(12) United States Patent
Crawley et al.

(10) Patent No.: US 12,240,899 B2
(45) Date of Patent: Mar. 4, 2025

(54) LAIR-1-BINDING AGENTS AND METHODS OF USE THEREOF

(71) Applicant: NGM Biopharmaceuticals, Inc., South San Francisco, CA (US)

(72) Inventors: Suzanne Christine Crawley, Brisbane, CA (US); Bin Fan, South San Francisco, CA (US); Betty Chan Li, Millbrae, CA (US); Lee Benjamin Rivera, South San Francisco, CA (US); James Robert Sissons, South San Francisco, CA (US); Jonathan Sitrin, South San Francisco, CA (US); Yan Wang, Foster City, CA (US); Xuan Zhao, South San Francisco, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 57 days.

(21) Appl. No.: 17/353,295

(22) Filed: Jun. 21, 2021

(65) Prior Publication Data
US 2022/0041711 A1 Feb. 10, 2022

Related U.S. Application Data

(60) Provisional application No. 63/122,877, filed on Dec. 8, 2020, provisional application No. 63/042,299, filed on Jun. 22, 2020.

(51) Int. Cl.
*C07K 16/28* (2006.01)
*A61P 35/00* (2006.01)
(52) U.S. Cl.
CPC .............. *C07K 16/28* (2013.01); *A61P 35/00* (2018.01); *C07K 16/2803* (2013.01);
(Continued)

(58) Field of Classification Search
CPC ................ C07K 16/28; C07K 16/2803; C07K 2317/24; C07K 2317/565; C07K 2317/74;
(Continued)

(56) References Cited

U.S. PATENT DOCUMENTS 6,140,076 A 10/2000 Adema et al.
6,479,638 B1 11/2002 Adema et al.
(Continued)

FOREIGN PATENT DOCUMENTS

EP 1264598 12/2002
EP 3315511 5/2018
(Continued)

OTHER PUBLICATIONS

Myoungsun Son, Understanding the contextual functions of C1q and LAIR-1 and their applications, May 13, 2022, Experimental & Molecular Medicine (2022) 54:567-572; (Year: 2022).*
(Continued)

*Primary Examiner* — Aurora M Fontainhas
*Assistant Examiner* — Selam Berhane
(74) *Attorney, Agent, or Firm* — Jones Day

(57) ABSTRACT

The present disclosure provides binding agents, such as antibodies, that specifically bind LAIR-1, including human LAIR-1, as well as compositions comprising the binding agents, and methods of their use. The disclosure also provides related polynucleotides and vectors encoding the binding agents and cells comprising the binding agents.

41 Claims, 25 Drawing Sheets
Specification includes a Sequence Listing.

(52) U.S. Cl.
CPC .... *C07K 2317/24* (2013.01); *C07K 2317/565* (2013.01); *C07K 2317/74* (2013.01); *C07K 2317/76* (2013.01); *C07K 2317/92* (2013.01)

(58) Field of Classification Search
CPC .. C07K 2317/76; C07K 2317/92; A61P 35/00
See application file for complete search history.

(56) References Cited

U.S. PATENT DOCUMENTS

| | | | |
|---|---|---|---|
| 7,999,078 | B2 | 8/2011 | Adema et al. |
| 9,605,070 | B2 | 3/2017 | Sabatos-Peyton et al. |
| 9,683,048 | B2 | 6/2017 | Freeman et al. |
| 10,280,225 | B2 | 5/2019 | Scadden et al. |
| 10,287,354 | B2 | 5/2019 | Brogdon et al. |
| 10,357,514 | B2 | 7/2019 | June et al. |
| 2003/0064072 | A9 | 4/2003 | Rosen et al. |
| 2007/0224663 | A1 | 9/2007 | Rosen et al. |
| 2009/0304686 | A1 | 12/2009 | Meyaard et al. |
| 2011/0268741 | A1 | 11/2011 | Tamada |
| 2014/0154252 | A1 | 6/2014 | Thompson et al. |
| 2014/0371086 | A1 | 12/2014 | Abbas et al. |
| 2016/0108045 | A1 | 4/2016 | Andres et al. |
| 2016/0144026 | A1 | 5/2016 | Lutteropp et al. |
| 2017/0065716 | A1 | 3/2017 | Brooks et al. |
| 2017/0121409 | A1 | 5/2017 | Verona et al. |
| 2017/0137783 | A1 | 5/2017 | Bedoya et al. |
| 2017/0198040 | A1 | 7/2017 | Balke et al. |
| 2017/0199198 | A1 | 7/2017 | Short |
| 2017/0209574 | A1 | 7/2017 | Cao et al. |
| 2017/0240638 | A1 | 8/2017 | Brooks et al. |
| 2017/0296659 | A1 | 10/2017 | Lebwohl et al. |
| 2017/0306038 | A1 | 10/2017 | Brogdon et al. |
| 2017/0335281 | A1 | 11/2017 | Loew et al. |
| 2017/0340733 | A1 | 11/2017 | Cao |
| 2017/0340735 | A1 | 11/2017 | Hicklin et al. |
| 2018/0016555 | A1 | 1/2018 | Borges et al. |
| 2018/0030137 | A1 | 2/2018 | Van Eenennaam et al. |
| 2018/0044424 | A1 | 2/2018 | June et al. |
| 2018/0044429 | A1 | 2/2018 | Keler et al. |
| 2018/0066053 | A1 | 3/2018 | Keler et al. |
| 2018/0071302 | A1 | 3/2018 | Abella et al. |
| 2018/0085472 | A1 | 3/2018 | Masteller et al. |
| 2018/0086830 | A1 | 3/2018 | Triebel et al. |
| 2018/0118834 | A1 | 5/2018 | Brogdon et al. |
| 2018/0140602 | A1 | 5/2018 | Angst et al. |
| 2018/0161302 | A1 | 6/2018 | Kremmidiotis et al. |
| 2018/0177808 | A1 | 6/2018 | Zebala et al. |
| 2018/0177847 | A1 | 6/2018 | Chen et al. |
| 2018/0179274 | A1 | 6/2018 | Lanzavecchia et al. |
| 2018/0186882 | A1 | 7/2018 | Freeman et al. |
| 2018/0228926 | A1 | 8/2018 | Kelly et al. |
| 2018/0230193 | A1 | 8/2018 | Loew et al. |
| 2018/0258149 | A1 | 9/2018 | Motz et al. |
| 2018/0271996 | A1 | 9/2018 | Bodyak et al. |
| 2018/0282423 | A1 | 10/2018 | Wang et al. |
| 2018/0289771 | A1 | 10/2018 | Shan et al. |
| 2018/0298068 | A1 | 10/2018 | Albelda |
| 2018/0312595 | A1 | 11/2018 | Brogdon et al. |
| 2018/0318417 | A1 | 11/2018 | Schuetz et al. |
| 2018/0333502 | A1 | 11/2018 | Lonberg et al. |
| 2018/0353483 | A1 | 12/2018 | Yeleswaram et al. |
| 2018/0363002 | A1 | 12/2018 | Deb et al. |
| 2019/0000880 | A1 | 1/2019 | Motz et al. |
| 2019/0062448 | A1 | 2/2019 | Soros et al. |
| 2019/0062783 | A1 | 2/2019 | Slepushkin et al. |
| 2019/0142967 | A1 | 5/2019 | Hicklin et al. |
| 2019/0151428 | A1 | 5/2019 | Stanford et al. |
| 2019/0183936 | A1 | 6/2019 | Shum, Shum et al. |
| 2019/0263925 | A1 | 8/2019 | Lavranos et al. |
| 2019/0276533 | A1 | 9/2019 | Zhang et al. |
| 2019/0338026 | A1 | 11/2019 | Liao et al. |

FOREIGN PATENT DOCUMENTS

| | | | |
|---|---|---|---|
| WO | WO 1998/024906 | 6/1998 | |
| WO | WO 2005/019258 | 3/2005 | |
| WO | WO 2014/116846 | 7/2014 | |
| WO | WO 2015/061752 | 4/2015 | |
| WO | WO 2017/125897 | 7/2017 | |
| WO | WO 2017/165683 | 9/2017 | |
| WO | WO 2017/181119 | 10/2017 | |
| WO | WO 2017/219934 | 12/2017 | |
| WO | WO 2017/219937 | 12/2017 | |
| WO | WO 2018/013918 | 1/2018 | |
| WO | WO-2018005967 A1 * | 1/2018 | ........... A61K 9/0019 |
| WO | WO 2018/025178 | 2/2018 | |
| WO | WO 2018/027039 | 2/2018 | |
| WO | WO 2018/033135 | 2/2018 | |
| WO | WO 2018/059437 | 4/2018 | |
| WO | WO 2018/059549 | 4/2018 | |
| WO | WO 2018/093907 | 5/2018 | |
| WO | WO 2018/111340 | 6/2018 | |
| WO | WO 2018/126259 | 7/2018 | |
| WO | WO 2018/140725 | 8/2018 | |
| WO | WO 2018/142322 | 8/2018 | |
| WO | WO 2018/160731 | 9/2018 | |
| WO | WO 2018/165228 | 9/2018 | |
| WO | WO 2018/175733 | 9/2018 | |
| WO | WO 2018/183889 | 10/2018 | |
| WO | WO 2018/189382 | 10/2018 | |
| WO | WO 2018/195348 | 10/2018 | |
| WO | WO 2018/215936 | 11/2018 | |
| WO | WO 2018/215937 | 11/2018 | |
| WO | WO 2018/215938 | 11/2018 | |
| WO | WO 2018/218056 | 11/2018 | |
| WO | WO 2018/218072 | 11/2018 | |
| WO | WO 2018/229715 | 12/2018 | |
| WO | WO 2018/234367 | 12/2018 | |
| WO | WO 2019/051135 | 3/2019 | |
| WO | WO 2019/057744 | 3/2019 | |
| WO | WO 2019/061562 | 4/2019 | |
| WO | WO 2019/077062 | 4/2019 | |
| WO | WO 2019/079569 | 4/2019 | |
| WO | WO 2019/079777 | 4/2019 | |
| WO | WO 2019/081983 | 5/2019 | |
| WO | WO 2019/094983 | 5/2019 | |
| WO | WO 2019/104075 | 5/2019 | |
| WO | WO 2019/108733 | 6/2019 | |
| WO | WO 2019/109047 | 6/2019 | |
| WO | WO 2019/114762 | 6/2019 | |
| WO | WO 2019/126366 | 6/2019 | |
| WO | WO 2019/129851 | 7/2019 | |
| WO | WO 2019/139987 | 7/2019 | |
| WO | WO 2019/157524 | 8/2019 | |
| WO | WO 2019/160956 | 8/2019 | |
| WO | WO 2019/170727 | 9/2019 | |

OTHER PUBLICATIONS

International Search Report and Written Opinion for International Application No. PCT/US2021/038251, mailed Jan. 19, 2022.

Arase et al., "Direct recognition of cytomegalovirus by activating and inhibitory NK cell receptors," Science, May 17, 2002, 296(5571):1323-6.

Chanput et al., "THP-1 cell line: an in vitro cell model for immune modulation approach," International immunopharmacology, Nov. 1, 2014, 23(1):37-45.

Lebbink et al., "Collagens are functional, high affinity ligands for the inhibitory immune receptor LAIR-1," The Journal of experimental medicine, Jun. 12, 2006, 203(6):1419-25.

Meyaard et al., "LAIR-1, a novel inhibitory receptor expressed on human mononuclear leukocytes," Immunity, Aug. 1, 1997, 7(2):283-90.

Meyaard et al., "The epithelial cellular adhesion molecule (Ep-CAM) is a ligand for the leukocyte-associated immunoglobulin-like receptor (LAIR)," The Journal of experimental medicine, Jul. 2, 2001, 194(1):107-12.

Meyaard, "The inhibitory collagen receptor LAIR-1 (CD305)," Journal of leukocyte biology, Apr. 2008, 83(4):799-803.

(56) References Cited

OTHER PUBLICATIONS

Barrow et al., "OSCAR is a receptor for surfactant protein D that activates TNF-α release from human CCR2+ inflammatory monocytes," The Journal of Immunology, Apr. 2015, 194(7):3317-26.
Invitation to pay additional fees in International Appln. No. PCT/US2021/038251, dated Nov. 10, 2021, 21 pages.
Xu et al., "Cancer immunotherapy based on blocking immune suppression mediated by an immune modulator LAIR-1," OncoImmunology, Jan. 1, 2020 9(1):1740477, 9 pages.
Bonnans et al., "Antagonist antibodies targeting LAIR1 promotes inflammatory phenotype in myeloid cells and activate lymphocytes," Immune-Onc Therapeutics, Palo Alto, CA, The University of Texas Southwestern Medical Center, Dallas, TX, The University of Texas Health Science Center, Houston, TX, Sep. 2020, 1 page.
Dondelinger et al., 2018, "Understanding the Significance and Implications of Antibody Numbering and Antigen-Binding Surface/Residue Definition," Frontiers in Immunology 9:1-15.
Krieg et al., 2005, "Functional analysis of B and T lymphocyte attenuator engagement on CD4+ and CD8+ T cells," Journal of Immunology 175(10):6420-6427.
Morris, 1996, "Epitope Mapping of Protein Antigens by Competition ELISA," The Proteins Protocols Handbook 595-600.
Perez De La Lastra, et al., 1999, "Epitope mapping of 10 monoclonal antibodies against the pig analogue of human membrane cofactor protein (MCP)," Immunology 96(4):663-670.

\* cited by examiner

＃ LAIR-1-BINDING AGENTS AND METHODS OF USE THEREOF

CROSS-REFERENCE TO RELATED APPLICATIONS

This application claims the benefit of priority of U.S. Provisional Application 63/042,299, filed on Jun. 22, 2020, and U.S. Provisional Application 63/122,877, filed Dec. 8, 2020, the content of both of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Jun. 8, 2021, is named 47702-0095001_SL.txt and is 190,218 bytes in size.

FIELD OF THE DISCLOSURE

The present disclosure generally relates to agents that bind leukocyte-associated immunoglobulin-like receptor 1 (LAIR-1), particularly antibodies that bind human LAIR-1, as well as compositions comprising the LAIR-1-binding agents. Methods of making the agents and methods of using the agents and compositions are also disclosed.

BACKGROUND

The basis for immunotherapy is the manipulation and/or modulation of the immune system, including both innate immune responses and adaptive immune responses. The general aim of immunotherapy is to treat diseases by controlling the immune response to a "foreign agent", for example a pathogen or a tumor cell. However, in some instances immunotherapy is used to treat autoimmune diseases which may arise from an abnormal immune response against proteins, molecules, and/or tissues normally present in the body. Immunotherapy may include methods to induce or enhance specific immune responses (e.g., to boost anti-tumor responses) or to inhibit or reduce specific immune responses.

The immune system is a highly complex system made up of a great number of cell types, including but not limited to, T-cells, B-cells, natural killer (NK) cells, antigen-presenting cells (APCs), dendritic cells, monocytes, and macrophages. These cells possess complex and subtle systems for controlling their interactions and responses. The cells utilize both activating and inhibitory mechanisms and feedback loops to keep responses in check and not allow negative consequences of an uncontrolled immune response (e.g., autoimmune diseases or a cytokine storm).

Some of the inhibitory mechanisms of the immune system rely on signaling proteins that contain ITIMs (immunoreceptor tyrosine-based inhibitory motifs). These proteins are generally cell-surface receptors comprising the ITIMs in their cytoplasmic tails. The majority of cells in the immune system express at least one, and often many, inhibitory receptors. Inhibitory receptors (i) use specific intracellular effector pathways that affect a variety of activation signals, (ii) recognize distinct ligands across a range of locations cells and tissues, and (iii) are differentially expressed between cell types and during differentiation and activation of cells. This allows these receptors to have an important part in a myriad of immune responses throughout the body. Many of the receptors are members of the Ig superfamily and include leukocyte immunoglobulin-like receptor subfamily B members (e.g., LILRB1, LILRB2, LILRB3, LILRB4, and LILRB5) and leukocyte-associated immunoglobulin-like receptor-1 (LAIR-1; also known as CD305) and LAIR-2. (See, for example, Meyaard et al., 1997, *Immunity*, 7:283-290; Meyaard, 2008, *J. Leukocyte Biol.*, 83:799-803)

The concept of cancer immunosurveillance is based on the theory that the immune system can recognize tumor cells, mount an immune response, and suppress the development and/or growth of a tumor. However, it is clear that many cancerous cells have developed mechanisms and/or hijacked normal inhibitory mechanisms to evade the immune system which can allow for uninhibited growth of tumors. Cancer/tumor immunotherapy (immuno-oncology) focuses on the development of new and novel agents that can activate and/or boost the immune system to achieve a more effective attack against cancer/tumor cells resulting in increased killing of cancer/tumor cells and/or inhibition of cancer/tumor growth. New and novel agents to boost the immune response to uncontrolled cell proliferation, i.e., tumor growth or cancer, are still needed.

BRIEF SUMMARY

The present disclosure provides agents that bind leukocyte-associated immunoglobulin-like receptor (LAIR-1). The agents include, but are not limited to, polypeptides such as antibodies that specifically bind LAIR-1. The agents may be referred to herein as "LAIR-1-binding agents". The disclosure provides methods of making a LAIR-1-binding agent. The disclosure provides methods of using a LAIR-1-binding agent. In some embodiments, a LAIR-1-binding agent inhibits LAIR-1 activity. In some embodiments, a LAIR-1-binding agent enhances an immune response. In some embodiments, a LAIR-1-binding agent reverses suppression of an immune cell. In some embodiments, a LAIR-1-binding agent is used in a combination therapy. In some embodiments, a LAIR-1-binding agent is used in combination with at least one additional therapeutic agent.

The disclosure also provides compositions comprising the LAIR-1-binding agents described herein. In some embodiments, the disclosure provides pharmaceutical compositions comprising the LAIR-1-binding agents described herein. Polynucleotides and/or vectors encoding the LAIR-1-binding agents are provided. Cells comprising the polynucleotides and/or the vectors described herein are also provided. Cells comprising or producing the LAIR-1-binding agents described herein are provided. Methods of making the LAIR-1-binding agents described herein are also provided.

In one aspect, the present disclosure provides agents that bind LAIR-1. In some embodiments, an agent binds human LAIR-1. In some embodiments, an agent binds cynomolgus monkey ("cyno") LAIR-1. In some embodiments, a LAIR-1-binding agent binds human LAIR-1 and cyno LAIR-1. In some embodiments, a LAIR-1-binding agent binds SEQ ID NO:2, SEQ ID NO:3, and/or SEQ ID NO:4. In some embodiments, a LAIR-1-binding agent binds SEQ ID NO:6, SEQ ID NO:7, and/or SEQ ID NO:8. In some embodiments, a LAIR-1-binding agent is an antibody. In some embodiments, a LAIR-1-binding agent is an antibody that binds human LAIR-1. In some embodiments, a LAIR-1-binding agent is an antibody that binds cyno LAIR-1. In some embodiments, a LAIR-1-binding agent is an antibody that binds human LAIR-1 and cyno LAIR-1. In some embodiments, a LAIR-1-binding agent is an antibody that binds human LAIR-1, but does not bind mouse LAIR-1.

In some embodiments, a LAIR-1-binding agent binds within the extracellular domain of LAIR-1. In some embodiments, a LAIR-1-binding agent binds within amino acids 22-165 of SEQ ID NO:1. In some embodiments, a LAIR-1-binding agent binds within amino acids 29-117 of SEQ ID NO:1. In some embodiments, a LAIR-1-binding agent binds a conformational epitope within the extracellular domain of human LAIR-1. In some embodiments, a LAIR-1-binding agent binds a conformational epitope within the Ig-like C2-type domain of human LAIR-1. In some embodiments, a LAIR-1-binding agent binds within amino acids 22-165 of SEQ ID NO:5. In some embodiments, a LAIR-1-binding agent binds within amino acids 29-117 of SEQ ID NO:5. In some embodiments, a LAIR-1-binding agent binds a conformational epitope within the extracellular domain of cyno LAIR-1. In some embodiments, a LAIR-1-binding agent binds a conformational epitope within the Ig-like C2-type domain of cyno LAIR-1.

In one aspect, the present disclosure provides a LAIR-1 binding agent that specifically binds the extracellular domain of LAIR-1, wherein: (i) the binding agent binds to human LAIR-1 and to cynomolgus LAIR-1, (ii) the binding agent binds to human LAIR-1 with a dissociation constant ($K_D$) of less than $1 \times 10^{-9}$ M, and/or (iii) the binding agent binds to cynomolgus LAIR-1 with a $K_D$ of less than $1 \times 10^{-8}$ M; and wherein the binding agent is an antibody or an antigen-binding fragment thereof. In some instances, the binding agent is an antibody (e.g., an immunoglobulin). In some instances, the binding agent is an antigen-binding fragment. In some instances, the binding agent binds to human LAIR-1 with a dissociation constant of less than $1 \times 10^{-9}$ M (e.g., less than $9 \times 10^{-10}$ M, less than $8 \times 10^{-10}$ M, less than $7 \times 10^{-10}$ M, less than $6 \times 10^{-10}$ M, less than $5 \times 10^{-10}$ M, less than $4 \times 10^{-10}$ M, less than $3 \times 10^{-10}$ M, less than $2 \times 10^{-10}$ M, less than $1 \times 10^{-10}$ M, less than $1 \times 10^{-11}$ M, from $1 \times 10^{-11}$ M to $1 \times 10^{-9}$ M, from $1 \times 10^{-10}$ M to $1 \times 10^{-9}$ M, from $1 \times 10^{-10}$ M to $9 \times 10^{-10}$ M, from $1 \times 10^{-10}$ M to $8 \times 10^{-10}$ M, from $1 \times 10^{-10}$ M to $7 \times 10^{-10}$ M, from $1 \times 10^{-10}$ M to $6 \times 10^{-10}$ M, from $1 \times 10^{-10}$ M to $5 \times 10^{-10}$ M, from $1 \times 10^{-10}$ M to $4 \times 10^{-10}$ M, or from $1 \times 10^{-10}$ M to $3 \times 10^{-10}$ M). In some instances, the binding agent binds to cynomolgus LAIR-1 with a $K_D$ of less than $1 \times 10^{-8}$ M (e.g., less than $9 \times 10^{19}$ M, less than $8 \times 10^{-9}$ M, less than $7 \times 10^{-9}$ M, less than $6 \times 10^{-9}$ M, less than $5 \times 10^{-9}$ M, less than $4 \times 10^{-9}$ M, less than $3 \times 10^{-9}$ M, less than $2 \times 10^{-9}$ M, less than $1 \times 10^{-9}$ M, less than $1 \times 10^{-10}$ M, from $1 \times 10^{-10}$ M to $1 \times 10^{-8}$ M, from $1 \times 10^{-9}$ M to $1 \times 10^{-8}$ M, from $1 \times 10^{-9}$ M to $9 \times 10^{-8}$ M, from $1 \times 10^{-9}$ M to $8 \times 10^{-9}$ M, from $1 \times 10^{-9}$ M to $7 \times 10^{-9}$ M, from $1 \times 10^{-9}$ M to $6 \times 10^{-9}$ M, or from $1 \times 10^{-9}$ M to $5 \times 10^{-9}$ M). In some instances, the binding agent is an antigen-binding fragment. In some instances, the binding agent binds to human LAIR-1 with a dissociation constant of less than $1 \times 10^{-9}$ M (e.g., less than $9 \times 10^{-10}$ M, less than $8 \times 10^{-10}$ M, less than $7 \times 10^{-10}$ M, less than $6 \times 10^{-10}$ M, less than $5 \times 10^{-10}$ M, less than $4 \times 10^{-10}$ M, less than $3 \times 10^{-10}$ M, less than $2 \times 10^{-10}$ M, less than $1 \times 10^{-10}$ M, less than $1 \times 10^{-11}$ M, from $1 \times 10^{-11}$ M to $1 \times 10^{-9}$ M, from $1 \times 10^{-10}$ M to $1 \times 10^{-9}$ M, from $1 \times 10^{-10}$ M to $9 \times 10^{-10}$ M, from $1 \times 10^{-10}$ M to $8 \times 10^{-10}$ M, from $1 \times 10^{-10}$ M to $7 \times 10^{-10}$ M, from $1 \times 10^{-10}$ M to $6 \times 10^{-10}$ M, from $1 \times 10^{-10}$ M to $5 \times 10^{-10}$ M, from $1 \times 10^{-10}$ M to $4 \times 10^{-10}$ M, or from $1 \times 10^{-10}$ M to $3 \times 10^{-10}$ M) and binds to cynomolgus LAIR-1 with a $K_D$ of less than $1 \times 10^{-8}$ M (e.g., less than $9 \times 10^{-9}$ M, less than $8 \times 10^{-9}$ M, less than $7 \times 10^{-9}$ M, less than $6 \times 10^{-9}$ M, less than $5 \times 10^{-9}$ M, less than $4 \times 10^{-9}$ M, less than $3 \times 10^{-9}$ M, less than $2 \times 10^{-9}$ M, less than $1 \times 10^{-9}$ M, less than $1 \times 10^{-10}$ M, from $1 \times 10^{-10}$ M to $1 \times 10^{-8}$ M, from $1 \times 10^{-9}$ M to $1 \times 10^{-8}$ M, from $1 \times 10^{-9}$ M to $9 \times 10^{-8}$ M, from $1 \times 10^{-9}$ M to $8 \times 10^{-9}$ M, from $1 \times 10^{-9}$ M to $7 \times 10^{-9}$ M, from $1 \times 10^{-9}$ M to $6 \times 10^{-9}$ M, or from $1 \times 10^{-9}$ M to $5 \times 10^{-9}$ M). In some instances, the $K_D$ is determined using Biacore. In some instances, the binding agent is an antibody comprising a human IgG1 heavy chain constant region. In some instances, the binding agent is an antibody comprising a human kappa light chain constant region. In some instances, the binding agent is an antibody comprising a human IgG1 heavy chain constant region and a human kappa light chain constant region. In some instances, the binding agent is an antibody comprising a heavy chain constant region comprising the amino acid sequence of SEQ ID NO:145. In some instances, the binding agent is an antibody comprising a light chain constant region of the amino acid sequence of SEQ ID NO:147.

In one aspect, the present disclosure provides agents that have at least one or more (e.g., 1, 2, 3, 4, 5, 6, 7, 8, 9, 10, 11, 12, 13, 14, 15, 16, 17, 18) of the following properties: (i) binds human LAIR-1; (ii) binds cyno LAIR-1; (iii) does not bind mouse LAIR-1; (iv) does not bind human LAIR-2; (v) is a LAIR-1 antagonist; (vi) inhibits LAIR-1 activity; (vi) inhibits LAIR-1 signaling in cells that express LAIR-1; (viii) inhibits binding of LAIR-1 to collagen; (ix) inhibits binding of LAIR-1 to MARCO (macrophage receptor with collagenous structure); (x) inhibits binding of LAIR-1 to COLEC12 (collectin 12); (xi) inhibits LAIR-1-induced suppression of myeloid cells; (xii) inhibits LAIR-1-induced suppression of myeloid cell activity; (xiii) restores FcR activation in myeloid cells; (xiv) restores cytokine and/or chemokine production in myeloid cells; (xv) inhibits LAIR-1-induced suppression of natural killer (NK) cells; (xvi) inhibits LAIR-1-induced suppression of NK activity; (xvii) inhibits LAIR-1-induced suppression of T-cell activity; and/or (xviii) inhibits myeloid-derived suppressor cell (MDSC) activity.

In another aspect, the present disclosure provides agents that specifically bind LAIR-1. In some embodiments, a LAIR-1-binding agent comprises a heavy chain variable region comprising a heavy chain variable region CDR1 (VH CDR1), a heavy chain variable region CDR2 (VH CDR2), and a heavy chain variable region CDR3 (VH CDR3) from the amino acid sequence of SEQ ID NO:115; and a light chain variable region comprising a light chain variable region CDR1 (VL CDR1), a light chain variable region CDR2 (VL CDR2), and a light chain variable region CDR3 (VL CDR3) from the amino acid sequence of SEQ ID NO:116. In some embodiments, a LAIR-1-binding agent comprises: (a) a heavy chain variable region comprising a VH CDR1 comprising the amino acid sequence GFTFN-TYAIH (SEQ ID NO:9), a VH CDR2 comprising the amino acid sequence RIRSKSTNYATYYADSVKD (SEQ ID NO:10), and a VH CDR3 comprising the amino acid sequence ENWYYYALDY (SEQ ID NO:11), and/or (b) a light chain variable region comprising a VL CDR1 comprising the amino acid sequence RASGNIHNYLT (SEQ ID NO:12), a VL CDR2 comprising the amino acid sequence NAKTLED (SEQ ID NO:13), and a VL CDR3 comprising the amino acid sequence QHFWSTPFT (SEQ ID NO:14). In some embodiments, a LAIR-1-binding agent comprises: (a) a heavy chain variable region comprising a VH CDR1 comprising the amino acid sequence of SEQ ID NO:15, a VH CDR2 comprising the amino acid sequence of SEQ ID NO:16, and a VH CDR3 comprising the amino acid sequence of SEQ ID NO:11, and/or (b) a light chain variable region comprising a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14. In some embodiments, a LAIR-1-binding agent comprises: (a) a heavy chain variable region comprising a VH CDR1 comprising the amino acid sequence of SEQ ID NO:9, a VH CDR2 comprising the amino acid sequence of SEQ ID NO:17, and a VH CDR3 comprising the amino acid sequence of SEQ ID NO:11, and/or (b) a light chain variable region comprising a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14. In some embodiments, a LAIR-1-binding agent comprises: (a) a heavy chain variable region comprising a VH CDR1 comprising the amino acid sequence of SEQ ID NO:18, a VH CDR2 comprising the amino acid sequence of SEQ ID NO:10, and a VH CDR3 comprising the amino acid sequence of SEQ ID NO:11, and/or (b) a light chain variable region comprising a VL CDR1 comprising the amino acid sequence of SEQ ID NO:12, a VL CDR2 comprising the amino acid sequence of SEQ ID NO:13, and a VL CDR3 comprising the amino acid sequence of SEQ ID NO:14. In some embodiments, a LAIR-1-binding agent comprises: (a) a heavy chain variable region comprising a VH CDR1 comprising the amino acid sequence of SEQ ID NO:19, a VH CDR2 comprising the amino acid sequence of SEQ ID NO:20, and a VH CDR3 comprising the amino acid sequence of SEQ ID NO:21, and/or (b) a light chain variable region comprising a VL CDR1 comprising the amino acid sequence of SEQ ID NO:22, a VL CDR2 comprising the amino acid sequence of SEQ ID NO:23, and a VL CDR3 comprising the amino acid sequence of SEQ ID NO:24.

In some embodiments, a LAIR-1-binding agent comprises: (a) a heavy chain variable region having at least 80% sequence identity to the amino acid sequence of SEQ ID NO:115; and/or (b) a light chain variable region having at least 80% sequence identity to the amino acid sequence of SEQ ID NO:116. In some embodiments, a LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:115 and/or a light chain variable region having at least 85%, at least 90%, at least 95%, at least 96%, at least 97%, at least 98%, or at least 99% sequence identity to the amino acid sequence of SEQ ID NO:116. In some embodiments, a LAIR-1-binding agent comprises a heavy chain variable region of amino acid sequence SEQ ID NO:115 and/or a light chain variable region of amino acid sequence SEQ ID NO:116. In some embodiments, the LAIR-1-binding agent comprises a heavy chain variable region of amino acid sequence SEQ ID NO:115 and a light chain variable region of amino acid sequence SEQ ID NO:116.

In some embodiments, the LAIR-1-binding agent is antibody 47A1. In some embodiments, the LAIR-1-binding agent is a humanized version of antibody 47A1. In some embodiments, the LAIR-1-binding agent is a variant of antibody 47A1 or a variant of a humanized version of 47A1.

In some embodiments, a LAIR-1-binding agent comprises a heavy chain variable region comprising a VH CDR1, a VH CDR2, and a VH CDR3 from the amino acid sequence of SEQ ID NO:117; and/or a light chain variable region comprising a VL CDR1, a VL CDR2, and a VL CDR3 from the amino acid sequence of SEQ ID NO:118. In some embodiments, a LAIR-1-binding agent comprises: (a) a heavy chain variable region comprising a VH CDR1 comprising the amino acid sequence GFTFNINAMN (SEQ ID NO:25), a VH CDR2 comprising the amino acid sequence RIRTKNNNYATFYADSVKD (SEQ ID NO:26), and a VH CDR3 comprising the amino acid sequence DRAGFFAY (SEQ ID NO:27), and/or (b) a light chain variable region comprising a VL CDR1 comprising the amino acid sequence LASQTIGTWLG (SEQ ID NO:28), a VL CDR2 comprising the amino acid sequence AATSLAD (SEQ ID NO:29), and a VL CDR3 comprising the amino acid sequence QQLYSTPLT (SEQ ID NO:30). In some embodiments, a LAIR-1-binding agent comprises: (a) a heavy chain variable region comprising a VH CDR1 comprising the amino acid sequence GFTFNINAMN (SEQ ID NO:25), a VH CDR2 comprising the amino acid sequence RIRTKNNNYATFYADSVKD (SEQ ID NO:26), and a VH CDR3 comprising the amino acid sequence DRAGFFAY (SEQ ID NO:27), and/or (b) a light chain variable region comprising a VL CDR1 comprising the amino acid sequence LASQTIGTWLG (SEQ ID NO:28), a VL CDR2 comprising the amino acid sequence AATSLAD (SEQ ID NO:29), and a VL CDR3 comprising the amino acid sequence QQLYSTPLT (SEQ ID NO:30). In some embodiments, a LAIR-1-binding agent comprises: (a) a heavy chain variable region comprising a VH CDR1 comprising the amino acid sequence of SEQ ID NO:31, a VH CDR2 comprising the amino acid sequence of SEQ ID NO:32, and a VH CDR3 comprising the amino acid sequence of SEQ ID NO:27, and/or (b) a light chain variable region comprising a VL CDR1 comprising the amino acid sequence of SEQ ID NO:28, a VL CDR2 comprising the amino acid sequence of SEQ ID NO:29, and a VL CDR3 comprising the amino acid sequence of SEQ ID NO:30. In some embodiments, a LAIR-1-binding agent comprises: (a) a heavy chain variable region comprising a VH CDR1 comprising the amino acid sequence of SEQ ID NO:25, a VH CDR2 comprising the amino acid sequence of SEQ ID NO:33, and a VH CDR3 comprising the amino acid sequence of SEQ ID NO:27, and/or (b) a light chain variable region comprising a VL CDR1 comprising the amino acid sequence of SEQ ID NO:28, a VL CDR2 comprising the amino acid sequence of SEQ ID NO:29, and a VL CDR3 comprising the amino acid sequence of SEQ ID NO:30. In some embodiments, a LAIR-1-binding agent comprises: (a) a heavy chain variable region comprising a VH CDR1 comprising the amino acid sequence of SEQ ID NO:34, a VH CDR2 comprising the amino acid sequence of SEQ ID NO:26, and a VH CDR3 comprising the amino acid sequence of SEQ ID NO:27, and/or (b) a light chain variable region comprising a VL CDR1 comprising the amino acid sequence of SEQ ID NO:28, a VL CDR2 comprising the amino acid sequence of SEQ ID NO:29, and a VL CDR3 comprising the amino acid sequence of SEQ ID NO:30. In some embodiments, a LAIR-1-binding agent comprises: (a) a heavy chain variable region comprising a VH CDR1 comprising the amino acid sequence of SEQ ID NO:35, a VH CDR2 comprising the amino acid sequence of SEQ ID NO:36, and a VH CDR3 comprising the amino acid sequence of SEQ ID NO:37, and/or (b) a light chain variable region comprising a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40. In some instances, the LAIR-1-binding agent comprises the VH comprising the VH CDR1, the VH CDR2, and the VH CDR3, and the VL comprising the VL CDR1, the VL CDR2, and the VL CDR3.

In some embodiments, a LAIR-1-binding agent comprises a heavy chain variable region comprising a VH CDR1, a VH CDR2, and a VH CDR3 from the amino acid sequence of SEQ ID NO:119; and/or a light chain variable region comprising a VL CDR1, a VL CDR2, and a VL CDR3 from the amino acid sequence of SEQ ID NO:120. In some embodiments, a LAIR-1-binding agent comprises: (a) a heavy chain variable region comprising a VH CDR1 comprising the amino acid sequence GFTFNINAMN (SEQ ID NO:25), a VH CDR2 comprising the amino acid sequence RIRTKNYNYATFYADSVKD (SEQ ID NO:41), and a VH CDR3 comprising the amino acid sequence DRAGFFAY (SEQ ID NO:27), and/or (b) a light chain variable region comprising a VL CDR1 comprising the amino acid sequence LASQTIGTWLG (SEQ ID NO:28), a VL CDR2 comprising the amino acid sequence AATSLAE (SEQ ID NO:42), and a VL CDR3 comprising the amino acid sequence QQLYSTPLT (SEQ ID NO:30). In some embodiments, a LAIR-1-binding agent comprises: (a) a heavy chain variable region comprising a VH CDR1 comprising the amino acid sequence of SEQ ID NO:31, a VH CDR2 comprising the amino acid sequence of SEQ ID NO:43, and a VH CDR3 comprising the amino acid sequence of SEQ ID NO:27, and/or (b) a light chain variable region comprising a VL CDR1 comprising the amino acid sequence of SEQ ID NO:28, a VL CDR2 comprising the amino acid sequence of SEQ ID NO:42, and a VL CDR3 comprising the amino acid sequence of SEQ ID NO:30. In some embodiments, a LAIR-1-binding agent comprises: (a) a heavy chain variable region comprising a VH CDR1 comprising the amino acid sequence of SEQ ID NO:25, a VH CDR2 comprising the amino acid sequence of SEQ ID NO:44, and a VH CDR3 comprising the amino acid sequence of SEQ ID NO:27, and/or (b) a light chain variable region comprising a VL CDR1 comprising the amino acid sequence of SEQ ID NO:28, a VL CDR2 comprising the amino acid sequence of SEQ ID NO:42, and a VL CDR3 comprising the amino acid sequence of SEQ ID NO:30. In some embodiments, a LAIR-1-binding agent comprises: (a) a heavy chain variable region comprising a VH CDR1 comprising the amino acid sequence of SEQ ID NO:34, a VH CDR2 comprising the amino acid sequence of SEQ ID NO:41, and a VH CDR3 comprising the amino acid sequence of SEQ ID NO:27, and/or (b) a light chain variable region comprising a VL CDR1 comprising the amino acid sequence of SEQ ID NO:28, a VL CDR2 comprising the amino acid sequence of SEQ ID NO:42, and a VL CDR3 comprising the amino acid sequence of SEQ ID NO:30. In some embodiments, a LAIR-1-binding agent comprises: (a) a heavy chain variable region comprising a VH CDR1 comprising the amino acid sequence of SEQ ID NO:35, a VH CDR2 comprising the amino acid sequence of SEQ ID NO:45, and a VH CDR3 comprising the amino acid sequence of SEQ ID NO:37, and/or (b) a light chain variable region comprising a VL CDR1 comprising the amino acid sequence of SEQ ID NO:38, a VL CDR2 comprising the amino acid sequence of SEQ ID NO:39, and a VL CDR3 comprising the amino acid sequence of SEQ ID NO:40. In some instances, the LAIR-1-binding agent comprises the VH comprising the VH CDR1, the VH CDR2, and the VH CDR3, and the VL comprising the VL CDR1, the VL CDR2, and the VL CDR3.

In some embodiments, a LAIR-1-binding agent comprises: (a) a heavy chain variable region having at least 80% sequence identity to the amino acid sequence of SEQ ID NO:117; and/or (b) a light chain variable region having at least 80% sequence identity to the amino acid sequence of SEQ ID NO:118. In some embodiments, a LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:117 and/or a light chain variable region having at least 85%, at least 90%, at least 95%, at least 96%, at least 97%, at least 98%, or at least 99% sequence identity to the amino acid sequence of SEQ ID NO:118. In some embodiments, a LAIR-1-binding agent comprises a heavy chain variable region of amino acid sequence SEQ ID NO:117 and/or a light chain variable region of amino acid sequence SEQ ID NO:118. In some embodiments, the LAIR-1-binding agent comprises a heavy chain variable region of amino acid sequence SEQ ID NO:117 and a light chain variable region of amino acid sequence SEQ ID NO:118.

In some embodiments, a LAIR-1-binding agent comprises: (a) a heavy chain variable region having at least 80% sequence identity to the amino acid sequence of SEQ ID NO:119; and/or (b) a light chain variable region having at least 80% sequence identity to the amino acid sequence of SEQ ID NO:120. In some embodiments, a LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:119 and/or a light chain variable region having at least 85%, at least 90%, at least 95%, at least 96%, at least 97%, at least 98%, or at least 99% sequence identity to the amino acid sequence of SEQ ID NO:120. In some embodiments, a LAIR-1-binding agent comprises a heavy chain variable region of amino acid sequence SEQ ID NO:119 and/or a light chain variable region of amino acid sequence SEQ ID NO:120. In some embodiments, the LAIR-1-binding agent comprises a heavy chain variable region of amino acid sequence SEQ ID NO:119 and a light chain variable region of amino acid sequence SEQ ID NO:120.

In some embodiments, a LAIR-1-binding agent comprises a heavy chain with an amino acid sequence at least 80% (e.g., at least 85%, at least 90%, at least 95%, at least 96%, at least 97%, at least 98%, or at least 99%) identical to SEQ ID NO:134, and/or a light chain with an amino acid sequence at least 80% (e.g., at least 85%, at least 90%, at least 95%, at least 96%, at least 97%, at least 98%, or at least 99%) identical to SEQ ID NO:136. In some embodiments, a LAIR-1-binding agent is an antibody comprising a heavy chain with an amino acid sequence at least 80% (e.g., at least 85%, at least 90%, at least 95%, at least 96%, at least 97%, at least 98%, or at least 99%) identical to SEQ ID NO:134, and/or a light chain with an amino acid sequence at least 80% (e.g., at least 85%, at least 90%, at least 95%, at least 96%, at least 97%, at least 98%, or at least 99%) identical to SEQ ID NO:136. In some embodiments, a LAIR-1-binding agent comprises a heavy chain comprising the amino acid sequence of SEQ ID NO:134, and/or a light chain comprising the amino acid sequence of SEQ ID NO:136. In some embodiments, a LAIR-1-binding agent is an antibody comprising a heavy chain comprising the amino acid sequence of SEQ ID NO:134 and/or a light chain comprising the amino acid sequence of SEQ ID NO:136. In some embodiments, a LAIR-1-binding agent is an antibody comprising a heavy chain comprising the amino acid sequence of SEQ ID NO:134 and a light chain comprising the amino acid sequence of SEQ ID NO:136.

In some embodiments, the LAIR-1-binding agent is antibody 47H1. In some embodiments, the LAIR-1-binding agent is a humanized version of antibody 47H1 (e.g., Hz47H1, e.g., Hz47H1.v4). In some embodiments, the LAIR-1-binding agent is a variant of antibody 47H1 or a variant of a humanized version of 47H1. In some embodiments, the LAIR-1-binding agent is antibody Hz47H1.v4.

In some embodiments, a LAIR-1-binding agent comprises a heavy chain variable region comprising a VH CDR1, a VH CDR2, and a VH CDR3 from the amino acid sequence of SEQ ID NO:121; and/or a light chain variable region comprising a VL CDR1, a VL CDR2, and a VL CDR3 from the amino acid sequence of SEQ ID NO:122. In some embodiments, a LAIR-1-binding agent comprises: (a) a heavy chain variable region comprising a VH CDR1 comprising the amino acid sequence GYSFTSFGIS (SEQ ID NO:46), a VH CDR2 comprising the amino acid sequence EIYPRSDNTFYNEKFKG (SEQ ID NO:47), and a VH CDR3 comprising the amino acid sequence HFGSSSFDY (SEQ ID NO:48), and/or (b) a light chain variable region comprising a VL CDR1 comprising the amino acid sequence SASSSVSSIYFH (SEQ ID NO:49), a VL CDR2 comprising the amino acid sequence RASNLAS (SEQ ID NO:50), and a VL CDR3 comprising the amino acid sequence QQWSGYPLT (SEQ ID NO:51). In some embodiments, a LAIR-1-binding agent comprises: (a) a heavy chain variable region comprising a VH CDR1 comprising the amino acid sequence of SEQ ID NO:52, a VH CDR2 comprising the amino acid sequence of SEQ ID NO:53, and a VH CDR3 comprising the amino acid sequence of SEQ ID NO:48, and/or (b) a light chain variable region comprising a VL CDR1 comprising the amino acid sequence of SEQ ID NO:49, a VL CDR2 comprising the amino acid sequence of SEQ ID NO:50, and a VL CDR3 comprising the amino acid sequence of SEQ ID NO:51. In some embodiments, a LAIR-1-binding agent comprises: (a) a heavy chain variable region comprising a VH CDR1 comprising the amino acid sequence of SEQ ID NO:46, a VH CDR2 comprising the amino acid sequence of SEQ ID NO:54, and a VH CDR3 comprising the amino acid sequence of SEQ ID NO:48, and/or (b) a light chain variable region comprising a VL CDR1 comprising the amino acid sequence of SEQ ID NO:49, a VL CDR2 comprising the amino acid sequence of SEQ ID NO:50, and a VL CDR3 comprising the amino acid sequence of SEQ ID NO:51. In some embodiments, a LAIR-1-binding agent comprises: (a) a heavy chain variable region comprising a VH CDR1 comprising the amino acid sequence of SEQ ID NO:55, a VH CDR2 comprising the amino acid sequence of SEQ ID NO:47, and a VH CDR3 comprising the amino acid sequence of SEQ ID NO:48, and/or (b) a light chain variable region comprising a VL CDR1 comprising the amino acid sequence of SEQ ID NO:49, a VL CDR2 comprising the amino acid sequence of SEQ ID NO:50, and a VL CDR3 comprising the amino acid sequence of SEQ ID NO:51. In some embodiments, a LAIR-1-binding agent comprises: (a) a heavy chain variable region comprising a VH CDR1 comprising the amino acid sequence of SEQ ID NO:56, a VH CDR2 comprising the amino acid sequence of SEQ ID NO:57, and a VH CDR3 comprising the amino acid sequence of SEQ ID NO:58, and/or (b) a light chain variable region comprising a VL CDR1 comprising the amino acid sequence of SEQ ID NO:59, a VL CDR2 comprising the amino acid sequence of SEQ ID NO:60, and a VL CDR3 comprising the amino acid sequence of SEQ ID NO:61. In some instances, the LAIR-1-binding agent comprises the VH comprising the VH CDR1, the VH CDR2, and the VH CDR3, and the VL comprising the VL CDR1, the VL CDR2, and the VL CDR3.

In some embodiments, a LAIR-1-binding agent comprises: (a) a heavy chain variable region having at least 80% sequence identity to the amino acid sequence of SEQ ID NO:121; and/or (b) a light chain variable region having at least 80% sequence identity to the amino acid sequence of SEQ ID NO:122. In some embodiments, a LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:121 and/or a light chain variable region having at least 85%, at least 90%, at least 95%, at least 96%, at least 97%, at least 98%, or at least 99% sequence identity to the amino acid sequence of SEQ ID NO:122. In some embodiments, a LAIR-1-binding agent comprises a heavy chain variable region of amino acid sequence SEQ ID NO:121 and/or a light chain variable region of amino acid sequence SEQ ID NO:122. In some embodiments, the LAIR-1-binding agent comprises a heavy chain variable region of amino acid sequence SEQ ID NO:121 and a light chain variable region of amino acid sequence SEQ ID NO:122.

In some embodiments, the LAIR-1-binding agent is antibody 57D12. In some embodiments, the LAIR-1-binding agent is a humanized version of antibody 57D12. In some embodiments, the LAIR-1-binding agent is a variant of antibody 57D12 or a variant of a humanized version of 57D12.

In some embodiments, a LAIR-1-binding agent comprises a heavy chain variable region comprising a VH CDR1, a VH CDR2, and a VH CDR3 from the amino acid sequence of SEQ ID NO:123; and/or a light chain variable region comprising a VL CDR1, a VL CDR2, and a VL CDR3 from the amino acid sequence of SEQ ID NO:124. In some embodiments, a LAIR-1-binding agent comprises (a) a heavy chain variable region comprising a VH CDR1 comprising the amino acid sequence GYTFTDYYYMN (SEQ ID NO:62), a VH CDR2 comprising the amino acid sequence YIYPNNGATSYNQKFKG (SEQ ID NO:63), and a VH CDR3 comprising the amino acid sequence DGYSSNYYTMDY (SEQ ID NO:64), and/or (b) a light chain variable region comprising a VL CDR1 comprising the amino acid sequence QASQGTSINLN (SEQ ID NO:65), a VL CDR2 comprising the amino acid sequence GASNLED (SEQ ID NO:66), and a VL CDR3 comprising the amino acid sequence LQHTYLPYT (SEQ ID NO:67). In some embodiments, a LAIR-1-binding agent comprises: (a) a heavy chain variable region comprising a VH CDR1 comprising the amino acid sequence of SEQ ID NO:68, a VH CDR2 comprising the amino acid sequence of SEQ ID NO:69, and a VH CDR3 comprising the amino acid sequence of SEQ ID NO:64, and/or (b) a light chain variable region comprising a VL CDR1 comprising the amino acid sequence of SEQ ID NO:65, a VL CDR2 comprising the amino acid sequence of SEQ ID NO:66, and a VL CDR3 comprising the amino acid sequence of SEQ ID NO:67. In some embodiments, a LAIR-1-binding agent comprises: (a) a heavy chain variable region comprising a VH CDR1 comprising the amino acid sequence of SEQ ID NO:62, a VH CDR2 comprising the amino acid sequence of SEQ ID NO:70, and a VH CDR3 comprising the amino acid sequence of SEQ ID NO:64, and/or (b) a light chain variable region comprising a VL CDR1 comprising the amino acid sequence of SEQ ID NO:65, a VL CDR2 comprising the amino acid sequence of SEQ ID NO:66, and a VL CDR3 comprising the amino acid sequence of SEQ ID NO:67. In some embodiments, a LAIR-1-binding agent comprises: (a) a heavy chain variable region comprising a VH CDR1 comprising the amino acid sequence of SEQ ID NO:71, a VH CDR2 comprising the amino acid sequence of SEQ ID NO:63, and a VH CDR3 comprising the amino acid sequence of SEQ ID NO:64, and/or (b) a light chain variable region comprising a VL CDR1 comprising the amino acid sequence of SEQ ID NO:65, a VL CDR2 comprising the amino acid sequence of SEQ ID NO:66, and a VL CDR3 comprising the amino acid sequence of SEQ ID NO:67. In some embodiments, a LAIR-1-binding agent comprises: (a) a heavy chain variable region comprising a VH CDR1 comprising the amino acid sequence of SEQ ID NO:72, a VH CDR2 comprising the amino acid sequence of SEQ ID NO:73, and a VH CDR3 comprising the amino acid sequence of SEQ ID NO:74, and/or (b) a light chain variable region comprising a VL CDR1 comprising the amino acid sequence of SEQ ID NO:75, a VL CDR2 comprising the amino acid sequence of SEQ ID NO:76, and a VL CDR3 comprising the amino acid sequence of SEQ ID NO:77. In some instances, the LAIR-1-binding agent comprises the VH comprising the VH CDR1, the VH CDR2, and the VH CDR3, and the VL comprising the VL CDR1, the VL CDR2, and the VL CDR3.

In some embodiments, a LAIR-1-binding agent comprises: (a) a heavy chain variable region having at least 80% sequence identity to the amino acid sequence of SEQ ID NO:123; and/or (b) a light chain variable region having at least 80% sequence identity to the amino acid sequence of SEQ ID NO:124. In some embodiments, a LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:123 and/or a light chain variable region having at least 85%, at least 90%, at least 95%, at least 96%, at least 97%, at least 98%, or at least 99% sequence identity to the amino acid sequence of SEQ ID NO:124. In some embodiments, a LAIR-1-binding agent comprises a heavy chain variable region of amino acid sequence SEQ ID NO:123 and/or a light chain variable region of amino acid sequence SEQ ID NO:124. In some embodiments, the LAIR-1-binding agent comprises a heavy chain variable region of amino acid sequence SEQ ID NO:123 and a light chain variable region of amino acid sequence SEQ ID NO:124.

In some embodiments, the LAIR-1-binding agent is antibody 61H4. In some embodiments, the LAIR-1-binding agent is a humanized version of antibody 61H4. In some embodiments, the LAIR-1-binding agent is a variant of antibody 61H4 or a variant of a humanized antibody 61H4.

In some embodiments, a LAIR-1-binding agent comprises a heavy chain variable region comprising a VH CDR1, a VH CDR2, and a VH CDR3 from the amino acid sequence of SEQ ID NO:125 or SEQ ID NO: 127; and/or a light chain variable region comprising a VL CDR1, a VL CDR2, and a VL CDR3 from the amino acid sequence of SEQ ID NO:126 or SEQ ID NO: 128. In some embodiments, a LAIR-1-binding agent comprises a heavy chain variable region comprising a VH CDR1, a VH CDR2, and a VH CDR3 from the amino acid sequence of SEQ ID NO: 127; and/or a light chain variable region comprising a VL CDR1, a VL CDR2, and a VL CDR3 from the amino acid sequence of SEQ ID NO: 128. In some embodiments, a LAIR-1-binding agent comprises (a) a heavy chain variable region comprising a VH CDR1 comprising the amino acid sequence GFTFNI-NAMN (SEQ ID NO:25), a VH CDR2 comprising the amino acid sequence RIRTKNNNFATYYADSVKD (SEQ ID NO:78), and a VH CDR3 comprising the amino acid sequence GPYFDY (SEQ ID NO:79), and/or (b) a light chain variable region comprising a VL CDR1 comprising the amino acid sequence LASQTIGTWLA (SEQ ID NO:80), a VL CDR2 comprising the amino acid sequence AATSLAD (SEQ ID NO:29), and a VL CDR3 comprising the amino acid sequence QQLYSTPYT (SEQ ID NO:81). In some embodiments, a LAIR-1-binding agent comprises: (a) a heavy chain variable region comprising a VH CDR1 comprising the amino acid sequence of SEQ ID NO:31, a VH CDR2 comprising the amino acid sequence of SEQ ID NO:82, and a VH CDR3 comprising the amino acid sequence of SEQ ID NO:79, and/or (b) a light chain variable region comprising a VL CDR1 comprising the amino acid sequence of SEQ ID NO:80, a VL CDR2 comprising the amino acid sequence of SEQ ID NO:29, and a VL CDR3 comprising the amino acid sequence of SEQ ID NO:81. In some embodiments, a LAIR-1-binding agent comprises: (a) a heavy chain variable region comprising a VH CDR1 comprising the amino acid sequence of SEQ ID NO:25, a VH CDR2 comprising the amino acid sequence of SEQ ID NO:83, and a VH CDR3 comprising the amino acid sequence of SEQ ID NO:79, and/or (b) a light chain variable region comprising a VL CDR1 comprising the amino acid sequence of SEQ ID NO:80, a VL CDR2 comprising the amino acid sequence of SEQ ID NO:29, and a VL CDR3 comprising the amino acid sequence of SEQ ID NO:81. In some embodiments, a LAIR-1-binding agent comprises: (a) a heavy chain variable region comprising a VH CDR1 comprising the amino acid sequence of SEQ ID NO:34, a VH CDR2 comprising the amino acid sequence of SEQ ID NO:78, and a VH CDR3 comprising the amino acid sequence of SEQ ID NO:79, and/or (b) a light chain variable region comprising a VL CDR1 comprising the amino acid sequence of SEQ ID NO:80, a VL CDR2 comprising the amino acid sequence of SEQ ID NO:29, and a VL CDR3 comprising the amino acid sequence of SEQ ID NO:81. In some embodiments, a LAIR-1-binding agent comprises: (a) a heavy chain variable region comprising a VH CDR1 comprising the amino acid sequence of SEQ ID NO:35, a VH CDR2 comprising the amino acid sequence of SEQ ID NO:84, and a VH CDR3 comprising the amino acid sequence of SEQ ID NO:85, and/or (b) a light chain variable region comprising a VL CDR1 comprising the amino acid sequence of SEQ ID NO:86, a VL CDR2 comprising the amino acid sequence of SEQ ID NO:39, and a VL CDR3 comprising the amino acid sequence of SEQ ID NO:87. In some instances, the LAIR-1-binding agent comprises the VH comprising the VH CDR1, the VH CDR2, and the VH CDR3, and the VL comprising the VL CDR1, the VL CDR2, and the VL CDR3.

In some embodiments, a LAIR-1-binding agent comprises: (a) a heavy chain variable region having at least 80% sequence identity to the amino acid sequence of SEQ ID NO:125; and/or (b) a light chain variable region having at least 80% sequence identity to the amino acid sequence of SEQ ID NO:126. In some embodiments, a LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:125 and/or a light chain variable region having at least 85%, at least 90%, at least 95%, at least 96%, at least 97%, at least 98%, or at least 99% sequence identity to the amino acid sequence of SEQ ID NO:126. In some embodiments, a LAIR-1-binding agent comprises a heavy chain variable region of amino acid sequence SEQ ID NO:125 and/or a light chain variable region of amino acid sequence SEQ ID NO:126. In some embodiments, the LAIR-1-binding agent comprises a heavy chain variable region of amino acid sequence SEQ ID NO:125 and a light chain variable region of amino acid sequence SEQ ID NO:126.

In some embodiments, a LAIR-1-binding agent comprises: (a) a heavy chain variable region having at least 80% sequence identity to the amino acid sequence of SEQ ID NO:127; and/or (b) a light chain variable region having at least 80% sequence identity to the amino acid sequence of SEQ ID NO:128. In some embodiments, a LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:127 and/or a light chain variable region having at least 85%, at least 90%, at least 95%, at least 96%, at least 97%, at least 98%, or at least 99% sequence identity to the amino acid sequence of SEQ ID NO:128. In some embodiments, a LAIR-1-binding agent comprises a heavy chain variable region of amino acid sequence SEQ ID NO:127 and/or a light chain variable region of amino acid sequence SEQ ID NO:128. In some embodiments, the LAIR-1-binding agent comprises a heavy chain variable region of amino acid sequence SEQ ID NO:127 and a light chain variable region of amino acid sequence SEQ ID NO:128.

In some embodiments, a LAIR-1-binding agent comprises a heavy chain with an amino acid sequence at least 80% (e.g., at least 85%, at least 90%, at least 95%, at least 96%, at least 97%, at least 98%, or at least 99%) identical to SEQ ID NO:138, and/or a light chain with an amino acid sequence at least 80% (e.g., at least 85%, at least 90%, at least 95%, at least 96%, at least 97%, at least 98%, or at least 99%) identical to SEQ ID NO:140. In some embodiments, a LAIR-1-binding agent is an antibody comprising a heavy chain with an amino acid sequence at least 80% (e.g., at least 85%, at least 90%, at least 95%, at least 96%, at least 97%, at least 98%, or at least 99%) identical to SEQ ID NO:138, and/or a light chain with an amino acid sequence at least 80% (e.g., at least 85%, at least 90%, at least 95%, at least 96%, at least 97%, at least 98%, or at least 99%) identical to SEQ ID NO:140. In some embodiments, a LAIR-1-binding agent comprises a heavy chain comprising the amino acid sequence of SEQ ID NO:138, and/or a light chain comprising the amino acid sequence of SEQ ID NO:140. In some embodiments, a LAIR-1-binding agent is an antibody comprising a heavy chain comprising the amino acid sequence of SEQ ID NO:138 and/or a light chain comprising the amino acid sequence of SEQ ID NO:140. In some embodiments, a LAIR-1-binding agent is an antibody comprising a heavy chain comprising the amino acid sequence of SEQ ID NO:138 and a light chain comprising the amino acid sequence of SEQ ID NO:140.

In some embodiments, the LAIR-1-binding agent is antibody 62G10. In some embodiments, the LAIR-1-binding agent is a humanized version of antibody 62G10 (e.g., Hz62G10, e.g., Hz62G10.v1). In some embodiments, the LAIR-1-binding agent is a variant of antibody 62G10 or a variant of humanized antibody 62G10. In some embodiments, the LAIR-1-binding agent is antibody Hz62G10.v1.

In some embodiments, a LAIR-1-binding agent comprises a heavy chain variable region comprising a VH CDR1, a VH CDR2, and a VH CDR3 from the amino acid sequence of SEQ ID NO:129; and/or a light chain variable region comprising a VL CDR1, a VL CDR2, and a VL CDR3 from the amino acid sequence of SEQ ID NO:130. In some embodiments, a LAIR-1-binding agent comprises (a) a heavy chain variable region comprising a VH CDR1 comprising the amino acid sequence GFTFNINAMN (SEQ ID NO:25), a VH CDR2 comprising the amino acid sequence RIRTKNNNYATYYADSVKD (SEQ ID NO:88), and a VH CDR3 comprising the amino acid sequence DRYGGAMAY (SEQ ID NO:89), and/or (b) a light chain variable region comprising a VL CDR1 comprising the amino acid sequence KASEDIYNRLA (SEQ ID NO:90), a VL CDR2 comprising the amino acid sequence SATSLET (SEQ ID NO:91), and a VL CDR3 comprising the amino acid sequence QQYWTIPYT (SEQ ID NO:92). In some embodiments, a LAIR-1-binding agent comprises: (a) a heavy chain variable region comprising a VH CDR1 comprising the amino acid sequence of SEQ ID NO:31, a VH CDR2 comprising the amino acid sequence of SEQ ID NO:32, and a VH CDR3 comprising the amino acid sequence of SEQ ID NO:89, and/or (b) a light chain variable region comprising a VL CDR1 comprising the amino acid sequence of SEQ ID NO:90, a VL CDR2 comprising the amino acid sequence of SEQ ID NO:91, and a VL CDR3 comprising the amino acid sequence of SEQ ID NO:92. In some embodiments, a LAIR-1-binding agent comprises: (a) a heavy chain variable region comprising a VH CDR1 comprising the amino acid sequence of SEQ ID NO:25, a VH CDR2 comprising the amino acid sequence of SEQ ID NO:93, and a VH CDR3 comprising the amino acid sequence of SEQ ID NO:89, and/or (b) a light chain variable region comprising a VL CDR1 comprising the amino acid sequence of SEQ ID NO:90, a VL CDR2 comprising the amino acid sequence of SEQ ID NO:91, and a VL CDR3 comprising the amino acid sequence of SEQ ID NO:92. In some embodiments, a LAIR-1-binding agent comprises: (a) a heavy chain variable region comprising a VH CDR1 comprising the amino acid sequence of SEQ ID NO:34, a VH CDR2 comprising the amino acid sequence of SEQ ID NO:88, and a VH CDR3 comprising the amino acid sequence of SEQ ID NO:89, and/or (b) a light chain variable region comprising a VL CDR1 comprising the amino acid sequence of SEQ ID NO:90, a VL CDR2 comprising the amino acid sequence of SEQ ID NO:91, and a VL CDR3 comprising the amino acid sequence of SEQ ID NO:92. In some embodiments, a LAIR-1-binding agent comprises: (a) a heavy chain variable region comprising a VH CDR1 comprising the amino acid sequence of SEQ ID NO:35, a VH CDR2 comprising the amino acid sequence of SEQ ID NO:94, and a VH CDR3 comprising the amino acid sequence of SEQ ID NO:95, and/or (b) a light chain variable region comprising a VL CDR1 comprising the amino acid sequence of SEQ ID NO:96, a VL CDR2 comprising the amino acid sequence of SEQ ID NO:97, and a VL CDR3 comprising the amino acid sequence of SEQ ID NO:98. In some instances, the LAIR-1-binding agent comprises the VH comprising the VH CDR1, the VH CDR2, and the VH CDR3, and the VL comprising the VL CDR1, the VL CDR2, and the VL CDR3.

In some embodiments, a LAIR-1-binding agent comprises: (a) a heavy chain variable region having at least 80% sequence identity to the amino acid sequence of SEQ ID NO:129; and/or (b) a light chain variable region having at least 80% sequence identity to the amino acid sequence of SEQ ID NO:130. In some embodiments, a LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:129 and/or a light chain variable region having at least 85%, at least 90%, at least 95%, at least 96%, at least 97%, at least 98%, or at least 99% sequence identity to the amino acid sequence of SEQ ID NO:130. In some embodiments, a LAIR-1-binding agent comprises a heavy chain variable region of amino acid sequence SEQ ID NO:129 and/or a light chain variable region of amino acid sequence SEQ ID NO:130. In some embodiments, the LAIR-1-binding agent comprises a heavy chain variable region of amino acid sequence SEQ ID NO:129 and a light chain variable region of amino acid sequence SEQ ID NO:130.

In some embodiments, the LAIR-1-binding agent is antibody 108D10. In some embodiments, the LAIR-1-binding agent is a humanized version of antibody 108D10. In some embodiments, the LAIR-1-binding agent is a variant of antibody 108D10 or a variant of humanized antibody 108D10.

In another aspect, the present disclosure provides agents that specifically bind mouse LAIR-1. In some embodiments, a mouse LAIR-1-binding agent comprises a heavy chain variable region comprising a VH CDR1, a VH CDR2, and a VH CDR3 from the amino acid sequence of SEQ ID NO:131; and/or a light chain variable region comprising a VL CDR1, a VL CDR2, and a VL CDR3 from the amino acid sequence of SEQ ID NO:132. In some embodiments, a mouse LAIR-1-binding agent comprises (a) a heavy chain variable region comprising a VH CDR1 comprising the amino acid sequence GFTFSNYGIH (SEQ ID NO:99), a VH CDR2 comprising the amino acid sequence SISPS-GRSTYFRDSVKG (SEQ ID NO:100), and a VH CDR3 comprising the amino acid sequence GINYSSFDY (SEQ ID NO:101), and/or (b) a light chain variable region comprising a VL CDR1 comprising the amino acid sequence KASQNVGSHVD (SEQ ID NO:102), a VL CDR2 comprising the amino acid sequence TASNRYT (SEQ ID NO:103), and a VL CDR3 comprising the amino acid sequence MQSNSYPPT (SEQ ID NO:104). In some embodiments, a mouse LAIR-1-binding agent comprises: (a) a heavy chain variable region comprising a VH CDR1 comprising the amino acid sequence of SEQ ID NO:105, a VH CDR2 comprising the amino acid sequence of SEQ ID NO:106, and a VH CDR3 comprising the amino acid sequence of SEQ ID NO:101, and/or (b) a light chain variable region comprising a VL CDR1 comprising the amino acid sequence of SEQ ID NO:102, a VL CDR2 comprising the amino acid sequence of SEQ ID NO:103, and a VL CDR3 comprising the amino acid sequence of SEQ ID NO:104. In some embodiments, a mouse LAIR-1-binding agent comprises: (a) a heavy chain variable region comprising a VH CDR1 comprising the amino acid sequence of SEQ ID NO:99, a VH CDR2 comprising the amino acid sequence of SEQ ID NO:107, and a VH CDR3 comprising the amino acid sequence of SEQ ID NO:101, and/or (b) a light chain variable region comprising a VL CDR1 comprising the amino acid sequence of SEQ ID NO:102, a VL CDR2 comprising the amino acid sequence of SEQ ID NO:103, and a VL CDR3 comprising the amino acid sequence of SEQ ID NO:104. In some embodiments, a mouse LAIR-1-binding agent comprises: (a) a heavy chain variable region comprising a VH CDR1 comprising the amino acid sequence of SEQ ID NO:108, a VH CDR2 comprising the amino acid sequence of SEQ ID NO:100, and a VH CDR3 comprising the amino acid sequence of SEQ ID NO:101, and/or (b) a light chain variable region comprising a VL CDR1 comprising the amino acid sequence of SEQ ID NO:102, a VL CDR2 comprising the amino acid sequence of SEQ ID NO:103, and a VL CDR3 comprising the amino acid sequence of SEQ ID NO:104. In some embodiments, a mouse LAIR-1-binding agent comprises: (a) a heavy chain variable region comprising a VH CDR1 comprising the amino acid sequence of SEQ ID NO:109, a VH CDR2 comprising the amino acid sequence of SEQ ID NO:110, and a VH CDR3 comprising the amino acid sequence of SEQ ID NO:111, and/or (b) a light chain variable region comprising a VL CDR1 comprising the amino acid sequence of SEQ ID NO:112, a VL CDR2 comprising the amino acid sequence of SEQ ID NO:113, and a VL CDR3 comprising the amino acid sequence of SEQ ID NO:114. In some instances, the mouse LAIR-1-binding agent comprises the VH comprising the VH CDR1, the VH CDR2, and the VH CDR3, and the VL comprising the VL CDR1, the VL CDR2, and the VL CDR3.

In some embodiments, a mouse LAIR-1-binding agent comprises: (a) a heavy chain variable region having at least 80% sequence identity to the amino acid sequence of SEQ ID NO:131; and/or (b) a light chain variable region having at least 80% sequence identity to the amino acid sequence of SEQ ID NO:132. In some embodiments, a mouse LAIR-1-binding agent comprises a heavy chain variable region having at least 85%, at least 90%, at least 95%, at least 96%, at least 97%, at least 98%, or at least 99% sequence identity to the amino acid sequence of SEQ ID NO:131 and/or a light chain variable region having at least 85%, at least 90%, at least 95%, at least 96%, at least 97%, at least 98%, or at least 99% sequence identity to the amino acid sequence of SEQ ID NO:132. In some embodiments, a mouse LAIR-1-binding agent comprises a heavy chain variable region of amino acid sequence SEQ ID NO:131 and/or a light chain variable region of amino acid sequence SEQ ID NO:132. In some embodiments, the mouse LAIR-1-binding agent comprises a heavy chain variable region of amino acid sequence SEQ ID NO:131 and a light chain variable region of amino acid sequence SEQ ID NO:132.

In some embodiments, the LAIR-1-binding agent is antibody 43H2. In some embodiments, the LAIR-1-binding agent is a humanized version of antibody 43H2. In some embodiments, the LAIR-1-binding agent is a variant of antibody 43H2 or humanized antibody 43H2.

In another aspect of the disclosure, provided herein is a binding agent that competes for binding to LAIR-1 with any of the LAIR-1-binding agents described herein. In some embodiments, provided herein is an agent that competes for binding to LAIR-1 with a reference antibody, wherein the reference antibody comprises: (a) a heavy chain variable region comprising a VH CDR1 comprising the amino acid sequence GFTFNINAMN (SEQ ID NO:25), a VH CDR2 comprising the amino acid sequence RIRTKNNNYATFY-ADSVKD (SEQ ID NO:26) or RIRTKNYNYATFY-ADSVKD (SEQ ID NO:41), and a VH CDR3 comprising the amino acid sequence DRAGFFAY (SEQ ID NO:27), and (b) a light chain variable region comprising a VL CDR1 comprising the amino acid sequence LASQTIGTWLG (SEQ ID NO:28), a VL CDR2 comprising the amino acid sequence AATSLAD (SEQ ID NO:29) or AATSLAE (SEQ ID NO:42), and a VL CDR3 comprising the amino acid sequence QQLYSTPLT (SEQ ID NO:30). In some embodiments, the reference antibody comprises a heavy chain variable region comprising a VH CDR1, a VH CDR2, and a VH CDR3 from the amino acid sequence of SEQ ID NO:119; and a light chain variable region comprising a VL CDR1, a VL CDR2, and a VL CDR3 from the amino acid sequence of SEQ ID NO:120.

In some embodiments of each of the aforementioned aspects and embodiments, as well as other aspects and embodiments described herein, a LAIR-1-binding agent is an antibody. In some embodiments, the antibody is a monoclonal antibody. In some embodiments, the antibody is a humanized antibody. In some embodiments, the antibody is a human antibody. In some embodiments, the antibody is a chimeric antibody. In some embodiments, the antibody is a whole or intact antibody. In some embodiments, the antibody is a bispecific antibody or a multispecific antibody. In some embodiments, the antibody is an antibody fragment comprising at least one antigen-binding site. In some embodiments, the antibody or antibody fragment is a Fab, Fab', F(ab')$_2$, Fv, scFv, (scFv)$_2$, single chain antibody, dual variable region antibody, single variable region antibody, linear antibody, diabody, nanobody, or a V region antibody. In some embodiments, the antibody is an IgG antibody. In some embodiments, the antibody is an IgG1 antibody, an IgG2 antibody, an IgG3 antibody, or an IgG4 antibody. In some embodiments, the antibody comprises a kappa light chain. In some embodiments, the antibody comprises a lambda light chain.

In some embodiments of each of the aforementioned aspects and embodiments, as well as other aspects and embodiments described herein, a LAIR-1-binding agent is attached (either directly or indirectly) to a half-life extending moiety.

In some embodiments of each of the aforementioned aspects and embodiments, as well as other aspects and embodiments described herein, a LAIR-1-binding agent described herein is an antagonist of LAIR-1. In some embodiments, a LAIR-1-binding agent inhibits LAIR-1 activity. In some embodiments, the LAIR-1-binding agent is an antagonistic antibody. In some embodiments, the LAIR-1-binding agent is an antibody that inhibits LAIR-1-induced immune cell suppression. In some embodiments, the LAIR-1-binding agent is an antibody that inhibits LAIR-1-induced suppression of myeloid cells. In some embodiments, the LAIR-1-binding agent is an antibody that inhibits LAIR-1-induced suppression of NK cells. In some embodiments, the LAIR-1-binding agent is an antibody that inhibits LAIR-1-induced suppression of T-cells (e.g., CTLs). In some embodiments, the LAIR-1-binding agent is an antibody that inhibits MDSCs. In some embodiments, the LAIR-1-binding agent is an antibody that inhibits regulatory T-cells (Tregs).

In another aspect, the disclosure provides compositions comprising a LAIR-1-binding agent described herein. In some embodiments, a composition comprises an anti-LAIR-1 antibody described herein. In some embodiments, a composition comprises a monoclonal anti-LAIR-1 antibody described herein. In some embodiments, a composition comprises an anti-LAIR-1 antibody selected from the group consisting of: 47A1, 47H1, Hz47H1.v4, 57D12, 61H4, 62G10, Hz62G10.v1, 108D10, and 43H2.

In another aspect, the disclosure provides pharmaceutical compositions comprising a LAIR-1-binding agent described herein and a pharmaceutically acceptable carrier. In some embodiments, a pharmaceutical composition comprises an anti-LAIR-1 antibody described herein and a pharmaceutically acceptable carrier. In some embodiments, a pharmaceutical composition comprises a monoclonal anti-LAIR-1 antibody described herein and a pharmaceutically acceptable carrier. In some embodiments, a pharmaceutical composition comprises an anti-LAIR-1 antibody selected from the group consisting of: 47A1, 47H1, Hz47H1.v4, 57D12, 61H4, 62G10, Hz62G10.v1, 108D10, and 43H2 and a pharmaceutically acceptable carrier. In some embodiments, a pharmaceutical composition comprises the anti-LAIR-1 antibody Hz47H1.v4 and a pharmaceutically acceptable carrier.

In some embodiments of each of the aforementioned aspects, as well as other aspects and/or embodiments described elsewhere herein, the LAIR-1-binding agent is isolated. In some embodiments, the LAIR-1-binding agent is substantially pure.

In another aspect, the disclosure provides polynucleotides comprising a polynucleotide that encodes a LAIR-1-binding agent described herein. In another aspect, the disclosure provides one or more polynucleotides that encode a LAIR-1-binding agent described herein. In some embodiments, the one or more polynucleotides encode an anti-LAIR-1 antibody described herein. In some embodiments, the one or more polynucleotides are isolated. In another aspect, the disclosure provides one or more vectors comprising one or more polynucleotides that encode a LAIR-1-binding agent described herein. In some embodiments, an isolated cell comprises the one or more polynucleotides that encode a LAIR-1-binding agent described herein. In some embodiments, an isolated cell comprises the one or more vectors comprising the one or more polynucleotides that encode a LAIR-1-binding agent described herein. In some embodiments, a cell comprises a LAIR-1-binding agent described herein. In some embodiments, a cell produces a LAIR-1-binding agent described herein. In some embodiments, a cell produces an anti-LAIR-1 antibody described herein. In some embodiments, a cell is a monoclonal cell line. In some embodiments, a cell is a hybridoma.

In another aspect, the disclosure provides methods of using the LAIR-1-binding agents described herein. In some embodiments, a method comprises using a composition comprising a LAIR-1-binding agent described herein. In some embodiments, a method comprises using a pharmaceutical composition comprising a LAIR-1-binding agent described herein.

In some embodiments, methods of disrupting, inhibiting, or blocking the binding of LAIR-1 to a ligand and/or binding partner are provided. In some embodiments, a method of disrupting, inhibiting, or blocking the binding of LAIR-1 to collagen in a cell mixture comprises contacting the cell mixture with a LAIR-1-binding agent described herein. In some embodiments, a method of disrupting, inhibiting, or blocking the binding of LAIR-1 to MARCO in a cell mixture comprises contacting the cell mixture with a LAIR-1-binding agent described herein. In some embodiments, a method of disrupting, inhibiting, or blocking the binding of LAIR-1 to COLEC12 in a cell mixture comprises contacting the cell mixture with a LAIR-1-binding agent described herein.

In some embodiments, a method of disrupting, inhibiting, or blocking the binding of LAIR-1 to collagen in a cell mixture comprises contacting the cell mixture with a LAIR-binding agent described herein. In some embodiments, a method of disrupting, inhibiting, or blocking the binding of LAIR-1 to MARCO in a cell mixture comprises contacting the cell mixture with a LAIR-binding agent described herein. In some embodiments, a method of disrupting, inhibiting, or blocking the binding of LAIR-1 to COLEC12 in a cell mixture comprises contacting the cell mixture with a LAIR-binding agent described herein. In some embodiments, a method of disrupting, inhibiting, or blocking collagen-induced LAIR-1 activity in a cell comprises contacting the cell with a LAIR-binding agent described herein. In some embodiments, a method of disrupting, inhibiting, or blocking LAIR-1-induced suppression of a myeloid cell or myeloid cell activity comprises contacting the myeloid cell with a LAIR-binding agent described herein. In some embodiments, the myeloid cell may include, but is not limited to, a monocyte, a macrophage, a dendritic cells, and/or an APC. In some embodiments, a method of disrupting, inhibiting, or blocking LAIR-1-induced suppression of a natural killer cell or natural killer cell activity comprises contacting the natural killer cell with a LAIR-binding agent described herein. In some embodiments, a method of disrupting, inhibiting, or blocking LAIR-1-induced suppression of a T-cell or T-cell activity comprises contacting the T-cell with a LAIR-binding agent described herein. In some embodiments, the T-cell is a cytotoxic T-cell (CTL). In some embodiments, a method of disrupting, inhibiting, or blocking the activity of a myeloid-derived suppressor cell (MDSC) comprises contacting the MDSC with a LAIR-binding agent described herein. In some embodiments, a method of disrupting, inhibiting, or blocking the activity of a regulatory T-cell (Treg) comprises contacting the regulatory T-cell with a LAIR-binding agent described herein.

In some embodiments, a method of disrupting, inhibiting, or blocking the binding of LAIR-1 to collagen in a subject comprises administering to the subject a therapeutically effective amount of a LAIR-1-binding agent described herein. In some embodiments, a method of disrupting, inhibiting, or blocking the binding of LAIR-1 to MARCO in a subject comprises administering to the subject a therapeutically effective amount of a LAIR-1-binding agent described herein. In some embodiments, a method of disrupting, inhibiting, or blocking the binding of LAIR-1 to COLEC12 in a subject comprises administering to the subject a therapeutically effective amount of a LAIR-1-binding agent described herein. In some embodiments, a method of disrupting, inhibiting, or blocking collagen-induced LAIR-1 activity in a subject comprises administering to the subject a therapeutically effective amount of a LAIR-1-binding agent described herein. In some embodiments, a method of disrupting, inhibiting, or blocking LAIR-1-induced suppression of a myeloid cell or myeloid cell activity in a subject comprises administering to the subject a therapeutically effective amount of a LAIR-1-binding agent described herein. In some embodiments, the myeloid cell may include, but is not limited to, a monocyte, a macrophage, a dendritic cell, and/or an APC. In some embodiments, a method of disrupting, inhibiting, or blocking LAIR-1-induced suppression of a natural killer cell or natural killer cell activity in a subject comprises administering to the subject a therapeutically effective amount of a LAIR-1-binding agent described herein. In some embodiments, a method of disrupting, inhibiting, or blocking LAIR-1-induced suppression of a T-cell or T-cell activity in a subject comprises administering to the subject a therapeutically effective amount of a LAIR-1-binding agent described herein. In some embodiments, the T-cell is a cytotoxic T-cell or CTL. In some embodiments, a method of disrupting, inhibiting, or blocking the activity of a MDSC in a subject comprises administering to the subject a therapeutically effective amount of a LAIR-1-binding agent described herein. In some embodiments, a method of disrupting, inhibiting, or blocking the activity of a regulatory T-cell (Treg) in a subject comprises administering to the subject a therapeutically effective amount of a LAIR-1-binding agent described herein.

In some embodiments, a method of treating cancer in a subject comprises administering to the subject a therapeutically effective amount of a LAIR-1-binding agent described herein. In some embodiments, the cancer is a solid tumor (e.g., an advanced solid tumor). In some embodiments, the cancer is pancreatic cancer, breast cancer, lung cancer (e.g., non-small cell lung cancer (NSCLC)), head and neck cancer (e.g., squamous cell carcinoma of the head and neck (SCCHN)), colorectal cancer (CRC), prostate cancer, skin cancer, melanoma, stomach cancer, gastric cancer, intestinal cancer, ovarian cancer, cervical and endocervical cancer, biliary cancer, uterine cancer, endometrial cancer, urinary bladder cancer, brain cancer, mesothelioma, esophageal cancer, liver cancer, kidney cancer (e.g., renal cell carcinoma (RCC)), or testicular cancer. In some embodiments, the cancer is gastric cancer. In some embodiments, the cancer is pancreatic cancer. In some embodiments, the cancer is bladder cancer. In some embodiments, the cancer is insensitive to treatment with an immune-checkpoint inhibitor (e.g., an anti-PD-1 antibody). In some embodiments, the cancer has become resistant to treatment with an immune-checkpoint inhibitor (e.g., an anti-PD-1 antibody).

In some embodiments, a method of inhibiting tumor growth in a subject comprises administering to the subject a therapeutically effective amount of a LAIR-1-binding agent described herein. In some embodiments, a method of increasing or enhancing an immune response to a tumor or tumor cells in a subject comprises administering to the subject a therapeutically effective amount of a LAIR-1-binding agent described herein. In some embodiments, a method of activating or enhancing a persistent or long-term immune response to a tumor or tumor cells in a subject comprises administering to the subject a therapeutically effective amount of a LAIR-1-binding agent described herein. In some embodiments, a method of inhibiting tumor relapse or tumor regrowth in a subject comprises administering to the subject a therapeutically effective amount of a LAIR-1-binding agent described herein. In some embodiments, a method of inducing a persistent or long-term immunity that inhibits tumor relapse or tumor regrowth in a subject comprises administering to the subject a therapeutically effective amount of a LAIR-1-binding agent described herein. In some embodiments, the tumor is a pancreatic cancer, breast cancer, lung cancer (e.g., non-small cell lung cancer (NSCLC)), head and neck cancer (e.g., squamous cell carcinoma of the head and neck (SCCHN)), colorectal cancer (CRC), prostate cancer, skin cancer, melanoma, stomach cancer, gastric cancer, intestinal cancer, ovarian cancer, cervical and endocervical cancer, biliary cancer, uterine cancer, endometrial cancer, urinary bladder cancer, brain cancer, mesothelioma, esophageal cancer, liver cancer, kidney cancer (e.g., renal cell carcinoma (RCC)), or testicular cancer. In some embodiments, the tumor is a gastric tumor. In some embodiments, the tumor is a pancreatic tumor. In some embodiments, the tumor is a bladder tumor.

In some embodiments, a method of activating myeloid cells in the tumor microenvironment in a subject with a tumor, wherein the method comprises administering to the subject a therapeutically effective amount of a LAIR-1-binding agent described herein. In some embodiments, the myeloid cells are dendritic cells. In some embodiments, the myeloid cells are monocytes or macrophages. In some embodiments, a method of activating T-cells in the tumor microenvironment in a subject with a tumor comprises administering to the subject a therapeutically effective amount of a LAIR-1-binding agent described herein. In some embodiments, the T-cells are cytotoxic T-cells (CTLs).

In some embodiments of any of the methods described herein, a LAIR-1 binding agent or antibody described herein is administered as part of a combination therapy. In some embodiments, the combination therapy comprises at least one additional therapeutic agent. In some embodiments, the combination therapy comprises at least one immunotherapeutic agent.

In some embodiments of each of the aforementioned aspects and embodiments, as well as other aspects and embodiments described herein, the subject is human.

The present disclosure also provides agents that bind macrophage receptor with collagenous structure (MARCO). The agents include, but are not limited to, polypeptides such as antibodies that specifically bind MARCO. The agents may be referred to herein as "MARCO-binding agents". The disclosure provides methods of making a MARCO-binding agent. The disclosure provides methods of using a MARCO-binding agent.

In one aspect, the present disclosure provides agents that bind MARCO. In some embodiments, a MARCO-binding agent binds human MARCO. In some embodiments, a MARCO-binding agent binds SEQ ID NO:155, SEQ ID NO:156, and/or SEQ ID NO:157. In some embodiments, a MARCO-binding agent is an antibody. In some embodiments, a MARCO-binding agent is an antibody that binds human MARCO. In some embodiments, a MARCO-binding agent binds within the extracellular domain of MARCO. In some embodiments, a MARCO-binding agent binds within amino acids 65-520 of SEQ ID NO:154. In some embodiments, a MARCO-binding agent binds within SEQ ID NO:155. In some embodiments, a MARCO-binding agent binds within amino acids 147-419 of SEQ ID NO:154. In some embodiments, a MARCO-binding agent binds within SEQ ID NO:156. In some embodiments, a MARCO-binding agent binds within amino acids 424-519 of SEQ ID NO:154. In some embodiments, a MARCO-binding agent binds within SEQ ID NO:157. In some embodiments, an agent binds a conformational epitope within the extracellular domain of human MARCO. In some embodiments, an agent binds a conformational epitope within the collagen-like domain of MARCO. In some embodiments, an agent binds a conformational epitope within the scavenger receptor cysteine-rich (SRCR) domain of MARCO.

In another aspect, the present disclosure provide agents that specifically bind the extracellular domain of MARCO. In some embodiments, a MARCO-binding agent comprises a heavy chain variable region comprising a VH CDR1, a VH CDR2, and a VH CDR3 from the amino acid sequence of SEQ ID NO:160; and/or a light chain variable region comprising a VL CDR1, a VL CDR2, and a VL CDR3 from the amino acid sequence of SEQ ID NO:161. In some embodiments, a MARCO-binding agent comprises: (a) a heavy chain variable region comprising a VH CDR1 comprising the amino acid sequence GFSLTNYAIS (SEQ ID NO:178), a VH CDR2 comprising the amino acid sequence VIWTGGGTNYNSTLKS (SEQ ID NO:179), and a VH CDR3 comprising the amino acid sequence NSGDWYFDV (SEQ ID NO:180); and/or (b) a light chain variable region comprising a VL CDR1 comprising the amino acid sequence KSSQSLLYSSNQKNYLA (SEQ ID NO:181), a VL CDR2 comprising the amino acid sequence WASTRES (SEQ ID NO:182), and a VL CDR3 comprising the amino acid sequence QQYYDYPPT (SEQ ID NO:183). In some embodiments, a MARCO binding agent comprises: (a) a heavy chain variable region comprising a VH CDR1 comprising the amino acid sequence of SEQ ID NO:184, a VH CDR2 comprising the amino acid sequence of SEQ ID NO:185, and a VH CDR3 comprising the amino acid sequence of SEQ ID NO:180, and/or (b) a light chain variable region comprising a VL CDR1 comprising the amino acid sequence of SEQ ID NO:181, a VL CDR2 comprising the amino acid sequence of SEQ ID NO:182, and a VL CDR3 comprising the amino acid sequence of SEQ ID NO:183. In some embodiments, a MARCO binding agent comprises: (a) a heavy chain variable region comprising a VH CDR1 comprising the amino acid sequence of SEQ ID NO:178, a VH CDR2 comprising the amino acid sequence of SEQ ID NO:186, and a VH CDR3 comprising the amino acid sequence of SEQ ID NO:180, and/or (b) a light chain variable region comprising a VL CDR1 comprising the amino acid sequence of SEQ ID NO:181, a VL CDR2 comprising the amino acid sequence of SEQ ID NO:182, and a VL CDR3 comprising the amino acid sequence of SEQ ID NO:183. In some embodiments, a MARCO binding agent comprises: (a) a heavy chain variable region comprising a VH CDR1 comprising the amino acid sequence of SEQ ID NO:187, a VH CDR2 comprising the amino acid sequence of SEQ ID NO:179, and a VH CDR3 comprising the amino acid sequence of SEQ ID NO:180, and/or (b) a light chain variable region comprising a VL CDR1 comprising the amino acid sequence of SEQ ID NO:181, a VL CDR2 comprising the amino acid sequence of SEQ ID NO:182, and a VL CDR3 comprising the amino acid sequence of SEQ ID NO:183. In some embodiments, a MARCO binding agent comprises: (a) a heavy chain variable region comprising a VH CDR1 comprising the amino acid sequence of SEQ ID NO:188, a VH CDR2 comprising the amino acid sequence of SEQ ID NO:189, and a VH CDR3 comprising the amino acid sequence of SEQ ID NO:190, and/or (b) a light chain variable region comprising a VL CDR1 comprising the amino acid sequence of SEQ ID NO:191, a VL CDR2 comprising the amino acid sequence of SEQ ID NO:192, and a VL CDR3 comprising the amino acid sequence of SEQ ID NO:193. In some instances, the MARCO-binding agent comprises the VH comprising the VH CDR1, the VH CDR2, and the VH CDR3, and the VL comprising the VL CDR1, the VL CDR2, and the VL CDR3.

In some embodiments, a MARCO-binding agent comprises: (a) a heavy chain variable region having at least 80% sequence identity to the amino acid sequence of SEQ ID NO:160; and/or (b) a light chain variable region having at least 80% sequence identity to the amino acid sequence of SEQ ID NO:161. In some embodiments, a MARCO-binding agent comprises a heavy chain variable region having at least 85%, at least 90%, at least 95%, at least 96%, at least 97%, at least 98%, or at least 99% sequence identity to the amino acid sequence of SEQ ID NO:160 and/or a light chain variable region having at least 85%, at least 90%, at least 95%, at least 96%, at least 97%, at least 98%, or at least 99% sequence identity to the amino acid sequence of SEQ ID NO:161. In some embodiments, a MARCO-binding agent comprises a heavy chain variable region of amino acid sequence SEQ ID NO:160 and/or a light chain variable region of amino acid sequence SEQ ID NO:161. In some embodiments, the MARCO-binding agent comprises a heavy chain variable region of amino acid sequence SEQ ID NO:160 and a light chain variable region of amino acid sequence SEQ ID NO:161.

In some embodiments, the MARCO-binding agent is antibody 6D8. In some embodiments, the MARCO-binding agent is a variant of antibody 6D8.

In some embodiments, a MARCO-binding agent comprises a heavy chain variable region comprising a VH CDR1, a VH CDR2, and a VH CDR3 from the amino acid sequence of SEQ ID NO:162; and/or a light chain variable region comprising a VL CDR1, a VL CDR2, and a VL CDR3 from the amino acid sequence of SEQ ID NO:163. In some embodiments, a MARCO-binding agent comprises: (a) a heavy chain variable region comprising a VH CDR1 comprising the amino acid sequence GFSLSSYPIS (SEQ ID NO:194), a VH CDR2 comprising the amino acid sequence IIWTGGGTNYNSALKS (SEQ ID NO:195), and a VH CDR3 comprising the amino acid sequence QNWDVN-SALDY (SEQ ID NO:196); and/or (b) a light chain variable region comprising a VL CDR1 comprising the amino acid sequence RASENIYSNLA (SEQ ID NO:197), a VL CDR2 comprising the amino acid sequence TATNLAD (SEQ ID NO:198), and a VL CDR3 comprising the amino acid sequence QHFWNAPWT (SEQ ID NO:199). In some embodiments, a MARCO binding agent comprises: (a) a heavy chain variable region comprising a VH CDR1 comprising the amino acid sequence of SEQ ID NO:200, a VH CDR2 comprising the amino acid sequence of SEQ ID NO:185, and a VH CDR3 comprising the amino acid sequence of SEQ ID NO:196, and/or (b) a light chain variable region comprising a VL CDR1 comprising the amino acid sequence of SEQ ID NO:197, a VL CDR2 comprising the amino acid sequence of SEQ ID NO:198, and a VL CDR3 comprising the amino acid sequence of SEQ ID NO:199. In some embodiments, a MARCO binding agent comprises: (a) a heavy chain variable region comprising a VH CDR1 comprising the amino acid sequence of SEQ ID NO:194, a VH CDR2 comprising the amino acid sequence of SEQ ID NO:201, and a VH CDR3 comprising the amino acid sequence of SEQ ID NO:196, and/or (b) a light chain variable region comprising a VL CDR1 comprising the amino acid sequence of SEQ ID NO:197, a VL CDR2 comprising the amino acid sequence of SEQ ID NO:198, and a VL CDR3 comprising the amino acid sequence of SEQ ID NO:199. In some embodiments, a MARCO binding agent comprises: (a) a heavy chain variable region comprising a VH CDR1 comprising the amino acid sequence of SEQ ID NO:202, a VH CDR2 comprising the amino acid sequence of SEQ ID NO:195, and a VH CDR3 comprising the amino acid sequence of SEQ ID NO:196, and/or (b) a light chain variable region comprising a VL CDR1 comprising the amino acid sequence of SEQ ID NO:197, a VL CDR2 comprising the amino acid sequence of SEQ ID NO:198, and a VL CDR3 comprising the amino acid sequence of SEQ ID NO:199. In some embodiments, a MARCO binding agent comprises: (a) a heavy chain variable region comprising a VH CDR1 comprising the amino acid sequence of SEQ ID NO:203, a VH CDR2 comprising the amino acid sequence of SEQ ID NO:204, and a VH CDR3 comprising the amino acid sequence of SEQ ID NO:205, and/or (b) a light chain variable region comprising a VL CDR1 comprising the amino acid sequence of SEQ ID NO:206, a VL CDR2 comprising the amino acid sequence of SEQ ID NO:207, and a VL CDR3 comprising the amino acid sequence of SEQ ID NO:208. In some instances, the MARCO-binding agent comprises the VH comprising the VH CDR1, the VH CDR2, and the VH CDR3, and the VL comprising the VL CDR1, the VL CDR2, and the VL CDR3.

In some embodiments, a MARCO-binding agent comprises: (a) a heavy chain variable region having at least 80% sequence identity to the amino acid sequence of SEQ ID NO:162; and/or (b) a light chain variable region having at least 80% sequence identity to the amino acid sequence of SEQ ID NO:163. In some embodiments, a MARCO-binding agent comprises a heavy chain variable region having at least 85%, at least 90%, at least 95%, at least 96%, at least 97%, at least 98%, or at least 99% sequence identity to the amino acid sequence of SEQ ID NO:162 and/or a light chain variable region having at least 85%, at least 90%, at least 95%, at least 96%, at least 97%, at least 98%, or at least 99% sequence identity to the amino acid sequence of SEQ ID NO:163. In some embodiments, a MARCO-binding agent comprises a heavy chain variable region of amino acid sequence SEQ ID NO:162 and/or a light chain variable region of amino acid sequence SEQ ID NO:163. In some embodiments, the MARCO-binding agent comprises a heavy chain variable region of amino acid sequence SEQ ID NO:162 and a light chain variable region of amino acid sequence SEQ ID NO:163.

In some embodiments, the MARCO-binding agent is antibody 10G4. In some embodiments, the MARCO-binding agent is a variant of antibody 10G4.

In some embodiments, a MARCO-binding agent comprises a heavy chain variable region comprising a VH CDR1, a VH CDR2, and a VH CDR3 from the amino acid sequence of SEQ ID NO:164; and/or a light chain variable region comprising a VL CDR1, a VL CDR2, and a VL CDR3 from the amino acid sequence of SEQ ID NO:165. In some embodiments, a MARCO-binding agent comprises: (a) a heavy chain variable region comprising a VH CDR1 comprising the amino acid sequence GYSFTDYNMY (SEQ ID NO:209), a VH CDR2 comprising the amino acid sequence YIDPYNGGTSYNQKFKG (SEQ ID NO:210), and a VH CDR3 comprising the amino acid sequence LRSPYDYDRGDYVMDY (SEQ ID NO:211); and (b) a light chain variable region comprising a VL CDR1 comprising the amino acid sequence RASKSVSTSGYTYMH (SEQ ID NO:212), a VL CDR2 comprising the amino acid sequence LASNLES (SEQ ID NO:213), and a VL CDR3 comprising the amino acid sequence QHSRELPLT (SEQ ID NO:214). In some embodiments, a MARCO binding agent comprises: (a) a heavy chain variable region comprising a VH CDR1 comprising the amino acid sequence of SEQ ID NO:215, a VH CDR2 comprising the amino acid sequence of SEQ ID NO:216, and a VH CDR3 comprising the amino acid sequence of SEQ ID NO:211, and/or (b) a light chain variable region comprising a VL CDR1 comprising the amino acid sequence of SEQ ID NO:212, a VL CDR2 comprising the amino acid sequence of SEQ ID NO:213, and a VL CDR3 comprising the amino acid sequence of SEQ ID NO:214. In some embodiments, a MARCO binding agent comprises: (a) a heavy chain variable region comprising a VH CDR1 comprising the amino acid sequence of SEQ ID NO:209, a VH CDR2 comprising the amino acid sequence of SEQ ID NO:217, and a VH CDR3 comprising the amino acid sequence of SEQ ID NO:211, and/or (b) a light chain variable region comprising a VL CDR1 comprising the amino acid sequence of SEQ ID NO:212, a VL CDR2 comprising the amino acid sequence of SEQ ID NO:213, and a VL CDR3 comprising the amino acid sequence of SEQ ID NO:214. In some embodiments, a MARCO binding agent comprises: (a) a heavy chain variable region comprising a VH CDR1 comprising the amino acid sequence of SEQ ID NO:218, a VH CDR2 comprising the amino acid sequence of SEQ ID NO:210, and a VH CDR3 comprising the amino acid sequence of SEQ ID NO:211, and/or (b) a light chain variable region comprising a VL CDR1 comprising the amino acid sequence of SEQ ID NO:212, a VL CDR2 comprising the amino acid sequence of SEQ ID NO:213, and a VL CDR3 comprising the amino acid sequence of SEQ ID NO:214. In some embodiments, a MARCO binding agent comprises: (a) a heavy chain variable region comprising a VH CDR1 comprising the amino acid sequence of SEQ ID NO:219, a VH CDR2 comprising the amino acid sequence of SEQ ID NO:220, and a VH CDR3 comprising the amino acid sequence of SEQ ID NO:221, and/or (b) a light chain variable region comprising a VL CDR1 comprising the amino acid sequence of SEQ ID NO:222, a VL CDR2 comprising the amino acid sequence of SEQ ID NO:223, and a VL CDR3 comprising the amino acid sequence of SEQ ID NO:224. In some instances, the MARCO-binding agent comprises the VH comprising the VH CDR1, the VH CDR2, and the VH CDR3, and the VL comprising the VL CDR1, the VL CDR2, and the VL CDR3.

In some embodiments, a MARCO-binding agent comprises: (a) a heavy chain variable region having at least 80% sequence identity to the amino acid sequence of SEQ ID NO:164; and/or (b) a light chain variable region having at least 80% sequence identity to the amino acid sequence of SEQ ID NO:165. In some embodiments, a MARCO-binding agent comprises a heavy chain variable region having at least 85%, at least 90%, at least 95%, at least 96%, at least 97%, at least 98%, or at least 99% sequence identity to the amino acid sequence of SEQ ID NO:164 and/or a light chain variable region having at least 85%, at least 90%, at least 95%, at least 96%, at least 97%, at least 98%, or at least 99% sequence identity to the amino acid sequence of SEQ ID NO:165. In some embodiments, a MARCO-binding agent comprises a heavy chain variable region of amino acid sequence SEQ ID NO:164 and/or a light chain variable region of amino acid sequence SEQ ID NO:165. In some embodiments, the MARCO-binding agent comprises a heavy chain variable region of amino acid sequence SEQ ID NO:164 and a light chain variable region of amino acid sequence SEQ ID NO:165.

In some embodiments, the MARCO-binding agent is antibody 15A3. In some embodiments, the MARCO-binding agent is a variant of antibody 15A3.

In some embodiments of each of the aforementioned aspects and embodiments, as well as other aspects and embodiments described herein, a MARCO-binding agent is an antibody. In some embodiments, the antibody is a monoclonal antibody. In some embodiments, the antibody is a humanized antibody. In some embodiments, the antibody is a human antibody. In some embodiments, the antibody is a chimeric antibody. In some embodiments, the antibody is a whole or intact antibody. In some embodiments, the antibody is a bispecific antibody or a multispecific antibody. In some embodiments, the antibody is an antibody fragment comprising at least one antigen-binding site. In some embodiments, the antibody or antibody fragment is a Fab, Fab', F(ab')$_2$, Fv, scFv, (scFv)$_2$, single chain antibody, dual variable region antibody, single variable region antibody, linear antibody, diabody, nanobody, or a V region antibody. In some embodiments, the antibody is an IgG antibody. In some embodiments, the antibody is an IgG1 antibody, an IgG2 antibody, an IgG3 antibody, or an IgG4 antibody. In some embodiments, the antibody comprises a kappa light chain. In some embodiments, the antibody comprises a lambda light chain.

In another aspect, the disclosure provides compositions comprising a MARCO-binding agent described herein. In some embodiments, a composition comprises an anti-MARCO antibody described herein. In some embodiments, a composition comprises a monoclonal anti-MARCO antibody described herein. In some embodiments, a composition comprises an anti-MARCO antibody selected from the group consisting of: 6D8, 10G4, and 15A3.

In some embodiments of each of the aforementioned aspects, as well as other aspects and/or embodiments described elsewhere herein, the MARCO-binding agent is isolated. In some embodiments, the MARCO-binding agent is substantially pure.

In another aspect, the disclosure provides polynucleotides comprising a polynucleotide that encodes a MARCO-binding agent described herein. In another aspect, the disclosure provides one or more polynucleotides that encode a MARCO-binding agent described herein. In some embodiments, the one or more polynucleotides encode an anti-MARCO antibody described herein. In some embodiments, the one or more polynucleotides are isolated. In another aspect, the disclosure provides one or more vectors comprising one or more polynucleotides that encode a MARCO-binding agent described herein. In some embodiments, a vector comprises the one or more polynucleotides that encode a MARCO-binding agent described herein. In some embodiments, an isolated cell comprises the one or more polynucleotides that encode a MARCO-binding agent described herein. In some embodiments, an isolated cell comprises one or more vectors comprising the one or more polynucleotides that encode a MARCO-binding agent described herein. In some embodiments, a cell comprises a MARCO-binding agent described herein. In some embodiments, a cell produces a MARCO-binding agent described herein. In some embodiments, a cell produces an anti-MARCO antibody described herein. In some embodiments, a cell is a monoclonal cell line. In some embodiments, a cell is a hybridoma.

In another aspect, the disclosure provides methods of using the MARCO-binding agents described herein. In some embodiments, a method comprises using a composition comprising a MARCO-binding agent described herein. In some embodiments, a MARCO-binding agent described herein is used in flow cytometry. In some embodiments, a MARCO-binding agent described herein is used in immunohistochemistry assays.

In one aspect, this disclosure features an antibody that binds human LAIR-1 and inhibits binding of LAIR-1 to one or more LAIR ligands (e.g., collagen 1, collagen 4, tumor cell collagens, polymerized collagen matrix, MARCO, COLEC12, MBL, SPD, and C1 complex). In some instances, this antibody also has one or more (e.g., 1, 2, 3, 4, 5, 6, 7, 8, 9, 10, 11, or 12) of the following properties in any combination or permutation: (i) binds cyno LAIR-1; (ii) does not bind mouse LAIR-1; (iii) does not bind human LAIR-2; (iv) is a LAIR-1 antagonist; (v) inhibits LAIR-1 activity; (vi) inhibits LAIR-1 signaling in cells that express LAIR-1; (vii) inhibits LAIR-1-induced suppression of myeloid cells; (viii) inhibits LAIR-1-induced suppression of myeloid cell activity; (ix) restores FcR activation in myeloid cells; (x) restores cytokine and/or chemokine production in myeloid cells; (xi) inhibits LAIR-1-induced suppression of NK cells; (xii) inhibits LAIR-1-induced suppression of NK activity; (xiii) inhibits LAIR-1-induced suppression of T-cell activity; and/or (xiv) inhibits MDSC activity.

In another aspect, the disclosure features a pharmaceutical composition comprising the antibody as described above, and a pharmaceutically acceptable carrier.

In another aspect, the disclosure features a pharmaceutical composition comprising: (a) a means for inhibiting the interaction between LAIR1 and a LAIR-1 ligand; and (b) a pharmaceutically acceptable carrier. In some instances, the LAIR-1 ligand is collagen, MBL, SPD, C1 complex, MARCO, or COLEC12. In some instances, the collagen is Collagen 1, Collagen 4, a Tumor Cell Collagen, or a Polymerized Collagen Matrix. In some instances, wherein the means for inhibiting the interaction between LAIR1 and a LAIR-1 ligand is an anti-LAIR-1 antibody. In some instances, the antibody comprises a heavy chain variable region comprising a VH CDR1, a VH CDR2, and a VH CDR3, and a light chain variable region comprising a VL CDR1, a VL CDR2, and a VL CDR3 of any one of Hz47H1.v4, Hz62G10.v1, or 57D12.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

DETAILED DESCRIPTION

Figure 1:
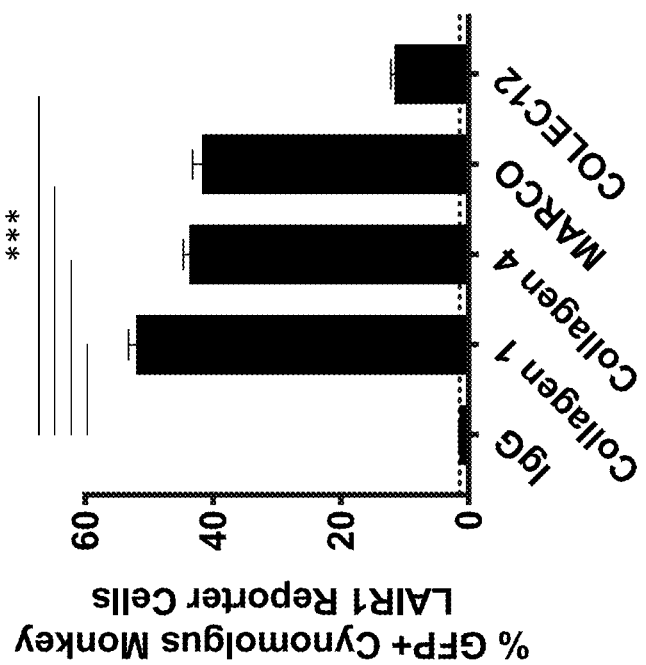
FIG. 1. Characterization of LAIR-1 ligands. 96-well Maxisorp plates were coated with 1 μg/mL human collagen type 1, 1 μg/mL human collagen type 4, 2 μg/mL recombinant human MARCO-his protein. 1 μg/mL recombinant human COLEC12 protein, 2 μg/mL recombinant MBL protein, 2 μg/mL recombinant SP-D protein, or 3 μg/mL C1 protein. Human LAIR-1-CD3ζ-NFAT-GFP reporter cells or cyno LAIR-1-CD3ζ-NFAT-GFP reporter were added to coated plates. GFP expression was measured by flow cytometry and analyzed using FlowJo software. ***=p<0.001
Figure 1:
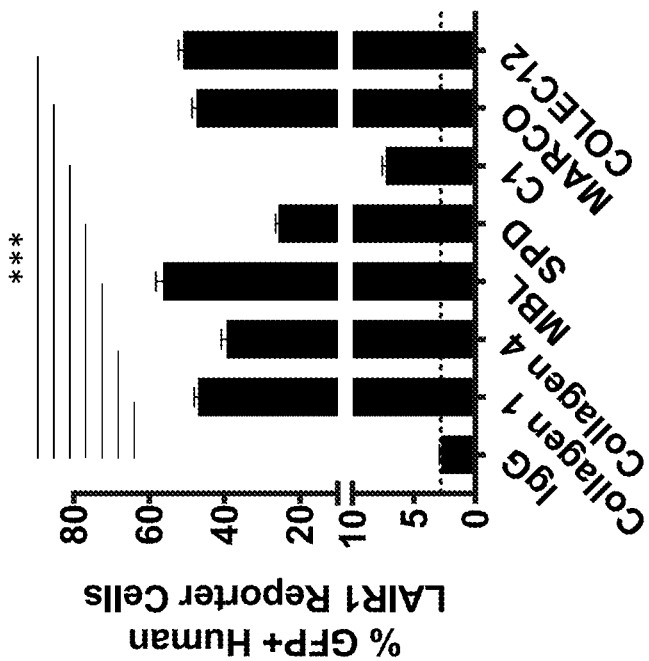

The present disclosure provides novel agents, including but not limited to polypeptides such as antibodies, that bind leukocyte-associated immunoglobulin-like receptor 1 (LAIR-1). The LAIR-1-binding agents include, but are not limited to, polypeptides, antibodies and antigen-binding fragments thereof, scaffold proteins, and heterodimeric molecules. LAIR-1-binding agents include, but are not limited to, antagonists of LAIR-1 activity, inhibitors of LAIR-1 activity, and/or agents that inhibit LAIR-1 suppressive activity. Related polypeptides, polynucleotides, vectors, compositions comprising the agents, cells comprising the related polynucleotides or vectors, and methods of making the agents are provided. Methods of using the novel LAIR-1-binding agents are also provided.

The present disclosure also provides novel agents, including but not limited to polypeptides such as antibodies, that bind macrophage receptor with collagenous structure (MARCO). The MARCO-binding agents include, but are not limited to, polypeptides, antibodies and antigen-binding fragments thereof, scaffold proteins, and heterodimeric molecules. Related polypeptides, polynucleotides, vectors, compositions comprising the agents, cells comprising the related polynucleotides or vectors, and methods of making the agents are provided. Methods of using the novel MARCO-binding agents are also provided.

I. Definitions

Unless otherwise defined herein, technical and scientific terms used in the present description have the meanings that are commonly understood by those of ordinary skill in the art. Whenever appropriate, terms used in the singular will also include the plural and vice versa. In the event that any description of a term set forth conflicts with any document incorporated herein by reference, the description of the term set forth below shall control.

The term "binding agent" as used herein refers to a molecule that binds a specific antigen or target (e.g., LAIR-1). A binding agent may comprise a protein, peptide, nucleic acid, carbohydrate, lipid, or small molecular weight compound. In some embodiments, a binding agent comprises a full-length antibody. In some embodiments, a binding agent is an antigen-binding fragment of an antibody. In some embodiments, a binding agent comprises an alternative protein scaffold or artificial scaffold (e.g., a non-immunoglobulin backbone). In some embodiments, a binding agent is a fusion protein comprising an antigen-binding site. In some embodiments, a binding agent is a bispecific or multispecific molecule comprising at least one antigen-binding site.

The term "antibody" is used herein in the broadest sense and encompasses various antibody structures, including but not limited to, an immunoglobulin molecule that recognizes and binds a target through at least one antigen-binding site, polyclonal antibodies, recombinant antibodies, monoclonal antibodies, chimeric antibodies, humanized antibodies, human antibodies, bispecific antibodies, multispecific antibodies, diabodies, tribodies, tetrabodies, single chain Fv (scFv) antibodies, and antibody fragments as long as they exhibit the desired antigen-binding activity.

The term "intact antibody" or "full-length antibody" refers to an antibody having a structure substantially similar to a native antibody structure. This includes, for example, an antibody comprising two light chains each comprising a variable region and a light chain constant region (CL) and two heavy chains each comprising a variable region and at least heavy chain constant regions CH1, CH2, and CH3. Depending on the isotype of antibody, an intact antibody may include a hinge region (or a portion thereof) between the CH1 and CH2 regions.

The term "antibody fragment" as used herein refers to a molecule other than an intact antibody that comprises a portion of an antibody and generally an antigen-binding site. Examples of antibody fragments include, but are not limited to, Fab, Fab', F(ab')$_2$, Fv, single chain antibody molecules, scFv, sc(Fv)$_2$, disulfide-linked scFv (dsscFv), diabodies, tribodies, tetrabodies, minibodies, dual variable domain antibodies (DVD), single variable domain antibodies (e.g., camelid antibodies), and multispecific antibodies formed from antigen-binding antibody fragments.

The term "monoclonal antibody" as used herein refers to a substantially homogenous antibody population involved in the highly specific recognition and binding of a single antigenic determinant or epitope. The term "monoclonal antibody" encompasses intact and full-length antibodies as well as antibody fragments (e.g., Fab, Fab', F(ab')$_2$, Fv), single chain antibodies, scFv, fusion proteins comprising an antigen-binding antibody fragment, and any other modified immunoglobulin molecule comprising at least one antigen-binding site. Furthermore, "monoclonal antibody" refers to such antibodies made by any number of techniques, including but not limited to, hybridoma production, phage library display, recombinant expression, and transgenic animals.

The term "chimeric antibody" refers to an antibody in which a portion of the heavy and/or light chain is derived from a first source or species, while the remainder of the heavy and/or light chain is derived from a different source or species.

The term "humanized antibody" as used herein refers to an antibody that comprises a human heavy chain variable region and a light chain variable region wherein the native CDR amino acid residues are replaced by residues from corresponding CDRs from a non-human antibody (e.g., mouse, rat, rabbit, or non-human primate), wherein the non-human antibody has the desired specificity, affinity, and/or activity. In some embodiments, one or more framework region amino acid residues of the human heavy chain or light chain variable regions are replaced by corresponding residues from the non-human antibody. Furthermore, humanized antibodies can comprise amino acid residues that are not found in the human antibody or in the non-human antibody. In some embodiments, these modifications are made to further refine and/or optimize antibody characteristics. In some embodiments, the humanized antibody comprises at least a portion of a human immunoglobulin constant region (e.g., CH1, CH2, CH3, Fc, and/or hinge region).

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but not limited to, phage display libraries, yeast display libraries, transgenic animals, recombinant protein production, and B-cell hybridoma technology.

The terms "epitope" and "antigenic determinant" are used interchangeably herein and refer to that portion of an antigen or target capable of being recognized and bound by a particular antibody. When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of publicly available bioinformatic software tools. X-ray crystallography may be used to characterize an epitope on a target protein by analyzing the amino acid residue interactions of an antigen/antibody complex.

The term "specifically binds" as used herein refers to an agent that interacts more frequently, more rapidly, with greater duration, with greater affinity, or with some combination of the above to a particular antigen, epitope, protein, or target molecule than with alternative substances. A binding agent that specifically binds an antigen can be identified, for example, by immunoassays, ELISAs, surface plasmon resonance (SPR), or other techniques known to those of skill in the art. In some embodiments, an agent that specifically binds an antigen (e.g., human LAIR-1) can bind related antigens (e.g., cyno LAIR-1). Generally, a binding agent that specifically binds an antigen will bind the target antigen at a higher affinity than its affinity for a different antigen. The different antigen can be a related antigen. In some embodiments, a binding agent that specifically binds an antigen can bind the target antigen with an affinity that is at least 20 times greater, at least 30 times greater, at least 40 times greater, at least 50 times greater, at least 60 times greater, at least 70 times greater, at least 80 times greater, at least 90 times greater, or at least 100 times greater, than its affinity for a different antigen. In some embodiments, a binding agent that specifically binds a particular antigen binds a different antigen at such a low affinity that binding cannot be detected using an assay described herein or otherwise known in the art. In some embodiments, affinity is measured using SPR technology in a Biacore system as described herein or as known to those of skill in the art.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid identity, when compared and aligned for maximum correspondence, as measured using a sequence comparison algorithm or by visual inspection. In some embodiments, identity exists over a region of the sequences that is at least about 10, at least about 20, at least about 20-40, at least about 40-60, at least about 60-80 nucleotides or amino acids in length, or any integral value there between. In some embodiments, identity exists over a longer region than 60-80 nucleotides or amino acids, such as at least about 80-100 nucleotides or amino acids, and in some embodiments the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of an alanine for a valine is considered to be a conservative substitution. Methods of identifying nucleotide and amino acid conservative substitutions that do not eliminate binding are well-known in the art.

The term "vector" as used herein means a construct that is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

The term "isolated" as used herein refers to a polypeptide, soluble protein, antibody, polynucleotide, vector, cell, or composition that is in a form not found in nature. An "isolated" antibody is substantially free of material from the cellular source from which it is derived. In some embodiments, isolated polypeptides, soluble proteins, antibodies, polynucleotides, vectors, cells, or compositions are those that have been purified to a degree that they are no longer in a form in which they are found in nature. In some embodiments, a polypeptide, soluble protein, antibody, polynucleotide, vector, cell, or composition that is isolated is substantially pure. A polypeptide, soluble protein, antibody, polynucleotide, vector, cell, or composition can be isolated from a natural source (e.g., tissue) or from a source such as an engineered cell line.

The term "substantially pure" as used herein refers to material that is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, rabbits, rodents, and the like.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject, together with at least one therapeutic agent, and that is generally safe, non-toxic, and has no effect on the pharmacological activity of the therapeutic agent. In general, those of skill in the art and government agencies consider a pharmaceutically acceptable excipient, carrier, or adjuvant to be an inactive ingredient of any formulation or any pharmaceutical composition.

The term "pharmaceutical formulation" or "pharmaceutical composition" as used herein refers to a preparation that is in such form as to permit the biological activity of the agent to be effective. A pharmaceutical formulation or composition generally comprises additional components, such as a pharmaceutically acceptable excipient, carrier, adjuvant, buffers, etc.

The term "effective amount" or "therapeutically effective amount" as used herein refers to the amount of an agent that is sufficient to reduce and/or ameliorate the severity and/or duration of (i) a disease, disorder or condition in a subject, and/or (ii) a symptom in a subject. The term also encompasses an amount of an agent necessary for the (i) reduction or amelioration of the advancement or progression of a given disease, disorder, or condition, (ii) reduction or amelioration of the recurrence, development, or onset of a given disease, disorder, or condition, and/or (iii) the improvement or enhancement of the prophylactic or therapeutic effect(s) of another agent or therapy (e.g., an agent other than the binding agents provided herein).

The term "therapeutic effect" as used herein refers to the effect and/or ability of an agent to reduce and/or ameliorate the severity and/or duration of (i) a disease, disorder, or condition in a subject, and/or (ii) a symptom in a subject. The term also encompasses the ability of an agent to (i) reduce or ameliorate the advancement or progression of a given disease, disorder, or condition, (ii) reduce or ameliorate the recurrence, development, or onset of a given disease, disorder, or condition, and/or (iii) to improve or enhance the prophylactic or therapeutic effect(s) of another agent or therapy (e.g., an agent other than the binding agents provided herein).

The term "treat" or "treatment" or "treating" or "to treat" or "alleviate" or "alleviation" or "alleviating" or "to alleviate" as used herein refers to therapeutic measures that aim to cure, slow down, lessen symptoms of, and/or halt progression of a pathologic condition or disorder. Thus, those in need of treatment include those already with the disorder.

The term "prevent" or "prevention" or "preventing" as used herein refers to the partial or total inhibition of the development, recurrence, onset, or spread of a disease, disorder, or condition, or a symptom thereof in a subject.

The term "immune response" as used herein includes responses from both the innate immune system and the adaptive immune system. It includes both cell-mediated and/or humoral immune responses. It includes both T-cell and B-cell responses, as well as responses from other cells of the immune system such as natural killer (NK) cells, monocytes, macrophages, dendritic cells, etc.

As used herein, reference to "about" or "approximately" a value or parameter includes (and describes) embodiments that are directed to that value or parameter. For example, a description referring to "about X" includes description of "X".

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. LAIR-1 Ligands

Collagens are known to be high affinity ligands for LAIR-1 (see, e.g., Lebbink et al., 2006, *Journal of Exp. Med.*, 203:1419-1425). The present disclosure provides MARCO (macrophage receptor with collagenous structure) as a newly identified ligand for LAIR-1. In addition, there is preliminary evidence that COLEC12 is also a newly identified ligand for LAIR-1.

As disclosed herein, MARCO was identified as a ligand for LAIR-1. In some embodiments, LAIR-1 binds MARCO. In some embodiments, LAIR-1 binds SEQ ID NO:154. In some embodiments, LAIR-1 binds the extracellular domain of MARCO. In some embodiments, LAIR-1 binds within amino acid 65-520 of SEQ ID NO:154. In some embodiments, LAIR-1 binds within SEQ ID NO:155. In some embodiments, LAIR-1 binds within the collagen-like domain of MARCO. In some embodiments, LAIR-1 binds within amino acids 147-419 of SEQ ID NO:154. In some embodiments, LAIR-1 binds within SEQ ID NO:156. In some embodiments, LAIR-1 binds within the SRCR domain of MARCO. In some embodiments, LAIR-1 binds within amino acids 424-519 of SEQ ID NO:154. In some embodiments, LAIR-1 binds within SEQ ID NO:157.

In some embodiments, a LAIR-1-binding agent described herein inhibits, disrupts, or blocks binding of LAIR-1 to collagen. In some embodiments, a LAIR-1-binding agent described herein blocks the interaction of LAIR-1 to collagen. In some embodiments, a LAIR-1-binding agent described herein inhibits binding of LAIR-1 to collagen. In some embodiments, a LAIR-1-binding agent described herein blocks or inhibits a functional interaction between LAIR-1 to collagen. In some embodiments, a LAIR-1-binding agent described herein inhibits, disrupts, or blocks binding of LAIR-1 to MARCO. In some embodiments, a LAIR-1-binding agent described herein blocks the interaction of LAIR-1 to MARCO. In some embodiments, a LAIR-1-binding agent described herein inhibits binding of LAIR-1 to MARCO. In some embodiments, a LAIR-1-binding agent described herein blocks or inhibits a functional interaction between LAIR-1 to MARCO. In some embodiments, a LAIR-1-binding agent described herein inhibits, disrupts, or blocks binding of LAIR-1 to COLEC12. In some embodiments, a LAIR-1-binding agent described herein blocks the interaction of LAIR-1 to COLEC12. In some embodiments, a LAIR-1-binding agent described herein inhibits binding of LAIR-1 to COLEC12. In some embodiments, a LAIR-1-binding agent described herein blocks or inhibits a functional interaction between LAIR-1 to COLEC12.

In some embodiments, a LAIR-1-binding agent described herein inhibits collagen-induced LAIR-1 activity. In some embodiments, a LAIR-1-binding agent described herein inhibits collagen-induced LAIR-1 suppressive activity. In some embodiments, a LAIR-1-binding agent described herein inhibits collagen-induced LAIR-1 suppression of myeloid cells. In some embodiments, a LAIR-1-binding agent described herein inhibits collagen-induced LAIR-1 suppression of myeloid cell activity. In some embodiments, a LAIR-1-binding agent described herein inhibits collagen-induced LAIR-1 suppression of APCs. In some embodiments, a LAIR-1-binding agent described herein inhibits collagen-induced LAIR-1 suppression of APC activity. In some embodiments, a LAIR-1-binding agent described herein inhibits collagen-induced LAIR-1 suppression of dendritic cells. In some embodiments, a LAIR-1-binding agent described herein inhibits collagen-induced LAIR-1 suppression of dendritic cell activity. In some embodiments, the myeloid cells, dendritic cells, or APCs are tumor-associated cells. In some embodiments, the myeloid cells, dendritic cells, or APCs are residing in the tumor microenvironment. In some embodiments, the myeloid cells, dendritic cells, or APCs are residing within a tumor.

In some embodiments, a LAIR-1-binding agent described herein inhibits MARCO-induced LAIR-1 activity. In some embodiments, a LAIR-1-binding agent described herein inhibits MARCO-induced LAIR-1 suppressive activity. In some embodiments, a LAIR-1-binding agent described herein inhibits MARCO-induced LAIR-1 suppression of myeloid cells. In some embodiments, a LAIR-1-binding agent described herein inhibits MARCO-induced LAIR-1 suppression of myeloid cell activity. In some embodiments, a LAIR-1-binding agent described herein inhibits MARCO-induced LAIR-1 suppression of APCs. In some embodiments, a LAIR-1-binding agent described herein inhibits MARCO-induced LAIR-1 suppression of APC activity. In some embodiments, a LAIR-1-binding agent described herein inhibits MARCO-induced LAIR-1 suppression of dendritic cells. In some embodiments, a LAIR-1-binding agent described herein inhibits MARCO-induced LAIR-1 suppression of dendritic cell activity. In some embodiments, the myeloid cells, dendritic cells, or APCs are tumor-associated cells. In some embodiments, the myeloid cells, dendritic cells, or APCs are residing in the tumor microenvironment. In some embodiments, the myeloid cells, dendritic cells, or APCs are residing within a tumor.

III. LAIR-1-Binding Agents

Amino acid (aa) sequences for human LAIR-1 (UniProtKB No. Q6GTX8), cynomolgus monkey ("cyno") LAIR-1 (UniProtKB No. A0A2K5TN26), and mouse LAIR-1 (UniProtKB No. Q8BG84) are provided herein as SEQ ID NO:1, SEQ ID NO:5, and SEQ ID NO:149, respectively. As used herein, reference to amino acid positions of LAIR-1 refer to the numbering of amino acid sequences including the signal sequence.

LAIR-1 is a single pass type I transmembrane protein with a predicted molecular weight of approximately 32 kDa. As characterized within UniProtKB, human LAIR-1 is a protein of 287 amino acids (aa)—the signal sequence is aa 1-21, the extracellular domain is aa 22-165, the transmembrane region is aa 166-186, and the cytoplasmic domain is aa 187-287. Within the extracellular domain, the Ig-like C2-type domain is aa 29-117 and the "stem region" is aa 118-165. Within the cytoplasmic domain, ITIMs are positioned at aa 249-254 and 279-284. LAIR-1 is expressed on almost all immune cells, including NK cells, T-cells, B-cells, monocytes, dendritic cells, eosinophils, basophils, and mast cells. LAIR-1 is characterized by an extracellular domain comprising one Ig-like C2 type domain, a transmembrane domain, and a cytoplasmic domain containing 2 ITIM domains (see, e.g., Meyaard et al., 1997, *Immunity.* 7:283-290; Meyaard et al., 2008, *J. Leuk. Biol.,* 83:799-803). LAIR-1 is known to bind to multiple transmembrane and extracellular matrix collagens. As described herein, MARCO and COLEC12 were identified as new and novel ligands for LAIR-1.

Cyno LAIR-1 has an amino acid sequence identity to human LAIR-1 of 88%. As characterized within UniProtKB, cyno LAIR-1 is a protein of 287 amino acids and it is believed that the structural characteristics of cyno LAIR-1 are similar to human LAIR-1. Thus, for cyno LAIR-1 the signal sequence is predicted to be aa 1-21, the extracellular domain is predicted to be aa 22-165, the transmembrane region is predicted to be aa 166-186, and the cytoplasmic domain is predicted to be aa 187-287. Within the extracellular domain, the Ig-like C2-type domain is predicted to be aa 29-117 and the "stem region" is predicted to be aa 118-165. Within the cytoplasmic domain, ITIMs are positioned at aa 249-254 and 279-284.

Mouse LAIR-1 has an amino acid sequence identity to human LAIR-1 of 42%. As characterized within UniProtKB, mouse LAIR-1 is a protein of 263 amino acids and has structural characteristics similar to human LAIR-1. Thus, for mouse LAIR-1 the signal sequence is aa 1-21, the extracellular domain is aa 22-144, the transmembrane region is aa 145-165, and the cytoplasmic domain is aa 166-263. Within the extracellular domain, the Ig-like C2-type domain is aa 27-114 and the "stem region" is aa 115-144. Within the cytoplasmic domain, ITIMs are positioned at aa 226-231 and 255-260.

In some embodiments, a LAIR-1-binding agent binds LAIR-1 or a fragment of LAIR-1. In some embodiments, a fragment of LAIR-1 comprises the extracellular domain. In some embodiments, a fragment of LAIR-1 comprises the Ig-like C2 type domain (D1). In some embodiments, a fragment of LAIR-1 comprises the Ig-like C2 type domain and the stem region (D1-stem). In some embodiments, the extracellular domain of human LAIR-1 comprises amino acids 22-165 of SEQ ID NO:1. In some embodiments, D1 of human LAIR-1 comprises amino acids 29-117 of SEQ ID NO:1. In some embodiments, D1-stem of human LAIR-1 comprises amino acids 29-165 of SEQ ID NO:1. In some embodiments, a fragment of human LAIR-1 comprises the amino acid sequence of SEQ ID NO:3. In some embodiments, a fragment of human LAIR-1 comprises the amino acid sequence of SEQ ID NO:4. In some embodiments, the extracellular domain of cyno LAIR-1 comprises amino acids 22-165 of SEQ ID NO:5. In some embodiments, D1 of cyno LAIR-1 comprises amino acids 29-117 of SEQ ID NO:5. In some embodiments, D1-stem of cyno LAIR-1 comprises amino acids 29-165 of SEQ ID NO:5. In some embodiments, a fragment of cyno LAIR-1 comprises the amino acid sequence of SEQ ID NO:7. In some embodiments, a fragment of cyno LAIR-1 comprises the amino acid sequence of SEQ ID NO:8. In some embodiments, the extracellular domain of mouse LAIR-1 comprises amino acids 22-144 of SEQ ID NO:149. In some embodiments, D1 of mouse LAIR-1 comprises amino acids 27-114 of SEQ ID NO:149. In some embodiments, D1-stem of mouse LAIR-1 comprises amino acids 27-144 of SEQ ID NO:149. In some embodiments, a fragment of mouse LAIR-1 comprises the amino acid sequence of SEQ ID NO:151. In some embodiments, a fragment of mouse LAIR-1 comprises the amino acid sequence of SEQ ID NO:152.

It is understood that the regions and/or domains of LAIR-1 (e.g., human LAIR-1, cyno LAIR-1, or mouse LAIR-1) may be defined differently by those of skill in the art, therefore the N-terminal amino acids and the C-terminal amino acids of any LAIR-1 domain or region may vary by 1, 2, 3, 4, 5, or more amino acid residues.

The present disclosure provides agents that bind LAIR-1. In some embodiments, a LAIR-1-binding agent binds a fragment of LAIR-1. In some embodiments, a LAIR-1-binding agent binds within a specific region of LAIR-1. In some embodiments, a LAIR-1-binding agent binds within the extracellular domain of LAIR-1. In some embodiments, a LAIR-1-binding agent binds within the D1 domain of LAIR-1. In some embodiments, a LAIR-1-binding agent binds within the D1-stem domain of LAIR-1. In some embodiments, a LAIR-1-binding agent binds an epitope on LAIR-1. In some embodiments, a LAIR-1-binding agent binds a conformational epitope on LAIR-1.

In some embodiments, a LAIR-1-binding agent binds human LAIR-1. In some embodiments, a LAIR-1-binding agent binds cyno LAIR-1. In some embodiments, a LAIR-1-binding agent binds mouse LAIR-1. In some embodiments, a LAIR-1-binding agent binds human LAIR-1 and cyno LAIR-1. In some embodiments, a LAIR-1-binding agent binds human LAIR-1 and cyno LAIR-1, but does not bind mouse LAIR-1. In some embodiments, a LAIR-1-binding agent binds SEQ ID NO:1. In some embodiments, a LAIR-1-binding agent binds SEQ ID NO:2. In some embodiments, a LAIR-1-binding agent binds within amino acids 22-165 of SEQ ID NO:1. In some embodiments, a LAIR-1-binding agent binds within amino acids 29-117 of SEQ ID NO:1. In some embodiments, a LAIR-1-binding agent binds within amino acids 29-165 of SEQ ID NO:1. In some embodiments, a LAIR-1-binding agent binds SEQ ID NO:3. In some embodiments, a LAIR-1-binding agent binds SEQ ID NO:4. In some embodiments, a LAIR-1-binding agent binds SEQ ID NO:5. In some embodiments, a LAIR-1-binding agent binds SEQ ID NO:6. In some embodiments, a LAIR-1-binding agent binds within amino acids 22-165 of SEQ ID NO:5. In some embodiments, a LAIR-1-binding agent binds within amino acids 29-117 of SEQ ID NO:5. In some embodiments, a LAIR-1-binding agent binds within amino acids 29-165 of SEQ ID NO:5. In some embodiments, a LAIR-1-binding agent binds SEQ ID NO:7. In some embodiments, a LAIR-1-binding agent binds SEQ ID NO:8. In some embodiments, a LAIR-1-binding agent binds SEQ ID NO:149. In some embodiments, a LAIR-1-binding agent binds SEQ ID NO:150. In some embodiments, a LAIR-1-binding agent binds within amino acids 22-144 of SEQ ID NO:149. In some embodiments, a LAIR-1-binding agent binds within amino acids 27-114 of SEQ ID NO:149. In some embodiments, a LAIR-1-binding agent binds within amino acids 27-144 of SEQ ID NO:149. In some embodiments, a LAIR-1-binding agent binds SEQ ID NO:151. In some embodiments, a LAIR-1-binding agent binds SEQ ID NO:152.

In some embodiments, a LAIR-1-binding agent binds a polypeptide comprising the amino acid sequence of SEQ ID NO:2. In some embodiments, a LAIR-1-binding agent binds a polypeptide comprising the amino acid sequence of SEQ ID NO:3. In some embodiments, a LAIR-1-binding agent binds a polypeptide comprising the amino acid sequence of SEQ ID NO:4. In some embodiments, a LAIR-1-binding agent binds a polypeptide comprising the amino acid sequence of SEQ ID NO:6. In some embodiments, a LAIR-1-binding agent binds a polypeptide comprising the amino acid sequence of SEQ ID NO:7. In some embodiments, a LAIR-1-binding agent binds a polypeptide comprising the amino acid sequence of SEQ ID NO:8. In some embodiments, a LAIR-1-binding agent binds a polypeptide comprising the amino acid sequence of SEQ ID NO:150. In some embodiments, a LAIR-1-binding agent binds a polypeptide comprising the amino acid sequence of SEQ ID NO:151. In some embodiments, a LAIR-1-binding agent binds a polypeptide comprising the amino acid sequence of SEQ ID NO:152.

In some embodiments, a LAIR-1-binding agent binds an epitope comprising amino acids within SEQ ID NO:2. In some embodiments, a LAIR-1-binding agent binds an epitope comprising amino acids within SEQ ID NO:3. In some embodiments, a LAIR-1-binding agent binds an epitope comprising amino acids within SEQ ID NO:4. In some embodiments, a LAIR-1-binding agent binds an epitope comprising at least one amino acid within amino acids 70-80 of SEQ ID NO:1. In some embodiments, a LAIR-1-binding agent binds an epitope comprising at least one amino acid within amino acids 61-80 of SEQ ID NO:1. In some embodiments, a LAIR-1-binding agent binds an epitope comprising amino acids within SEQ ID NO:6. In some embodiments, a LAIR-1-binding agent binds an epitope comprising amino acids within SEQ ID NO:7. In some embodiments, a LAIR-1-binding agent binds an epitope comprising amino acids within SEQ ID NO:8. In some embodiments, a LAIR-1-binding agent binds an epitope comprising amino acids within SEQ ID NO:150. In some embodiments, a LAIR-1-binding agent binds an epitope comprising amino acids within SEQ ID NO:151. In some embodiments, a LAIR-1-binding agent binds an epitope comprising amino acids within SEQ ID NO:152.

In some embodiments, a LAIR-1-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgG antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some embodiments, the antibody comprises an IgG heavy chain. In some embodiments, the antibody comprises an IgG1 heavy chain. In some embodiments, the antibody comprises an IgG2 heavy chain. In some embodiments, the antibody comprises an IgG4 heavy chain. In some embodiments, the antibody comprises a human IgG1 heavy chain. In some embodiments, the antibody comprises a human IgG2 heavy chain. In some embodiments, the antibody comprises a human IgG4 heavy chain. In some embodiments, the antibody comprises a kappa light chain. In some embodiments, the antibody comprises a kappa light chain constant region. In some embodiments, the antibody comprises a human kappa light chain constant region. In some embodiments, the antibody comprises a lambda light chain. In some embodiments, the antibody comprises a lambda light chain constant region. In some embodiments, the antibody comprises a human lambda light chain constant region.

In some embodiments, the antibody is an antibody fragment comprising an antigen-binding site. In some embodiments, the antibody is a scFv. In some embodiments, the antibody is a disulfide-linked scFv. In some embodiments, the antibody is a disulfide-linked sc(Fv)$_2$. In some embodiments, the antibody is a Fab, Fab', or a F(ab)$_2$ antibody. In some embodiments, the antibody is a diabody. In some embodiments, the antibody is a nanobody.

In some embodiments, the antibody is a monospecific antibody. In some embodiments, the antibody is a bispecific antibody. In some embodiments, the antibody is a multispecific antibody. In some embodiments, the antibody is a monovalent antibody. In some embodiments, the antibody is a bivalent antibody. In some embodiments, the antibody is a tetravalent antibody.

In some embodiments, the antibody is isolated. In some embodiments, the antibody is substantially pure.

In some embodiments, a LAIR-1-binding agent is a polyclonal antibody. Polyclonal antibodies can be prepared by any method known to those of skill in the art. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a period of time, polyclonal antibodies are recovered from the immunized animal (e.g., from blood or ascites). In some embodiments, the polyclonal antibodies are purified from serum or ascites according to standard methods in the art including, but not limited to, affinity chromatography, ion-exchange chromatography, gel electrophoresis, and/or dialysis.

In some embodiments, a LAIR-1-binding agent is a monoclonal antibody. Monoclonal antibodies can be prepared by any method known to those of skill in the art. In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a mouse protein or a fragment thereof. In some embodiments, the immunizing antigen is a cyno protein or a fragment thereof. In some embodiments, the immunizing antigen is a combination of two or more (e.g., 2, 3, 4) related proteins or fragments thereof.

Following immunization, lymphocytes are isolated and fused with a suitable myeloma cell line using, for example, polyethylene glycol or electrofusion. The hybridoma cells are selected using specialized media as known in the art and unfused lymphocytes and myeloma cells do not survive the selection process. Hybridomas that produce monoclonal antibodies directed specifically against a chosen antigen can be identified by a variety of methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution techniques. In some embodiments, high-throughput methods are used to distribute single cell hybridoma cells into plates. In some embodiments, high-throughput methods are used to directly distribute single cells from original fusion into plates. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins.

In some embodiments, recombinant monoclonal antibodies are isolated from phage display libraries expressing variable domains or CDRs of a desired species. Screening of phage libraries can be accomplished by various techniques known in the art.

In some embodiments, a monoclonal antibody is modified by using recombinant DNA technology to generate alternative antibodies. In some embodiments, the constant domains of the light chain and heavy chain of a mouse monoclonal antibody are substituted for constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and affinity of a monoclonal antibody.

In some embodiments, a LAIR-1-binding agent is a humanized antibody. Various methods for generating humanized antibodies are known in the art. In some embodiments, a humanized antibody comprises one or more amino acid residues that have been introduced into it from a source that is non-human. In some embodiments, humanization is performed by substituting one or more non-human CDR sequences for the corresponding CDR sequences of a human antibody. In some embodiments, the humanized antibodies are constructed by substituting all six CDRs of a non-human antibody (e.g., a mouse antibody) for the corresponding CDRs of a human antibody.

The choice of which human heavy chain variable region and/or light chain variable region to use for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, a method called "superhumanization" which is described as the direct transfer of CDRs to a human germline framework, a method termed Human String Content (HSC) which is based on a metric of "antibody humanness", methods based on generation of large libraries of humanized variants (including phage, ribosomal, and yeast display libraries), and methods based on framework region shuffling.

In some embodiments, a LAIR-1-binding agent is a human antibody. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized human donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, a LAIR-1-binding agent is an antibody fragment. Examples of antibody fragments include, but are not limited to, Fab, Fab', F(ab')$_2$, Fv, single chain antibody molecules, scFv, disulfide-linked scFv (dsscFv), nanobodies, diabodies, tribodies, tetrabodies, minibodies, dual variable domain antibodies (DVD), and single variable domain antibodies.

In some embodiments, a LAIR-1-binding agent is a scFv antibody. In some embodiments, the scFv is a disulfide-linked scFv (dsscFv). DsscFv antibodies comprise an engineered disulfide bond between the light chain variable region and heavy chain variable region of the scFv. In some embodiments, the disulfide bond increases stability of the scFv molecule. In some embodiments, the disulfide bond increases thermostability of the scFv molecule.

In some embodiments, a LAIR-1-binding agent is a Fv. In some embodiments, a LAIR-1-binding agent is a Fab. In some embodiments, a LAIR-1-binding agent is a F(ab')$_2$. In some embodiments, a LAIR-1-binding agent is a F(ab').

Antibody fragments can be made by various techniques, including but not limited to proteolytic digestion of an intact antibody. In some embodiments, antibody fragments are produced using recombinant technologies known in the art (e.g., *E. coli* or phage expression).

In some embodiments, a LAIR-1-binding agent is a bispecific antibody. Bispecific antibodies are capable of recognizing and binding at least two different antigens or epitopes. The different epitopes can either be within the same molecule (e.g., two epitopes on LAIR-1) or on different molecules (e.g., one epitope on LAIR-1 and one epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject. In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Many techniques for making bispecific antibodies are known to those skilled in the art. In some embodiments, a bispecific antibody comprises heavy chain constant regions with modifications in the amino acids that are part of the interface between the two heavy chains. These modifications are made to enhance heterodimer formation and generally reduce or eliminate homodimer formation. In some embodiments, the bispecific antibody is generated using a knobs-into-holes (KIH) strategy. In some embodiments, the bispecific antibody comprises variant hinge regions incapable of forming disulfide linkages between identical heavy chains (e.g., reduce homodimer formation). In some embodiments, the bispecific antibody comprises heavy chains with changes in amino acids that result in altered electrostatic interactions. In some embodiments, the bispecific antibodies comprise heavy chains with changes in amino acids that result in altered hydrophobic/hydrophilic interactions.

Bispecific antibodies can be intact antibodies or antibody fragments comprising antigen-binding sites.

In some embodiments, a LAIR-1-binding agent is an antibody that binds LAIR-1. In some embodiments, an anti-LAIR-1 antibody binds human LAIR-1. In some embodiments, an anti-LAIR-1 antibody binds cyno LAIR-1. In some embodiments, an anti-LAIR-1 antibody binds mouse LAIR-1. In some embodiments, an anti-LAIR-1 antibody binds human LAIR-1 and cyno LAIR-1. In some embodiments, an anti-LAIR-1 antibody binds human LAIR-1 and cyno LAIR-1, and does not bind mouse LAIR-1. In some embodiments, an anti-LAIR-1 antibody binds an LAIR-1 epitope. In some embodiments, an anti-LAIR-1 antibody binds an LAIR-1 epitope within the extracellular domain of human LAIR-1. In some embodiments, an anti-LAIR-1 antibody binds an LAIR-1 epitope within the extracellular domain of cyno LAIR-1.

In some embodiments, an anti-LAIR-1 antibody binds an epitope comprising at least one amino acid (e.g., 1, 2, 3, 4, 5, 6, 7, 8, 9) within amino acids 22-165 of SEQ ID NO:1. In some embodiments, an anti-LAIR-1 antibody binds an epitope comprising at least one amino acid within amino acids 22-117 of SEQ ID NO:1. In some embodiments, an anti-LAIR-1 antibody binds an epitope comprising at least one amino acid within amino acids 29-117 of SEQ ID NO:1. In some embodiments, an anti-LAIR-1 antibody binds an epitope comprising amino acids within SEQ ID NO:3. In some embodiments, an anti-LAIR-1 antibody binds an epitope comprising amino acids within SEQ ID NO:4.

In some embodiments, an anti-LAIR-1 antibody binds an epitope comprising at least one amino acid (e.g., 1, 2, 3, 4, 5, 6, 7, 8, 9) within amino acids 22-165 of SEQ ID NO:5. In some embodiments, an anti-LAIR-1 antibody binds an epitope comprising at least one amino acid within amino acids 22-117 of SEQ ID NO:5. In some embodiments, an anti-LAIR-1 antibody binds an epitope comprising at least one amino acid within amino acids 29-117 of SEQ ID NO:5. In some embodiments, an anti-LAIR-1 antibody binds an epitope comprising amino acids within SEQ ID NO:7. In some embodiments, an anti-LAIR-1 antibody binds an epitope comprising amino acids within SEQ ID NO:8.

In some embodiments, an anti-LAIR-1 antibody binds an epitope comprising at least one amino acid (e.g., 1, 2, 3, 4, 5, 6, 7, 8, 9) within amino acids 22-144 of SEQ ID NO:149. In some embodiments, an anti-LAIR-1 antibody binds an epitope comprising at least one amino acid within amino acids 22-114 of SEQ ID NO:149. In some embodiments, an anti-LAIR-1 antibody binds an epitope comprising at least one amino acid within amino acids 27-114 of SEQ ID NO:149. In some embodiments, an anti-LAIR-1 antibody binds an epitope comprising amino acids within SEQ ID NO:151. In some embodiments, an anti-LAIR-1 antibody binds an epitope comprising amino acids within SEQ ID NO:152.

In some embodiments, the epitope is a conformational epitope. In some embodiments, the epitope is a linear epitope.

In some embodiments, an anti-LAIR-1 antibody competes with a second agent for binding within the extracellular domain of human LAIR-1. In some embodiments, an anti-LAIR-1 antibody competes with a second agent for binding within the extracellular domain of cyno LAIR-1. In some embodiments, an anti-LAIR-1 antibody competes with a second agent for binding within amino acids 22-165 of SEQ ID NO:1. In some embodiments, an anti-LAIR-1 antibody competes with a second agent for binding within amino acids 22-117 of SEQ ID NO:1. In some embodiments, an anti-LAIR-1 antibody competes with a second agent for binding within amino acid sequence SEQ ID NO:3. In some embodiments, an anti-LAIR-1 antibody competes with a second agent for binding within amino acid sequence SEQ ID NO:4.

In some embodiments, a LAIR-1-binding agent is an anti-LAIR-1 antibody described herein. In some embodiments, the LAIR-1-binding agent is a variant of an anti-LAIR-1 antibody described herein. In some embodiments, a variant of an anti-LAIR-1 antibody comprises one to thirty amino acid substitutions. In some embodiments, a variant of the anti-LAIR-1 antibody comprises one to twenty-five amino acid substitutions. In some embodiments, a variant of the anti-LAIR-1 antibody comprises one to twenty amino acid substitutions. In some embodiments, a variant of the anti-LAIR-1 antibody comprises one to fifteen amino acid substitutions. In some embodiments, a variant of the anti-LAIR-1 antibody comprises one to ten amino acid substitutions. In some embodiments, a variant of the anti-LAIR-1 antibody comprises one to five amino acid substitutions. In some embodiments, the variant of the anti-LAIR-1 antibody comprises one to three amino acid substitutions. In some embodiments, the amino acid substitution(s) is in a CDR of the antibody. In some embodiments, the amino acid substitution(s) is not in a CDR of the antibody. In some embodiments, the amino acid substitution(s) is in a framework region of the antibody. In some embodiments, the amino acid substitution(s) is a conservative amino acid substitution.

CDRs of an antibody are defined using a variety of methods/systems by those skilled in the art. These systems and/or definitions have been developed and refined over a number of years and include Kabat, Chothia, IMGT, AbM, and Contact. The Kabat definition is based on sequence variability and is commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis) are available and known to those of skill in the art for analysis of antibody sequence and determination of CDRs.

The specific CDR sequences defined herein are generally based on a combination of Kabat and Chothia definitions (Exemplary definition). However, it will be understood that reference to a heavy chain variable region CDR or CDRs and/or a light chain variable region CDR or CDRs of a specific antibody will encompass all CDR definitions as known to those of skill in the art.

In some embodiments, an anti-LAIR-1 antibody described herein comprises the six CDRs of antibody 47A1, 47H1, Hz47H1.v4, 57D12, 61H4, 62G10, 108D10, or 43H2 based on the Kabat definition. In some embodiments, an anti-LAIR-1 antibody described herein comprises the six CDRs of antibody 47A1, 47H1, Hz47H1.v4, 57D12, 61H4, 62G10, 108D10, or 43H2 based on the Chothia definition. In some embodiments, an anti-LAIR-1 antibody described herein comprises the six CDRs of antibody 47A1, 47H1, Hz47H1.v4, 57D12, 61H4, 62G10, 108D10, or 43H2 based on the AbM definition. In some embodiments, an anti-LAIR-1 antibody described herein comprises the six CDRs of antibody 47A1, 47H1, Hz47H1.v4, 57D12, 61H4, 62G10, 108D10, or 43H2 based on the IMGT definition. In some embodiments, an anti-LAIR-1 antibody described herein comprises the six CDRs of antibody 47A1, 47H1, Hz47H1.v4, 57D12, 61H4, 62G10, 108D10, or 43H2 based on the Contact definition. In some embodiments, an anti-LAIR-1 antibody described herein comprises the six CDRs of antibody 47A1, 47H1, Hz47H1.v4, 57D12, 61H4, 62G10, 108D10, or 43H2 based on the Exemplary definition.

In some embodiments, a LAIR-1-binding agent is an anti-LAIR-1 antibody that comprises one, two, three, four, five, and/or six CDRs of any one of the antibodies described herein. In some embodiments, an anti-LAIR-1 antibody comprises (i) a heavy chain variable region comprising one, two, and/or three heavy chain variable region CDRs from Table 1, and/or (ii) a light chain variable region comprising one, two, and/or three light chain variable region CDRs from Table 1. In some embodiments, an anti-LAIR-1 antibody comprises (i) a heavy chain variable region comprising one, two, and/or three heavy chain variable region CDRs from Table 2A, and/or (ii) a light chain variable region comprising one, two, and/or three light chain variable region CDRs from Table 2A. In some embodiments, an anti-LAIR-1 antibody comprises (i) a heavy chain variable region comprising one, two, and/or three heavy chain variable region CDRs from Table 2B, and/or (ii) a light chain variable region comprising one, two, and/or three light chain variable region CDRs from Table 2B. In some embodiments, an anti-LAIR-1 antibody comprises (i) a heavy chain variable region comprising one, two, and/or three heavy chain variable region CDRs from Table 3, and/or (ii) a light chain variable region comprising one, two, and/or three light chain variable region CDRs from Table 3. In some embodiments, an anti-LAIR-1 antibody comprises (i) a heavy chain variable region comprising one, two, and/or three heavy chain variable region CDRs from Table 4, and/or (ii) a light chain variable region comprising one, two, and/or three light chain variable region CDRs from Table 4. In some embodiments, an anti-LAIR-1 antibody comprises (i) a heavy chain variable region comprising one, two, and/or three heavy chain variable region CDRs from Table 5, and/or (ii) a light chain variable region comprising one, two, and/or three light chain variable region CDRs from Table 5. In some embodiments, an anti-LAIR-1 antibody comprises (i) a heavy chain variable region comprising one, two, and/or three heavy chain variable region CDRs from Table 6, and/or (ii) a light chain variable region comprising one, two, and/or three light chain variable region CDRs from Table 6. In some embodiments, an anti-LAIR-1 antibody comprises (i) a heavy chain variable region comprising one, two, and/or three heavy chain variable region CDRs from Table 7, and/or (ii) a light chain variable region comprising one, two, and/or three light chain variable region CDRs from Table 7.

In some embodiments, an anti-LAIR-1 antibody comprises (i) a heavy chain variable region comprising three heavy chain variable region CDRs from Table 1, and (ii) a light chain variable region comprising three light chain variable region CDRs from Table 1. In some embodiments, an anti-LAIR-1 antibody comprises (i) a heavy chain variable region comprising three heavy chain variable region CDRs from Table 2A, and (ii) a light chain variable region comprising three light chain variable region CDRs from Table 2A. In some embodiments, an anti-LAIR-1 antibody comprises (i) a heavy chain variable region comprising three heavy chain variable region CDRs from Table 2B, and (ii) a light chain variable region comprising three light chain variable region CDRs from Table 2B. In some embodiments, an anti-LAIR-1 antibody comprises (i) a heavy chain variable region comprising three heavy chain variable region CDRs from Table 3, and (ii) a light chain variable region comprising three light chain variable region CDRs from Table 3. In some embodiments, an anti-LAIR-1 antibody comprises (i) a heavy chain variable region comprising three heavy chain variable region CDRs from Table 4, and (ii) a light chain variable region comprising three light chain variable region CDRs from Table 4. In some embodiments, an anti-LAIR-1 antibody comprises (i) a heavy chain variable region comprising three heavy chain variable region CDRs from Table 5, and (ii) a light chain variable region comprising three light chain variable region CDRs from Table 5. In some embodiments, an anti-LAIR-1 antibody comprises (i) a heavy chain variable region comprising three heavy chain variable region CDRs from Table 6, and (ii) a light chain variable region comprising three light chain variable region CDRs from Table 6. In some embodiments, an anti-LAIR-1 antibody comprises (i) a heavy chain variable region comprising three heavy chain variable region CDRs from Table 7, and (ii) a light chain variable region comprising three light chain variable region CDRs from Table 7.

TABLE 1

Antibody 47A1 Sequences

| | Exemplary | Chothia | AbM | Kabat | Contact |
|---|---|---|---|---|---|
| VH CDR1 | GFTFNTYAIH (SEQ ID NO: 9) | GFTFNTY (SEQ ID NO: 15) | GFTFNTYAIH (SEQ ID NO: 9) | TYAIH (SEQ ID NO: 18) | NTYAIH (SEQ ID NO: 19) |
| VH CDR2 | RIRSKSTNYATYYADRSKSTNYASVKD (SEQ ID NO: 10) | RIRSKSTNYATY (SEQ ID NO: 16) | RIRSKSTNYATY (SEQ ID NO: 17) | RIRSKSTNYATYYADWVARIRSKSTNYATYSVK (SEQ ID NO: 10) | (SEQ ID NO: 20) |
| VH CDR3 | ENWYYYALDY (SEQ ID NO: 11) | ENWYYYALDY (SEQ ID NO: 11) | ENWYYYALDY (SEQ ID NO: 11) | ENWYYYALDY (SEQ ID NO: 11) | VRENWYYYALD (SEQ ID NO: 21) |
| VL CDR1 | RASGNIHNYLT (SEQ ID NO: 12) | RASGNIHNYLT (SEQ ID NO: 12) | RASGNIHNYLT (SEQ ID NO: 12) | RASGNIHNYLT (SEQ ID NO: 12) | HNYLTWY (SEQ ID NO: 22) |
| VL CDR2 | NAKTLED (SEQ ID NO: 13) | NAKTLED (SEQ ID NO: 13) | NAKTLED (SEQ ID NO: 13) | NAKTLED (SEQ ID NO: 13) | VLVYNAKTLE (SEQ ID NO: 23) |
| VL CDR3 | QHFWSTPFT (SEQ ID NO: 14) | QHFWSTPFT (SEQ ID NO: 14) | QHFWSTPFT (SEQ ID NO: 14) | QHFWSTPFT (SEQ ID NO: 14) | QHFWSTPF (SEQ ID NO: 24) |

47A1 Heavy chain variable region (SEQ ID NO: 115)
EVQLVESGGGLVQPKGSLKLSCAASGFTFNTYAIHWVRQAPGKGLEWVARIRSKSTNYAT
YYADSVKDRFTISRDDSQSMVFLQMNNLKTEDTAMYYCVRENWYYYALDYWGQGTSVTVSS 47A1 Light chain variable region (SEQ ID NO: 116)
DIQMTQSPASLSASVGETVTITCRASGNIHNYLTWYQQKQGKSPQVLVYNAKTLEDGVPS
RFSGSESGTQYSLKINSLQPEDFGSYYCQHFWSTPFTFGSGTKLEIK

TABLE 2A

Antibody 47H1 Sequences

| | Exemplary | Chothia | AbM | Kabat | Contact |
|---|---|---|---|---|---|
| VH CDR1 | GFTFNINAMN (SEQ ID NO: 25) | GFTFNIN (SEQ ID NO: 31) | GFTFNINAMN (SEQ ID NO: 25) | INAMN (SEQ ID NO: 34) | NINAMN (SEQ ID NO: 35) |
| VH CDR2 | RIRTKNNNYATFYADSVKD (SEQ ID NO: 26) | RTKNNNYA (SEQ ID NO: 32) | RIRTKNNNYATF (SEQ ID NO: 33) | RIRTKNNNYATFYADSVKD (SEQ ID NO: 26) | WVARIRTKNNNYATF (SEQ ID NO: 36) |
| VH CDR3 | DRAGFFAY (SEQ ID NO: 27) | DRAGFFAY (SEQ ID NO: 27) | DRAGFFAY (SEQ ID NO: 27) | DRAGFFAY (SEQ ID NO: 27) | VRDRAGFFA (SEQ ID NO: 37) |
| VL CDR1 | LASQTIGTWLG (SEQ ID NO: 28) | LASQTIGTWLG (SEQ ID NO: 28) | LASQTIGTWLG (SEQ ID NO: 28) | LASQTIGTWLG (SEQ ID NO: 28) | GTWLGWY (SEQ ID NO: 38) |

TABLE 2A-continued

Antibody 47H1 Sequences

| | Exemplary | Chothia | AbM | Kabat | Contact |
|---|---|---|---|---|---|
| VL CDR2 | AATSLAD (SEQ ID NO: 29) | AATSLAD (SEQ ID NO: 29) | AATSLAD (SEQ ID NO: 29) | AATSLAD (SEQ ID NO: 29) | LLIYAATSLA (SEQ ID NO: 39) |
| VL CDR3 | QQLYSTPLT (SEQ ID NO: 30) | QQLYSTPLT (SEQ ID NO: 30) | QQLYSTPLT (SEQ ID NO: 30) | QQLYSTPLT (SEQ ID NO: 30) | QQLYSTPL (SEQ ID NO: 40) |

47H1 Heavy chain variable region (SEQ ID NO: 117)
EVQLVETGGGLVQPKGSLKLSCAASGFTFNINAMNWVRQAPGKGLEWVARIRTKNNNYAT
FYADSVKDRFTISRDDSQSMLYLQMNNLKTDDTAMYYCVRDRAGFFAYWGQGTPVTVSA 47H1 Light chain variable region (SEQ ID NO: 118)
DIQMTQSPASQSASLGESVTITCLASQTIGTWLGWYRQKPGKSPQLLIYAATSLADGVPS
RFSGSGSGTKFSFKISSLQAEDFVIYYCQQLYSTPLTFGSGTKLEIK

TABLE 2B

Antibody Hz47H1.v4 Sequences

| | Exemplary | Chothia | AbM | Kabat | Contact |
|---|---|---|---|---|---|
| VH CDR1 | GFTFNINAMN (SEQ ID NO: 25) | GFTFNIN (SEQ ID NO: 31) | GFTFNINAMN (SEQ ID NO: 25) | INAMN (SEQ ID NO: 34) | NINAMN (SEQ ID NO: 35) |
| VH CDR2 | RIRTKNYNYATFYADSVKD (SEQ ID NO: 41) | RTKNYNYA (SEQ ID NO: 43) | RIRTKNYNYATF (SEQ ID NO: 44) | RIRTKNYNYATFYADSVKD (SEQ ID NO: 41) | WVARIRTKNYNYATF (SEQ ID NO: 45) |
| VH CDR3 | DRAGFFAY (SEQ ID NO: 27) | DRAGFFAY (SEQ ID NO: 27) | DRAGFFAY (SEQ ID NO: 27) | DRAGFFAY (SEQ ID NO: 27) | VRDRAGFFA (SEQ ID NO: 37) |
| VL CDR1 | LASQTIGTWLG (SEQ ID NO: 28) | LASQTIGTWLG (SEQ ID NO: 28) | LASQTIGTWLG (SEQ ID NO: 28) | LASQTIGTWLG (SEQ ID NO: 28) | GTWLGWY (SEQ ID NO: 38) |
| VL CDR2 | AATSLAE (SEQ ID NO: 42) | AATSLAE (SEQ ID NO: 42) | AATSLAE (SEQ ID NO: 42) | AATSLAE (SEQ ID NO: 42) | LLIYAATSLA (SEQ ID NO: 39) |
| VL CDR3 | QQLYSTPLT (SEQ ID NO: 30) | QQLYSTPLT (SEQ ID NO: 30) | QQLYSTPLT (SEQ ID NO: 30) | QQLYSTPLT (SEQ ID NO: 30) | QQLYSTPL (SEQ ID NO: 40) |

Hz47H1.v4 Heavy chain variable region (SEQ ID NO: 119)
EVQLVESGGGLVQPGGSLRLSCAASGFTFNINAMNWVRQAPGKGLEWVARIRTKNYNYAT
FYADSVKDRFTISRDDSKNSLYLQMNSLKTEDTAVYYCVRDRAGFFAYWGQGTTVTVSS Hz47H1.v4 Light chain variable region (SEQ ID NO: 120)
DIQMTQSPSSLSASVGDRVTITCLASQTIGTWLGWYQQKPGKAPKLLIYAATSLAEGVPS
RFSGSGSGTDFTLTISSLQPEDFATYYCQQLYSTPLTFGGGTKVEIK

TABLE 3

Antibody 57D12 Sequences

| | Exemplary | Chothia | AbM | Kabat | Contact |
|---|---|---|---|---|---|
| VHCDR1 | GYSFTSFGIS (SEQ ID NO: 46) | GYSFTSF (SEQ ID NO: 52) | GYSFTSFGIS (SEQ ID NO: 46) | SFGIS (SEQ ID NO: 55) | TSFGIS (SEQ ID NO: 56) |
| VHCDR2 | EIYPRSDNTFYNEKFKG (SEQ ID NO: 47) | YPRSDN (SEQ ID NO: 53) | EIYPRSDNTF (SEQ ID NO: 54) | EIYPRSDNTFYNEKFKG (SEQ ID NO: 47) | WIGEIYPRSDNTF (SEQ ID NO: 57) |
| VHCDR3 | HFGSSSFDY (SEQ ID NO: 48) | HFGSSSFDY (SEQ ID NO: 48) | HFGSSSFDY (SEQ ID NO: 48) | HFGSSSFDY (SEQ ID NO: 48) | ARHFGSSSFD (SEQ ID NO: 58) |
| VL CDR1 | SASSSVSSIYFH (SEQ ID NO: 49) | SASSSVSSIYFH (SEQ ID NO: 49) | SASSSVSSIYFH (SEQ ID NO: 49) | SASSSVSSIYFH (SEQ ID NO: 49) | SSIYFHWY (SEQ ID NO: 59) |

TABLE 3 -continued

Antibody 57D12 Sequences

| | Exemplary | Chothia | AbM | Kabat | Contact |
|---|---|---|---|---|---|
| VL CDR2 | RASNLAS (SEQ ID NO: 50) | RASNLAS (SEQ ID NO: 50) | RASNLAS (SEQ ID NO: 50) | RASNLAS (SEQ ID NO: 50) | PLIHRASNLA (SEQ ID NO: 60) |
| VL CDR3 | QQWSGYPLT (SEQ ID NO: 51) | QQWSGYPLT (SEQ ID NO: 51) | QQWSGYPLT (SEQ ID NO: 51) | QQWSGYPLT (SEQ ID NO: 51) | QQWSGYPL (SEQ ID NO: 61) |

57D12 Heavy chain variable region (SEQ ID NO: 121)
QVQLQQSGAELARPGASVNLSCRASGYSFTSFGISWVKQRTGQGLEWIGETYPRSDNTFY
NEKFKGKATLTADKSSSTAYMELRSLTSEDSAVYFCARHFGSSSFDYWGQGTTLTVSS 57D12 Light chain variable region (SEQ ID NO: 122)
ENVLTQSPPIMAASLGQKVTMTCSASSSVSSIYFHWYQQKSGTSPKPLIHRASNLASGVP
ARFSGSGSGTSYSLTISSVEAEDDATYYCQQWSGYPLTFGGGTKLEIK

TABLE 4

Antibody 61H4 Sequences

| | Exemplary | Chothia | AbM | Kabat | Contact |
|---|---|---|---|---|---|
| VH CDR1 | GYTFTDYYYMN (SEQ ID NO: 62) | GYTFTDYY (SEQ ID NO: 68) | GYTFTDYYYMN (SEQ ID NO: 62) | DYYYMN (SEQ ID NO: 71) | TDYYYMN (SEQ ID NO: 72) |
| VH CDR2 | YIYPNNGATSYNQKFKG (SEQ ID NO: 63) | YPNNGA (SEQ ID NO: 69) | YIYPNNGATS (SEQ ID NO: 70) | YIYPNNGATSYNQKFKG (SEQ ID NO: 63) | WIGYIYPNNGATS (SEQ ID NO: 73) |
| VH CDR3 | DGYSSNYYTMDY (SEQ ID NO: 64) | DGYSSNYYTMDY (SEQ ID NO: 64) | DGYSSNYYTMDY (SEQ ID NO: 64) | DGYSSNYYTMD (SEQ ID NO: 64) | ARDGYSSNYYTMD (SEQ ID NO: 74) |
| VL CDR1 | QASQGTSINLN (SEQ ID NO: 65) | QASQGTSINLN (SEQ ID NO: 65) | QASQGTSINLN (SEQ ID NO: 65) | QASQGTSINLN (SEQ ID NO: 65) | SINLNWF (SEQ ID NO: 75) |
| VL CDR2 | GASNLED (SEQ ID NO: 66) | GASNLED (SEQ ID NO: 66) | GASNLED (SEQ ID NO: 66) | GASNLED (SEQ ID NO: 66) | LLIYGASNLE (SEQ ID NO: 76) |
| VL CDR3 | LQHTYLPYT (SEQ ID NO: 67) | LQHTYLPYT (SEQ ID NO: 67) | LQHTYLPYT (SEQ ID NO: 67) | LQHTYLPYT (SEQ ID NO: 67) | LQHTYLPY (SEQ ID NO: 77) |

61H4 Heavy chain variable region (SEQ ID NO: 123)
EVQLQQSGPEVLKPGASVKISCKASGYTFTDYYYMNWVKQSHGKSLEWIGYIYPNNGATS
YNQKFKGKATLTVDKSSSTAYMELRSLTSEDSAVYYCARDGYSSNYYTMDYWGQGTSVTVSS 61H4 Light chain variable region (SEQ ID NO: 124)
DVQMIQSPSSLSASLGDIVTMTCQASQGTSINLNWFQQKPGKAPKWYGASNLEDGVPS
RFSGSRYGTDFTLTISSLEDEDMATYFCLQHTYLPYTFGGGTKLEIK

TABLE 5

Antibody 62G10 and Hz62G10.v1 Sequences

| | Exemplary | Chothia | AbM | Kabat | Contact |
|---|---|---|---|---|---|
| VH CDR1 | GFTFNINAMN (SEQ ID NO: 25) | GFTFNIN (SEQ ID NO: 31) | GFTFNINAMN (SEQ ID NO: 25) | INAMN (SEQ ID NO: 34) | NINAMN (SEQ ID NO: 35) |
| VH CDR2 | RIRTKNNNFATYYADSV (SEQ ID NO: 78) | RTKNNNFA (SEQ ID NO: 82) | RIRTKNNNFATY (SEQ ID NO: 83) | RIRTKNNNFATYYADSVK (SEQ ID NO: 78) | WVARIRTKNNNFATY (SEQ ID NO: 84) |
| VH CDR 3 | GPYFDY (SEQ ID NO: 79) | GPYFDY (SEQ ID NO: 79) | GPYFDY (SEQ ID NO: 79) | GPYFDY (SEQ ID NO: 79) | VRGPYFD (SEQ ID NO: 85) |
| VL CDR1 | LASQTIGTWLA (SEQ ID NO: 80) | LASQTIGTWLA (SEQ ID NO: 80) | LASQTIGTWLA (SEQ ID NO: 80) | LASQTIGTWLA (SEQ ID NO: 80) | GTWLAWY (SEQ ID NO: 86) |
| VL CDR2 | AATSLAD (SEQ ID NO: 29) | AATSLAD (SEQ ID NO: 29) | AATSLAD (SEQ ID NO: 29) | AATSLAD (SEQ ID NO: 29) | LLIYAATSLA (SEQ ID NO: 39) |

TABLE 5 -continued

Antibody 62G10 and Hz62G10.v1 Sequences

| | Exemplary | Chothia | AbM | Kabat | Contact |
|---|---|---|---|---|---|
| VL CDR3 | QQLYSTPYT (SEQ ID NO: 81) | QQLYSTPYT (SEQ ID NO: 81) | QQLYSTPYT (SEQ ID NO: 81) | QQLYSTPYT (SEQ ID NO: 81) | QQLYSTPY (SEQ ID NO: 87) |

62G10 Heavy chain variable region (SEQ ID NO: 125)
EVQLVETGGGLVQPKGSLKLSCATSGFTFNINAMNWVRQAPGKGLEWVARIRTKNNNFAT
YYADSVKDRFTISRDDSQSMLYLQMNNLKTEDTAMYYCVRGPYFDYWGQGTTLTVSS 62G10 Light chain variable region (SEQ ID NO: 126)
DIQMTQSPASQSASLGESVTITCLASQTIGTWLAWYQQKPGKSPQLLIYAATSLADGVPS
RFSGSGSGTKFSFKISNLQAEDFVTYYCQQLYSTPYTFGGGTKLEIK Hz62G10.v1 Heavy chain variable region (SEQ ID NO: 127)
EVQLVESGGGLVKPGGSLRLSCAASGFTFNINAMNWVRQAPGKGLEWVARIRTKNNNFAT
YYADSVKDRFTISRDDSKNTLYLQMNSLKTEDTAVYYCVRGPYFDYWGQGTLVTVSS Hz62G10.v1 Light chain variable region (SEQ ID NO: 128)
DIQMTQSPSSLSASVGDRVTITCLASQTIGTWLAWYQQKPGKAPKLLIYAATSLADGVPS
RFSGSGSGTDFTLTISSLQPEDFATYYCQQLYSTPYTFGGGTKVEIK

TABLE 6

Antibody 108D10 Sequences

| | Exemplary | Chothia | AbM | Kabat | Contact |
|---|---|---|---|---|---|
| VH CDR1 | GFTFNINAMN (SEQ ID NO: 25) | GFTFNIN (SEQ ID NO: 31) | GFTFNINAMN (SEQ ID NO: 25) | INAMN (SEQ ID NO: 34) | NINAMN (SEQ ID NO: 35) |
| VH CDR2 | RIRTKNNNYATYYADSVKD (SEQ ID NO: 88) | RTKNNNYA (SEQ ID NO: 32) | RIRTKNNNYATY (SEQ ID NO: 93) | RIRTKNNNYATYYADSVKD (SEQ ID NO: 88) | WVARIRTKNNNYATY (SEQ ID NO: 94) |
| VH CDR3 | DRYGGAMAY (SEQ ID NO: 89) | DRYGGAMAY (SEQ ID NO: 89) | DRYGGAMAY (SEQ ID NO: 89) | DRYGGAMAY (SEQ ID NO: 89) | VRDRYGGAMA (SEQ ID NO: 95) |
| VL CDR1 | KASEDIYNRLA (SEQ ID NO: 90) | KASEDIYNRLA (SEQ ID NO: 90) | KASEDIYNRLA (SEQ ID NO: 90) | KASEDIYNRLA (SEQ ID NO: 90) | YNRLAWY (SEQ ID NO: 96) |
| VL CDR2 | SATSLET (SEQ ID NO: 91) | SATSLET (SEQ ID NO: 91) | SATSLET (SEQ ID NO: 91) | SATSLET (SEQ ID NO: 91) | LLISSATSLE (SEQ ID NO: 97) |
| VL CDR3 | QQYWTIPYT (SEQ ID NO: 92) | QQYWTIPYT (SEQ ID NO: 92) | QQYWTIPYT (SEQ ID NO: 92) | QQYWTIPYT (SEQ ID NO: 92) | QQYWTIPY (SEQ ID NO: 98) |

108D10 Heavy chain variable region (SEQ ID NO: 129)
EVQLVETGGGLVQPKGSLKLSCAASGFTFNINAMNWVRQAPGKGLEWVARIRTKNNNYAT
YYADSVKDRFTISRDDSESMLYLQMNNLKTEDTAMYYCVRDRYGGAMAYWGQGTSVTVSS 108D10 Light chain variable region (SEQ ID NO: 130)
DIQMTQSSSSFSVSLGDRVTITCKASEDIYNRLAWYQQKPGNVPRLLISSATSLETGVPS
RFSGSGSGKDYTLSLTSLQSEDVATYYCQQYWTIPYTFGGGTKLEIK

TABLE 7

Antibody 43H2 Sequences

| | Exemplary | Chothia | AbM | Kabat | Contact |
|---|---|---|---|---|---|
| VH CDR1 | GFTFSNYGIH (SEQ ID NO: 99) | GFTFSNY (SEQ ID NO: 105) | GFTFSNYGIH (SEQ ID NO: 99) | NYGIH (SEQ ID NO: 108) | SNYGIH (SEQ ID NO: 109) |
| VH CDR2 | SISPSGRSTYFRDSVKG (SEQ ID NO: 100) | SPSGRS (SEQ ID NO: 106) | SISPSGRSTY (SEQ ID NO: 107) | SISPSGRSTYFRDSVKG (SEQ ID NO: 100) | WVASISPSGRSTY (SEQ ID NO: 110) |
| VH CDR3 | GINYSSFDY (SEQ ID NO: 101) | GINYSSFDY (SEQ ID NO: 101) | GINYSSFDY (SEQ ID NO: 101) | GINYSSFDY (SEQ ID NO: 101) | ATGINYSSFD (SEQ ID NO: 111) |

TABLE 7 -continued

Antibody 43H2 Sequences

|        | Exemplary                       | Chothia                         | AbM                             | Kabat                           | Contact                       |
|--------|---------------------------------|---------------------------------|---------------------------------|---------------------------------|-------------------------------|
| VL CDR1 | KASQNVGSHVD<br>(SEQ ID NO: 102) | KASQNVGSHVD<br>(SEQ ID NO: 102) | KASQNVGSHVD<br>(SEQ ID NO: 102) | KASQNVGSHVD<br>(SEQ ID NO: 102) | GSHVDWY<br>(SEQ ID NO: 112)   |
| VL CDR2 | TASNRYT<br>(SEQ ID NO: 103)     | TASNRYT<br>(SEQ ID NO: 103)     | TASNRYT<br>(SEQ ID NO: 103)     | TASNRYT<br>(SEQ ID NO: 103)     | LLISTASNRY<br>(SEQ ID NO: 113) |
| VL CDR3 | MQSNSYPPT<br>(SEQ ID NO: 104)   | MQSNSYPPT<br>(SEQ ID NO: 104)   | MQSNSYPPT<br>(SEQ ID NO: 104)   | MQSNSYPPT<br>(SEQ ID NO: 104)   | MQSNSYPP<br>(SEQ ID NO: 114)  |

43H2 Heavy chain variable region (SEQ ID NO: 131)
EVQLVESGGGLVQPGRSLKVSCAASGFTFSNYGIHWIRQAPTKGLEWVASISPSGRSTYF
RDSVKGRFTISRDNAKNTLYLQLDSLRSEDTATYYCATGINYSSFDYWGQGVMVTVSS 43H2 Light chain variable region (SEQ ID NO: 132)
DIVMTQSPTSMSISVGDRVTMNCKASQNVGSHVDWYQQKTGQSPKLLISTASNRYTGVPD
RFTGSGSGTDFTFTINNMQTEDLAVYYCMQSNSYPPTFGGGTKLELK In some embodiments, a LAIR-1-binding agent comprises a heavy chain variable region CDR1, CDR2, and CDR3 and/or a light chain variable region CDR1, CDR2, and CDR3 from an antibody described herein. In some embodiments, a LAIR-1-binding agent comprises a heavy chain variable region CDR1, CDR2, and CDR3 and a light chain variable region CDR1, CDR2, and CDR3 from an antibody described herein. In some embodiments, a LAIR-1-binding agent comprises: (a) a heavy chain variable region comprising a heavy chain variable region CDR1, CDR2, and CDR3; and (b) a light chain variable region comprising a light chain variable region CDR1, CDR2, and CDR3 from an antibody described herein.

In some embodiments, a LAIR-1-binding agent is a variant of a LAIR-1-binding agent described herein. In some embodiments, the LAIR-1-binding agent variant comprises amino acid substitutions in the heavy chain variable region and/or the light chain variable region as compared to a LAIR-1-binding agent described herein. In some embodiments, the LAIR-1-binding agent variant comprises amino acid substitutions in the heavy chain variable region CDR1, CDR2, and/or CDR3 and/or the light chain variable region CDR1, CDR2, and/or CDR3 as compared to a LAIR-1-binding agent described herein. In some embodiments, a LAIR-1-binding agent comprises one or more (e.g., 1, 2, 3, 4, etc.) amino acid substitutions in a CDR of an antibody described herein. In some embodiments, the amino acid substitutions are conservative substitutions. In some embodiments, a CDR comprises one amino acid substitution. In some embodiments, a CDR comprises two amino acid substitutions. In some embodiments, a CDR comprises three amino acid substitutions. In some embodiments, a CDR comprises four amino acid substitutions. In some embodiments, the CDR is a heavy chain variable region CDR1. In some embodiments, the CDR is a heavy chain variable region CDR2. In some embodiment, the CDR is a heavy chain variable region CDR3. In some embodiments, the CDR is a light chain variable region CDR1. In some embodiments, the CDR is a light chain variable region CDR2. In some embodiments, the CDR is a light chain variable region CDR3. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, a LAIR-1-binding agent comprises one or more heavy chain variable region CDRs or light chain variable region CDRs that have been modified to reduce deamidation within the CDR sequence. Deamidation is a chemical reaction in which an amide functional group in the side chain of the amino acids asparagine (Asn or N) or glutamine (Gln or Q) is removed or converted to another functional group. Generally, asparagine is converted to aspartic acid or isoaspartic acid and glutamine is converted to glutamic acid or polyglutamic acid. In some situations, deamidation may change the structure, function, and/or stability of a polypeptide, potentially resulting in decreased biological activity. In some embodiments, the heavy chain variable region CDR1, CDR2, and/or CDR3 of an antibody described herein is modified to reduce deamidation. In some embodiments, the light chain variable region CDR1, CDR2, and/or CDR3 of an antibody described herein is modified to reduce deamidation.

In some embodiments, a LAIR-1-binding agent comprises one or more heavy chain variable region CDRs or light chain variable region CDRs that have been modified to reduce isomerization. Isomerization is a chemical process by which a compound is transformed into any of its isomeric forms, i.e., forms with the same chemical composition but with different structure or configuration and, potentially with different physical and chemical properties. Studies have shown that aspartate (Asp or D) isomerization within a CDR can impact antibody binding and/or stability. In some embodiments, the heavy chain variable region CDR1, CDR2, and/or CDR3 of an antibody described herein is modified to reduce isomerization. In some embodiments, the light chain variable region CDR1, CDR2, and/or CDR3 is modified to reduce isomerization.

In some embodiments, a LAIR-1-binding agent comprises one or more heavy chain variable region CDRs or light chain variable region CDRs that have been modified to reduce oxidation. Oxidation is a chemical process by which an oxygen is added to an atom, for example, methionine is converted to methionine sulfoxide by addition of an oxygen to the sulfur atom. Oxidation of one or more amino acids can potentially affect the physical and chemical properties of a protein. Studies have shown that oxidation of methionine (Met or M) within a CDR has the potential to impact antibody binding and/or stability. In some embodiments, the heavy chain variable region CDR1, CDR2, and/or CDR3 of an antibody described herein is modified to reduce oxidation. In some embodiments, the light chain variable region CDR1, CDR2, and/or CDR3 of an antibody described herein is modified to reduce oxidation.

In some embodiments, a LAIR-1-binding agent comprises a heavy chain variable region and/or a light chain variable region that comprises a modification within the amino acid sequence wherein the modification eliminates a glycosylation site. In some embodiments, a LAIR-1-binding agent comprises one or more heavy chain variable region CDRs or light chain variable region CDRs that have been modified to eliminate a glycosylation site. The consensus glycosylation site for N-linked glycans is N-X-S/T, wherein X can be any amino acid except proline. Generally, a glycosylation site within a variable region and/or within a CDR will impact antibody structure, binding, and/or stability.

In some embodiments, a LAIR-1-binding agent comprises a heavy chain variable region CDR1, CDR2, and CDR3 and/or a light chain variable region CDR1, CDR2, and CDR3 from antibody 47A1, a humanized version thereof, or variants thereof. In some embodiments, a LAIR-1-binding agent comprises a heavy chain variable region comprising a heavy chain variable region CDR1, a heavy chain variable region CDR2, and a heavy chain variable region CDR3 from antibody 47A1. In other embodiments, a LAIR-1-binding agent comprises a light chain variable region comprising a light chain variable region CDR1, a light chain variable region CDR2, and a light chain variable region CDR3 from antibody 47A1. In some embodiments, a LAIR-1-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 47A1.

In some embodiments, a LAIR-1-binding agent comprises: (a) a heavy chain variable region CDR1 comprising the amino acid sequence GFTFNTYAIH (SEQ ID NO:9), a heavy chain variable region CDR2 comprising the amino acid sequence RIRSKSTNYATYYADSVKD (SEQ ID NO:10), a heavy chain variable region CDR3 comprising the amino acid sequence ENWYYYALDY (SEQ ID NO:11), a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14); (b) a heavy chain variable region CDR1 comprising the amino acid sequence GFTFNTY (SEQ ID NO:15), a heavy chain variable region CDR2 comprising the amino acid sequence RSKSTNYA (SEQ ID NO:16), a heavy chain variable region CDR3 comprising the amino acid sequence ENWYYYALDY (SEQ ID NO:11), a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14); (c) a heavy chain variable region CDR1 comprising the amino acid sequence GFTFNTYAIH (SEQ ID NO:9), a heavy chain variable region CDR2 comprising the amino acid sequence RIRSKSTNYATY (SEQ ID NO:17), a heavy chain variable region CDR3 comprising the amino acid sequence ENWYYYALDY (SEQ ID NO:11), a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14); (d) a heavy chain variable region CDR1 comprising the amino acid sequence TYAIH (SEQ ID NO:18), a heavy chain variable region CDR2 comprising the amino acid sequence RIRSKSTNYATYYADSVKD (SEQ ID NO:10), a heavy chain variable region CDR3 comprising the amino acid sequence ENWYYYALDY (SEQ ID NO:11), a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14); or (e) a heavy chain variable region CDR1 comprising the amino acid sequence NTYAIH (SEQ ID NO:19), a heavy chain variable region CDR2 comprising the amino acid sequence WVARIRSKSTNYATY (SEQ ID NO:20), a heavy chain variable region CDR3 comprising the amino acid sequence VRENWYYYALD (SEQ ID NO:21), a light chain variable region CDR1 comprising the amino acid sequence HNYLTWY (SEQ ID NO:22), a light chain variable region CDR2 comprising the amino acid sequence VLVYNAKTLE (SEQ ID NO:23), and a light chain variable region CDR3 comprising the amino acid sequence QHFWSTPF (SEQ ID NO:24).

In some embodiments, a LAIR-1-binding agent comprises: (a) a heavy chain variable region comprising a heavy chain variable region CDR1 comprising the amino acid sequence GFTFNTYAIH (SEQ ID NO:9), a heavy chain variable region CDR2 comprising the amino acid sequence RIRSKSTNYATYYADSVKD (SEQ ID NO:10), and a heavy chain variable region CDR3 comprising the amino acid sequence ENWYYYALDY (SEQ ID NO:11), and a light chain variable region comprising a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14); (b) a heavy chain variable region comprising a heavy chain variable region CDR1 comprising the amino acid sequence GFTFNTY (SEQ ID NO:15), a heavy chain variable region CDR2 comprising the amino acid sequence RSKSTNYA (SEQ ID NO:16), and a heavy chain variable region CDR3 comprising the amino acid sequence ENWYYYALDY (SEQ ID NO:11), and a light chain variable region comprising a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14); (c) a heavy chain variable region comprising a heavy chain variable region CDR1 comprising the amino acid sequence GFTFNTYAIH (SEQ ID NO:9), a heavy chain variable region CDR2 comprising the amino acid sequence RIRSKSTNYATY (SEQ ID NO:17), and a heavy chain variable region CDR3 comprising the amino acid sequence ENWYYYALDY (SEQ ID NO:11), and a light chain variable region comprising a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFW-STPFT (SEQ ID NO:14); (d) a heavy chain variable region comprising a heavy chain variable region CDR1 comprising the amino acid sequence TYAIH (SEQ ID NO:18), a heavy chain variable region CDR2 comprising the amino acid sequence RIRSKSTNYATYYADSVKD (SEQ ID NO:10), and a heavy chain variable region CDR3 comprising the amino acid sequence ENWYYYALDY (SEQ ID NO:11), and a light chain variable region comprising a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFW-STPFT (SEQ ID NO:14); or (e) a heavy chain variable region comprising a heavy chain variable region CDR1 comprising the amino acid sequence NTYAIH (SEQ ID NO:19), a heavy chain variable region CDR2 comprising the amino acid sequence WVARIRSKSTNYATY (SEQ ID NO:20), and a heavy chain variable region CDR3 comprising the amino acid sequence VRENWYYYALD (SEQ ID NO:21), and a light chain variable region comprising a light chain variable region CDR1 comprising the amino acid sequence HNYLTWY (SEQ ID NO:22), a light chain variable region CDR2 comprising the amino acid sequence VLVYNAKTLE (SEQ ID NO:23), and a light chain variable region CDR3 comprising the amino acid sequence QHFW-STPF (SEQ ID NO:24).

In some embodiments, a LAIR-1-binding agent comprises: (a) a heavy chain variable region comprising a heavy chain variable region CDR1 comprising the amino acid sequence GFTFNTYAIH (SEQ ID NO:9), a heavy chain variable region CDR2 comprising the amino acid sequence RIRSKSTNYATYYADSVKD (SEQ ID NO:10), and a heavy chain variable region CDR3 comprising the amino acid sequence ENWYYYALDY (SEQ ID NO:11), and/or (b) a light chain variable region comprising a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFW-STPFT (SEQ ID NO:14). In some embodiments, a LAIR-1-binding agent comprises a heavy chain variable region comprising a heavy chain variable region CDR1 comprising the amino acid sequence GFTFNTYAIH (SEQ ID NO:9), a heavy chain variable region CDR2 comprising the amino acid sequence RIRSKSTNYATYYADSVKD (SEQ ID NO:10), and a heavy chain variable region CDR3 comprising the amino acid sequence ENWYYYALDY (SEQ ID NO:11). In some embodiments, a LAIR-1-binding agent comprises a light chain variable region comprising a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFW-STPFT (SEQ ID NO:14). In some embodiments, a LAIR-1-binding agent comprises (a) a heavy chain variable region comprising a heavy chain variable region CDR1 comprising the amino acid sequence GFTFNTYAIH (SEQ ID NO:9), a heavy chain variable region CDR2 comprising the amino acid sequence RIRSKSTNYATYYADSVKD (SEQ ID NO:10), and a heavy chain variable region CDR3 comprising the amino acid sequence ENWYYYALDY (SEQ ID NO:11), and (b) a light chain variable region comprising a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFW-STPFT (SEQ ID NO:14).

In some embodiments, a LAIR-1-binding agent comprises a heavy chain variable region having at least 80%, at least 85%, at least 90%, at least 95%, at least 96%, at least 97%, at least 98%, or at least 99% identity to the amino acid sequence of SEQ ID NO:115. In some embodiments, a LAIR-1-binding agent comprises a heavy chain variable region comprising an amino acid sequence of SEQ ID NO:115. In some embodiments, a LAIR-1-binding agent comprises a light chain variable region having at least 80%, at least 85%, at least 90%, at least 95%, at least 96%, at least 97%, at least 98%, or at least 99% identity to the amino acid sequence of SEQ ID NO:116. In some embodiments, a LAIR-1-binding agent comprises a light chain variable region comprising an amino acid sequence of SEQ ID NO:116.

In some embodiments, a LAIR-1-binding agent comprises a heavy chain variable region having at least 80% sequence identity to the amino acid sequence of SEQ ID NO:115 and a light chain variable region having at least 80% sequence identity to the amino acid sequence of SEQ ID NO:116. In some embodiments, a LAIR-1-binding agent comprises a heavy chain variable region having at least 90% sequence identity to the amino acid sequence of SEQ ID NO:115 and a light chain variable region having at least 90% sequence identity to the amino acid sequence of SEQ ID NO:116. In some embodiments, a LAIR-1-binding agent comprises a heavy chain variable region having at least 95% sequence identity to the amino acid sequence of SEQ ID NO:115 and a light chain variable region having at least 95% sequence identity to the amino acid sequence of SEQ ID NO:116. In some embodiments, a LAIR-1-binding agent comprises a heavy chain variable region comprising an amino acid sequence of SEQ ID NO:115 and a light chain variable region comprising an amino acid sequence of SEQ ID NO:116.

In some embodiments, the LAIR-1-binding agent is antibody 47A1. In some embodiments, the LAIR-1-binding agent is a humanized version of antibody 47A1. In some embodiments, the LAIR-1-binding agent is a variant of antibody 47A1 or a variant of a humanized version of 47A1.

In some embodiments, a LAIR-1-binding agent comprises a heavy chain variable region CDR1, CDR2, and CDR3 and/or a light chain variable region CDR1, CDR2, and CDR3 from antibody 47H1, a humanized version thereof, or variants thereof. In some embodiments, a LAIR-1-binding agent comprises a heavy chain variable region comprising a heavy chain variable region CDR1, a heavy chain variable region CDR2, and a heavy chain variable region CDR3 from antibody 47H1. In other embodiments, a LAIR-1-binding agent comprises a light chain variable region comprising a light chain variable region CDR1, a light chain variable region CDR2, and a light chain variable region CDR3 from antibody 47H1. In some embodiments, a LAIR-1-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 47H1. In some embodiments, a LAIR-1-binding agent comprises a heavy chain variable region comprising a heavy chain variable region CDR1, a heavy chain variable region CDR2, and a heavy chain variable region CDR3 from antibody Hz47H1.v4. In other embodiments, a LAIR-1-binding agent comprises a light chain variable region comprising a light chain variable region CDR1, a light chain variable region CDR2, and a light chain variable region CDR3 from antibody Hz47H1.v4. In some embodiments, a LAIR-1-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody Hz47H1.v4.

In some embodiments, a LAIR-1-binding agent comprises: (a) a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26) or RIRTKNYNYATFYADSVKD (SEQ ID NO:41), a heavy chain variable region CDR3 comprising the amino acid sequence DRAGFFAY (SEQ ID NO:27), a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30); (b) a heavy chain variable region CDR1 comprising the amino acid sequence GFTFNIN (SEQ ID NO:31), a heavy chain variable region CDR2 comprising the amino acid sequence RTKNNNYA (SEQ ID NO:32) or RTKNYNYA (SEQ ID NO:43), a heavy chain variable region CDR3 comprising the amino acid sequence DRAGFFAY (SEQ ID NO:27), a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30); (c) a heavy chain variable region CDR1 comprising the amino acid sequence GFTFNINAMN (SEQ ID NO:25), a heavy chain variable region CDR2 comprising the amino acid sequence RIRTKNNNYATF (SEQ ID NO:33) or RIRTKNYNYATF (SEQ ID NO:44), a heavy chain variable region CDR3 comprising the amino acid sequence DRAGFFAY (SEQ ID NO:27), a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30); (d) a heavy chain variable region CDR1 comprising the amino acid sequence INAMN (SEQ ID NO:34), a heavy chain variable region CDR2 comprising the amino acid sequence RIRTKNNNYATFYADSVKD (SEQ ID NO:26) or RIRTKNYNYATFYADSVKD (SEQ ID NO:41), a heavy chain variable region CDR3 comprising the amino acid sequence DRAGFFAY (SEQ ID NO:27), a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30); or (e) a heavy chain variable region CDR1 comprising the amino acid sequence NINAMN (SEQ ID NO:35), a heavy chain variable region CDR2 comprising the amino acid sequence WVARIRTKNNNYATF (SEQ ID NO:36) or WVARIRTKNYNYATF (SEQ ID NO:45), a heavy chain variable region CDR3 comprising the amino acid sequence VRDRAGFFA (SEQ ID NO:37), a light chain variable region CDR1 comprising the amino acid sequence GTWLGWY (SEQ ID NO:38), a light chain variable region CDR2 comprising the amino acid sequence LLIYAATSLA (SEQ ID NO:39), and a light chain variable region CDR3 comprising the amino acid sequence QQLYSTPL (SEQ ID NO:40).

In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26) or RIRTKNYNYATFYADSVKD (SEQ ID NO:41), and a heavy chain variable region CDR3 comprising the amino acid sequence DRAGFFAY (SEQ ID NO:27), and a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30); (b) a heavy chain variable region comprising a heavy chain variable region CDR1 comprising the amino acid sequence GFTFNIN (SEQ ID NO:31), a heavy chain variable region CDR2 comprising the amino acid sequence RTKNNNYA (SEQ ID NO:32) or RTKNYNYA (SEQ ID NO:43), and a heavy chain variable region CDR3 comprising the amino acid sequence DRAGFFAY (SEQ ID NO:27), and a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30); (c) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATF (SEQ ID NO:33) or RIRTKNYNYATF (SEQ ID NO:44), and a heavy chain variable region CDR3 comprising the amino acid sequence DRAGFFAY (SEQ ID NO:27), and a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30); (d) a heavy chain variable region comprising a heavy chain variable region CDR1 comprising the amino acid sequence INAMN (SEQ ID NO:34), a heavy chain variable region CDR2 comprising the amino acid sequence RIRTKNNNYATFYADSVKD (SEQ ID NO:26) or RIRTKNYNYATFYADSVKD (SEQ ID NO:41), and a heavy chain variable region CDR3 comprising the amino acid sequence DRAGFFAY (SEQ ID NO:27), and a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30); or (e) a heavy chain variable region comprising a heavy chain variable region CDR1 comprising the amino acid sequence NINAMN (SEQ ID NO:35), a heavy chain variable region CDR2 comprising the amino acid sequence WVARIRTKNNNYATF (SEQ ID NO:36) or WVARIRTKNYNYATF (SEQ ID NO:45), and a heavy chain variable region CDR3 comprising the amino acid sequence VRDRAGFFA (SEQ ID NO:37), and a light chain variable region comprising a light chain variable region CDR1 comprising the amino acid sequence GTWLGWY (SEQ ID NO:38), a light chain variable region CDR2 comprising the amino acid sequence LLIYAATSLA (SEQ ID NO:39), and a light chain variable region CDR3 comprising the amino acid sequence QQLYSTPL (SEQ ID NO:40).

In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26) or RIRTKNYNYATFYADSVKD (SEQ ID NO:41), and a heavy chain variable region CDR3 comprising the amino acid sequence DRAGFFAY (SEQ ID NO:27), and/or (b) a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30). In some embodiments, the LAIR-1-binding agent comprises a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26), and a heavy chain variable region CDR3 comprising the amino acid sequence DRAGFFAY (SEQ ID NO:27). In some embodiments, the LAIR-1-binding agent comprises a heavy chain variable region comprising a heavy chain variable region CDR1 comprising the amino acid sequence GFTFNINAMN (SEQ ID NO:25), a heavy chain variable region CDR2 comprising the amino acid sequence RIRTKNYNYATFYADSVKD (SEQ ID NO:41), and a heavy chain variable region CDR3 comprising the amino acid sequence DRAGFFAY (SEQ ID NO:27). In some embodiments, the LAIR-1-binding agent comprises a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29), and a light chain variable region CDR3 comprising the amino acid sequence QQLYSTPLT (SEQ ID NO:30). In some embodiments, the LAIR-1-binding agent comprises a light chain variable region comprising a light chain variable region CDR1 comprising the amino acid sequence LASQTIGTWLG (SEQ ID NO:28), a light chain variable region CDR2 comprising the amino acid sequence AATSLAE (SEQ ID NO:42), and a light chain variable region CDR3 comprising the amino acid sequence QQLYSTPLT (SEQ ID NO:30). In some embodiments, the LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26), and a heavy chain variable region CDR3 comprising the amino acid sequence DRAGFFAY (SEQ ID NO:27), and (b) a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29), and a light chain variable region CDR3 comprising the amino acid sequence QQLYSTPLT (SEQ ID NO:30). In some embodiments, the LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNYNYATFYADSVKD (SEQ ID NO:41), and a heavy chain variable region CDR3 comprising the amino acid sequence DRAGFFAY (SEQ ID NO:27), and (b) a light chain variable region comprising a light chain variable region CDR1 comprising the amino acid sequence LASQTIGTWLG (SEQ ID NO:28), a light chain variable region CDR2 comprising the amino acid sequence AATSLAE (SEQ ID NO:42), and a light chain variable region CDR3 comprising the amino acid sequence QQLYSTPLT (SEQ ID NO:30).

In some embodiments, a LAIR-1-binding agent comprises: (a) a heavy chain variable region CDR1 comprising the amino acid sequence GFTFNINAMN (SEQ ID NO:25), or a variant thereof comprising 1, 2, 3, or 4 amino acid substitutions, a heavy chain variable region CDR2 comprising the amino acid sequence RIRTKNNNYATFYADSVKD (SEQ ID NO:26), RIRTKNYNYATFYADSVKD (SEQ ID NO:41), or a variant thereof comprising 1, 2, 3, or 4 amino acid substitutions, and a heavy chain variable region CDR3 comprising the amino acid sequence DRAGFFAY (SEQ ID NO:27), or a variant thereof comprising 1, 2, 3, or 4 amino acid substitutions; and (b) a light chain variable region CDR1 comprising the amino acid sequence LASQTIGTWLG (SEQ ID NO:28), or a variant thereof comprising 1, 2, 3, or 4 amino acid substitutions, a light chain variable region CDR2 comprising the amino acid sequence AATSLAD (SEQ ID NO:29), AATSLAE (SEQ ID NO:42), or a variant thereof comprising 1, 2, 3, or 4 amino acid substitutions, and a light chain variable region CDR3 comprising the amino acid sequence QQLYSTPLT (SEQ ID NO:30), or a variant thereof comprising 1, 2, 3, or 4 amino acid substitutions.

In some embodiments, a LAIR-1-binding agent comprises one or more heavy chain variable region CDRs or light chain variable region CDRs that have been modified to reduce deamidation within the CDR sequence. In some embodiments, the heavy chain variable region CDR2 of antibody 47H1 or Hz47H1 is modified to reduce deamidation.

In some embodiments, a LAIR-1-binding agent comprises one or more heavy chain variable region CDRs or light chain variable region CDRs that have been modified to reduce isomerization. In some embodiments, the light chain variable region CDR2 of antibody 47H1 or Hz47H1 is modified to reduce isomerization.

In some embodiments, a LAIR-1-binding agent comprises a heavy chain variable region having at least 80%, at least 85%, at least 90%, at least 95%, at least 96%, at least 97%, at least 98%, or at least 99% identity to the amino acid sequence of SEQ ID NO:117. In some embodiments, a LAIR-1-binding agent comprises a light chain variable region having at least 80%, at least 85%, at least 90%, at least 95%, at least 96%, at least 97%, at least 98%, or at least 99% identity to the amino acid sequence of SEQ ID NO:118.

In some embodiments, a LAIR-1-binding agent comprises a heavy chain variable region having at least 80%, at least 85%, at least 90%, at least 95%, at least 96%, at least 97%, at least 98%, or at least 99% identity to the amino acid sequence of SEQ ID NO:119. In some embodiments, a LAIR-1-binding agent comprises a light chain variable region having at least 80%, at least 85%, at least 90%, at least 95%, at least 96%, at least 97%, at least 98%, or at least 99% identity to the amino acid sequence of SEQ ID NO:120.

In some embodiments, a LAIR-1-binding agent comprises a heavy chain variable region comprising an amino acid sequence of SEQ ID NO:117. In some embodiments, a LAIR-1-binding agent comprises a light chain variable region comprising an amino acid sequence of SEQ ID NO:118. In some embodiments, a LAIR-1-binding agent comprises a heavy chain variable region comprising an amino acid sequence of SEQ ID NO:119. In some embodiments, a LAIR-1-binding agent comprises a light chain variable region comprising an amino acid sequence of SEQ ID NO:120.

In some embodiments, a LAIR-1-binding agent comprises a heavy chain variable region having at least 80% sequence identity to the amino acid sequence of SEQ ID NO:117 and a light chain variable region having at least 80% sequence identity to the amino acid sequence of SEQ ID NO:118. In some embodiments, a LAIR-1-binding agent comprises a heavy chain variable region having at least 90% sequence identity to the amino acid sequence of SEQ ID NO:117 and a light chain variable region having at least 90% sequence identity to the amino acid sequence of SEQ ID NO:118. In some embodiments, a LAIR-1-binding agent comprises a heavy chain variable region having at least 95% sequence identity to the amino acid sequence of SEQ ID NO:117 and a light chain variable region having at least 95% sequence identity to the amino acid sequence of SEQ ID NO:118. In some embodiments, a LAIR-1-binding agent comprises a heavy chain variable region comprising an amino acid sequence of the amino acid sequence of SEQ ID NO:117 and a light chain variable region comprising an amino acid sequence of the amino acid sequence of SEQ ID NO:118.

In some embodiments, a LAIR-1-binding agent comprises a heavy chain variable region having at least 80% sequence identity to the amino acid sequence of SEQ ID NO:119 and a light chain variable region having at least 80% sequence identity to the amino acid sequence of SEQ ID NO:120. In some embodiments, a LAIR-1-binding agent comprises a heavy chain variable region having at least 90% sequence identity to the amino acid sequence of SEQ ID NO:119 and a light chain variable region having at least 90% sequence identity to the amino acid sequence of SEQ ID NO:120. In some embodiments, a LAIR-1-binding agent comprises a heavy chain variable region having at least 95% sequence identity to the amino acid sequence of SEQ ID NO:119 and a light chain variable region having at least 95% sequence identity to the amino acid sequence of SEQ ID NO:120. In some embodiments, a LAIR-1-binding agent comprises a heavy chain variable region comprising the amino acid sequence of SEQ ID NO:119 and a light chain variable region comprising the amino acid sequence of SEQ ID NO:120.

In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26), and a heavy chain variable region CDR3 comprising the amino acid sequence DRAGFFAY (SEQ ID NO:27), and (b) a light chain variable region comprising at least 80%, at least 85%, at least 90%, at least 95%, at least 96%, at least 97%, or at least 98% sequence identity to the amino acid sequence of SEQ ID NO:118. In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26), and a heavy chain variable region CDR3 comprising the amino acid sequence DRAGFFAY (SEQ ID NO:27), wherein the heavy chain variable region comprises at least 80%, at least 85%, at least 90%, at least 95%, at least 96%, at least 97%, or at least 98% sequence identity to the amino acid sequence of SEQ ID NO:117, and (b) a light chain variable region comprising at least 80%, at least 85%, at least 90%, at least 95%, at least 96%, at least 97%, or at least 98% sequence identity to the amino acid sequence of SEQ ID NO:118. In some embodiments, a LAIR-1-binding agent comprises: (a) a heavy chain variable region comprising at least 80%, at least 85%, at least 90%, at least 95%, at least 96%, at least 97%, or at least 98% sequence identity to the amino acid sequence of SEQ ID NO:117, and (b) a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29), and a light chain variable region CDR3 comprising the amino acid sequence QQLYSTPLT (SEQ ID NO:30). In some embodiments, a LAIR-1-binding agent comprises: (a) a heavy chain variable region comprising at least 80%, at least 85%, at least 90%, at least 95%, at least 96%, at least 97%, or at least 98% sequence identity to the amino acid sequence of SEQ ID NO:117, and (b) a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29), and a light chain variable region CDR3 comprising the amino acid sequence QQLYSTPLT (SEQ ID NO:30), wherein the light chain variable region comprises at least 80%, at least 85%, at least 90%, at least 95%, at least 96%, at least 97%, or at least 98% sequence identity to the amino acid sequence of SEQ ID NO: 118.

In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNYNYATFYADSVKD (SEQ ID NO:41), and a heavy chain variable region CDR3 comprising the amino acid sequence DRAGFFAY (SEQ ID NO:27), and (b) a light chain variable region comprising at least 80%, at least 85%, at least 90%, at least 95%, at least 96%, at least 97%, or at least 98% sequence identity to the amino acid sequence of SEQ ID NO:120. In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNYNYATFYADSVKD (SEQ ID NO:41), and a heavy chain variable region CDR3 comprising the amino acid sequence DRAGFFAY (SEQ ID NO:27), wherein the heavy chain variable region comprises at least 80%, at least 85%, at least 90%, at least 95%, at least 96%, at least 97%, or at least 98% sequence identity to the amino acid sequence of SEQ ID NO:119, and (b) a light chain variable region comprising at least 80%, at least 85%, at least 90%, at least 95%, at least 96%, at least 97%, or at least 98% sequence identity to the amino acid sequence of SEQ ID NO:120. In some embodiments, a LAIR-1-binding agent comprises: (a) a heavy chain variable region comprising at least 80%, at least 85%, at least 90%, at least 95%, at least 96%, at least 97%, or at least 98% sequence identity to the amino acid sequence of SEQ ID NO:119, and (b) a light chain variable region comprising a light chain variable region CDR1 comprising the amino acid sequence LASQTIGTWLG (SEQ ID NO:28), a light chain variable region CDR2 comprising the amino acid sequence AATSLAE (SEQ ID NO:42), and a light chain variable region CDR3 comprising the amino acid sequence QQLYSTPLT (SEQ ID NO:30). In some embodiments, a LAIR-1-binding agent comprises: (a) a heavy chain variable region comprising at least 80%, at least 85%, at least 90%, at least 95%, at least 96%, at least 97%, or at least 98% sequence identity to the amino acid sequence of SEQ ID NO:119, and (b) a light chain variable region comprising a light chain variable region CDR1 comprising the amino acid sequence LASQTIGTWLG (SEQ ID NO:28), a light chain variable region CDR2 comprising the amino acid sequence AATSLAE (SEQ ID NO:42), and a light chain variable region CDR3 comprising the amino acid sequence QQLYSTPLT (SEQ ID NO:30), wherein the light chain variable region comprises at least 80%, at least 85%, at least 90%, at least 95%, at least 96%, at least 97%, or at least 98% sequence identity to the amino acid sequence of SEQ ID NO:120.

In some embodiments, a LAIR-1-binding agent comprises: (a) a heavy chain comprising a heavy chain variable region CDR1 comprising the amino acid sequence GFTFNINAMN (SEQ ID NO:25), a heavy chain variable region CDR2 comprising the amino acid sequence RIRTKNYNYATFYADSVKD (SEQ ID NO:41), and a heavy chain variable region CDR3 comprising the amino acid sequence DRAGFFAY (SEQ ID NO:27), and (b) a light chain comprising a light chain variable region CDR1 comprising the amino acid sequence LASQTIGTWLG (SEQ ID NO:28), a light chain variable region CDR2 comprising the amino acid sequence AATSLAE (SEQ ID NO:42), and a light chain variable region CDR3 comprising the amino acid sequence QQLYSTPLT (SEQ ID NO:30), wherein the heavy chain comprises at least 80%, at least 85%, at least 90%, at least 95%, at least 96%, at least 97%, at least 98%, at least 99%, or 100% sequence identity to the amino acid sequence of SEQ ID NO:134, and wherein the light chain comprises at least 80%, at least 85%, at least 90%, at least 95%, at least 96%, at least 97%, at least 98%, at least 99%, or 100% sequence identity to the amino acid sequence of SEQ ID NO:136. In some embodiments, a LAIR-1-binding agent comprises: (a) a heavy chain comprising a heavy chain variable region CDR1 comprising the amino acid sequence GFTFNINAMN (SEQ ID NO:25), a heavy chain variable region CDR2 comprising the amino acid sequence RIRTKNYNYATFYADSVKD (SEQ ID NO:41), and a heavy chain variable region CDR3 comprising the amino acid sequence DRAGFFAY (SEQ ID NO:27), and (b) a light chain comprising a light chain variable region CDR1 comprising the amino acid sequence LASQTIGTWLG (SEQ ID NO:28), a light chain variable region CDR2 comprising the amino acid sequence AATSLAE (SEQ ID NO:42), and a light chain variable region CDR3 comprising the amino acid sequence QQLYSTPLT (SEQ ID NO:30), wherein the heavy chain comprises at least 95% sequence identity to the amino acid sequence of SEQ ID NO:134, and wherein the light chain comprises at least 95% sequence identity to the amino acid sequence of SEQ ID NO:136. In some embodiments, a LAIR-1-binding agent comprises: (a) a heavy chain comprising the amino acid sequence of SEQ ID NO:134 and (b) a light chain comprising a light chain variable region CDR1 comprising the amino acid sequence LASQTIGTWLG (SEQ ID NO:28), a light chain variable region CDR2 comprising the amino acid sequence AATSLAE (SEQ ID NO:42), and a light chain variable region CDR3 comprising the amino acid sequence QQLYSTPLT (SEQ ID NO:30), wherein the light chain comprises at least 80%, at least 85%, at least 90%, at least 95%, at least 96%, at least 97%, at least 98%, at least 99%, or at least 100% sequence identity to the amino acid sequence of SEQ ID NO:136. In some embodiments, a LAIR-1-binding agent comprises: (a) a heavy chain comprising a heavy chain variable region CDR1 comprising the amino acid sequence GFTFNINAMN (SEQ ID NO:25), a heavy chain variable region CDR2 comprising the amino acid sequence RIRTKNYNYATFYADSVKD (SEQ ID NO:41), and a heavy chain variable region CDR3 comprising the amino acid sequence DRAGFFAY (SEQ ID NO:27), wherein the heavy chain comprises at least 80%, at least 85%, at least 90%, at least 95%, at least 96%, at least 97%, at least 98%, at least 99%, or at least 100% sequence identity to the amino acid sequence of SEQ ID NO:134, and (b) a light chain comprising the amino acid sequence of SEQ ID NO:136. In some embodiments, a LAIR-1-binding agent is an antibody comprising a heavy chain comprising the amino acid sequence of SEQ ID NO:134 and a light chain comprising the amino acid sequence of SEQ ID NO:136.

In some embodiments, the LAIR-1-binding agent is antibody 47H1. In some embodiments, the LAIR-1-binding agent is a humanized version of antibody 47H1 (e.g., Hz47H1.v4). In some embodiments, the LAIR-1-binding agent is a variant of antibody 47H1 or a variant of a humanized version of 47H1. In some embodiments, the LAIR-1-binding agent is antibody Hz47H1.v4.

In some embodiments, a LAIR-1-binding agent comprises a heavy chain variable region CDR1, CDR2, and CDR3 and/or a light chain variable region CDR1, CDR2, and CDR3 from antibody 57D12, a humanized version thereof, or variants thereof. In some embodiments, a LAIR-1-binding agent comprises a heavy chain variable region comprising a heavy chain variable region CDR1, a heavy chain variable region CDR2, and a heavy chain variable region CDR3 from antibody 57D12. In other embodiments, a LAIR-1-binding agent comprises a light chain variable region comprising a light chain variable region CDR1, a light chain variable region CDR2, and a light chain variable region CDR3 from antibody 57D12. In some embodiments, a LAIR-1-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 57D12.

In some embodiments, a LAIR-1-binding agent comprises: (a) a heavy chain variable region CDR1 comprising the amino acid sequence GYSFTSFGIS (SEQ ID NO:46), a heavy chain variable region CDR2 comprising the amino acid sequence EIYPRSDNTFYNEKFKG (SEQ ID NO:47), a heavy chain variable region CDR3 comprising the amino acid sequence HFGSSSFDY (SEQ ID NO:48), a light chain variable region CDR1 comprising the amino acid sequence SASSSVSSIYFH (SEQ ID NO:49), a light chain variable region CDR2 comprising the amino acid sequence RASN- LAS (SEQ ID NO:50), and a light chain variable region CDR3 comprising the amino acid sequence QQWSGYPLT (SEQ ID NO:51); (b) a heavy chain variable region CDR1 comprising the amino acid sequence GYSFTSF (SEQ ID NO:52), a heavy chain variable region CDR2 comprising the amino acid sequence YPRSDN (SEQ ID NO:53), a heavy chain variable region CDR3 comprising the amino acid sequence HFGSSSFDY (SEQ ID NO:48), a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51); (c) a heavy chain variable region CDR1 comprising the amino acid sequence GYSFTSFGIS (SEQ ID NO:46), a heavy chain variable region CDR2 comprising the amino acid sequence EIYPRSDNTF (SEQ ID NO:54), a heavy chain variable region CDR3 comprising the amino acid sequence HFGSSSFDY (SEQ ID NO:48), a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51); (d) a heavy chain variable region CDR1 comprising the amino acid sequence SFGIS (SEQ ID NO:55), a heavy chain variable region CDR2 comprising the amino acid sequence EIYPRSDNTFYNEKFKG (SEQ ID NO:47), a heavy chain variable region CDR3 comprising the amino acid sequence HFGSSSFDY (SEQ ID NO:48), a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51); or (e) a heavy chain variable region CDR1 comprising the amino acid sequence TSFGIS (SEQ ID NO:56), a heavy chain variable region CDR2 comprising the amino acid sequence WIGEIYPRSDNTF (SEQ ID NO:57), a heavy chain variable region CDR3 comprising the amino acid sequence ARHFGSSSFD (SEQ ID NO:58), a light chain variable region CDR1 comprising the amino acid sequence SSIYFHWY (SEQ ID NO:59), a light chain variable region CDR2 comprising the amino acid sequence PLIHRASNLA (SEQ ID NO:60), and a light chain variable region CDR3 comprising the amino acid sequence QQWSGYPL (SEQ ID NO:61).

In some embodiments, a LAIR-1-binding agent comprises: (a) a heavy chain variable region comprising a heavy chain variable region CDR1 comprising the amino acid sequence GYSFTSFGIS (SEQ ID NO:46), a heavy chain variable region CDR2 comprising the amino acid sequence EIYPRSDNTFYNEKFKG (SEQ ID NO:47), and a heavy chain variable region CDR3 comprising the amino acid sequence HFGSSSFDY (SEQ ID NO:48), and a light chain variable region comprising a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51); (b) a heavy chain variable region comprising a heavy chain variable region CDR1 comprising the amino acid sequence GYSFTSF (SEQ ID NO:52), a heavy chain variable region CDR2 comprising the amino acid sequence YPRSDN (SEQ ID NO:53), and a heavy chain variable region CDR3 comprising the amino acid sequence HFGSSSFDY (SEQ ID NO:48), and a light chain variable region comprising a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51); (c) a heavy chain variable region comprising a heavy chain variable region CDR1 comprising the amino acid sequence GYSFTSFGIS (SEQ ID NO:46), a heavy chain variable region CDR2 comprising the amino acid sequence EIYPRSDNTF (SEQ ID NO:54), and a heavy chain variable region CDR3 comprising the amino acid sequence HFGSSSFDY (SEQ ID NO:48), and a light chain variable region comprising a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51); (d) a heavy chain variable region comprising a heavy chain variable region CDR1 comprising the amino acid sequence SFGIS (SEQ ID NO:55), a heavy chain variable region CDR2 comprising the amino acid sequence EIYPRSDNTFYNEKFKG (SEQ ID NO:47), and a heavy chain variable region CDR3 comprising the amino acid sequence HFGSSSFDY (SEQ ID NO:48), and a light chain variable region comprising a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51); or (e) a heavy chain variable region comprising a heavy chain variable region CDR1 comprising the amino acid sequence TSFGIS (SEQ ID NO:56), a heavy chain variable region CDR2 comprising the amino acid sequence WIGEIYPRSDNTF (SEQ ID NO:57), and a heavy chain variable region CDR3 comprising the amino acid sequence ARHFGSSSFD (SEQ ID NO:58), and a light chain variable region comprising a light chain variable region CDR1 comprising the amino acid sequence SSIYFHWY (SEQ ID NO:59), a light chain variable region CDR2 comprising the amino acid sequence PLIHRASNLA (SEQ ID NO:60), and a light chain variable region CDR3 comprising the amino acid sequence QQWSGYPL (SEQ ID NO:61).

In some embodiments, a LAIR-1-binding agent comprises: (a) a heavy chain variable region comprising a heavy chain variable region CDR1 comprising the amino acid sequence GYSFTSFGIS (SEQ ID NO:46), a heavy chain variable region CDR2 comprising the amino acid sequence EIYPRSDNTFYNEKFKG (SEQ ID NO:47), and a heavy chain variable region CDR3 comprising the amino acid sequence HFGSSSFDY (SEQ ID NO:48), and/or (b) a light chain variable region comprising a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51). In some embodiments, a LAIR-1-binding agent comprises a heavy chain variable region comprising a heavy chain variable region CDR1 comprising the amino acid sequence GYSFTSFGIS (SEQ ID NO:46), a heavy chain variable region CDR2 comprising the amino acid sequence EIYPRSDNTFYNEKFKG (SEQ ID NO:47), and a heavy chain variable region CDR3 comprising the amino acid sequence HFGSSSFDY (SEQ ID NO:48). In some embodiments, a LAIR-1-binding agent comprises a light chain variable region comprising a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51). In some embodiments, a LAIR-1-binding agent comprises (a) a heavy chain variable region comprising a heavy chain variable region CDR1 comprising the amino acid sequence GYSFTSFGIS (SEQ ID NO:46), a heavy chain variable region CDR2 comprising the amino acid sequence EIYPRSDNTFYNEKFKG (SEQ ID NO:47), and a heavy chain variable region CDR3 comprising the amino acid sequence HFGSSSFDY (SEQ ID NO:48), and (b) a light chain variable region comprising a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51).

In some embodiments, a LAIR-1-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:121. In some embodiments, a LAIR-1-binding agent comprises a heavy chain variable region comprising the amino acid sequence of SEQ ID NO:121. In some embodiments, a LAIR-1-binding agent comprises a light chain variable region having at least 80%, at least 85%, at least 90%, at least 95%, at least 96%, at least 97%, at least 98%, or at least 99% sequence identity to the amino acid sequence of SEQ ID NO:122. In some embodiments, a LAIR-1-binding agent comprises a light chain variable region comprising the amino acid sequence of SEQ ID NO:122.

In some embodiments, a LAIR-1-binding agent comprises a heavy chain variable region having at least 80% sequence identity to the amino acid sequence of SEQ ID NO:121 and a light chain variable region having at least 80% sequence identity to the amino acid sequence of SEQ ID NO:122. In some embodiments, a LAIR-1-binding agent comprises a heavy chain variable region having at least 90% sequence identity to the amino acid sequence of SEQ ID NO:121 and a light chain variable region having at least 90% sequence identity to the amino acid sequence of SEQ ID NO:122. In some embodiments, a LAIR-1-binding agent comprises a heavy chain variable region having at least 95% sequence identity to the amino acid sequence of SEQ ID NO:121 and a light chain variable region having at least 95% sequence identity to the amino acid sequence of SEQ ID NO:122. In some embodiments, a LAIR-1-binding agent comprises a heavy chain variable region comprising the amino acid sequence of SEQ ID NO:121 and a light chain variable region comprising the amino acid sequence of SEQ ID NO:122.

In some embodiments, the LAIR-1-binding agent is antibody 57D12. In some embodiments, the LAIR-1-binding agent is a humanized version of antibody 57D12. In some embodiments, the LAIR-1-binding agent is a variant of antibody 57D12 or a variant of a humanized version of antibody 57D12.

In some embodiments, a LAIR-1-binding agent comprises a heavy chain variable region CDR1, CDR2, and CDR3 and/or a light chain variable region CDR1, CDR2, and CDR3 from antibody 61H4, a humanized version thereof, or variants thereof. In some embodiments, a LAIR-1-binding agent comprises a heavy chain variable region comprising a heavy chain variable region CDR1, a heavy chain variable region CDR2, and a heavy chain variable region CDR3 from antibody 61H4. In other embodiments, a LAIR-1-binding agent comprises a light chain variable region comprising a light chain variable region CDR1, a light chain variable region CDR2, and a light chain variable region CDR3 from antibody 61H4. In some embodiments, a LAIR-1-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 61H4.

In some embodiments, a LAIR-1-binding agent comprises: (a) a heavy chain variable region CDR1 comprising the amino acid sequence GYTFTDYYYMN (SEQ ID NO:62), a heavy chain variable region CDR2 comprising the amino acid sequence YIYPNNGATSYNQKFKG (SEQ ID NO:63), a heavy chain variable region CDR3 comprising the amino acid sequence DGYSSNYYTMDY (SEQ ID NO:64), a light chain variable region CDR1 comprising the amino acid sequence QASQGTSINLN (SEQ ID NO:65), a light chain variable region CDR2 comprising the amino acid sequence GASNLED (SEQ ID NO:66), and a light chain variable region CDR3 comprising the amino acid sequence LQHTYLPYT (SEQ ID NO:67); (b) a heavy chain variable region CDR1 comprising the amino acid sequence GYTFTDYY (SEQ ID NO:68), a heavy chain variable region CDR2 comprising the amino acid sequence YPNNGA (SEQ ID NO:69), a heavy chain variable region CDR3 comprising the amino acid sequence DGYSSNYYTMDY (SEQ ID NO:64), a light chain variable region CDR1 comprising the amino acid sequence QASQGTSINLN (SEQ ID NO:65), a light chain variable region CDR2 comprising the amino acid sequence GASNLED (SEQ ID NO:66), and a light chain variable region CDR3 comprising the amino acid sequence LQHTYLPYT (SEQ ID NO:67); (c) a heavy chain variable region CDR1 comprising the amino acid sequence GYTFTDYYYMN (SEQ ID NO:62), a heavy chain variable region CDR2 comprising the amino acid sequence YIYPNNGATS (SEQ ID NO:70), a heavy chain variable region CDR3 comprising the amino acid sequence DGYSSNYYTMDY (SEQ ID NO:64), a light chain variable region CDR1 comprising the amino acid sequence QASQGTSINLN (SEQ ID NO:65), a light chain variable region CDR2 comprising the amino acid sequence GASNLED (SEQ ID NO:66), and a light chain variable region CDR3 comprising the amino acid sequence LQHTYLPYT (SEQ ID NO:67); (d) a heavy chain variable region CDR1 comprising the amino acid sequence DYYYMN (SEQ ID NO:71), a heavy chain variable region CDR2 comprising the amino acid sequence YIYPNNGATSYNQKFKG (SEQ ID NO:63), a heavy chain variable region CDR3 comprising the amino acid sequence DGYSSNYYTMDY (SEQ ID NO:64), a light chain variable region CDR1 comprising the amino acid sequence QASQGTSINLN (SEQ ID NO:65), a light chain variable region CDR2 comprising the amino acid sequence GASNLED (SEQ ID NO:66), and a light chain variable region CDR3 comprising the amino acid sequence LQHTYLPYT (SEQ ID NO:67); or (e) a heavy chain variable region CDR1 comprising the amino acid sequence TDYYYMN (SEQ ID NO:72), a heavy chain variable region CDR2 comprising the amino acid sequence WIGYIYPNNGATS (SEQ ID NO:73), a heavy chain variable region CDR3 comprising the amino acid sequence ARDGYSSNYYTMD (SEQ ID NO:74), a light chain variable region CDR1 comprising the amino acid sequence SINLNWF (SEQ ID NO:75), a light chain variable region CDR2 comprising the amino acid sequence LLIY-GASNLE (SEQ ID NO:76), and a light chain variable region CDR3 comprising the amino acid sequence LQHTYLPY (SEQ ID NO:77).

In some embodiments, a LAIR-1-binding agent comprises: (a) a heavy chain variable region comprising a heavy chain variable region CDR1 comprising the amino acid sequence GYTFTDYYYMN (SEQ ID NO:62), a heavy chain variable region CDR2 comprising the amino acid sequence YIYPNNGATSYNQKFKG (SEQ ID NO:63), and a heavy chain variable region CDR3 comprising the amino acid sequence DGYSSNYYTMDY (SEQ ID NO:64), and a light chain variable region comprising a light chain variable region CDR1 comprising the amino acid sequence QASQGTSINLN (SEQ ID NO:65), a light chain variable region CDR2 comprising the amino acid sequence GASN-LED (SEQ ID NO:66), and a light chain variable region CDR3 comprising the amino acid sequence LQHTYLPYT (SEQ ID NO:67); (b) a heavy chain variable region comprising a heavy chain variable region CDR1 comprising the amino acid sequence GYTFTDYY (SEQ ID NO:68), a heavy chain variable region CDR2 comprising the amino acid sequence YPNNGA (SEQ ID NO:69), and a heavy chain variable region CDR3 comprising the amino acid sequence DGYSSNYYTMDY (SEQ ID NO:64), and a light chain variable region comprising a light chain variable region CDR1 comprising the amino acid sequence QASQGTSINLN (SEQ ID NO:65), a light chain variable region CDR2 comprising the amino acid sequence GASN-LED (SEQ ID NO:66), and a light chain variable region CDR3 comprising the amino acid sequence LQHTYLPYT (SEQ ID NO:67); (c) a heavy chain variable region comprising a heavy chain variable region CDR1 comprising the amino acid sequence GYTFTDYYYMN (SEQ ID NO:62), a heavy chain variable region CDR2 comprising the amino acid sequence YIYPNNGATS (SEQ ID NO:70), and a heavy chain variable region CDR3 comprising the amino acid sequence DGYSSNYYTMDY (SEQ ID NO:64), and a light chain variable region comprising a light chain variable region CDR1 comprising the amino acid sequence QASQGTSINLN (SEQ ID NO:65), a light chain variable region CDR2 comprising the amino acid sequence GASN-LED (SEQ ID NO:66), and a light chain variable region CDR3 comprising the amino acid sequence LQHTYLPYT (SEQ ID NO:67); (d) a heavy chain variable region comprising a heavy chain variable region CDR1 comprising the amino acid sequence DYYYMN (SEQ ID NO:71), a heavy chain variable region CDR2 comprising the amino acid sequence YIYPNNGATSYNQKFKG (SEQ ID NO:63), and a heavy chain variable region CDR3 comprising the amino acid sequence DGYSSNYYTMDY (SEQ ID NO:64), and a light chain variable region comprising a light chain variable region CDR1 comprising the amino acid sequence QASQGTSINLN (SEQ ID NO:65), a light chain variable region CDR2 comprising the amino acid sequence GASN-LED (SEQ ID NO:66), and a light chain variable region CDR3 comprising the amino acid sequence LQHTYLPYT (SEQ ID NO:67); or (e) a heavy chain variable region comprising a heavy chain variable region CDR1 comprising the amino acid sequence TDYYYMN (SEQ ID NO:72), a heavy chain variable region CDR2 comprising the amino acid sequence WIGYIYPNNGATS (SEQ ID NO:73), and a heavy chain variable region CDR3 comprising the amino acid sequence ARDGYSSNYYTMD (SEQ ID NO:74), and a light chain variable region comprising a light chain variable region CDR1 comprising the amino acid sequence SINLNWF (SEQ ID NO:75), a light chain variable region CDR2 comprising the amino acid sequence LLIYGASNLE (SEQ ID NO:76), and a light chain variable region CDR3 comprising the amino acid sequence LQHTYLPY (SEQ ID NO:77).

In some embodiments, a LAIR-1-binding agent comprises: (a) a heavy chain variable region comprising a heavy chain variable region CDR1 comprising the amino acid sequence GYTFTDYYYMN (SEQ ID NO:62), a heavy chain variable region CDR2 comprising the amino acid sequence YIYPNNGATSYNQKFKG (SEQ ID NO:63), and a heavy chain variable region CDR3 comprising the amino acid sequence DGYSSNYYTMDY (SEQ ID NO:64), and/or (b) a light chain variable region comprising a light chain variable region CDR1 comprising the amino acid sequence QASQGTSINLN (SEQ ID NO:65), a light chain variable region CDR2 comprising the amino acid sequence GASN-LED (SEQ ID NO:66), and a light chain variable region CDR3 comprising the amino acid sequence LQHTYLPYT (SEQ ID NO:67). In some embodiments, a LAIR-1-binding agent comprises a heavy chain variable region comprising a heavy chain variable region CDR1 comprising the amino acid sequence GYTFTDYYYMN (SEQ ID NO:62), a heavy chain variable region CDR2 comprising the amino acid sequence YIYPNNGATSYNQKFKG (SEQ ID NO:63), and a heavy chain variable region CDR3 comprising the amino acid sequence DGYSSNYYTMDY (SEQ ID NO:64). In some embodiments, a LAIR-1-binding agent comprises a light chain variable region comprising a light chain variable region CDR1 comprising the amino acid sequence QASQGTSINLN (SEQ ID NO:65), a light chain variable region CDR2 comprising the amino acid sequence GASN-LED (SEQ ID NO:66), and a light chain variable region CDR3 comprising the amino acid sequence LQHTYLPYT (SEQ ID NO:67). In some embodiments, a LAIR-1-binding agent comprises: (a) a heavy chain variable region comprising a heavy chain variable region CDR1 comprising the amino acid sequence GYTFTDYYYMN (SEQ ID NO:62), a heavy chain variable region CDR2 comprising the amino acid sequence YIYPNNGATSYNQKFKG (SEQ ID NO:63), and a heavy chain variable region CDR3 comprising the amino acid sequence DGYSSNYYTMDY (SEQ ID NO:64), and (b) a light chain variable region comprising a light chain variable region CDR1 comprising the amino acid sequence QASQGTSINLN (SEQ ID NO:65), a light chain variable region CDR2 comprising the amino acid sequence GASNLED (SEQ ID NO:66), and a light chain variable region CDR3 comprising the amino acid sequence LQHTYLPYT (SEQ ID NO:67).

In some embodiments, a LAIR-1-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:123. In some embodiments, a LAIR-1-binding agent comprises a heavy chain variable region comprising the amino acid sequence of SEQ ID NO:123. In some embodiments, a LAIR-1-binding agent comprises a light chain variable region having at least 80%, at least 85%, at least 90%, at least 95%, at least 96%, at least 97%, at least 98%, or at least 99% sequence identity to the amino acid sequence of SEQ ID NO:124. In some embodiments, a LAIR-1-binding agent comprises a light chain variable region comprising the amino acid sequence of SEQ ID NO:124.

In some embodiments, a LAIR-1-binding agent comprises a heavy chain variable region having at least 80% sequence identity to the amino acid sequence of SEQ ID NO:123 and a light chain variable region having at least 80% sequence identity to the amino acid sequence of SEQ ID NO:124. In some embodiments, a LAIR-1-binding agent comprises a heavy chain variable region having at least 90% sequence identity to the amino acid sequence of SEQ ID NO:123 and a light chain variable region having at least 90% sequence identity to the amino acid sequence of SEQ ID NO:124. In some embodiments, a LAIR-1-binding agent comprises a heavy chain variable region having at least 95% sequence identity to the amino acid sequence of SEQ ID NO:123 and a light chain variable region having at least 95% sequence identity to the amino acid sequence of SEQ ID NO:124. In some embodiments, a LAIR-1-binding agent comprises a heavy chain variable region comprising the amino acid sequence of SEQ ID NO:123 and a light chain variable region comprising the amino acid sequence of SEQ ID NO:124.

In some embodiments, the LAIR-1-binding agent is antibody 61H4. In some embodiments, the LAIR-1-binding agent is a humanized version of antibody 61H4. In some embodiments, the LAIR-1-binding agent is a variant of antibody 61H4 or a variant of a humanized antibody 61H4.

In some embodiments, a LAIR-1-binding agent comprises a heavy chain variable region CDR1, CDR2, and CDR3 and/or a light chain variable region CDR1, CDR2, and CDR3 from antibody 62G10, a humanized version thereof, or variants thereof. In some embodiments, a LAIR-1-binding agent comprises a heavy chain variable region comprising a heavy chain variable region CDR1, a heavy chain variable region CDR2, and a heavy chain variable region CDR3 from antibody 62G10. In other embodiments, a LAIR-1-binding agent comprises a light chain variable region comprising a light chain variable region CDR1, a light chain variable region CDR2, and a light chain variable region CDR3 from antibody 62G10. In some embodiments, a LAIR-1-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 62G10.

In some embodiments, a LAIR-1-binding agent comprises: (a) a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), a heavy chain variable region CDR3 comprising the amino acid sequence GPYFDY (SEQ ID NO:79), a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81); (b) a heavy chain variable region CDR1 comprising the amino acid sequence GFTFNIN (SEQ ID NO:31), a heavy chain variable region CDR2 comprising the amino acid sequence RTKNNNFA (SEQ ID NO:82), a heavy chain variable region CDR3 comprising the amino acid sequence GPYFDY (SEQ ID NO:79), a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81); (c) a heavy chain variable region CDR1 comprising the amino acid sequence GFTFNINAMN (SEQ ID NO:25), a heavy chain variable region CDR2 comprising the amino acid sequence RIRTKNNNFATY (SEQ ID NO:83), a heavy chain variable region CDR3 comprising the amino acid sequence GPYFDY (SEQ ID NO:79), a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81); (d) a heavy chain variable region CDR1 comprising the amino acid sequence INAMN (SEQ ID NO:34), a heavy chain variable region CDR2 comprising the amino acid sequence RIRTKNNNFATYYADSVKD (SEQ ID NO:78), a heavy chain variable region CDR3 comprising the amino acid sequence GPYFDY (SEQ ID NO:79), a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81); or (e) a heavy chain variable region CDR1 comprising the amino acid sequence NINAMN (SEQ ID NO:35), a heavy chain variable region CDR2 comprising the amino acid sequence WVARIRTKNNNFATY (SEQ ID NO:84), a heavy chain variable region CDR3 comprising the amino acid sequence VRGPYFD (SEQ ID NO:85), a light chain variable region CDR1 comprising the amino acid sequence GTWLAWY (SEQ ID NO:86), a light chain variable region CDR2 comprising the amino acid sequence LLIYAATSLA (SEQ ID NO:39), and a light chain variable region CDR3 comprising the amino acid sequence QQLYSTPY (SEQ ID NO:87).

In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), and a heavy chain variable region CDR3 comprising the amino acid sequence GPYFDY (SEQ ID NO:79), and a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81); (b) a heavy chain variable region comprising a heavy chain variable region CDR1 comprising the amino acid sequence GFTFNIN (SEQ ID NO:31), a heavy chain variable region CDR2 comprising the amino acid sequence RTKNNNFA (SEQ ID NO:82), and a heavy chain variable region CDR3 comprising the amino acid sequence GPYFDY (SEQ ID NO:79), and a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81); (c) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNFATY (SEQ ID NO:83), and a heavy chain variable region CDR3 comprising the amino acid sequence GPYFDY (SEQ ID NO:79), and a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81); (d) a heavy chain variable region comprising a heavy chain variable region CDR1 comprising the amino acid sequence INAMN (SEQ ID NO:34), a heavy chain variable region CDR2 comprising the amino acid sequence RIRTKNNNFATYYADSVKD (SEQ ID NO:78), and a heavy chain variable region CDR3 comprising the amino acid sequence GPYFDY (SEQ ID NO:79), and a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81); or (e) a heavy chain variable region comprising a heavy chain variable region CDR1 comprising the amino acid sequence NINAMN (SEQ ID NO:35), a heavy chain variable region CDR2 comprising the amino acid sequence WVARIRTKNNNFATY (SEQ ID NO:84), and a heavy chain variable region CDR3 comprising the amino acid sequence VRGPYFD (SEQ ID NO:85), and a light chain variable region comprising a light chain variable region CDR1 comprising the amino acid sequence GTWLAWY (SEQ ID NO:86), a light chain variable region CDR2 comprising the amino acid sequence LLIYAATSLA (SEQ ID NO:39), and a light chain variable region CDR3 comprising the amino acid sequence QQLYSTPY (SEQ ID NO:87).

In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), and a heavy chain variable region CDR3 comprising the amino acid sequence GPYFDY (SEQ ID NO:79), and/or (b) a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81). In some embodiments, a LAIR-1-binding agent comprises a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), and a heavy chain variable region CDR3 comprising the amino acid sequence GPYFDY (SEQ ID NO:79). In some embodiments, a LAIR-1-binding agent comprises a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81). In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), and a heavy chain variable region CDR3 comprising the amino acid sequence GPYFDY (SEQ ID NO:79), and (b) a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81).

In some embodiments, a LAIR-1-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:125. In some embodiments, a LAIR-1-binding agent comprises a heavy chain variable region comprising the amino acid sequence of SEQ ID NO:125. In some embodiments, a LAIR-1-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:127. In some embodiments, a LAIR-1-binding agent comprises a heavy chain variable region comprising the amino acid sequence of SEQ ID NO:127. In some embodiments, a LAIR-1-binding agent comprises a light chain variable region having at least 80%, at least 85%, at least 90%, at least 95%, at least 96%, at least 97%, at least 98%, or at least 99% sequence identity to the amino acid sequence of SEQ ID NO:126. In some embodiments, a LAIR-1-binding agent comprises a light chain variable region comprising the amino acid sequence of SEQ ID NO:126. In some embodiments, a LAIR-1-binding agent comprises a light chain variable region having at least 80%, at least 85%, at least 90%, at least 95%, at least 96%, at least 97%, at least 98%, or at least 99% sequence identity to the amino acid sequence of SEQ ID NO:128. In some embodiments, a LAIR-1-binding agent comprises a light chain variable region comprising the amino acid sequence of SEQ ID NO:128.

In some embodiments, a LAIR-1-binding agent comprises a heavy chain variable region having at least 80% sequence identity to the amino acid sequence of SEQ ID NO:125 and a light chain variable region having at least 80% sequence identity to the amino acid sequence of SEQ ID NO:126. In some embodiments, a LAIR-1-binding agent comprises a heavy chain variable region having at least 90% sequence identity to the amino acid sequence of SEQ ID NO:125 and a light chain variable region having at least 90% sequence identity to the amino acid sequence of SEQ ID NO:126. In some embodiments, a LAIR-1-binding agent comprises a heavy chain variable region having at least 95% sequence identity to the amino acid sequence of SEQ ID NO:125 and a light chain variable region having at least 95% sequence identity to the amino acid sequence of SEQ ID NO:126. In some embodiments, a LAIR-1-binding agent comprises a heavy chain variable region comprising the amino acid sequence of SEQ ID NO:125 and a light chain variable region comprising the amino acid sequence of SEQ ID NO:126.

In some embodiments, a LAIR-1-binding agent comprises a heavy chain variable region having at least 80% sequence identity to the amino acid sequence of SEQ ID NO:127 and a light chain variable region having at least 80% sequence identity to the amino acid sequence of SEQ ID NO:128. In some embodiments, a LAIR-1-binding agent comprises a heavy chain variable region having at least 90% sequence identity to the amino acid sequence of SEQ ID NO:127 and a light chain variable region having at least 90% sequence identity to the amino acid sequence of SEQ ID NO:128. In some embodiments, a LAIR-1-binding agent comprises a heavy chain variable region having at least 95% sequence identity to the amino acid sequence of SEQ ID NO:127 and a light chain variable region having at least 95% sequence identity to the amino acid sequence of SEQ ID NO:128. In some embodiments, a LAIR-1-binding agent comprises a heavy chain variable region comprising the amino acid sequence of SEQ ID NO:127 and a light chain variable region comprising the amino acid sequence of SEQ ID NO:128.

In some embodiments, a LAIR-1-binding agent comprises: (a) a heavy chain comprising a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), and a heavy chain variable region CDR3 comprising the amino acid sequence GPYFDY (SEQ ID NO:79), and (b) a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81), wherein the heavy chain comprises at least 80%, at least 85%, at least 90%, at least 95%, at least 96%, at least 97%, at least 98%, at least 99%, or 100% sequence identity to the amino acid sequence of SEQ ID NO:138, and wherein the light chain comprises at least 80%, at least 85%, at least 90%, at least 95%, at least 96%, at least 97%, at least 98%, at least 99%, or 100% sequence identity to the amino acid sequence of SEQ ID NO:140. In some embodiments, a LAIR-1-binding agent comprises: (a) a heavy chain comprising a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), and a heavy chain variable region CDR3 comprising the amino acid sequence GPYFDY (SEQ ID NO:79), and (b) a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81), wherein the heavy chain comprises at least 95% sequence identity to the amino acid sequence of SEQ ID NO:138, and wherein the light chain comprises at least 95% sequence identity to the amino acid sequence of SEQ ID NO:140. In some embodiments, a LAIR-1-binding agent comprises: (a) a heavy chain comprising the amino acid sequence of SEQ ID NO:138 and (b) a light chain comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81), wherein the light chain comprises at least 80%, at least 85%, at least 90%, at least 95%, at least 96%, at least 97%, at least 98%, at least 99%, or at least 100% sequence identity to the amino acid sequence of SEQ ID NO:140. In some embodiments, a LAIR-1-binding agent comprises: (a) a heavy chain comprising a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), and a heavy chain variable region CDR3 comprising the amino acid sequence GPYFDY (SEQ ID NO:79), wherein the heavy chain comprises at least 80%, at least 85%, at least 90%, at least 95%, at least 96%, at least 97%, at least 98%, at least 99%, or at least 100% sequence identity to the amino acid sequence of SEQ ID NO:138, and (b) a light chain comprising the amino acid sequence of SEQ ID NO:140. In some embodiments, a LAIR-1-binding agent is an antibody comprising a heavy chain comprising the amino acid sequence of SEQ ID NO:138 and a light chain comprising the amino acid sequence of SEQ ID NO:140.

In some embodiments, the LAIR-1-binding agent is antibody 62G10. In some embodiments, the LAIR-1-binding agent is a humanized version of antibody 62G10 (e.g., Hz62G10.v1). In some embodiments, the LAIR-1-binding agent is a variant of antibody 62G10 or a variant of humanized antibody 62G10. In some embodiments, the LAIR-1-binding agent is antibody Hz62G10.v1.

In some embodiments, a LAIR-1-binding agent comprises a heavy chain variable region CDR1, CDR2, and CDR3 and/or a light chain variable region CDR1, CDR2, and CDR3 from antibody 108D10, a humanized version thereof, or variants thereof. In some embodiments, a LAIR-1-binding agent comprises a heavy chain variable region comprising a heavy chain variable region CDR1, a heavy chain variable region CDR2, and a heavy chain variable region CDR3 from antibody 108D10. In other embodiments, a LAIR-1-binding agent comprises a light chain variable region comprising a light chain variable region CDR1, a light chain variable region CDR2, and a light chain variable region CDR3 from antibody 108D10. In some embodiments, a LAIR-1-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 108D10.

In some embodiments, a LAIR-1-binding agent comprises: (a) a heavy chain variable region CDR1 comprising the amino acid sequence GFTFNINAMN (SEQ ID NO:25), a heavy chain variable region CDR2 comprising the amino acid sequence RIRTKNNNYATYYADSVKD (SEQ ID NO:88), a heavy chain variable region CDR3 comprising the amino acid sequence DRYGGAMAY (SEQ ID NO:89), a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92); (b) a heavy chain variable region CDR1 comprising the amino acid sequence GFTFNIN (SEQ ID NO:31), a heavy chain variable region CDR2 comprising the amino acid sequence RTKNNNYA (SEQ ID NO:32), a heavy chain variable region CDR3 comprising the amino acid sequence DRYGGAMAY (SEQ ID NO:89), a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92); (c) a heavy chain variable region CDR1 comprising the amino acid sequence GFTFNINAMN (SEQ ID NO:25), a heavy chain variable region CDR2 comprising the amino acid sequence RIRTKNNNYATY (SEQ ID NO:93), a heavy chain variable region CDR3 comprising the amino acid sequence DRYGGAMAY (SEQ ID NO:89), a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92); (d) a heavy chain variable region CDR1 comprising the amino acid sequence INAMN (SEQ ID NO:34), a heavy chain variable region CDR2 comprising the amino acid sequence RIRTKNN-NYATYYADSVKD (SEQ ID NO:88), a heavy chain variable region CDR3 comprising the amino acid sequence DRYGGAMAY (SEQ ID NO:89), a light chain variable region CDR1 comprising the amino acid sequence KASEDIYNRLA (SEQ ID NO:90), a light chain variable region CDR2 comprising the amino acid sequence SATS-LET (SEQ ID NO:91), and a light chain variable region CDR3 comprising the amino acid sequence QQYWTIPYT (SEQ ID NO:92); or (e) a heavy chain variable region CDR1 comprising the amino acid sequence NINAMN (SEQ ID NO:35), a heavy chain variable region CDR2 comprising the amino acid sequence WVARIRTKNNNYATY (SEQ ID NO:94), a heavy chain variable region CDR3 comprising the amino acid sequence VRDRYGGAMA (SEQ ID NO:95), a light chain variable region CDR1 comprising the amino acid sequence YNRLAWY (SEQ ID NO:96), a light chain variable region CDR2 comprising the amino acid sequence LLISSATSLE (SEQ ID NO:97), and a light chain variable region CDR3 comprising the amino acid sequence QQYW-TIPY (SEQ ID NO:98).

In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATYYADSVKD (SEQ ID NO:88), and a heavy chain variable region CDR3 comprising the amino acid sequence DRYGGAMAY (SEQ ID NO:89), and a light chain variable region comprising a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92); (b) a heavy chain variable region comprising a heavy chain variable region CDR1 comprising the amino acid sequence GFTFNIN (SEQ ID NO:31), a heavy chain variable region CDR2 comprising the amino acid sequence RTKNNNYA (SEQ ID NO:32), and a heavy chain variable region CDR3 comprising the amino acid sequence DRYGGAMAY (SEQ ID NO:89), and a light chain variable region comprising a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92); (c) a heavy chain variable region comprising a heavy chain variable region CDR1 comprising the amino acid sequence GFTFNINAMN (SEQ ID NO:25), a heavy chain variable region CDR2 comprising the amino acid sequence RIRT-KNNNYATY (SEQ ID NO:93), and a heavy chain variable region CDR3 comprising the amino acid sequence DRYG-GAMAY (SEQ ID NO:89), and a light chain variable region comprising a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92); (d) a heavy chain variable region comprising a heavy chain variable region CDR1 comprising the amino acid sequence INAMN (SEQ ID NO:34), a heavy chain variable region CDR2 comprising the amino acid sequence RIRTKNNNYATYYADSVKD (SEQ ID NO:88), and a heavy chain variable region CDR3 comprising the amino acid sequence DRYGGAMAY (SEQ ID NO:89), and a light chain variable region comprising a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYW-TIPYT (SEQ ID NO:92); or (e) a heavy chain variable region comprising a heavy chain variable region CDR1 comprising the amino acid sequence NINAMN (SEQ ID NO:35), a heavy chain variable region CDR2 comprising the amino acid sequence WVARIRTKNNNYATY (SEQ ID NO:94), and a heavy chain variable region CDR3 comprising the amino acid sequence VRDRYGGAMA (SEQ ID NO:95), and a light chain variable region comprising a light chain variable region CDR1 comprising the amino acid sequence YNRLAWY (SEQ ID NO:96), a light chain variable region CDR2 comprising the amino acid sequence LLISSATSLE (SEQ ID NO:97), and a light chain variable region CDR3 comprising the amino acid sequence QQYW-TIPY (SEQ ID NO:98).

In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATYYADSVKD (SEQ ID NO:88), and a heavy chain variable region CDR3 comprising the amino acid sequence DRYGGAMAY (SEQ ID NO:89), and/or (b) a light chain variable region comprising a light chain variable region CDR1 comprising the amino acid sequence KASEDIYNRLA (SEQ ID NO:90), a light chain variable region CDR2 comprising the amino acid sequence SATS-LET (SEQ ID NO:91), and a light chain variable region CDR3 comprising the amino acid sequence QQYWTIPYT (SEQ ID NO:92). In some embodiments, a LAIR-1-binding agent comprises a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATYYADSVKD (SEQ ID NO:88), and a heavy chain variable region CDR3 comprising the amino acid sequence DRYGGAMAY (SEQ ID NO:89). In some embodiments, a LAIR-1-binding agent comprises a light chain variable region comprising a light chain variable region CDR1 comprising the amino acid sequence KASEDIYNRLA (SEQ ID NO:90), a light chain variable region CDR2 comprising the amino acid sequence SATS-LET (SEQ ID NO:91), and a light chain variable region CDR3 comprising the amino acid sequence QQYWTIPYT (SEQ ID NO:92). In some embodiments, a LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATYYADSVKD (SEQ ID NO:88), and a heavy chain variable region CDR3 comprising the amino acid sequence DRYGGAMAY (SEQ ID NO:89), and (b) a light chain variable region comprising a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92).

In some embodiments, a LAIR-1-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:129. In some embodiments, a LAIR-1-binding agent comprises a heavy chain variable region comprising the amino acid sequence of SEQ ID NO:129. In some embodiments, a LAIR-1-binding agent comprises a light chain variable region having at least 80%, at least 85%, at least 90%, at least 95%, at least 96%, at least 97%, at least 98%, or at least 99% sequence identity to the amino acid sequence of SEQ ID NO:130. In some embodiments, a LAIR-1-binding agent comprises a light chain variable region comprising the amino acid sequence of SEQ ID NO:130.

In some embodiments, a LAIR-1-binding agent comprises a heavy chain variable region having at least 80% sequence identity to the amino acid sequence of SEQ ID NO:129 and a light chain variable region having at least 80% sequence identity to the amino acid sequence of SEQ ID NO:130. In some embodiments, a LAIR-1-binding agent comprises a heavy chain variable region having at least 90% sequence identity to the amino acid sequence of SEQ ID NO:129 and a light chain variable region having at least 90% sequence identity to the amino acid sequence of SEQ ID NO:130. In some embodiments, a LAIR-1-binding agent comprises a heavy chain variable region having at least 95% sequence identity to the amino acid sequence of SEQ ID NO:129 and a light chain variable region having at least 95% sequence identity to the amino acid sequence of SEQ ID NO:130. In some embodiments, a LAIR-1-binding agent comprises a heavy chain variable region comprising the amino acid sequence of SEQ ID NO:129 and a light chain variable region comprising the amino acid sequence of SEQ ID NO:130.

In some embodiments, the LAIR-1-binding agent is antibody 108D10. In some embodiments, the LAIR-1-binding agent is a humanized version of antibody 108D10. In some embodiments, the LAIR-1-binding agent is a variant of antibody 108D10 or a variant of humanized antibody 108D10.

In some embodiments, a LAIR-1 binding agent binds mouse LAIR-1. In some embodiments, a LAIR-1-binding agent comprises a heavy chain variable region CDR1, CDR2, and CDR3 and/or a light chain variable region CDR1, CDR2, and CDR3 from antibody 43H2 or variants thereof. In some embodiments, a LAIR-1-binding agent comprises a heavy chain variable region comprising a heavy chain variable region CDR1, a heavy chain variable region CDR2, and a heavy chain variable region CDR3 from antibody 43H2. In other embodiments, a LAIR-1-binding agent comprises a light chain variable region comprising a light chain variable region CDR1, a light chain variable region CDR2, and a light chain variable region CDR3 from antibody 43H2. In some embodiments, a LAIR-1-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 43H2.

In some embodiments, a LAIR-1-binding agent comprises: (a) a heavy chain variable region CDR1 comprising the amino acid sequence GFTFSNYGIH (SEQ ID NO:99), a heavy chain variable region CDR2 comprising the amino acid sequence SISPSGRSTYFRDSVKG (SEQ ID NO:100), a heavy chain variable region CDR3 comprising the amino acid sequence GINYSSFDY (SEQ ID NO:101), a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104); (b) a heavy chain variable region CDR1 comprising the amino acid sequence GFTFSNY (SEQ ID NO:105), a heavy chain variable region CDR2 comprising the amino acid sequence SPSGRS (SEQ ID NO:106), a heavy chain variable region CDR3 comprising the amino acid sequence GINYSSFDY (SEQ ID NO:101), a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104); (c) a heavy chain variable region CDR1 comprising the amino acid sequence GFTFSNYGIH (SEQ ID NO:99), a heavy chain variable region CDR2 comprising the amino acid sequence SISPSGRSTY (SEQ ID NO:107), a heavy chain variable region CDR3 comprising the amino acid sequence GINYSSFDY (SEQ ID NO:101), a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104); (d) a heavy chain variable region CDR1 comprising the amino acid sequence NYGIH (SEQ ID NO:108), a heavy chain variable region CDR2 comprising the amino acid sequence SISPSGRSTYFRDSVKG (SEQ ID NO:100), a heavy chain variable region CDR3 comprising the amino acid sequence GINYSSFDY (SEQ ID NO:101), a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104); or (e) a heavy chain variable region CDR1 comprising the amino acid sequence SNYGIH (SEQ ID NO:109), a heavy chain variable region CDR2 comprising the amino acid sequence WVASISPSGRSTY (SEQ ID NO:110), a heavy chain variable region CDR3 comprising the amino acid sequence ATGINYSSFD (SEQ ID NO:111), a light chain variable region CDR1 comprising the amino acid sequence GSHVDWY (SEQ ID NO:112), a light chain variable region CDR2 comprising the amino acid sequence LLISTASNRY (SEQ ID NO:113), and a light chain variable region CDR3 comprising the amino acid sequence MQSNSYPP (SEQ ID NO:114).

In some embodiments, a LAIR-1-binding agent comprises: (a) a heavy chain variable region comprising a heavy chain variable region CDR1 comprising the amino acid sequence GFTFSNYGIH (SEQ ID NO:99), a heavy chain variable region CDR2 comprising the amino acid sequence SISPSGRSTYFRDSVKG (SEQ ID NO:100), and a heavy chain variable region CDR3 comprising the amino acid sequence GINYSSFDY (SEQ ID NO:101), and a light chain variable region comprising a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104); (b) a heavy chain variable region comprising a heavy chain variable region CDR1 comprising the amino acid sequence GFTFSNY (SEQ ID NO:105), a heavy chain variable region CDR2 comprising the amino acid sequence SPSGRS (SEQ ID NO:106), and a heavy chain variable region CDR3 comprising the amino acid sequence GINYSSFDY (SEQ ID NO:101), and a light chain variable region comprising a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104); (c) a heavy chain variable region comprising a heavy chain variable region CDR1 comprising the amino acid sequence GFTFSNYGIH (SEQ ID NO:99), a heavy chain variable region CDR2 comprising the amino acid sequence SISPSGRSTY (SEQ ID NO:107), and a heavy chain variable region CDR3 comprising the amino acid sequence GINYSSFDY (SEQ ID NO:101), and a light chain variable region comprising a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104); (d) a heavy chain variable region comprising a heavy chain variable region CDR1 comprising the amino acid sequence NYGIH (SEQ ID NO:108), a heavy chain variable region CDR2 comprising the amino acid sequence SISPSGRSTYFRDSVKG (SEQ ID NO:100), and a heavy chain variable region CDR3 comprising the amino acid sequence GINYSSFDY (SEQ ID NO:101), and a light chain variable region comprising a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104); or (e) a heavy chain variable region comprising a heavy chain variable region CDR1 comprising the amino acid sequence SNYGIH (SEQ ID NO:109), a heavy chain variable region CDR2 comprising the amino acid sequence WVASISPSGRSTY (SEQ ID NO:110), and a heavy chain variable region CDR3 comprising the amino acid sequence ATGINYSSFD (SEQ ID NO:111), and a light chain variable region comprising a light chain variable region CDR1 comprising the amino acid sequence GSHVDWY (SEQ ID NO:112), a light chain variable region CDR2 comprising the amino acid sequence LLISTASNRY (SEQ ID NO:113), and a light chain variable region CDR3 comprising the amino acid sequence MQSNSYPP (SEQ ID NO:114).

In some embodiments, a LAIR-1-binding agent comprises: (a) a heavy chain variable region comprising a heavy chain variable region CDR1 comprising the amino acid sequence GFTFSNYGIH (SEQ ID NO:99), a heavy chain variable region CDR2 comprising the amino acid sequence SISPSGRSTYFRDSVKG (SEQ ID NO:100), and a heavy chain variable region CDR3 comprising the amino acid sequence GINYSSFDY (SEQ ID NO:101), and/or (b) a light chain variable region comprising a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104). In some embodiments, a LAIR-1-binding agent comprises a heavy chain variable region comprising a heavy chain variable region CDR1 comprising the amino acid sequence GFTFSNYGIH (SEQ ID NO:99), a heavy chain variable region CDR2 comprising the amino acid sequence SISPSGRSTYFRDSVKG (SEQ ID NO:100), and a heavy chain variable region CDR3 comprising the amino acid sequence GINYSSFDY (SEQ ID NO:101). In some embodiments, a LAIR-1-binding agent comprises a light chain variable region comprising a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104). In some embodiments, a LAIR-1-binding agent comprises: (a) a heavy chain variable region comprising a heavy chain variable region CDR1 comprising the amino acid sequence GFTFSNYGIH (SEQ ID NO:99), a heavy chain variable region CDR2 comprising the amino acid sequence SISPSGRSTYFRDSVKG (SEQ ID NO:100), and a heavy chain variable region CDR3 comprising the amino acid sequence GINYSSFDY (SEQ ID NO:101), and (b) a light chain variable region comprising a light chain variable region CDR1 comprising the amino acid sequence KASQNVGSHVD (SEQ ID NO:102), a light chain variable region CDR2 comprising the amino acid sequence TASNRYT (SEQ ID NO:103), and a light chain variable region CDR3 comprising the amino acid sequence MQSNSYPPT (SEQ ID NO:104).

In some embodiments, a LAIR-1-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:131. In some embodiments, a LAIR-1-binding agent comprises a heavy chain variable region comprising the amino acid sequence of SEQ ID NO:131. In some embodiments, a LAIR-1-binding agent comprises a light chain variable region having at least 80%, at least 85%, at least 90%, at least 95%, at least 96%, at least 97%, at least 98%, or at least 99% sequence identity to the amino acid sequence of SEQ ID NO:132. In some embodiments, a LAIR-1-binding agent comprises a light chain variable region comprising the amino acid sequence of SEQ ID NO:132.

In some embodiments, a LAIR-1-binding agent comprises a heavy chain variable region having at least 80% sequence identity to the amino acid sequence of SEQ ID NO:131 and a light chain variable region having at least 80% sequence identity to the amino acid sequence of SEQ ID NO:132. In some embodiments, a LAIR-1-binding agent comprises a heavy chain variable region having at least 90% sequence identity to the amino acid sequence of SEQ ID NO:131 and a light chain variable region having at least 90% sequence identity to the amino acid sequence of SEQ ID NO:132. In some embodiments, a LAIR-1-binding agent comprises a heavy chain variable region having at least 95% sequence identity to the amino acid sequence of SEQ ID NO:131 and a light chain variable region having at least 95% sequence identity to the amino acid sequence of SEQ ID NO:132. In some embodiments, a LAIR-1-binding agent comprises a heavy chain variable region comprising the amino acid sequence of SEQ ID NO:131 and a light chain variable region comprising the amino acid sequence of SEQ ID NO:132.

In some embodiments, the LAIR-1-binding agent is antibody 43H2. In some embodiments, the LAIR-1-binding agent is a humanized version of antibody 43H2. In some embodiments, the LAIR-1-binding agent is a variant of antibody 43H2 or a variant of humanized antibody 43H2.

Provided herein are agents that compete with one or more of the binding agents described herein for binding to LAIR-1. In some embodiments, an agent competes with one or more of the binding agents described herein for binding to LAIR-1. In some embodiments, an agent competes with one or more of the binding agents described herein for binding to human LAIR-1. In some embodiments, an agent that competes with one or more of the binding agents described herein is an antibody. In some embodiments, an agent binds the same epitope as one of the LAIR-1-binding agents described herein. In some embodiments, an agent binds an epitope overlapping with an epitope bound by one of the LAIR-1-binding agents described herein. Antibodies and antigen-binding fragments that compete with or bind the same epitope as the LAIR-1-binding agents described herein are expected to show similar functional properties.

In some embodiments, an agent competes for binding to human LAIR-1 with a reference antibody, wherein the reference antibody comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26) or RIRTKNYNYATFYADSVKD (SEQ ID NO:41), and a heavy chain variable region CDR3 comprising the amino acid sequence DRAGFFAY (SEQ ID NO:27), and a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30). In some embodiments, the reference antibody is antibody 47H1 or Hz47H1.v4.

In some embodiments, an agent competes for binding to human LAIR-1 with a reference antibody, wherein the reference antibody comprises: (a) a heavy chain variable region comprising a heavy chain variable region CDR1 comprising the amino acid sequence GFTFNTYAIH (SEQ ID NO:9), a heavy chain variable region CDR2 comprising the amino acid sequence RIRSKSTNYATYYADSVKD (SEQ ID NO:10), and a heavy chain variable region CDR3 comprising the amino acid sequence ENWYYYALDY (SEQ ID NO:11), and a light chain variable region comprising a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14). In some embodiments, the reference antibody is antibody 47A1.

In some embodiments, a LAIR-1-binding agent described herein comprises an antibody in which at least one or more of the constant regions of the antibody has been modified or deleted. In some embodiments, an antibody comprises one or more modifications to one or more of the heavy chain constant regions (CH1, CH2, CH3, or CH4) and/or to the light chain constant region (CL). In some embodiments, an antibody comprises one or more modifications to the hinge region. In some embodiments, the heavy chain constant region of the modified antibody comprises at least one human constant region. In some embodiments, the heavy chain constant region of the modified antibody comprises more than one human constant region. In some embodiments, modifications to the constant region comprise additions, deletions, or substitutions of one or more amino acids in one or more regions. In some embodiments, one or more regions are partially or entirely deleted from the constant regions of a modified antibody. In some embodiments, the entire CH2 domain has been removed from an antibody (ΔCH2 constructs). In some embodiments, one or more regions are partially or entirely deleted from the hinge region of a modified antibody. In some embodiments, a deleted constant region is replaced by a short amino acid spacer that provides some of the molecular flexibility typically imparted by the absent constant region. In some embodiments, a deleted hinge region is replaced by a short amino acid spacer that provides some of the molecular flexibility typically imparted by the absent hinge region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions and these effector functions can vary depending on the isotype of the antibody. For example, binding of the C1q component of complement to the Fc region of IgG or IgM antibodies when the antibodies are bound to antigen activates the complement system. Activation of complement is important in the opsonization and lysis of cell pathogens. The activation of complement also stimulates the inflammatory immune response and can be involved in autoimmune hypersensitivity. In addition, the Fc region of an antibody can bind a cell expressing a Fc receptor (FcR). There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including, but not limited to, engulfment and destruction of antibody-coated particles, clearance of immune complexes, lysis of antibody-coated target cells by killer cells (i.e., antibody-dependent cell cytotoxicity or ADCC), release of inflammatory mediators, placental transfer, and control of immunoglobulin production.

In some embodiments, a LAIR-1-binding agent comprises a variant constant region or Fc region. The amino acid sequences of the constant region or Fc region of human IgG1, IgG2, IgG3, and IgG4 are known to those of ordinary skill in the art (e.g., a representative human IgG1 constant region is SEQ ID NO:141). In some cases, constant regions or Fc regions with amino acid variations have been identified in native antibodies. In some embodiments, a variant constant region or Fc region is engineered with substitutions at specific amino acid positions as compared to a native constant region or Fc region. Variant constant region or Fc regions are well-known in the art and include, but are not limited to, SEQ ID NO:142, SEQ ID NO:143, SEQ ID NO:144, SEQ ID NO:145, SEQ ID NO:146, SEQ ID NO:158, and SEQ ID NO:159.

In some embodiments, a modified antibody provides for altered effector functions that, in turn, affect the biological profile of the antibody. For example, in some embodiments, the deletion or inactivation (through point mutations or other means) of a constant region reduces binding of a modified antibody to a Fc receptor. In some embodiments, constant region modifications increase the serum half-life of an antibody. In some embodiments, constant region modifications reduce the serum half-life of an antibody. In some embodiments, constant region modifications decrease or remove ADCC and/or complement-dependent cytotoxicity (CDC) of an antibody. In some embodiments, a human IgG1 Fc region with specific amino acid substitutions corresponding to IgG2 or IgG4 residues reduce effector functions (e.g., ADCC and CDC) in a modified antibody. In some embodiments, a modified antibody does not have one or more effector functions. In some embodiments, a modified antibody has no ADCC activity and/or no CDC activity. In some embodiments, a modified antibody does not bind an Fc receptor and/or complement factors. In some embodiments, a modified antibody does not have any detectable effector functions (e.g., an "effectorless" antibody). In some embodiments, constant region modifications increase or enhance ADCC and/or CDC of an antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites.

Modifications to the constant region of antibodies described herein may be made using well-known biochemical or molecular engineering techniques. In some embodiments, antibody variants are prepared by introducing appropriate nucleotide changes into the encoding DNA, and/or by synthesis of the desired antibody or polypeptide. Using these engineering techniques to modify an antibody it may be possible to disrupt the activity or effector function provided by a specific sequence or region while substantially maintaining the structure, binding activity, and other desired characteristics of the modified antibody.

The present disclosure further embraces additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine (i.e., conservative amino acid replacements). In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant are determined by systematically making insertions, deletions, or substitutions in the sequence and testing the resulting variant proteins for activity as compared to the parental antibody.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein to create a fusion protein. In some embodiments, a variant is engineered to be detectable and may comprise a detectable label and/or protein (e.g., a fluorescent tag, a fluorescent protein, or an enzyme).

In some embodiments, a cysteine residue not involved in maintaining the proper conformation of an antibody is substituted or deleted to modulate the antibody's characteristics, for example, to improve oxidative stability and/or prevent aberrant disulfide crosslinking. Conversely, in some embodiments, one or more cysteine residues are added to create disulfide bond(s) to improve stability.

In some embodiments, an antibody of the present disclosure is "deimmunized". The deimmunization of antibodies generally consists of introducing specific amino acid mutations (e.g., substitutions, deletions, additions) that result in removal of T-cell epitopes (known or predicted) without significantly reducing the binding affinity or other desired activities of the antibody.

The variant antibodies or polypeptides described herein may be generated using methods known in the art, including but not limited to, site-directed mutagenesis, alanine scanning mutagenesis, and PCR mutagenesis.

In some embodiments, a LAIR-1-binding agent described herein is chemically modified. In some embodiments, a LAIR-1-binding agent is an anti-LAIR-1 antibody that is chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques. In some embodiments, a LAIR-1-binding agent is attached (either directly or indirectly) to a half-life extending moiety including, but not limited to, polyethylene glycol (PEG), a PEG mimetic, XTEN®, serum albumin, polysialic acid, N-(2-hydroxypropyl)methacrylamide, or dextran. In some embodiments, a LAIR-1-binding agent is an antibody, wherein the antibody is attached (either directly or indirectly) to a half-life extending moiety including, but not limited to, polyethylene glycol (PEG), a PEG mimetic, XTEN®, serum albumin, polysialic acid, N-(2-hydroxypropyl)methacrylamide, or dextran. In some embodiments, a LAIR-1-binding agent is an antibody fragment (e.g., scFv, Fv, Fab, F(ab')$_2$, or F(ab')), wherein the antibody fragment is attached (either directly or indirectly) to a half-life extending moiety including, but not limited to, polyethylene glycol (PEG), a PEG mimetic, XTEN®, serum albumin, polysialic acid, N-(2-hydroxypropyl)methacrylamide, or dextran.

The present disclosure encompasses LAIR-1-binding agents built upon non-immunoglobulin backbones, wherein the agents bind the same epitope or essentially the same epitope as an anti-LAIR-1 antibody disclosed herein. In some embodiments, a non-immunoglobulin-based binding agent is an agent that competes with a LAIR-1-binding agent described herein in a competitive binding assay. In some embodiments, alternative LAIR-1-binding agents comprise a scaffold protein. Generally, scaffold proteins can be assigned to one of three groups based on the architecture of their backbone (1) scaffolds consisting of α-helices; (2) small scaffolds with few secondary structures or an irregular architecture of α-helices and β-sheets; and (3) scaffolds consisting of predominantly n-sheets. Scaffold proteins include, but are not limited to, (i) anticalins, which are based upon the lipocalin scaffold; (ii) adnectins, which are based on the 10$^{th}$ domain of human fibronectin type 3; (iii) affibodies, which are based on the B-domain in the Ig-binding region of *Staphylococcus aureus* protein A; (iv) darpins, which are based on ankyrin repeat domain proteins; (v) fynomers, which are based on the SH3 domain of the human Fyn protein kinase; (vi) affitins, which are based on Sac7d from *Sulfolobus acidocaldarius*; (vii) affilins, which are based on human γ-B-crystallin or human ubiquitin; (viii) avimers, which are based on the A-domains of membrane receptor proteins; (ix) knottins (cysteine knot miniproteins), which are based upon a stable 30-amino acid anti-parallel β-strand protein fold; and (x) Kunitz domain inhibitor scaffolds, which are based upon a structure that contains three disulfide bonds and three loops.

In some embodiments, a LAIR-1-binding agent comprises an engineered scaffold protein comprising a heavy chain variable region CDR1, CDR2, and CDR3 and a light chain variable region CDR1, CDR2, and CDR3 shown in Table 1. In some embodiments, a LAIR-1-binding agent comprises an engineered scaffold protein comprising a heavy chain variable region CDR1 comprising the amino acid sequence GFTFNTYAIH (SEQ ID NO:9), a heavy chain variable region CDR2 comprising the amino acid sequence RIRSKSTNYATYYADSVKD (SEQ ID NO:10), a heavy chain variable region CDR3 comprising the amino acid sequence ENWYYYALDY (SEQ ID NO:11), a light chain variable region CDR1 comprising the amino acid sequence RASGNIHNYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14). In some embodiments, a LAIR-1-binding agent comprises an engineered scaffold protein comprising a heavy chain variable region CDR1, CDR2, and CDR3 and a light chain variable region CDR1, CDR2, and CDR3 from antibody 47A1.

In some embodiments, a LAIR-1-binding agent comprises an engineered scaffold protein comprising a heavy chain variable region CDR1, CDR2, and CDR3 and a light chain variable region CDR1, CDR2, and CDR3 shown in Table 2A or 2B. In some embodiments, a LAIR-1-binding agent comprises an engineered scaffold protein comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26) or RIRTKNYNYATFYADSVKD (SEQ ID NO:41), a heavy chain variable region CDR3 comprising the amino acid sequence DRAGFFAY (SEQ ID NO:27), a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30). In some embodiments, a LAIR-1-binding agent comprises an engineered scaffold protein comprising a heavy chain variable region CDR1, CDR2, and CDR3 and a light chain variable region CDR1, CDR2, and CDR3 from antibody 47H1 or Hz47H1.v4.

In some embodiments, a LAIR-1-binding agent comprises an engineered scaffold protein comprising a heavy chain variable region CDR1, CDR2, and CDR3 and a light chain variable region CDR1, CDR2, and CDR3 shown in Table 3. In some embodiments, a LAIR-1-binding agent comprises an engineered scaffold protein comprising a heavy chain variable region CDR1 comprising the amino acid sequence GYSFTSFGIS (SEQ ID NO:46), a heavy chain variable region CDR2 comprising the amino acid sequence EIYPRSDNTFYNEKFKG (SEQ ID NO:47), a heavy chain variable region CDR3 comprising the amino acid sequence HFGSSSFDY (SEQ ID NO:48), a light chain variable region CDR1 comprising the amino acid sequence SASSSVSSIYFH (SEQ ID NO:49), a light chain variable region CDR2 comprising the amino acid sequence RASNLAS (SEQ ID NO:50), and a light chain variable region CDR3 comprising the amino acid sequence QQWSGYPLT (SEQ ID NO:51). In some embodiments, a LAIR-1-binding agent comprises an engineered scaffold protein comprising a heavy chain variable region CDR1, CDR2, and CDR3 and a light chain variable region CDR1, CDR2, and CDR3 from antibody 57D12.

In some embodiments, a LAIR-1-binding agent comprises an engineered scaffold protein comprising a heavy chain variable region CDR1, CDR2, and CDR3 and a light chain variable region CDR1, CDR2, and CDR3 shown in Table 4. In some embodiments, a LAIR-1-binding agent comprises an engineered scaffold protein comprising a heavy chain variable region CDR1 comprising the amino acid sequence GYTFTDYYYMN (SEQ ID NO:62), a heavy chain variable region CDR2 comprising the amino acid sequence YIYPNNGATSYNQKFKG (SEQ ID NO:63), a heavy chain variable region CDR3 comprising the amino acid sequence DGYSSNYYTMDY (SEQ ID NO:64), a light chain variable region CDR1 comprising the amino acid sequence QASQGTSINLN (SEQ ID NO:65), a light chain variable region CDR2 comprising the amino acid sequence GASNLED (SEQ ID NO:66), and a light chain variable region CDR3 comprising the amino acid sequence LQHTYLPYT (SEQ ID NO:67). In some embodiments, a LAIR-1-binding agent comprises an engineered scaffold protein comprising a heavy chain variable region CDR1, CDR2, and CDR3 and a light chain variable region CDR1, CDR2, and CDR3 from antibody 61H4.

In some embodiments, a LAIR-1-binding agent comprises an engineered scaffold protein comprising a heavy chain variable region CDR1, CDR2, and CDR3 and a light chain variable region CDR1, CDR2, and CDR3 shown in Table 5. In some embodiments, a LAIR-1-binding agent comprises an engineered scaffold protein comprising a heavy chain variable region CDR1 comprising the amino acid sequence GFTFNINAMN (SEQ ID NO:25), a heavy chain variable region CDR2 comprising the amino acid sequence RIRTKNNNFATYYADSVKD (SEQ ID NO:78), a heavy chain variable region CDR3 comprising the amino acid sequence GPYFDY (SEQ ID NO:79), a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81). In some embodiments, a LAIR-1-binding agent comprises an engineered scaffold protein comprising a heavy chain variable region CDR1, CDR2, and CDR3 and a light chain variable region CDR1, CDR2, and CDR3 from antibody 62G10 or Hz62G10.v1.

In some embodiments, a LAIR-1-binding agent comprises an engineered scaffold protein comprising a heavy chain variable region CDR1, CDR2, and CDR3 and a light chain variable region CDR1, CDR2, and CDR3 shown in Table 6. In some embodiments, a LAIR-1-binding agent comprises an engineered scaffold protein comprising a heavy chain variable region CDR1 comprising the amino acid sequence GFTFNINAMN (SEQ ID NO:25), a heavy chain variable region CDR2 comprising the amino acid sequence RIRTKNNNYATYYADSVKD (SEQ ID NO:88), a heavy chain variable region CDR3 comprising the amino acid sequence DRYGGAMAY (SEQ ID NO:89), a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92). In some embodiments, a LAIR-1-binding agent comprises an engineered scaffold protein comprising a heavy chain variable region CDR1, CDR2, and CDR3 and a light chain variable region CDR1, CDR2, and CDR3 from antibody 108D10.

In some embodiments, a composition comprises a LAIR-1-binding agent described herein. In some embodiments, a composition comprises an anti-LAIR-1 antibody described herein. In some embodiments, a composition comprises a monoclonal anti-LAIR-1 antibody described herein. In some embodiments, a composition comprises an antibody selected from the group consisting of: antibody 47A1, antibody 47H1, antibody 57D12, antibody 61H4, antibody 62G10, or antibody 108D10, or humanized versions thereof. In some embodiments, a composition comprises the antibody 47A1, antibody 47H1, antibody Hz47H1.v4, antibody 57D12, antibody 61H4, antibody 62G10, antibody Hz62G10.v1, or antibody 108D10.

In some embodiments, a pharmaceutical composition comprises a LAIR-1-binding agent described herein and a pharmaceutically acceptable carrier. In some embodiments, a pharmaceutical composition comprises an anti-LAIR-1 antibody described herein and a pharmaceutically acceptable carrier. In some embodiments, a pharmaceutical composition comprises a monoclonal anti-LAIR-1 antibody described herein and a pharmaceutically acceptable carrier. In some embodiments, a pharmaceutical composition comprises an antibody selected from the group consisting of: antibody 47A1, antibody 47H1, antibody 57D12, antibody 61H4, antibody 62G10, or antibody 108D10, or humanized versions thereof and a pharmaceutically acceptable carrier. In some embodiments, a pharmaceutical composition comprises the antibody 47A1, antibody 47H1, antibody Hz47H1.v4, antibody 57D12, antibody 61H4, antibody 62G10, antibody Hz62G10.v1, or antibody 108D10 and a pharmaceutically acceptable carrier. In some embodiments, a pharmaceutical composition comprises antibody Hz47H1.v4 and a pharmaceutically acceptable carrier. In some embodiments, a pharmaceutical composition comprises antibody Hz62G10.v1 and a pharmaceutically acceptable carrier.

In some embodiments, a LAIR-1-binding agent is isolated. In some embodiments, a LAIR-1-binding agent is substantially pure.

Generally speaking, antigen-antibody interactions are non-covalent and reversible, formed by a combination of hydrogen bonds, hydrophobic interactions, electrostatic and van der Waals forces. When describing the strength of an antigen-antibody complex, the terms affinity and/or avidity are commonly used. The binding of an antibody to its antigen is a reversible process, and the affinity of the binding is typically reported as an equilibrium dissociation constant ($K_D$). $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. In some embodiments, affinity is measured using SPR technology in a Biacore system. Avidity gives a measure of the overall strength of an antibody-antigen complex. It is dependent on three major parameters: (i) affinity of the antibody for the target, (ii) valency of both the antibody and antigen, and (iii) structural arrangement of the parts that interact.

In some embodiments, a LAIR-1-binding agent binds LAIR-1 with a dissociation constant ($K_D$) of 1 µM or less, 100 nM or less, 40 nM or less, 20 nM or less, 10 nM or less, 1 nM or less, 0.1 nM or less, 50 pM or less, 10 pM or less, or 1 pM or less. In some embodiments, a LAIR-1-binding agent binds LAIR-1 with a $K_D$ of about 20 nM or less. In some embodiments, a LAIR-1-binding agent binds LAIR-1 with a $K_D$ of 10 nM or less. In some embodiments, a LAIR-1-binding agent binds LAIR-1 with a $K_D$ of 5 nM or less. In some embodiments, a LAIR-1-binding agent binds LAIR-1 with a $K_D$ of 3 nM or less. In some embodiments, a LAIR-1-binding agent binds LAIR-1 with a $K_D$ of 2 nM or less. In some embodiments, a LAIR-1-binding agent binds LAIR-1 with a $K_D$ of 1 nM or less. In some embodiments, a LAIR-1-binding agent binds LAIR-1 with a $K_D$ of 0.5 nM or less. In some embodiments, a LAIR-1-binding agent binds LAIR-1 with a $K_D$ of 0.1 nM or less. In some embodiments, a LAIR-1-binding agent binds LAIR-1 with a $K_D$ of 50 pM or less. In some embodiments, a LAIR-1-binding agent binds LAIR-1 with a $K_D$ of 25 pM or less. In some embodiments, a LAIR-1-binding agent binds LAIR-1 with a $K_D$ of 10 pM or less. In some embodiments, a LAIR-1-binding agent binds LAIR-1 with a $K_D$ of 1 pM or less. In some embodiments, a LAIR-1-binding agent binds LAIR-1 with a $K_D$ of 0.01 nM to 2.5 nM. In some embodiments, a LAIR-1-binding agent binds LAIR-1 with a $K_D$ of 0.1 nM to 5 nM. In some embodiments, a LAIR-1-binding agent binds LAIR-1 with a $K_D$ of 1 nM to 5 nM. In some embodiments, the dissociation constant of the binding agent for LAIR-1 is the dissociation constant determined using an LAIR-1 protein immobilized on a Biacore chip and the binding agent flowed over the chip. In some embodiments, the dissociation constant of the binding agent for LAIR-1 is the dissociation constant determined using the binding agent captured by an anti-human IgG antibody on a Biacore chip and soluble LAIR-1 flowed over the chip.

In some embodiments, a LAIR-1-binding agent binds LAIR-1 with a half maximal effective concentration (EC50) of 1 µM or less, 100 nM or less, 40 nM or less, 20 nM or less, 10 nM or less, 1 nM or less, or 0.1 nM or less. In some embodiments, a LAIR-1-binding agent binds human LAIR-1 with an EC50 of 1 µM or less, 100 nM or less, 40 nM or less, 20 nM or less, 10 nM or less, 1 nM or less, or 0.1 nM or less. In some embodiments, a LAIR-1-binding agent binds cyno LAIR-1 and/or human LAIR-1 with an EC50 of 40 nM or less, 20 nM or less, 10 nM or less, 1 nM or less or 0.1 nM or less. In some embodiments, a LAIR-1-binding agent binds LAIR-1 with an EC50 of 0.1 nM to about 3 nM, 0.1 nM to 2 nM, 0.1 nM to 1 nM, 0.5 nM to 3 nM, 0.5 nM to 2 nM, or 0.5 nM to 1 nM.

In some embodiments, a LAIR-1-binding agent has at least one or more of the following properties: (i) binds human LAIR-1; (ii) binds cyno LAIR-1; (iii) does not bind mouse LAIR-1; (iv) does not bind human LAIR-2; (v) is a LAIR-1 antagonist; (vi) inhibits LAIR-1 activity; (vii) inhibits LAIR-1 signaling in cells that express LAIR-1; (viii) inhibits binding of LAIR-1 to collagen; (ix) inhibits binding of LAIR-1 to MARCO; (x) inhibits binding of LAIR-1 to COLEC12; (xi) inhibits LAIR-1-induced suppression of myeloid cells; (xii) inhibits LAIR-1-induced suppression of myeloid cell activity; (xiii) restores FcR activation in myeloid cells; (xiv) restores cytokine and/or chemokine production in myeloid cells; (xv) inhibits LAIR-1-induced suppression of NK cells; (xvi) inhibits LAIR-1-induced suppression of NK activity; (xvii) inhibits LAIR-1-induced suppression of T-cell activity; and/or (xviii) inhibits MDSC activity. In some embodiments, the myeloid cells are monocytes. In some embodiments, the myeloid cells are macrophages. In some embodiments, the myeloid cells are dendritic cells. In some embodiments, the myeloid cells are antigen-presenting cells (APCs).

The LAIR-1-binding agents described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host.

In some embodiments, recombinant expression vectors are used to amplify and express DNA encoding the LAIR-1-binding agents described herein. For example, recombinant expression vectors can be replicable DNA constructs which have synthetic or cDNA-derived DNA fragments encoding a polypeptide chain of a LAIR-1-binding agent, such as an anti-LAIR-1 antibody, or antigen-binding fragment thereof, operatively linked to suitable transcriptional and/or translational regulatory elements derived from mammalian, microbial, viral or insect genes. A transcriptional unit generally comprises an assembly of (i) a genetic element or elements having a regulatory role in gene expression, for example, transcriptional promoters or enhancers, (ii) a structural or coding sequence that is transcribed into mRNA and translated into protein, and (iii) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor that participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of a LAIR-1-binding agent or a LAIR-1 protein or fragment thereof to use as an antigen or immunogen include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described herein. Cell-free translation systems may also be employed. Appropriate cloning vectors and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexahistidine (His6; SEQ ID NO:153), maltose binding domain, influenza coat sequence, and glutathione-S-transferase can be attached to the protein to allow easy purification by passage over an appropriate affinity column. Affinity chromatography methods used for purifying immunoglobulins can include, but are not limited to, Protein A, Protein G, and Protein L chromatography. Isolated proteins can be physically characterized using techniques that include, but are not limited to, proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems that secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

LAIR-1-binding agents of the present disclosure may be analyzed for their physical/chemical properties and/or biological activities by various assays known in the art. In some embodiments, a LAIR-1-binding agent is tested for its ability to bind LAIR-1. Binding assays include, but are not limited to, SPR (e.g., Biacore), ELISA, and FACS. In some embodiments, a LAIR-1-binding agent is tested for its ability to inhibit, reduce, or block binding to collagen, MARCO, and/or COLEC12. In addition, binding agents may be evaluated for solubility, stability, thermostability, viscosity, expression levels, expression quality, and/or purification efficiency.

In some embodiments, monoclonal antibodies generated against LAIR-1 are grouped based upon the epitope each individual antibody recognizes, a process known as "epitope binning". Generally, antibodies are tested in a pairwise combinatorial manner and antibodies that compete with each other are grouped together into bins. For example, in a premix binning assay, a first antibody is immobilized on a surface and a premixed solution of a second antibody and antigen is flowed over the immobilized first antibody. In tandem, the antigen is immobilized on a surface and the two antibodies are flowed over the immobilized antigen and compete to bind. Using these techniques, antibodies that block one another can be identified. A competitive blocking profile is created for each antibody relative to the other antibodies. The blocking results determine which bin each antibody is placed in. High-throughput methods of epitope binning are known in the art and allow for screening and characterization of large numbers of antibodies within a short period of time. Antibodies that bind similar epitopes often share similar functions and/or capabilities. Conversely, antibodies that bind different epitopes may have different functional activities.

In some embodiments, an epitope bin comprises at least one antibody from the group consisting of: 47A1, 47H1, 57D12, 61H4, 62G10, and 108D10. In some embodiments, an epitope bin comprises at least antibodies 47A1, 57D12, and 61H4. In some embodiments, an epitope bin comprises antibodies 47A1, 57D12, and 61H4. In some embodiments, an epitope bin comprises at least antibodies 47H1, 62G10, and 108D10. In some embodiments, an epitope bin comprises antibodies 47H1, 62G10, and 108D10.

Epitope mapping is the process of identifying the binding site, or epitope on a target protein/antigen where an antibody (or other binding agent) binds. A variety of methods are known in the art for mapping epitopes on target proteins. These methods include (i) mutagenesis, including but not limited to, shotgun mutagenesis, site-directed mutagenesis, and alanine scanning; (ii) domain or fragment scanning; (iii) peptide scanning (e.g., Pepscan technology); (iv) display methods, including but not limited to, phage display, microbial display, and ribosome/mRNA display; (v) methods involving proteolysis and mass spectroscopy; (vi) methods involving amide hydrogen/deuterium exchange; and (vii) structural determination, including but not limited to, x-ray crystallography and NMR.

In some embodiments, purified anti-LAIR-1 antibodies are characterized by assays including, but not limited to, N-terminal sequencing, amino acid analysis, HPLC, mass spectrometry, differential scanning fluorimetry (DSF), nanoDSF, capillary isoelectric focusing (cIEF), ion exchange chromatography, and papain digestion.

In some embodiments, assays are provided for identifying LAIR-1-binding agents that affect LAIR-1 activity. In some embodiments, assays are provided for identifying an anti-LAIR-1 antibody that affects LAIR-1 activity. These assays may include, but are not limited to, cell activation assays (e.g., cell proliferation assays), cytotoxic T-cell (CTL)

assays, NK cell assays, mixed lymphocyte reaction (MLR) assays, cytokine/chemokine production assays, FcR binding assays, and cell migration assays. "Affect or affecting LAIR-1 activity" may include, for example, inhibiting, reducing, blocking, antagonizing, suppressing, and/or interfering with LAIR-1 activity. As LAIR-1 generally acts a negative regulator/inhibitory molecule, in some embodiments, inhibiting, reducing, blocking, antagonizing, suppressing, and/or interfering with LAIR-1 activity results in a release of LAIR-1-induced suppression of a biological function (e.g., an activation signal). As described herein, LAIR-1 is expressed on T-cells, B-cells, NK cells, and myeloid cells. Myeloid cells include, but may not be limited to, monocytes, macrophages, dendritic cells, and APCs. LAIR-1 activity or LAIR-1 signaling activity includes, but is not limited to, suppression of myeloid cells, suppression of myeloid cell activity, suppression of tumor-associated myeloid cells, suppression of NK cells, suppression of NK cell activity, suppression of T-cells, and suppression of T-cell activity. In some embodiments, inhibiting, reducing, blocking, antagonizing, suppressing, and/or interfering with LAIR-1 activity results in a release of LAIR-1-induced suppression of an activation signal. In some embodiments, an anti-LAIR-1 antibody inhibits LAIR-1 signaling. In some embodiments, an anti-LAIR-1 antibody inhibits LAIR-1 signaling thereby reversing an LAIR-1-induced suppressive effect. In some embodiments, an anti-LAIR-1 antibody inhibits an LAIR-1-induced extinction signal.

In some embodiments, an anti-LAIR-1 antibody disrupts the LAIR-1 signaling pathway. In some embodiments, an anti-LAIR-1 antibody disrupts the LAIR-1 signaling pathway and activates myeloid cells. In some embodiments, an anti-LAIR-1 antibody disrupts the LAIR-1 signaling pathway and activates APCs. In some embodiments, an anti-LAIR-1 antibody disrupts the LAIR-1 signaling pathway and activates dendritic cells. In some embodiments, an anti-LAIR-1 antibody disrupts the LAIR-1 signaling pathway and activates NK cells. In some embodiments, an anti-LAIR-1 antibody disrupts the LAIR-1 signaling pathway and activates T-cells. In some embodiments, an anti-LAIR-1 antibody disrupts the LAIR-1 signaling pathway and activates CTLs. In some embodiments, an anti-LAIR-1 antibody disrupts the LAIR-1 signaling pathway and activates tumor-associated T-cells.

In some embodiments, the terms "inhibiting", "reducing", "blocking", "antagonizing", "suppressing", and "interfering" are relative to levels and/or activity in the absence of treatment with the LAIR-1-binding agent. In some embodiments, the terms "inhibiting", "reducing", "blocking", "antagonizing", "suppressing", and "interfering" are relative to levels and/or activity prior to treatment with the LAIR-1-binding agent.

In some embodiments, a LAIR-1-binding agent inhibits human LAIR-1 activity. In some embodiments, an anti-LAIR-1 antibody inhibits human LAIR-1 activity. In some embodiments, an anti-LAIR-1 antibody that inhibits human LAIR-1 activity is antibody 47A1. In some embodiments, an anti-LAIR-1 antibody that inhibits human LAIR-1 activity is antibody 47H1. In some embodiments, an anti-LAIR-1 antibody that inhibits human LAIR-1 activity is antibody Hz47H1.v4. In some embodiments, an anti-LAIR-1 antibody that inhibits human LAIR-1 activity is antibody 57D12. In some embodiments, an anti-LAIR-1 antibody that inhibits human LAIR-1 activity is antibody 61H4. In some embodiments, an anti-LAIR-1 antibody that inhibits human LAIR-1 activity is antibody 62G10. In some embodiments, an anti-LAIR-1 antibody that inhibits human LAIR-1 activity is antibody Hz62H10.v1. In some embodiments, an anti-LAIR-1 antibody that inhibits human LAIR-1 activity is antibody 108D10.

In some embodiments, a LAIR-1-binding agent inhibits mouse LAIR-1 activity. In some embodiments, an anti-LAIR-1 antibody inhibits mouse LAIR-1 activity. In some embodiments, an anti-LAIR-1 antibody that inhibits mouse LAIR-1 activity is antibody 43H2.

The present disclosure also provides conjugates comprising a LAIR-1-binding agent described herein. In some embodiments, a conjugate comprises an anti-LAIR-1 antibody described herein. In some embodiments, the antibody is attached to a second molecule. In some embodiments, the antibody is conjugated to a cytotoxic agent or moiety. In some embodiments, the antibody is conjugated to a cytotoxic agent to form an antibody-drug conjugate (ADC). In some embodiments, the cytotoxic agent is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic agent is a microtubule inhibitor including, but not limited to, auristatins, maytansinoids (e.g., DM1 and DM4), and tubulysins. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleuites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC1065. A derivative of any one of these toxins may be used as long as the derivative retains the cytotoxic activity of the parent molecule.

Conjugates comprising a LAIR-1-binding agent (e.g., an anti-LAIR-1 antibody described herein) may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, a LAIR-1-binding agent described herein is conjugated to a detectable substance or molecule that allows the agent to be used for diagnosis and/or detection. In some embodiments, an anti-LAIR-1 antibody described herein is conjugated to a detectable substance or molecule that allows the antibody to be used for diagnosis and/or detection. In some embodiments, a labeled anti-LAIR-1 antibody is used to monitor immune cells in a tumor or in the microenvironment of a tumor. In some embodiments, a labeled anti-LAIR-1 antibody is used to monitor immune cells in a tumor or in the microenvironment of a tumor after treatment. A detectable substance can include but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}$Bi, $^{14}$C, $^{57}$Co, $^{51}$Cr, $^{67}$Cu, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$Sc, $^{75}$Se, $^{153}$Sm, $^{113}$Sn, $^{117}$Sn, $^{85}$Sr, $^{99m}$Tc, $^{201}$Ti, $^{133}$Xe, $^{90}$Y, $^{69}$Yb, $^{175}$Yb, $^{65}$Zn; positron emitting metals; and magnetic metal ions.

An anti-LAIR-1 antibody described herein can also be conjugated to a second antibody to form an antibody heteroconjugate.

A LAIR-1-binding agent as described herein may be attached to a solid support. In some embodiments, an anti-LAIR-1 antibody as described herein is attached to a solid support. Such solid supports include, but are not limited to, glass, cellulose, polyacrylamide, nylon, polystyrene, polyvinyl chloride, or polypropylene. In some embodiments, an immobilized anti-LAIR-1 antibody is used in an immunoassay. In some embodiments, an immobilized anti-LAIR-1 antibody is used in purification of the target antigen.

In some embodiments, an anti-LAIR-1 antibody described herein is used in an immunoassay. Immunoassays are known to those of skill in the art and include, but are not limited to, ELISA, SPR (e.g., Biacore), FACS, and immunohistochemistry (IHC). In some embodiments, an anti-LAIR-1 antibody described herein is used on a tissue sample or a tumor sample.

IV. MARCO-Binding Agents

An amino acid (aa) sequence for human MARCO (UniProtKB No. Q9UEW3) is provided herein as SEQ ID NO:154. As used herein, reference to amino acid positions of these proteins refer to the numbering of amino acid sequences including the signal sequence.

MARCO is a single pass type II transmembrane protein with a predicted molecular weight of approximately 44 kDa. As characterized within UniProtKB, human MARCO is a protein of 520 amino acids (aa)—the cytoplasmic region is aa 1-43, the signal-anchor transmembrane domain is aa 44-64, and the extracellular domain is aa 65-520. Within the extracellular domain, there is a collagen-like domain—aa 147-419 and a SRCR (scavenger receptor cysteine-rich) domain—aa 424-519. MARCO is expressed on macrophages, including tumor-associated macrophages.

In some embodiments, a MARCO-binding agent binds MARCO or a fragment of MARCO. In some embodiments, a fragment of MARCO comprises the extracellular domain. In some embodiments, a fragment of MARCO comprises the collagen-like domain. In some embodiments, a fragment of MARCO comprises the SRCR domain. In some embodiments, the extracellular domain of human MARCO comprises amino acids 65-520 of SEQ ID NO:154. In some embodiments, the collagen-like domain of human MARCO comprises amino acids 147-419 of SEQ ID NO:154. In some embodiments, the SRCR domain of human MARCO comprises amino acids 424-519 of SEQ ID NO:154. In some embodiments, a fragment of human MARCO comprises the amino acid sequence of SEQ ID NO:155. In some embodiments, a fragment of human MARCO comprises the amino acid sequence of SEQ ID NO:156.

It is understood that the regions and/or domains of MARCO may be defined differently by those of skill in the art, therefore the N-terminal amino acids and the C-terminal amino acids of any MARCO domain or region may vary by 1, 2, 3, 4, 5, or more amino acid residues.

In some embodiments, a MARCO-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgG antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some embodiments, the antibody comprises an IgG heavy chain. In some embodiments, the antibody comprises an IgG1 heavy chain. In some embodiments, the antibody comprises an IgG2 heavy chain. In some embodiments, the antibody comprises an IgG4 heavy chain. In some embodiments, the antibody comprises a human IgG1 heavy chain. In some embodiments, the antibody comprises a human IgG2 heavy chain. In some embodiments, the antibody comprises a human IgG4 heavy chain. In some embodiments, the antibody comprises a kappa light chain. In some embodiments, the antibody comprises a kappa light chain constant region. In some embodiments, the antibody comprises a human kappa light chain constant region. In some embodiments, the antibody comprises a lambda light chain. In some embodiments, the antibody comprises a lambda light chain constant region. In some embodiments, the antibody comprises a human lambda light chain constant region.

In some embodiments, an anti-MARCO antibody described herein comprises the six CDRs of antibody 6D8, 10G4, or 15A3 based on the Kabat definition. In some embodiments, an anti-MARCO antibody described herein comprises the six CDRs of antibody 6D8, 10G4, or 15A3 based on the Chothia definition. In some embodiments, an anti-MARCO antibody described herein comprises the six CDRs of antibody 6D8, 10G4, or 15A3 based on the AbM definition. In some embodiments, an anti-MARCO T antibody described herein comprises the six CDRs of antibody 6D8, 10G4, or 15A3 based on the IMGT definition. In some embodiments, an anti-MARCO antibody described herein comprises the six CDRs of antibody 6D8, 10G4, or 15A3 based on the Contact definition. In some embodiments, an anti-MARCO antibody described herein comprises the six CDRs of antibody 6D8, 10G4, or 15A3 based on the Exemplary definition.

In some embodiments, an MARCO-binding agent is an anti-MARCO antibody that comprises one, two, three, four, five, and/or six CDRs of any one of the anti-MARCO antibodies described herein. In some embodiments, an anti-MARCO antibody comprises (i) a heavy chain variable region comprising one, two, and/or three heavy chain variable region CDRs from Table 8, and/or (ii) a light chain variable region comprising one, two, and/or three light chain variable region CDRs from Table 8. In some embodiments, an anti-MARCO antibody comprises (i) a heavy chain variable region comprising one, two, and/or three heavy chain variable region CDRs from Table 9, and/or (ii) a light chain variable region comprising one, two, and/or three light chain variable region CDRs from Table 9. In some embodiments, an anti-MARCO antibody comprises (i) a heavy chain variable region comprising one, two, and/or three heavy chain variable region CDRs from Table 10, and/or (ii) a light chain variable region comprising one, two, and/or three light chain variable region CDRs from Table 10. In some embodiments, an anti-MARCO antibody comprises (i) a heavy chain variable region comprising three heavy chain variable region CDRs from Table 8, and (ii) a light chain variable region comprising three light chain variable region CDRs from Table 8. In some embodiments, an anti-MARCO antibody comprises (i) a heavy chain variable region comprising three heavy chain variable region CDRs from Table 9, and (ii) a light chain variable region comprising three light chain variable region CDRs from Table 9. In some embodiments, an anti-MARCO antibody comprises (i) a heavy chain variable region comprising three heavy chain variable region CDRs from Table 10, and (ii) a light chain variable region comprising three light chain variable region CDRs from Table 10.

TABLE 8

Anti-MARCO Antibody 6D8 Sequences

| | Exemplary | Chothia | AbM | Kabat | Contact |
|---|---|---|---|---|---|
| VH CDR1 | GFSLTNYAIS (SEQ ID NO: 178) | GFSLTNY (SEQ ID NO: 184) | GFSLTNYAIS (SEQ ID NO: 178) | NYAIS (SEQ ID NO: 187) | TNYAIS (SEQ ID NO: 188) |
| VH CDR2 | VIWTGGGTNYNSTLKS (SEQ ID NO: 179) | WTGGG (SEQ ID NO: 185) | VIWTGGGTN (SEQ ID NO: 186) | VIWTGGGTNYNSTLKS (SEQ ID NO: 179) | WLGVIWTGGGTN (SEQ ID NO: 189) |
| VH CDR3 | NSGDWYFDV (SEQ ID NO: 180) | NSGDWYFDV (SEQ ID NO: 180) | NSGDWYFDV (SEQ ID NO: 180) | NSGDWYFDV (SEQ ID NO: 180) | ARNSGDWYFD (SEQ ID NO: 190) |
| VL CDR1 | KSSQSLLYSSNQKNYLA (SEQ ID NO: 181) | KSSQSLLYSSNQKNYLA (SEQ ID NO: 181) | KSSQSLLYSSNQKNYLA (SEQ ID NO: 181) | KSSQSLLYSSNQKNYLA (SEQ ID NO: 181) | LYSSNQKNYLAWY (SEQ ID NO: 191) |
| VL CDR2 | WASTRES (SEQ ID NO: 182) | WASTRES (SEQ ID NO: 182) | WASTRES (SEQ ID NO: 182) | WASTRES (SEQ ID NO: 182) | LLIYWASTRE (SEQ ID NO: 192) |
| VL CDR3 | QQYYDYPPT (SEQ ID NO: 183) | QQYYDYPPT (SEQ ID NO: 183) | QQYYDYPPT (SEQ ID NO: 183) | QQYYDYPPT (SEQ ID NO: 183) | QQYYDYPP (SEQ ID NO: 193) |

6D8 Heavy chain variable region (SEQ ID NO: 160)
QVQLKESGPGLVAPSQSLSIACTVSGFSLTNYAISWVRQPPGKGLEWLGVIWTGGGTNYN
STLKSRLSISKDNSKSQVFLKMNSLQTDDTARYNCARNSGDWYFDVWGPGTTVTVSS 6D8 Light chain variable region (SEQ ID NO: 161)
DIVMSQSPSSLAVSVGEKVTMSCKSSQSLLYSSNQKNYLAWYQQKPGQSPHLLIYWASTR
ESGVPDRFIGSGSGTDFTLTISSVKAEDLAVYYCQQYYDYPPTFGSGTKLEIK

TABLE 9

Anti-MARCO Antibody 10G4 Sequences

| | Exemplary | Chothia | AbM | Kabat | Contact |
|---|---|---|---|---|---|
| VH CDR1 | GFSLSSYPIS (SEQ ID NO: 194) | GFSLSSY (SEQ ID NO: 200) | GFSLSSYPIS (SEQ ID NO: 194) | SYPIS (SEQ ID NO: 202) | SSYPIS (SEQ ID NO: 203) |
| VH CDR2 | IIWTGGGTNYNSALKS (SEQ ID NO: 195) | WTGGG (SEQ ID NO: 185) | IIWTGGGTN (SEQ ID NO: 201) | IIWTGGGTNYNSALKS (SEQ ID NO: 195) | WLGIIWTGGGTN (SEQ ID NO: 204) |
| VH CDR3 | QNWDVNSALDY (SEQ ID NO: 196) | QNWDVNSALDY (SEQ ID NO: 196) | QNWDVNSALDY (SEQ ID NO: 196) | QNWDVNSALDY (SEQ ID NO: 196) | ASQNWDVNSALD (SEQ ID NO: 205) |
| VL CDR1 | RASENIYSNLA (SEQ ID NO: 197) | RASENIYSNLA (SEQ ID NO: 197) | RASENIYSNLA (SEQ ID NO: 197) | RASENIYSNLA (SEQ ID NO: 197) | YSNLAWY (SEQ ID NO: 206) |
| VL CDR2 | TATNLAD (SEQ ID NO: 198) | TATNLAD (SEQ ID NO: 198) | TATNLAD (SEQ ID NO: 198) | TATNLAD (SEQ ID NO: 198) | LLVYTATNLA (SEQ ID NO: 207) |
| VL CDR 3 | QHFWNAPWT (SEQ ID NO: 199) | QHFWNAPWT (SEQ ID NO: 199) | QHFWNAPWT (SEQ ID NO: 199) | QHFWNAPWT (SEQ ID NO: 199) | QHFWNAPW (SEQ ID NO: 208) |

10G4 Heavy chain variable region (SEQ ID NO: 162)
QVQLKESGPGLVAPSQSLSITCTVSGFSLSSYPISWVRQPPGKGLEWLGIIWTGGGTNYN
SALKSRLSISKDNSKSQVFLKMNSLQTDDTARYYCASQNWDVNSALDYWGQGTSVTVSS 10G4 Light chain variable region (SEQ ID NO: 163)
DIQMTQSPASLSVSVGETVTITCRASENIYSNLAWYQQKQGKSPQLLVYTATNLADGVPS
RFSGSGSGTQYSLRINRLQSEDFGNYYCQHFWNAPWTFGGGTKLEIK

TABLE 10

Anti-MARCO Antibody 15A3 Sequences

|  | Exemplary | Chothia | AbM | Kabat | Contact |
|---|---|---|---|---|---|
| VH CDR1 | GYSFTDYNMY (SEQ ID NO: 209) | GYSFTDY (SEQ ID NO: 215) | GYSFTDYNMY (SEQ ID NO: 209) | DYNMY (SEQ ID NO: 218) | TDYNMY (SEQ ID NO: 219) |
| VH CDR2 | YIDPYNGGTSYNQKFKG (SEQ ID NO: 210) | DPYNGG (SEQ ID NO: 216) | YIDPYNGGTS (SEQ ID NO: 217) | YIDPYNGGTSYNQKFKG (SEQ ID NO: 210) | WIGYIDPYNGGTS (SEQ ID NO: 220) |
| VH CDR3 | LRSPYDYDRGDYVMDY (SEQ ID NO: 211) | LRSPYDYDRGDYVMDY (SEQ ID NO: 211) | LRSPYDYDRGDYVMDY (SEQ ID NO: 211) | LRSPYDYDRGDYVMDY (SEQ ID NO: 211) | ARLRSPYDYDRGDYVMD (SEQ ID NO: 221) |
| VL CDR1 | RASKSVSTSGYTYMH (SEQ ID NO: 212) | RASKSVSTSGYTYMH (SEQ ID NO: 212) | RASKSVSTSGYTYMH (SEQ ID NO: 212) | RASKSVSTSGYTYMH (SEQ ID NO: 212) | STSGYTYMHWY (SEQ ID NO: 222) |
| VL CDR2 | LASNLES (SEQ ID NO: 213) | LASNLES (SEQ ID NO: 213) | LASNLES (SEQ ID NO: 213) | LASNLES (SEQ ID NO: 213) | LLIYLASNLE (SEQ ID NO: 223) |
| VL CDR3 | QHSRELPLT (SEQ ID NO: 214) | QHSRELPLT (SEQ ID NO: 214) | QHSRELPLT (SEQ ID NO: 214) | QHSRELPLT (SEQ ID NO: 214) | QHSRELPL (SEQ ID NO: 224) |

15A3 Heavy chain variable region (SEQ ID NO: 164)
EIQLQQSGPELVKPGASVKVSCKASGYSFTDYNMYWVKQSHGKSLEWIGYIDPYNGGTSY
NQKFKGKATLTVDKSSSTAFMHLNSLTSEDSAVYYCARLRSPYDYDRGDYVMDYWGQGTSVTVSS 15A3 Light chain variable region (SEQ ID NO: 165)
DIVLTQSPASLAVSLGQRATISCRASKSVSTSGYTYMHWYQQKPGQPPKWYLASNLES
GVPARFSGSGSGTDFTLNIHPVEEEDAATYYCQHSRELPLTFGAGTKLELK In some embodiments, a MARCO-binding agent comprises a heavy chain variable region CDR1, CDR2, and CDR3 and/or a light chain variable region CDR1, CDR2, and CDR3 from antibody 6D8, a humanized version thereof, or variants thereof. In some embodiments, a MARCO-binding agent comprises a heavy chain variable region comprising a heavy chain variable region CDR1, a heavy chain variable region CDR2, and a heavy chain variable region CDR3 from antibody 6D8. In other embodiments, a MARCO-binding agent comprises a light chain variable region comprising a light chain variable region CDR1, a light chain variable region CDR2, and a light chain variable region CDR3 from antibody 6D8. In some embodiments, a MARCO-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 6D8.

In some embodiments, a MARCO-binding agent comprises: (a) a heavy chain variable region CDR1 comprising the amino acid sequence GFSLTNYAIS (SEQ ID NO:178), a heavy chain variable region CDR2 comprising the amino acid sequence VIWTGGGTNYNSTLKS (SEQ ID NO:179), a heavy chain variable region CDR3 comprising the amino acid sequence NSGDWYFDV (SEQ ID NO:180), a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183); (b) a heavy chain variable region CDR1 comprising the amino acid sequence GFSLTNY (SEQ ID NO:184), a heavy chain variable region CDR2 comprising the amino acid sequence WTGGG (SEQ ID NO:185), a heavy chain variable region CDR3 comprising the amino acid sequence NSGDWYFDV (SEQ ID NO:180), a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183); (c) a heavy chain variable region CDR1 comprising the amino acid sequence GFSLTNYAIS (SEQ ID NO:178), a heavy chain variable region CDR2 comprising the amino acid sequence VIWTGGGTN (SEQ ID NO:186), a heavy chain variable region CDR3 comprising the amino acid sequence NSGDWYFDV (SEQ ID NO:180), a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183); (d) a heavy chain variable region CDR1 comprising the amino acid sequence NYAIS (SEQ ID NO:187), a heavy chain variable region CDR2 comprising the amino acid sequence VIWTGGGTNYNSTLKS (SEQ ID NO:179), a heavy chain variable region CDR3 comprising the amino acid sequence NSGDWYFDV (SEQ ID NO:180), a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183); or (e) a heavy chain variable region CDR1 comprising the amino acid sequence TNYAIS (SEQ ID NO:188), a heavy chain variable region CDR2 comprising the amino acid sequence WLGVIWTGGGTN (SEQ ID NO:189), a heavy chain variable region CDR3 comprising the amino acid sequence ARNSGDWYFD (SEQ ID NO:190), a light chain variable region CDR1 comprising the amino acid sequence LYSSNQKNYLAWY (SEQ ID NO:191), a light chain variable region CDR2 comprising the amino acid sequence LLIYWASTRE (SEQ ID NO:192), and a light chain variable region CDR3 comprising the amino acid sequence QQYYDYPP (SEQ ID NO:193).

In some embodiments, a MARCO-binding agent comprises: (a) a heavy chain variable region comprising a heavy chain variable region CDR1 comprising the amino acid sequence GFSLTNYAIS (SEQ ID NO:178), a heavy chain variable region CDR2 comprising the amino acid sequence VIWTGGGTNYNSTLKS (SEQ ID NO:179), a heavy chain variable region CDR3 comprising the amino acid sequence NSGDWYFDV (SEQ ID NO:180), and a light chain variable region comprising a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183); (b) a heavy chain variable region comprising a heavy chain variable region CDR1 comprising the amino acid sequence GFSLTNY (SEQ ID NO:184), a heavy chain variable region CDR2 comprising the amino acid sequence WTGGG (SEQ ID NO:185), a heavy chain variable region CDR3 comprising the amino acid sequence NSGDWYFDV (SEQ ID NO:180), and a light chain variable region comprising a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183); (c) a heavy chain variable region comprising a heavy chain variable region CDR1 comprising the amino acid sequence GFSLTNYAIS (SEQ ID NO:178), a heavy chain variable region CDR2 comprising the amino acid sequence VIWTGGGTN (SEQ ID NO:186), a heavy chain variable region CDR3 comprising the amino acid sequence NSGDWYFDV (SEQ ID NO:180), and a light chain variable region comprising a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183); (d) a heavy chain variable region comprising a heavy chain variable region CDR1 comprising the amino acid sequence NYAIS (SEQ ID NO:187), a heavy chain variable region CDR2 comprising the amino acid sequence VIWTGGGTNYNSTLKS (SEQ ID NO:179), a heavy chain variable region CDR3 comprising the amino acid sequence NSGDWYFDV (SEQ ID NO:180), and a light chain variable region comprising a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183); or (e) a heavy chain variable region comprising a heavy chain variable region CDR1 comprising the amino acid sequence TNYAIS (SEQ ID NO:188), a heavy chain variable region CDR2 comprising the amino acid sequence WLGVIWTGGGTN (SEQ ID NO:189), a heavy chain variable region CDR3 comprising the amino acid sequence ARNSGDWYFD (SEQ ID NO:190), and a light chain variable region comprising a light chain variable region CDR1 comprising the amino acid sequence LYSSNQKNYLAWY (SEQ ID NO:191), a light chain variable region CDR2 comprising the amino acid sequence LLIYWASTRE (SEQ ID NO:192), and a light chain variable region CDR3 comprising the amino acid sequence QQYYDYPP (SEQ ID NO:193).

In some embodiments, a MARCO-binding agent comprises: (a) a heavy chain variable region comprising a heavy chain variable region CDR1 comprising the amino acid sequence GFSLTNYAIS (SEQ ID NO:178), a heavy chain variable region CDR2 comprising the amino acid sequence VIWTGGGTNYNSTLKS (SEQ ID NO:179), a heavy chain variable region CDR3 comprising the amino acid sequence NSGDWYFDV (SEQ ID NO:180), and/or (b) a light chain variable region comprising a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183). In some embodiments, a MARCO-binding agent comprises a heavy chain variable region comprising a heavy chain variable region CDR1 comprising the amino acid sequence GFSLTNYAIS (SEQ ID NO:178), a heavy chain variable region CDR2 comprising the amino acid sequence VIWTGGGTNYNSTLKS (SEQ ID NO:179), a heavy chain variable region CDR3 comprising the amino acid sequence NSGDWYFDV (SEQ ID NO:180). In some embodiments, a MARCO-binding agent comprises a light chain variable region comprising a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183). In some embodiments, a LAIR-1-binding agent comprises: (a) a heavy chain variable region comprising a heavy chain variable region CDR1 comprising the amino acid sequence GFSLTNYAIS (SEQ ID NO:178), a heavy chain variable region CDR2 comprising the amino acid sequence VIWTGGGTNYNSTLKS (SEQ ID NO:179), a heavy chain variable region CDR3 comprising the amino acid sequence NSGDWYFDV (SEQ ID NO:180), and (b) a light chain variable region comprising a light chain variable region CDR1 comprising the amino acid sequence KSSQSLLYSSNQKNYLA (SEQ ID NO:181), a light chain variable region CDR2 comprising the amino acid sequence WASTRES (SEQ ID NO:182), and a light chain variable region CDR3 comprising the amino acid sequence QQYYDYPPT (SEQ ID NO:183).

In some embodiments, a MARCO-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:160. In some embodiments, a MARCO-binding agent comprises a heavy chain variable region comprising the amino acid sequence of SEQ ID NO:160. In some embodiments, a MARCO-binding agent comprises a light chain variable region having at least 80%, at least 85%, at least 90%, at least 95%, at least 96%, at least 97%, at least 98%, or at least 99% sequence identity to the amino acid sequence of SEQ ID NO:161. In some embodiments, a MARCO-binding agent comprises a light chain variable region comprising the amino acid sequence of SEQ ID NO:161.

In some embodiments, a MARCO-binding agent comprises a heavy chain variable region having at least 80% sequence identity to the amino acid sequence of SEQ ID NO:160 and a light chain variable region having at least 80% sequence identity to the amino acid sequence of SEQ ID NO:161. In some embodiments, a MARCO-binding agent comprises a heavy chain variable region having at least 90% sequence identity to the amino acid sequence of SEQ ID NO:160 and a light chain variable region having at least 90% sequence identity to the amino acid sequence of SEQ ID NO:161. In some embodiments, a MARCO-binding agent comprises a heavy chain variable region having at least 95% sequence identity to the amino acid sequence of SEQ ID NO:160 and a light chain variable region having at least 95% sequence identity to the amino acid sequence of SEQ ID NO:161. In some embodiments, a MARCO-binding agent comprises a heavy chain variable region comprising the amino acid sequence of SEQ ID NO:160 and a light chain variable region comprising the amino acid sequence of SEQ ID NO:161.

In some embodiments, a MARCO-binding agent comprises a heavy chain having at least 80% sequence identity to the amino acid sequence of SEQ ID NO:167 and a light chain having at least 80% sequence identity to the amino acid sequence of SEQ ID NO:169. In some embodiments, a MARCO-binding agent comprises a heavy chain having at least 90% sequence identity to the amino acid sequence of SEQ ID NO:167 and a light chain having at least 90% sequence identity to the amino acid sequence of SEQ ID NO:169. In some embodiments, a MARCO-binding agent comprises a heavy chain having at least 95% sequence identity to the amino acid sequence of SEQ ID NO:167 and a light chain having at least 95% sequence identity to the amino acid sequence of SEQ ID NO:169. In some embodiments, a MARCO-binding agent comprises a heavy chain comprising the amino acid sequence of SEQ ID NO:167 and a light chain variable region comprising the amino acid sequence of SEQ ID NO:169.

In some embodiments, the MARCO-binding agent is antibody 6D8. In some embodiments, the MARCO-binding agent is a humanized version of antibody 6D8. In some embodiments, the MARCO-binding agent is a variant of antibody 6D8 or a variant of humanized antibody 6D8.

In some embodiments, a MARCO-binding agent comprises a heavy chain variable region CDR1, CDR2, and CDR3 and/or a light chain variable region CDR1, CDR2, and CDR3 from antibody 10G4, a humanized version thereof, or variants thereof. In some embodiments, a MARCO-binding agent comprises a heavy chain variable region comprising a heavy chain variable region CDR1, a heavy chain variable region CDR2, and a heavy chain variable region CDR3 from antibody 10G4. In other embodiments, a MARCO-binding agent comprises a light chain variable region comprising a light chain variable region CDR1, a light chain variable region CDR2, and a light chain variable region CDR3 from antibody 10G4. In some embodiments, a MARCO-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 10G4.

In some embodiments, a MARCO-binding agent comprises: (a) a heavy chain variable region CDR1 comprising the amino acid sequence GFSLSSYPIS (SEQ ID NO:194), a heavy chain variable region CDR2 comprising the amino acid sequence IIWTGGGTNYNSALKS (SEQ ID NO:195), a heavy chain variable region CDR3 comprising the amino acid sequence QNWDVNSALDY (SEQ ID NO:196), a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199); (b) a heavy chain variable region CDR1 comprising the amino acid sequence GFSLSSY (SEQ ID NO:200), a heavy chain variable region CDR2 comprising the amino acid sequence WTGGG (SEQ ID NO:185), a heavy chain variable region CDR3 comprising the amino acid sequence QNWDVNSALDY (SEQ ID NO:196), a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199); (c) a heavy chain variable region CDR1 comprising the amino acid sequence GFSLSSYPIS (SEQ ID NO:194), a heavy chain variable region CDR2 comprising the amino acid sequence IIWTGGGTN (SEQ ID NO:201), a heavy chain variable region CDR3 comprising the amino acid sequence QNWDVNSALDY (SEQ ID NO:196), a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199); (d) a heavy chain variable region CDR1 comprising the amino acid sequence SYPIS (SEQ ID NO:202), a heavy chain variable region CDR2 comprising the amino acid sequence IIWTGGGTNYNSALKS (SEQ ID NO:195), a heavy chain variable region CDR3 comprising the amino acid sequence QNWDVNSALDY (SEQ ID NO:196), a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199); or (e) a heavy chain variable region CDR1 comprising the amino acid sequence SSYPIS (SEQ ID NO:203), a heavy chain variable region CDR2 comprising the amino acid sequence WLGIIWTGGGTN (SEQ ID NO:204), a heavy chain variable region CDR3 comprising the amino acid sequence ASQNWDVNSALD (SEQ ID NO:205), a light chain variable region CDR1 comprising the amino acid sequence YSNLAWY (SEQ ID NO:206), a light chain variable region CDR2 comprising the amino acid sequence LLVYTATNLA (SEQ ID NO:207), and a light chain variable region CDR3 comprising the amino acid sequence QHFWNAPW (SEQ ID NO:208).

In some embodiments, a MARCO-binding agent comprises: (a) a heavy chain variable region comprising a heavy chain variable region CDR1 comprising the amino acid sequence GFSLSSYPIS (SEQ ID NO:194), a heavy chain variable region CDR2 comprising the amino acid sequence IIWTGGGTNYNSALKS (SEQ ID NO:195), a heavy chain variable region CDR3 comprising the amino acid sequence QNWDVNSALDY (SEQ ID NO:196), and a light chain variable region comprising a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199); (b) a heavy chain variable region comprising a heavy chain variable region CDR1 comprising the amino acid sequence GFSLSSY (SEQ ID NO:200), a heavy chain variable region CDR2 comprising the amino acid sequence WTGGG (SEQ ID NO:185), a heavy chain variable region CDR3 comprising the amino acid sequence QNWDVNSALDY (SEQ ID NO:196), and a light chain variable region comprising a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199); (c) a heavy chain variable region comprising a heavy chain variable region CDR1 comprising the amino acid sequence GFSLSSYPIS (SEQ ID NO:194), a heavy chain variable region CDR2 comprising the amino acid sequence IIWTGGGTN (SEQ ID NO:201), a heavy chain variable region CDR3 comprising the amino acid sequence QNWDVNSALDY (SEQ ID NO:196), and a light chain variable region comprising a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199); (d) a heavy chain variable region comprising a heavy chain variable region CDR1 comprising the amino acid sequence SYPIS (SEQ ID NO:202), a heavy chain variable region CDR2 comprising the amino acid sequence IIWTGGGTNYNSALKS (SEQ ID NO:195), a heavy chain variable region CDR3 comprising the amino acid sequence QNWDVNSALDY (SEQ ID NO:196), and a light chain variable region comprising a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199); or (e) a heavy chain variable region comprising a heavy chain variable region CDR1 comprising the amino acid sequence SSYPIS (SEQ ID NO:203), a heavy chain variable region CDR2 comprising the amino acid sequence WLGIIWTGGGTN (SEQ ID NO:204), a heavy chain variable region CDR3 comprising the amino acid sequence ASQNWDVNSALD (SEQ ID NO:205), and a light chain variable region comprising a light chain variable region CDR1 comprising the amino acid sequence YSNLAWY (SEQ ID NO:206), a light chain variable region CDR2 comprising the amino acid sequence LLVYTATNLA (SEQ ID NO:207), and a light chain variable region CDR3 comprising the amino acid sequence QHFWNAPW (SEQ ID NO:208).

In some embodiments, a MARCO-binding agent comprises: (a) a heavy chain variable region comprising a heavy chain variable region CDR1 comprising the amino acid sequence GFSLSSYPIS (SEQ ID NO:194), a heavy chain variable region CDR2 comprising the amino acid sequence IIWTGGGTNYNSALKS (SEQ ID NO:195), a heavy chain variable region CDR3 comprising the amino acid sequence QNWDVNSALDY (SEQ ID NO:196), and/or (b) a light chain variable region comprising a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199). In some embodiments, a MARCO-binding agent comprises a heavy chain variable region comprising a heavy chain variable region CDR1 comprising the amino acid sequence GFSLSSYPIS (SEQ ID NO:194), a heavy chain variable region CDR2 comprising the amino acid sequence IIWTGGGTNYNSALKS (SEQ ID NO:195), a heavy chain variable region CDR3 comprising the amino acid sequence QNWDVNSALDY (SEQ ID NO:196). In some embodiments, a MARCO-binding agent comprises a light chain variable region comprising a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199). In some embodiments, a MARCO-binding agent comprises: (a) a heavy chain variable region comprising a heavy chain variable region CDR1 comprising the amino acid sequence GFSLSSYPIS (SEQ ID NO:194), a heavy chain variable region CDR2 comprising the amino acid sequence IIWTGGGTNYNSALKS (SEQ ID NO:195), a heavy chain variable region CDR3 comprising the amino acid sequence QNWDVNSALDY (SEQ ID NO:196), and (b) a light chain variable region comprising a light chain variable region CDR1 comprising the amino acid sequence RASENIYSNLA (SEQ ID NO:197), a light chain variable region CDR2 comprising the amino acid sequence TATNLAD (SEQ ID NO:198), and a light chain variable region CDR3 comprising the amino acid sequence QHFWNAPWT (SEQ ID NO:199).

In some embodiments, a MARCO-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:162. In some embodiments, a MARCO-binding agent comprises a heavy chain variable region comprising the amino acid sequence of SEQ ID NO:162. In some embodiments, a MARCO-binding agent comprises a light chain variable region having at least 80%, at least 85%, at least 90%, at least 95%, at least 96%, at least 97%, at least 98%, or at least 99% sequence identity to the amino acid sequence of SEQ ID NO:163. In some embodiments, a MARCO-binding agent comprises a light chain variable region comprising the amino acid sequence of SEQ ID NO:163.

In some embodiments, a MARCO-binding agent comprises a heavy chain variable region having at least 80% sequence identity to the amino acid sequence of SEQ ID NO:162 and a light chain variable region having at least 80% sequence identity to the amino acid sequence of SEQ ID NO:163. In some embodiments, a MARCO-binding agent comprises a heavy chain variable region having at least 90% sequence identity to the amino acid sequence of SEQ ID NO:162 and a light chain variable region having at least 90% sequence identity to the amino acid sequence of SEQ ID NO:163. In some embodiments, a MARCO-binding agent comprises a heavy chain variable region having at least 95% sequence identity to the amino acid sequence of SEQ ID NO:162 and a light chain variable region having at least 95% sequence identity to the amino acid sequence of SEQ ID NO:163. In some embodiments, a MARCO-binding agent comprises a heavy chain variable region comprising the amino acid sequence of SEQ ID NO:162 and a light chain variable region comprising the amino acid sequence of SEQ ID NO:163.

In some embodiments, a MARCO-binding agent comprises a heavy chain having at least 80% sequence identity to the amino acid sequence of SEQ ID NO:171 and a light chain having at least 80% sequence identity to the amino acid sequence of SEQ ID NO:173. In some embodiments, a MARCO-binding agent comprises a heavy chain having at least 90% sequence identity to the amino acid sequence of SEQ ID NO:171 and a light chain having at least 90% sequence identity to the amino acid sequence of SEQ ID NO:173. In some embodiments, a MARCO-binding agent comprises a heavy chain having at least 95% sequence identity to the amino acid sequence of SEQ ID NO:171 and a light chain having at least 95% sequence identity to the amino acid sequence of SEQ ID NO:173. In some embodiments, a MARCO-binding agent comprises a heavy chain comprising the amino acid sequence of SEQ ID NO:171 and a light chain variable region comprising the amino acid sequence of SEQ ID NO:173.

In some embodiments, the MARCO-binding agent is antibody 10G4. In some embodiments, the MARCO-binding agent is a humanized version of antibody 10G4. In some embodiments, the MARCO-binding agent is a variant of antibody 10G4 or a variant of humanized antibody 10G4.

In some embodiments, a MARCO-binding agent comprises a heavy chain variable region CDR1, CDR2, and CDR3 and/or a light chain variable region CDR1, CDR2, and CDR3 from antibody 15A3, a humanized version thereof, or variants thereof. In some embodiments, a MARCO-binding agent comprises a heavy chain variable region comprising a heavy chain variable region CDR1, a heavy chain variable region CDR2, and a heavy chain variable region CDR3 from antibody 15A3. In other embodiments, a MARCO-binding agent comprises a light chain variable region comprising a light chain variable region CDR1, a light chain variable region CDR2, and a light chain variable region CDR3 from antibody 15A3. In some embodiments, a MARCO-binding agent comprises: (a) a heavy chain variable region comprising a heavy chain variable region CDR1, a heavy chain variable region CDR2, a heavy chain variable region CDR3; and (b) a light chain variable region comprising a light chain variable region CDR1, a light chain variable region CDR2, and a light chain variable region CDR3 from antibody 15A3.

In some embodiments, a MARCO-binding agent comprises: (a) a heavy chain variable region CDR1 comprising the amino acid sequence GYSFTDYNMY (SEQ ID NO:209), a heavy chain variable region CDR2 comprising the amino acid sequence YIDPYNGGTSYNQKFKG (SEQ ID NO:210), a heavy chain variable region CDR3 comprising the amino acid sequence LRSPYDYDRGDYVMDY (SEQ ID NO:211), a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214); (b) a heavy chain variable region CDR1 comprising the amino acid sequence GYSFTDY (SEQ ID NO:215), a heavy chain variable region CDR2 comprising the amino acid sequence DPYNGG (SEQ ID NO:216), a heavy chain variable region CDR3 comprising the amino acid sequence LRSPYDYDRGDYVMDY (SEQ ID NO:211), a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214); (c) a heavy chain variable region CDR1 comprising the amino acid sequence GYSFTDYNMY (SEQ ID NO:209), a heavy chain variable region CDR2 comprising the amino acid sequence YIDPYNGGTS (SEQ ID NO:217), a heavy chain variable region CDR3 comprising the amino acid sequence LRSPYDYDRGDYVMDY (SEQ ID NO:211), a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214); (d) a heavy chain variable region CDR1 comprising the amino acid sequence DYNMY (SEQ ID NO:218), a heavy chain variable region CDR2 comprising the amino acid sequence YIDPYNGGTSYNQKFKG (SEQ ID NO:210), a heavy chain variable region CDR3 comprising the amino acid sequence LRSPYDYDRGDYVMDY (SEQ ID NO:211), a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214); or (e) a heavy chain variable region CDR1 comprising the amino acid sequence TDYNMY (SEQ ID NO:219), a heavy chain variable region CDR2 comprising the amino acid sequence WIGYIDPYNGGTS (SEQ ID NO:220), a heavy chain variable region CDR3 comprising the amino acid sequence ARLRSPYDYDRGDYVMD (SEQ ID NO:221), a light chain variable region CDR1 comprising the amino acid sequence STSGYTYMHWY (SEQ ID NO:222), a light chain variable region CDR2 comprising the amino acid sequence LLIYLASNLE (SEQ ID NO:223), and a light chain variable region CDR3 comprising the amino acid sequence QHSRELPL (SEQ ID NO:224).

In some embodiments, a MARCO-binding agent comprises: (a) a heavy chain variable region comprising a heavy chain variable region CDR1 comprising the amino acid sequence GYSFTDYNMY (SEQ ID NO:209), a heavy chain variable region CDR2 comprising the amino acid sequence YIDPYNGGTSYNQKFKG (SEQ ID NO:210), a heavy chain variable region CDR3 comprising the amino acid sequence LRSPYDYDRGDYVMDY (SEQ ID NO:211), and a light chain variable region comprising a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214); (b) a heavy chain variable region comprising a heavy chain variable region CDR1 comprising the amino acid sequence GYSFTDY (SEQ ID NO:215), a heavy chain variable region CDR2 comprising the amino acid sequence DPYNGG (SEQ ID NO:216), a heavy chain variable region CDR3 comprising the amino acid sequence LRSPYDYDRGDYVMDY (SEQ ID NO:211), and a light chain variable region comprising a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214); (c) a heavy chain variable region comprising a heavy chain variable region CDR1 comprising the amino acid sequence GYSFTDYNMY (SEQ ID NO:209), a heavy chain variable region CDR2 comprising the amino acid sequence YIDPYNGGTS (SEQ ID NO:217), a heavy chain variable region CDR3 comprising the amino acid sequence LRSPYDYDRGDYVMDY (SEQ ID NO:211), and a light chain variable region comprising a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214); (d) a heavy chain variable region comprising a heavy chain variable region CDR1 comprising the amino acid sequence DYNMY (SEQ ID NO:218), a heavy chain variable region CDR2 comprising the amino acid sequence YIDPYNGGTSYNQKFKG (SEQ ID NO:210), a heavy chain variable region CDR3 comprising the amino acid sequence LRSPYDYDRGDYVMDY (SEQ ID NO:211), and a light chain variable region comprising a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214); or (e) a heavy chain variable region comprising a heavy chain variable region CDR1 comprising the amino acid sequence TDYNMY (SEQ ID NO:219), a heavy chain variable region CDR2 comprising the amino acid sequence WIGYIDPYNGGTS (SEQ ID NO:220), a heavy chain variable region CDR3 comprising the amino acid sequence ARLRSPYDYDRGDYVMD (SEQ ID NO:221), and a light chain variable region comprising a light chain variable region CDR1 comprising the amino acid sequence STSGYTYMHWY (SEQ ID NO:222), a light chain variable region CDR2 comprising the amino acid sequence LLIYLASNLE (SEQ ID NO:223), and a light chain variable region CDR3 comprising the amino acid sequence QHSRELPL (SEQ ID NO:224).

In some embodiments, a MARCO-binding agent comprises: (a) a heavy chain variable region comprising a heavy chain variable region CDR1 comprising the amino acid sequence GYSFTDYNMY (SEQ ID NO:209), a heavy chain variable region CDR2 comprising the amino acid sequence YIDPYNGGTSYNQKFKG (SEQ ID NO:210), a heavy chain variable region CDR3 comprising the amino acid sequence LRSPYDYDRGDYVMDY (SEQ ID NO:211), and/or (b) a light chain variable region comprising a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214). In some embodiments, a MARCO-binding agent comprises a heavy chain variable region comprising a heavy chain variable region CDR1 comprising the amino acid sequence GYSFTDYNMY (SEQ ID NO:209), a heavy chain variable region CDR2 comprising the amino acid sequence YIDPYNGGTSYNQKFKG (SEQ ID NO:210), a heavy chain variable region CDR3 comprising the amino acid sequence LRSPYDYDRGDYVMDY (SEQ ID NO:211). In some embodiments, a MARCO-binding agent comprises a light chain variable region comprising a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214). In some embodiments, a MARCO-binding agent comprises: (a) a heavy chain variable region comprising a heavy chain variable region CDR1 comprising the amino acid sequence GYSFTDYNMY (SEQ ID NO:209), a heavy chain variable region CDR2 comprising the amino acid sequence YIDPYNGGTSYNQKFKG (SEQ ID NO:210), a heavy chain variable region CDR3 comprising the amino acid sequence LRSPYDYDRGDYVMDY (SEQ ID NO:211), and (b) a light chain variable region comprising a light chain variable region CDR1 comprising the amino acid sequence RASKSVSTSGYTYMH (SEQ ID NO:212), a light chain variable region CDR2 comprising the amino acid sequence LASNLES (SEQ ID NO:213), and a light chain variable region CDR3 comprising the amino acid sequence QHSRELPLT (SEQ ID NO:214).

In some embodiments, a MARCO-binding agent comprises a heavy chain variable region having at least 80%, at least 85%, at least 90%, at least 95%, at least 96%, at least 97%, at least 98%, or at least 99% sequence identity to the amino acid sequence of SEQ ID NO:164. In some embodiments, a MARCO-binding agent comprises a heavy chain variable region comprising the amino acid sequence of SEQ ID NO:164. In some embodiments, a MARCO-binding agent comprises a light chain variable region having at least 80%, at least 85%, at least 90%, at least 95%, at least 96%, at least 97%, at least 98%, or at least 99% sequence identity to the amino acid sequence of SEQ ID NO:165. In some embodiments, a MARCO-binding agent comprises a light chain variable region comprising the amino acid sequence of SEQ ID NO:165.

In some embodiments, a MARCO-binding agent comprises a heavy chain variable region having at least 80% sequence identity to the amino acid sequence of SEQ ID NO:164 and a light chain variable region having at least 80% sequence identity to the amino acid sequence of SEQ ID NO:165. In some embodiments, a MARCO-binding agent comprises a heavy chain variable region having at least 90% sequence identity to the amino acid sequence of SEQ ID NO:164 and a light chain variable region having at least 90% sequence identity to the amino acid sequence of SEQ ID NO:165. In some embodiments, a MARCO-binding agent comprises a heavy chain variable region having at least 95% sequence identity to the amino acid sequence of SEQ ID NO:164 and a light chain variable region having at least 95% sequence identity to the amino acid sequence of SEQ ID NO:165. In some embodiments, a MARCO-binding agent comprises a heavy chain variable region comprising the amino acid sequence of SEQ ID NO:164 and a light chain variable region comprising the amino acid sequence of SEQ ID NO:165.

In some embodiments, a MARCO-binding agent comprises a heavy chain having at least 80% sequence identity to the amino acid sequence of SEQ ID NO:175 and a light chain having at least 80% sequence identity to the amino acid sequence of SEQ ID NO:177. In some embodiments, a MARCO-binding agent comprises a heavy chain having at least 90% sequence identity to the amino acid sequence of SEQ ID NO:175 and a light chain having at least 90% sequence identity to the amino acid sequence of SEQ ID NO:177. In some embodiments, a MARCO-binding agent comprises a heavy chain having at least 95% sequence identity to the amino acid sequence of SEQ ID NO:175 and a light chain having at least 95% sequence identity to the amino acid sequence of SEQ ID NO:177. In some embodiments, a MARCO-binding agent comprises a heavy chain comprising the amino acid sequence of SEQ ID NO:175 and a light chain variable region comprising the amino acid sequence of SEQ ID NO:177.

In some embodiments, the MARCO-binding agent is antibody 15A3. In some embodiments, the MARCO-binding agent is a humanized version of antibody 15A3. In some embodiments, the MARCO-binding agent is a variant of antibody 15A3 or a variant of humanized antibody 15A3.

In some embodiments, a MARCO-binding agent described herein comprises a detectable moiety. Detectable moieties, also referred to as detectable labels or detectable tags, are known to those of skill in the art. In some embodiments, the detectable moiety is a fluorescent label, a bioluminescent label, a chemiluminescent label, an enzyme, a small molecule, a radioisotope, or colloidal gold. In some embodiments, the detectable moiety is a fluorescent label.

In some embodiments, the MARCO-binding agents described herein are used in methods for detecting MARCO in a biological sample. In some embodiments, a method of detecting MARCO in a biological sample comprises: (a) contacting the biological sample with a MARCO-binding agent described herein; and (b) detecting the binding between the binding agent and MARCO in the sample. In some embodiments, the method uses flow cytometry, immunohistochemistry (IHC), western blot analysis, ELISA, or mass spectrometry. In some embodiments, the sample is a fresh sample, a frozen sample, or a formalin-fixed paraffin-embedded sample. In some embodiments, the sample is a tissue sample, a tissue biopsy, a cell pellet, a blood sample, or a pleural effusion.

V. Polynucleotides, Vectors, and Cells

In some embodiments, the disclosure encompasses polynucleotides comprising polynucleotides that encode a polypeptide (e.g., a LAIR-1-binding agent or a MARCO-binding agent) described herein. In some embodiments, the disclosure encompasses one or more polynucleotides that encode a binding agent (e.g., a LAIR-1-binding agent or a MARCO-binding agent) described herein. The term "polynucleotides that encode a polypeptide" encompasses a polynucleotide that includes only coding sequences for the polypeptide as well as a polynucleotide that includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, a polynucleotide comprises a polynucleotide encoding a heavy chain variable region and/or a light chain variable region of a LAIR-1-binding agent described herein. In some embodiments, a polynucleotide comprises a polynucleotide encoding a heavy chain variable region of a LAIR-1-binding agent described herein. In some embodiments, a polynucleotide comprises a polynucleotide encoding a light chain variable region of a LAIR-1-binding agent described herein. In some embodiments, a polynucleotide comprises a polynucleotide encoding a heavy chain variable region of a LAIR-1-binding agent described herein and a polynucleotide encoding a light chain variable region of the LAIR-1-binding agent.

In some embodiments, a polynucleotide comprises a polynucleotide encoding a heavy chain and/or a light chain of a LAIR-1-binding agent described herein. In some embodiments, a polynucleotide comprises a polynucleotide encoding a heavy chain of a LAIR-1-binding agent described herein. In some embodiments, a polynucleotide comprises a polynucleotide encoding a light chain of a LAIR-1-binding agent described herein. In some embodiments, a polynucleotide comprises a polynucleotide encoding a heavy chain of a LAIR-1-binding agent described herein and a polynucleotide encoding a light chain of the LAIR-1-binding agent.

In some embodiments, a polynucleotide comprises a polynucleotide encoding a heavy chain variable region and/or a light chain variable region of a MARCO-binding agent described herein. In some embodiments, a polynucleotide comprises a polynucleotide encoding a heavy chain variable region of a MARCO-binding agent described herein. In some embodiments, a polynucleotide comprises a polynucleotide encoding a light chain variable region of a MARCO-binding agent described herein. In some embodiments, a polynucleotide comprises a polynucleotide encoding a heavy chain variable region of a MARCO-binding agent described herein and a polynucleotide encoding a light chain variable region of the MARCO-binding agent.

In some embodiments, a polynucleotide comprises a polynucleotide encoding a heavy chain and/or a light chain of a MARCO-binding agent described herein. In some embodiments, a polynucleotide comprises a polynucleotide encoding a heavy chain of a MARCO-binding agent described herein. In some embodiments, a polynucleotide comprises a polynucleotide encoding a light chain of a MARCO-binding agent described herein. In some embodiments, a polynucleotide comprises a polynucleotide encoding a heavy chain of a MARCO-binding agent described herein and a polynucleotide encoding a light chain of the MARCO-binding agent.

In some embodiments, the polynucleotide comprises a polynucleotide encoding a polypeptide comprising an amino acid sequence selected from the group consisting of: SEQ ID NOs:115-140.

In some embodiments, the polynucleotide comprises a polynucleotide encoding a polypeptide comprising more than one amino acid sequence selected from the group consisting of: SEQ ID NOs:115-132. In some embodiments, the polynucleotide comprises a polynucleotide encoding (i) a polypeptide comprising an amino acid sequence of SEQ ID NO:115 and (ii) a polypeptide comprising an amino acid sequence of SEQ ID NO:116. In some embodiments, the polynucleotide comprises a polynucleotide encoding (i) a polypeptide comprising an amino acid sequence of SEQ ID NO:117 and (ii) a polypeptide comprising an amino acid sequence of SEQ ID NO:118. In some embodiments, the polynucleotide comprises a polynucleotide encoding (i) a polypeptide comprising an amino acid sequence of SEQ ID NO:119 and (ii) a polypeptide comprising an amino acid sequence of SEQ ID NO:120. In some embodiments, the polynucleotide comprises a polynucleotide encoding (i) a polypeptide comprising an amino acid sequence of SEQ ID NO:121 and (ii) a polypeptide comprising an amino acid sequence of SEQ ID NO:122. In some embodiments, the polynucleotide comprises a polynucleotide encoding (i) a polypeptide comprising an amino acid sequence of SEQ ID NO:123 and (ii) a polypeptide comprising an amino acid sequence of SEQ ID NO:124. In some embodiments, the polynucleotide comprises a polynucleotide encoding (i) a polypeptide comprising an amino acid sequence of SEQ ID NO:125 and (ii) a polypeptide comprising an amino acid sequence of SEQ ID NO:126. In some embodiments, the polynucleotide comprises a polynucleotide encoding (i) a polypeptide comprising an amino acid sequence of SEQ ID NO:127 and (ii) a polypeptide comprising an amino acid sequence of SEQ ID NO:128. In some embodiments, the polynucleotide comprises a polynucleotide encoding (i) a polypeptide comprising an amino acid sequence of SEQ ID NO:129 and (ii) a polypeptide comprising an amino acid sequence of SEQ ID NO:130. In some embodiments, the polynucleotide comprises a polynucleotide encoding (i) a polypeptide comprising an amino acid sequence of SEQ ID NO:131 and (ii) a polypeptide comprising an amino acid sequence of SEQ ID NO:132.

In some embodiments, the polynucleotide comprises a polynucleotide encoding a polypeptide comprising more than one amino acid sequence selected from the group consisting of: SEQ ID NOs:133-140. In some embodiments, the polynucleotide comprises a polynucleotide encoding (i) a polypeptide comprising an amino acid sequence of SEQ ID NO:133 and (ii) a polypeptide comprising an amino acid sequence of SEQ ID NO:135. In some embodiments, the polynucleotide comprises a polynucleotide encoding (i) a polypeptide comprising an amino acid sequence of SEQ ID NO:134 and (ii) a polypeptide comprising an amino acid sequence of SEQ ID NO:136. In some embodiments, the polynucleotide comprises a polynucleotide encoding (i) a polypeptide comprising an amino acid sequence of SEQ ID NO:137 and (ii) a polypeptide comprising an amino acid sequence of SEQ ID NO:139. In some embodiments, the polynucleotide comprises a polynucleotide encoding (i) a polypeptide comprising an amino acid sequence of SEQ ID NO:138 and (ii) a polypeptide comprising an amino acid sequence of SEQ ID NO:140.

In some embodiments, the polynucleotide comprises a polynucleotide encoding a polypeptide comprising an amino acid sequence selected from the group consisting of: SEQ ID NOs:160-177.

In some embodiments, the polynucleotide comprises a polynucleotide encoding a polypeptide comprising more than one amino acid sequence selected from the group consisting of: SEQ ID NOs:160-165. In some embodiments, the polynucleotide comprises a polynucleotide encoding (i) a polypeptide comprising an amino acid sequence of SEQ ID NO:160 and (ii) a polypeptide comprising an amino acid sequence of SEQ ID NO:161. In some embodiments, the polynucleotide comprises a polynucleotide encoding (i) a polypeptide comprising an amino acid sequence of SEQ ID NO:162 and (ii) a polypeptide comprising an amino acid sequence of SEQ ID NO:163. In some embodiments, the polynucleotide comprises a polynucleotide encoding (i) a polypeptide comprising an amino acid sequence of SEQ ID NO:164 and (ii) a polypeptide comprising an amino acid sequence of SEQ ID NO:165.

In some embodiments, the polynucleotide comprises a polynucleotide encoding a polypeptide comprising more than one amino acid sequence selected from the group consisting of: SEQ ID NOs:166-177. In some embodiments, the polynucleotide comprises a polynucleotide encoding (i) a polypeptide comprising an amino acid sequence of SEQ ID NO:166 and (ii) a polypeptide comprising an amino acid sequence of SEQ ID NO:168. In some embodiments, the polynucleotide comprises a polynucleotide encoding (i) a polypeptide comprising an amino acid sequence of SEQ ID NO:167 and (ii) a polypeptide comprising an amino acid sequence of SEQ ID NO:169. In some embodiments, the polynucleotide comprises a polynucleotide encoding (i) a polypeptide comprising an amino acid sequence of SEQ ID NO:170 and (ii) a polypeptide comprising an amino acid sequence of SEQ ID NO:172. In some embodiments, the polynucleotide comprises a polynucleotide encoding (i) a polypeptide comprising an amino acid sequence of SEQ ID NO:171 and (ii) a polypeptide comprising an amino acid sequence of SEQ ID NO:173. In some embodiments, the polynucleotide comprises a polynucleotide encoding (i) a polypeptide comprising an amino acid sequence of SEQ ID NO:174 and (ii) a polypeptide comprising an amino acid sequence of SEQ ID NO:176. In some embodiments, the polynucleotide comprises a polynucleotide encoding (i) a polypeptide comprising an amino acid sequence of SEQ ID NO:175 and (ii) a polypeptide comprising an amino acid sequence of SEQ ID NO:177.

The present disclosure also provides variants of the polynucleotides described herein, wherein the variant encodes, for example, fragments, analogs, and/or derivatives of a polypeptide. In some embodiments, the present disclosure provides a polynucleotide comprising a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding a polypeptide described herein.

In some embodiments, a polynucleotide comprises a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding an amino acid sequence selected from the group consisting of: SEQ ID NOs:115-140. Also provided is a polynucleotide that comprises a polynucleotide that hybridizes to a polynucleotide encoding an amino acid sequence selected from the group consisting of: SEQ ID NOs:115-140. In some embodiments, the hybridization is under conditions of high stringency as is known to those skilled in the art.

In some embodiments, a polynucleotide comprises a polynucleotide having a nucleotide sequence at least 80% identical, at least 85% identical, at least 90% identical, at least 95% identical, and in some embodiments, at least 96%, at least 97%, at least 98%, or at least 99% identical to a polynucleotide encoding an amino acid sequence selected from the group consisting of: SEQ ID NOs:160-177. Also provided is a polynucleotide that comprises a polynucleotide that hybridizes to a polynucleotide encoding an amino acid sequence selected from the group consisting of: SEQ ID NOs:160-177. In some embodiments, the hybridization is under conditions of high stringency as is known to those skilled in the art.

As used herein, the phrase "a polynucleotide having a nucleotide sequence at least 95% identical to a polynucleotide sequence" is intended to mean that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. It is understood by those of skill in the art that an appropriate calculation would be made for other "% identical" statements, for example, 90% identical or 85% identical. Mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations that produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). In some embodiments, a polynucleotide variant comprises one or more mutated codons comprising one or more (e.g., 1, 2, or 3) substitutions to the codon that change the amino acid encoded by that codon. Methods for introducing one or more substitutions into a codon are known in the art, including but not limited to, PCR mutagenesis and site-directed mutagenesis. Polynucleotide variants can be produced for a variety of reasons, for example, to optimize codon expression for a particular host (e.g., change codons in the human mRNA to those preferred by a bacterial host such as *E. coli*). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide comprises the coding sequence for a polypeptide fused in the same reading frame to a polynucleotide that aids in expression and secretion of a polypeptide from a host cell. In some embodiments, the polynucleotide that aids in expression and secretion is a leader sequence that functions as a secretory sequence for controlling transport of a polypeptide. In some embodiments, the polypeptide has a leader sequence cleaved by the host cell to form a "mature" form of the polypeptide.

In some embodiments, a polynucleotide comprises the coding sequence for a polypeptide fused in the same reading frame to a marker or tag sequence. For example, in some embodiments, a marker sequence is a hexa-histidine tag (HIS-tag; SEQ ID NO:153) that allows for efficient purification of the polypeptide fused to the marker. In some embodiments, a marker sequence is a hemagglutinin (HA) tag derived from the influenza hemagglutinin protein when a mammalian host is used. In some embodiments, the marker sequence is a FLAG™ tag. In some embodiments, a marker may be used in conjunction with other markers or tags.

In some embodiments, a polynucleotide is isolated. In some embodiments, a polynucleotide is substantially pure.

Vectors comprising any of the polynucleotides described herein are also provided. In some embodiments, a vector comprises a polynucleotide encoding a LAIR-1-binding agent described herein. In some embodiments, a vector comprises a polynucleotide encoding a polypeptide that is part of a LAIR-1-binding agent described herein. In some embodiments, a vector comprises a polynucleotide encoding an anti-LAIR-1 antibody described herein. In some embodiments, a vector comprises a polynucleotide encoding a heavy chain variable region described herein. In some embodiments, a vector comprises a polynucleotide encoding a light chain variable region described herein. In some embodiments, a vector comprises a first polynucleotide encoding a heavy chain variable region and a second polynucleotide encoding a light chain variable region described herein. In some embodiments, a vector comprises a polynucleotide encoding a heavy chain of an anti-LAIR antibody described herein. In some embodiments, a vector comprises a polynucleotide encoding a light chain of an anti-LAIR antibody described herein. In some embodiments, a vector comprises a polynucleotide encoding a heavy chain and a polynucleotide encoding a light chain of an anti-LAIR antibody described herein.

In some embodiments, a vector comprises a polynucleotide encoding a MARCO-binding agent described herein. In some embodiments, a vector comprises a polynucleotide encoding a polypeptide that is part of a MARCO-binding agent described herein. In some embodiments, a vector comprises a polynucleotide encoding an anti-MARCO antibody described herein. In some embodiments, a vector comprises a polynucleotide encoding a heavy chain variable region described herein. In some embodiments, a vector comprises a polynucleotide encoding a light chain variable region described herein. In some embodiments, a vector comprises a first polynucleotide encoding a heavy chain variable region and a second polynucleotide encoding a light chain variable region described herein. In some embodiments, a vector comprises a polynucleotide encoding a heavy chain of an anti-MARCO antibody described herein. In some embodiments, a vector comprises a polynucleotide encoding a light chain of an anti-MARCO antibody described herein. In some embodiments, a vector comprises a polynucleotide encoding a heavy chain and a polynucleotide encoding a light chain of an anti-MARCO antibody described herein.

Cells comprising any of the polynucleotides described herein are provided. In some embodiments, a cell comprises one or more polynucleotides encoding a LAIR-1-binding agent described herein. In some embodiments, a cell comprises one or more polynucleotides encoding a polypeptide that is part of a LAIR-1-binding agent described herein. In some embodiments, a cell comprises one or more polynucleotides encoding an anti-LAIR-1 antibody described herein. In some embodiments, a cell comprises a polynucleotide encoding a heavy chain variable region described herein. In some embodiments, a cell comprises a polynucleotide encoding a light chain variable region described herein. In some embodiments, a cell comprises a first polynucleotide encoding a heavy chain variable region and a second polynucleotide encoding a light chain variable region described herein. In some embodiments, a cell comprises a single polynucleotide encoding a heavy chain variable region and a light chain variable region described herein. In some embodiments, a cell comprises a polynucleotide encoding a heavy chain of an anti-LAIR antibody described herein. In some embodiments, a cell comprises a polynucleotide encoding a light chain of an anti-LAIR antibody described herein. In some embodiments, a cell comprises a first polynucleotide encoding a heavy chain and a second polynucleotide encoding a light chain of an anti-LAIR antibody described herein. In some embodiments, a cell comprises a single polynucleotide encoding a heavy chain and a light chain of an anti-LAIR antibody described herein.

In some embodiments, a cell comprises one or more polynucleotides encoding a MARCO-binding agent described herein. In some embodiments, a cell comprises one or more polynucleotides encoding a polypeptide that is part of a MARCO-binding agent described herein. In some embodiments, a cell comprises one or more polynucleotides encoding an anti-MARCO antibody described herein. In some embodiments, a cell comprises a polynucleotide encoding a heavy chain variable region described herein. In some embodiments, a cell comprises a polynucleotide encoding a light chain variable region described herein. In some embodiments, a cell comprises a first polynucleotide encoding a heavy chain variable region and a second polynucleotide encoding a light chain variable region described herein. In some embodiments, a cell comprises a single polynucleotide encoding a heavy chain variable region and a light chain variable region described herein. In some embodiments, a cell comprises a polynucleotide encoding a heavy chain of an anti-MARCO antibody described herein. In some embodiments, a cell comprises a polynucleotide encoding a light chain of an anti-MARCO antibody described herein. In some embodiments, a cell comprises a first polynucleotide encoding a heavy chain and a second polynucleotide encoding a light chain of an anti-MARCO antibody described herein. In some embodiments, a cell comprises a single polynucleotide encoding a heavy chain and a light chain of an anti-MARCO antibody described herein.

In addition, cells comprising the vectors described herein are provided. In some embodiments, a cell comprises one or more vectors expressing a LAIR-1-binding agent described herein. In some embodiments, a cell comprises one or more vectors expressing a polypeptide that is part of a LAIR-1-binding agent described herein. In some embodiments, a cell comprises one or more vectors expressing an anti-LAIR-1 antibody described herein. In some embodiments, a cell comprises a vector encoding a LAIR-1-binding agent described herein. In some embodiments, a cell comprises a first vector expressing a heavy chain variable region described herein and a second vector expressing a light chain variable region described herein. In some embodiments, a cell comprises a single vector expressing a heavy chain variable region and a light chain variable region described herein. In some embodiments, a cell comprises a first vector expressing a heavy chain of an anti-LAIR-1 antibody described herein and a second vector expressing a light chain of an anti-LAIR-1 antibody described herein. In some embodiments, a cell comprises a single vector expressing a heavy chain and a light chain of an anti-LAIR-1 antibody described herein.

In some embodiments, a cell comprises one or more vectors expressing a MARCO-binding agent described herein. In some embodiments, a cell comprises one or more vectors expressing a polypeptide that is part of a MARCO-binding agent described herein. In some embodiments, a cell comprises one or more vectors expressing an anti-MARCO antibody described herein. In some embodiments, a cell comprises a vector encoding a MARCO-binding agent described herein. In some embodiments, a cell comprises a first vector expressing a heavy chain variable region described herein and a second vector expressing a light chain variable region described herein. In some embodiments, a cell comprises a single vector expressing a heavy chain variable region and a light chain variable region described herein. In some embodiments, a cell comprises a first vector expressing a heavy chain of an anti-MARCO antibody described herein and a second vector expressing a light chain of an anti-MARCO antibody described herein. In some embodiments, a cell comprises a single vector expressing a heavy chain and a light chain of an anti-MARCO antibody described herein.

In some embodiments, a cell produces a LAIR-1-binding agent described herein. In some embodiments, a cell produces an anti-LAIR-1 antibody described herein. In some embodiments, a cell produces an antibody selected from the group consisting of: 47A1, 47H1, Hz47H1.v4, 57D12, 61H4, 62G10, Hz62G10.v1, 108D10, and 43H2. In some embodiments, the cell is a prokaryotic cell. In some embodiments, the cell is a eukaryotic cell. In some embodiments, the cell is a mammalian cell. In some embodiments, the cell is isolated. In some embodiments, the cell is a hybridoma. In some embodiments, a hybridoma produces an antibody selected from the group consisting of: 47A1, 47H1, Hz47H1.v4, 57D12, 61H4, 62G10, Hz62G10.v1, 108D10, and 43H2.

In some embodiments, a cell produces a MARCO-binding agent described herein. In some embodiments, a cell produces an anti-MARCO antibody described herein. In some embodiments, a cell produces an antibody selected from the group consisting of: 6D8, 10G4, and 15A3. In some embodiments, the cell is a prokaryotic cell. In some embodiments, the cell is a eukaryotic cell. In some embodiments, the cell is a mammalian cell. In some embodiments, the cell is isolated. In some embodiments, the cell is a hybridoma. In some embodiments, a hybridoma produces an antibody selected from the group consisting of: 6D8, 10G4, and 15A3.

VI. Methods of Making Binding Agents

The disclosure provides methods for making the LAIR-1-binding agents and the MARCO-binding agents described herein. In some embodiments, a method comprises providing a cell comprising a LAIR-1-binding agent described herein, culturing the cell under conditions that permit the expression of the binding agent, and isolating the binding agent. In some embodiments, a method comprises providing a cell comprising one or more polypeptides encoding a LAIR-1-binding agent described herein, culturing the cell under conditions that permit the expression of the binding agent, and isolating the binding agent. In some embodiments, a method comprises providing a cell comprising a heavy chain and a light chain of an anti-LAIR-1 antibody described herein, culturing the cell under conditions that permit the expression of the antibody, and isolating the antibody. In some embodiments, a method further comprises purifying the binding agent or antibody. In some embodiments, a method further comprises formulating the binding agent or antibody as a pharmaceutical composition (e.g., a sterile pharmaceutical composition).

In some embodiments, a method comprises providing a cell comprising a MARCO-binding agent described herein, culturing the cell under conditions that permit the expression of the binding agent, and isolating the binding agent. In some embodiments, a method comprises providing a cell comprising one or more polypeptides encoding a MARCO-binding agent described herein, culturing the cell under conditions that permit the expression of the binding agent, and isolating the binding agent. In some embodiments, a method comprises providing a cell comprising a heavy chain and a light chain of an anti-MARCO antibody described herein, culturing the cell under conditions that permit the expression of the antibody, and isolating the antibody. In some embodiments, a method further comprises purifying the binding agent or antibody. In some embodiments, a method further comprises formulating the binding agent or antibody as a pharmaceutical composition.

In some embodiments, a polynucleotide encoding a LAIR-1-binding agent described herein is transiently transfected into a cell. In some embodiments, a polynucleotide encoding a LAIR-1-binding agent described herein is stably transfected into a cell. In some embodiments, a vector comprising a polynucleotide encoding a LAIR-1-binding agent described herein is transiently transfected into a cell. In some embodiments, a vector comprising a polynucleotide encoding a LAIR-1-binding agent described herein is stably transfected into a cell.

In some embodiments, a polynucleotide encoding a MARCO-binding agent described herein is transiently transfected into a cell. In some embodiments, a polynucleotide encoding a MARCO-binding agent described herein is stably transfected into a cell. In some embodiments, a vector comprising a polynucleotide encoding a MARCO-binding agent described herein is transiently transfected into a cell. In some embodiments, a vector comprising a polynucleotide encoding a MARCO-binding agent described herein is stably transfected into a cell.

In some embodiments, the cell used to make a LAIR-1-binding agent or a MARCO-binding agent is a bacterial cell. In some embodiments, the cell used to make a LAIR-1-binding agent or a MARCO-binding agent is a yeast cell. In some embodiments, the cell used to make a LAIR-1-binding agent or a MARCO-binding agent is a mammalian cell. In some embodiments, the cell used to make a LAIR-1-binding agent or a MARCO-binding agent is a CHO cell. In other embodiments, the cell used to make a LAIR-1-binding agent or a MARCO-binding agent is a HEK-293 cell.

VII. Methods of Use and Pharmaceutical Compositions

The LAIR-1-binding agents of the disclosure are useful in a variety of applications including, but not limited to, therapeutic treatment methods, such as treatment of cancer. In some embodiments, the therapeutic treatment methods comprise immunotherapy for cancer. In some embodiments, a LAIR-1-binding agent is useful for activating, promoting, increasing, and/or enhancing an immune response to cancer or cancer cells. In some embodiments, a LAIR-1-binding agent is useful for activating, promoting, increasing, and/or enhancing an immune response to a tumor or tumor cells. The methods of use may be in vitro, ex vivo, or in vivo methods.

The present disclosure provides methods of disrupting, inhibiting, or blocking the binding of LAIR-1 to collagen. In some embodiments, a method of disrupting, inhibiting, or blocking the binding of LAIR-1 to collagen in a cell mixture comprises contacting the cell mixture with a LAIR-1-binding agent described herein. In some embodiments, a method of disrupting, inhibiting, or blocking the binding of LAIR-1 to collagen in a cell mixture comprises contacting the cell mixture with a LAIR-1-binding agent described herein, wherein the method results in disrupting, inhibiting, or blocking collagen-induced LAIR-1 activity. In some embodiments, a method of disrupting, inhibiting, or blocking the binding of LAIR-1 to collagen in a cell mixture comprises contacting the cell mixture with a LAIR-1-binding agent described herein, wherein the method results in disrupting, inhibiting, or blocking LAIR-1-induced suppression of myeloid cells. In some embodiments, a method of disrupting, inhibiting, or blocking the binding of LAIR-1 to collagen in a cell mixture comprises contacting the cell mixture with a LAIR-1-binding agent described herein, wherein the method results in disrupting, inhibiting, or blocking of LAIR-1-induced suppression of myeloid cell activity. In some embodiments, a method of disrupting, inhibiting, or blocking the binding of LAIR-1 to collagen in a cell mixture comprises contacting the cell mixture with a LAIR-1-binding agent described herein, wherein the method results in disrupting, inhibiting, or blocking of LAIR-1-induced suppression of NK cells or NK cell activity. In some embodiments, a method of disrupting, inhibiting, or blocking the binding of LAIR-1 to collagen in a cell mixture comprises contacting the cell mixture with a LAIR-1-binding agent described herein, wherein the method results in disrupting, inhibiting, or blocking of LAIR-1-induced suppression of T-cells or T-cell activity. In some embodiments, a method of disrupting, inhibiting, or blocking the binding of LAIR-1 to collagen: (i) restores FcR signaling activity in myeloid cells; (ii) restores cytokine and/or chemokine production by myeloid cells; and/or (iii) restores immune cell (e.g., T-cell) proliferation and/or activity. In some embodiments, the myeloid cell is a monocyte. In some embodiments, the myeloid cell is a macrophage. In some embodiments, the myeloid cell is a dendritic cell. In some embodiments, the myeloid cell is an APC.

The present disclosure provides methods of disrupting, inhibiting, or blocking the binding of LAIR-1 to MARCO. In some embodiments, a method of disrupting, inhibiting, or blocking the binding of LAIR-1 to MARCO in a cell mixture comprises contacting the cell mixture with a LAIR-1-binding agent described herein. In some embodiments, a method of disrupting, inhibiting, or blocking the binding of LAIR-1 to MARCO in a cell mixture comprises contacting the cell mixture with a LAIR-1-binding agent described herein, wherein the method results in disrupting, inhibiting, or blocking MARCO-induced LAIR-1 activity. In some embodiments, a method of disrupting, inhibiting, or blocking the binding of LAIR-1 to MARCO in a cell mixture comprises contacting the cell mixture with a LAIR-1-binding agent described herein, wherein the method results in disrupting, inhibiting, or blocking LAIR-1-induced suppression of myeloid cells. In some embodiments, a method of disrupting, inhibiting, or blocking the binding of LAIR-1 to MARCO in a cell mixture comprises contacting the cell mixture with a LAIR-1-binding agent described herein, wherein the method results in disrupting, inhibiting, or blocking of LAIR-1-induced suppression of myeloid cell activity. In some embodiments, a method of disrupting, inhibiting, or blocking the binding of LAIR-1 to MARCO in a cell mixture comprises contacting the cell mixture with a LAIR-1-binding agent described herein, wherein the method results in disrupting, inhibiting, or blocking of LAIR-1-induced suppression of NK cells or NK cell activity. In some embodiments, a method of disrupting, inhibiting, or blocking the binding of LAIR-1 to MARCO in a cell mixture comprises contacting the cell mixture with a LAIR-1-binding agent described herein, wherein the method results in disrupting, inhibiting, or blocking of LAIR-1-induced suppression of T-cells or T-cell activity. In some embodiments, a method of disrupting, inhibiting, or blocking the binding of LAIR-1 to MARCO: (i) restores FcR signaling activity in myeloid cells; (ii) restores cytokine and/or chemokine production by myeloid cells; and/or (iii) restores immune cell (e.g., T-cell) proliferation and/or activity. In some embodiments, the myeloid cell is a monocyte. In some embodiments, the myeloid cell is a macrophage. In some embodiments, the myeloid cell is a dendritic cell. In some embodiments, the myeloid cell is an APC.

The present disclosure provides methods of disrupting, inhibiting, or blocking the binding of LAIR-1 to COLEC12. In some embodiments, a method of disrupting, inhibiting, or blocking the binding of LAIR-1 to COLEC12 in a cell mixture comprises contacting the cell mixture with a LAIR-1-binding agent described herein.

In some embodiments, a method of disrupting, inhibiting, or blocking collagen-induced LAIR-1 activity in a cell comprises contacting the cell with a LAIR-1-binding agent described herein. In some embodiments, a method of disrupting and/or inhibiting LAIR-1 signaling in a cell comprises contacting the cell with a LAIR-1-binding agent described herein. In some embodiments, a method of disrupting, inhibiting, or blocking LAIR-1-induced suppression of a myeloid cell comprises contacting the myeloid cell with a LAIR-1-binding agent described herein. In some embodiments, a method of disrupting, inhibiting, or blocking LAIR-1-induced suppression of myeloid cell activity comprises contacting the cell with a LAIR-1-binding agent described herein. In some embodiments, the myeloid cell is a monocyte, a macrophage, a dendritic cell, or an APC.

In some embodiments, a method of disrupting, inhibiting, or blocking LAIR-1-induced suppression of a natural killer cell or natural killer cell activity comprises contacting the natural killer cell with a LAIR-1-binding agent described herein. In some embodiments, a method of disrupting, inhibiting, or blocking LAIR-1-induced suppression of a T-cell or T-cell activity comprises contacting the T-cell with a LAIR-1-binding agent described herein. In some embodiments, the T-cell is a cytotoxic T-cell (CTL). In some embodiments, a method of disrupting, inhibiting, or blocking the activity of a myeloid-derived suppressor cell (MDSC) comprises contacting the MDSC with a LAIR-1-binding agent described herein. In some embodiments, a method of disrupting, inhibiting, or blocking the activity of a regulatory T-cell (Treg) comprises contacting the regulatory T-cell with a LAIR-1-binding agent described herein.

The present disclosure provides methods of disrupting, inhibiting, or blocking the binding of LAIR-1 to collagen, MARCO, and/or COLEC12 in a subject. In some embodiments, a method of disrupting, inhibiting, or blocking the binding of LAIR-1 to collagen in a subject comprises administering to the subject a therapeutically effective amount of a LAIR-1-binding agent described herein. In some embodiments, a method of disrupting, inhibiting, or blocking the binding of LAIR-1 to MARCO in a subject comprises administering to the subject a therapeutically effective amount of a LAIR-1-binding agent described herein. In some embodiments, a method of disrupting, inhibiting, or blocking the binding of LAIR-1 to COLEC12 in a subject comprises administering to the subject a therapeutically effective amount of a LAIR-1-binding agent described herein.

In some embodiments, a method of disrupting, inhibiting, or blocking collagen-induced LAIR-1 activity in a subject comprises administering to the subject a therapeutically effective amount of a LAIR-1-binding agent described herein. In some embodiments, a method of disrupting, inhibiting, or blocking LAIR-1-induced suppression of a myeloid cell in a subject comprises administering to the subject a therapeutically effective amount of a LAIR-1-binding agent described herein. In some embodiments, a method of disrupting, inhibiting, or blocking LAIR-1-induced suppression of myeloid cell activity in a subject comprises administering to the subject a therapeutically effective amount of a LAIR-1-binding agent described herein. In some embodiments, a method of disrupting, inhibiting, or blocking LAIR-1-induced suppression of a myeloid cell or myeloid cell activity in a subject (i) restores FcR activity in myeloid cells; (ii) restores cytokine and/or chemokine production by myeloid cells; and/or (iii) restores immune cell (e.g., T-cell) proliferation and/or activity. In some embodiments, the myeloid cell is a monocyte. In some embodiments, the myeloid cell is a macrophage. In some embodiments, the myeloid cell is a dendritic cell. In some embodiments, the myeloid cell is an APC.

In some embodiments, a method of disrupting, inhibiting, or blocking LAIR-1-induced suppression of a natural killer cell or natural killer cell activity in a subject comprises administering to the subject a therapeutically effective amount of a LAIR-1-binding agent described herein. In some embodiments, a method of disrupting, inhibiting, or blocking LAIR-1-induced suppression of a T-cell or T-cell activity in a subject comprises administering to the subject a therapeutically effective amount of a LAIR-1-binding agent described herein. In some embodiments, the T-cell is a cytotoxic T-cell (CTL). In some embodiments, the T-cell is a tumor-associated T-cell.

In some embodiments, a method of disrupting, inhibiting, or blocking the activity of a MDSC in a subject comprises administering to the subject a therapeutically effective amount of a LAIR-1-binding agent described herein. In some embodiments, a method of disrupting, inhibiting, or blocking the activity of a regulatory T-cell (Treg) in a subject comprises administering to the subject a therapeutically effective amount of a LAIR-1-binding agent described herein.

The present disclosure provides methods for activating an immune response in a subject using a LAIR-1-binding agent described herein. In some embodiments, the disclosure provides methods for promoting an immune response in a subject using a LAIR-1-binding agent described herein. In some embodiments, the disclosure provides methods for increasing an immune response in a subject using a LAIR-1-binding agent described herein. In some embodiments, the disclosure provides methods for enhancing an immune response in a subject using a LAIR-1-binding agent described herein. In some embodiments, the activating, promoting, increasing, and/or enhancing of an immune response comprises stimulating myeloid cells. In some embodiments, the activating, promoting, increasing, and/or enhancing of an immune response comprises stimulating monocytes. In some embodiments, the activating, promoting, increasing, and/or enhancing of an immune response comprises stimulating macrophages. In some embodiments, the activating, promoting, increasing, and/or enhancing of an immune response comprises stimulating dendritic cells. In some embodiments, the activating, promoting, increasing, and/or enhancing of an immune response comprises stimulating APCs. In some embodiments, the activating, promoting, increasing, and/or enhancing of an immune response comprises increasing cell-mediated immunity. In some embodiments, the activating, promoting, increasing, and/or enhancing of an immune response comprises increasing effector T-cell activity. In some embodiments, the activating, promoting, increasing, and/or enhancing of an immune response comprises increasing CTL activity. In some embodiments, the activating, promoting, increasing, and/or enhancing of an immune response comprises inhibiting or decreasing the suppressive activity of Tregs. In some embodiments, the activating, promoting, increasing, and/or enhancing of an immune response comprises inhibiting or decreasing the suppressive activity of MDSCs. In some embodiments, the immune response is a result of antigenic stimulation. In some embodiments, the antigenic stimulation is a tumor cell. In some embodiments, the antigenic stimulation is cancer.

The present disclosure also provides methods for inhibiting growth of a tumor using a LAIR-1-binding agent described herein. In some embodiments, a method of inhibiting growth of a tumor comprises contacting a cell mixture with a LAIR-1-binding agent in vitro. For example, an immortalized cell line or a cancer cell line mixed with immune cells (e.g., T-cells or myeloid cells) is cultured in medium to which is added a test agent that binds LAIR-1. In some embodiments, tumor cells are isolated from a patient sample such as, for example, a tissue biopsy, pleural effusion, or blood sample, mixed with immune cells (e.g., T-cells or myeloid cells), and cultured in medium to which is added a test agent that binds LAIR-1. In some embodiments, the disclosure provides use of a LAIR-1-binding agent described herein in the manufacture or preparation of a medicament for inhibiting growth of a tumor or a tumor cell. In some embodiments, a LAIR-1-binding agent increases, promotes, and/or enhances the activity of effector immune cells. In some embodiments, a LAIR-1-binding agent inhibits tumor cell growth.

In some embodiments, a method of inhibiting tumor growth comprises contacting the tumor and/or tumor microenvironment with a LAIR-1-binding agent described herein in vivo. In some embodiments, contacting a tumor and/or tumor microenvironment with a LAIR-1-binding agent is undertaken in an animal model (e.g., a mouse model). In some embodiments, a test agent may be administered to mice that have tumors. In some embodiments, the test agent is a LAIR-1 binding agent that binds mouse LAIR-1. In some embodiments, the test agent is a surrogate antibody that binds mouse LAIR-1. In some embodiments, the test agent is an anti-mouse LAIR-1 antibody described herein. In some embodiments, the test agent is anti-mouse LAIR-1 antibody 43H2. In some embodiments, a LAIR-1-binding agent increases, promotes, and/or enhances the activity of immune cells in the mice. In some embodiments, a LAIR-1-binding agent inhibits tumor growth. In some embodiments, a LAIR-1-binding agent causes a tumor to regress. In some embodiments, a LAIR-1-binding agent is administered at the same time or shortly after introduction of tumor cells into the animal to prevent tumor growth ("preventative model"). In some embodiments, a LAIR-1-binding agent is administered after tumors have grown to a specified size or have become "established" for treatment ("therapeutic model"). In some embodiments, a LAIR-1-binding agent is administered to a transgenic animal (e.g., a transgenic mouse) that expresses human LAIR-1, wherein the transgenic animal has a tumor derived from human cells. In some embodiments, the LAIR-1-binding agent is an anti-mouse LAIR-1 antibody described herein. In some embodiments, the LAIR-1-binding agent is anti-mouse LAIR-1 antibody 43H2.

In some embodiments, a method of inhibiting tumor growth in a subject comprises administering to the subject a therapeutically effective amount of a LAIR-1-binding agent described herein. In some embodiments, a method of increasing or enhancing an immune response to a tumor or tumor cells in a subject comprises administering to the subject a therapeutically effective amount of a LAIR-1-binding agent described herein. In some embodiments, a method of activating or enhancing a persistent or long-term immune response to a tumor or tumor cells in a subject comprises administering to the subject a therapeutically effective amount of a LAIR-1-binding agent described herein. In some embodiments, a method of inhibiting tumor relapse or tumor regrowth in a subject comprises administering to the subject a therapeutically effective amount of a LAIR-1-binding agent described herein. In some embodiments, a method of inducing a persistent or long-term immunity that inhibits tumor relapse or tumor regrowth in a subject comprises administering to the subject a therapeutically effective amount of a LAIR-1-binding agent described herein.

In some embodiments, the disclosure provides use of a LAIR-1-binding agent described herein in the manufacture or preparation of a medicament for inhibiting growth of a tumor or tumor cell.

In some embodiments of the methods described herein, the tumor is a solid tumor. In some embodiments, the tumor is a pancreatic cancer, breast cancer, lung cancer (e.g., non-small cell lung cancer (NSCLC)), head and neck cancer (e.g., squamous cell carcinoma of the head and neck (SCCHN)), colorectal cancer (CRC), prostate cancer, skin cancer, melanoma, stomach cancer, gastric cancer, intestinal cancer, ovarian cancer, cervical and endocervical cancer, biliary cancer, uterine cancer, endometrial cancer, urinary bladder cancer, brain cancer, mesothelioma, esophageal cancer, liver cancer, kidney cancer (e.g., renal cell carcinoma (RCC)), or testicular cancer. In some embodiments, the tumor is a pancreatic tumor. In some embodiments, the tumor is an ovarian tumor. In some embodiments, the tumor is a breast tumor. In some embodiments, the tumor is a uterine tumor. In some embodiments, the subject has a tumor or the subject had a tumor that was at least partially removed.

The present disclosure provides methods of treating cancer. In some embodiments, a method of treating cancer in a subject comprises administering to the subject a therapeutically effective amount of a LAIR-1-binding agent described herein. In some embodiments, a LAIR-1-binding agent binds LAIR-1 and inhibits or reduces growth of the cancer. In some embodiments, a LAIR-1-binding agent binds LAIR-1-expressing cells, enhances an immune response to a cancer, and inhibits or reduces growth of the cancer. In some embodiments, a LAIR-1-binding agent binds LAIR-1-expressing cells, activates myeloid cells, enhances an immune response to a cancer, and inhibits or reduces growth of the cancer. In some embodiments, the subject has a cancerous tumor. In some embodiments, the subject has had a tumor at least partially removed.

In some embodiments, the disclosure provides use of a LAIR-1-binding agent described herein in the manufacture or preparation of a medicament for the treatment of cancer.

In some embodiments of the methods described herein, the cancer is pancreatic cancer, breast cancer, lung cancer (e.g., non-small cell lung cancer (NSCLC)), head and neck cancer (e.g., squamous cell carcinoma of the head and neck (SCCHN)), colorectal cancer (CRC), prostate cancer, skin cancer, melanoma, stomach cancer, gastric cancer, intestinal cancer, ovarian cancer, cervical and endocervical cancer, biliary cancer, uterine cancer, endometrial cancer, urinary bladder cancer, brain cancer, mesothelioma, esophageal cancer, liver cancer, kidney cancer (e.g., renal cell carcinoma (RCC)), or testicular cancer. In some embodiments, the cancer is pancreatic cancer. In some embodiments, the cancer is ovarian cancer. In some embodiments, the cancer is breast cancer. In some embodiments, the cancer is uterine cancer.

In some embodiments, the cancer is a hematologic cancer. In some embodiments, the cancer is a myelogenous leukemia. In some embodiments, the myelogenous cancer is acute myeloid leukemia (AML). In some embodiments, the myelogenous cancer is a chronic myeloid leukemia.

In some embodiments, the cancer is a myelodysplastic syndrome. Myelodysplastic syndromes (MDS) are a group of cancers in which immature blood cells in the bone marrow do not mature and therefore do not become healthy blood cells. In some embodiments, myelodysplastic syndrome develops into AML.

In some embodiments, the disclosure provides methods of activating myeloid cells in the tumor microenvironment. In some embodiments, a method of activating myeloid cells in the tumor microenvironment in a subject with a tumor comprises administering to the subject a therapeutically effective amount of a LAIR-1-binding agent described herein. In some embodiments, the myeloid cells are dendritic cells. In some embodiments, the myeloid cells are monocytes. In some embodiments, the myeloid cells are macrophages. In some embodiments, the myeloid cells are APCs.

In some embodiments, the disclosure provides methods of activating T-cells in the tumor microenvironment. In some embodiments, a method of activating T-cells in the tumor microenvironment in a subject with a tumor comprises administering to the subject a therapeutically effective amount of a LAIR-1-binding agent described herein. In some embodiments, the T-cells are CTLs. In some embodiments, the T-cells are tumor-associated T-cells.

In some embodiments of the methods described herein, a method is an in vitro method comprising contacting a cell with a LAIR-binding agent described herein. In some embodiments of the methods described herein, a method is an in vivo method comprising administering a therapeutically effective amount of a LAIR-1-binding agent described herein to a subject.

In some embodiments of the methods described herein, the LAIR-1-binding agent is an antibody selected from the group consisting of: Hz47H1.v4, Hz62G10.v1, 47A1, 47H1, 57D12, 61H4, 62G10, and 108D10. In some embodiments of the methods described herein, the LAIR-1-binding agent is antibody Hz47H1.v4.

In some embodiments of the methods described herein, the LAIR-1-binding agent comprises a heavy chain variable region CDR1, CDR2, and CDR3 and a light chain variable region CDR1, CDR2, and CDR3 of antibody 47H1. In some embodiments of the methods described herein, the LAIR-1-binding agent comprises a heavy chain variable region CDR1, CDR2, and CDR3 and a light chain variable region CDR1, CDR2, and CDR3 of antibody Hz47H1.v4.

In some embodiments of the methods described herein, the LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26) or RIRTKNYNYATFYADSVKD (SEQ ID NO:41), and a heavy chain variable region CDR3 comprising the amino acid sequence DRAGFFAY (SEQ ID NO:27), and (b) a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29) or AATSLAE (SEQ ID NO:42), and a light chain variable region CDR3 comprising the amino acid sequence QQLYSTPLT (SEQ ID NO:30). In some embodiments of the methods described herein, the LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATFYADSVKD (SEQ ID NO:26), and a heavy chain variable region CDR3 comprising the amino acid sequence DRAGFFAY (SEQ ID NO:27), and (b) a light chain variable region comprising a light chain variable region CDR1 comprising the amino acid sequence LASQTIGTWLG (SEQ ID NO:28), a light chain variable region CDR2 comprising the amino acid sequence AATSLAD (SEQ ID NO:29), and a light chain variable region CDR3 comprising the amino acid sequence QQLYSTPLT (SEQ ID NO:30). In some embodiments of the methods described herein, the LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNYNYATFYADSVKD (SEQ ID NO:41), and a heavy chain variable region CDR3 comprising the amino acid sequence DRAGFFAY (SEQ ID NO:27), and (b) a light chain variable region comprising a light chain variable region CDR1 comprising the amino acid sequence LASQTIGTWLG (SEQ ID NO:28), a light chain variable region CDR2 comprising the amino acid sequence AATSLAE (SEQ ID NO:42), and a light chain variable region CDR3 comprising the amino acid sequence QQLYSTPLT (SEQ ID NO:30).

In some embodiments of the methods described herein, the LAIR-1-binding agent comprises a heavy chain variable region of amino acid sequence SEQ ID NO:117 and a light chain variable region of amino acid sequence SEQ ID NO:118. In some embodiments of the methods described herein, the LAIR-1-binding agent comprises a polypeptide of amino acid sequence SEQ ID NO:117. In some embodiments of the methods described herein, the LAIR-1-binding agent comprises a polypeptide of amino acid sequence SEQ ID NO:118. In some embodiments of the methods described herein, the LAIR-1-binding agent comprises a polypeptide of amino acid sequence SEQ ID NO:117 and a polypeptide of amino acid sequence SEQ ID NO:118.

In some embodiments of the methods described herein, the LAIR-1-binding agent comprises a heavy chain variable region of amino acid sequence SEQ ID NO:119 and a light chain variable region of amino acid sequence SEQ ID NO:120. In some embodiments of the methods described herein, the LAIR-1-binding agent comprises a polypeptide of amino acid sequence SEQ ID NO:119. In some embodiments of the methods described herein, the LAIR-1-binding agent comprises a polypeptide of amino acid sequence SEQ ID NO:120. In some embodiments of the methods described herein, the LAIR-1-binding agent comprises a polypeptide of amino acid sequence SEQ ID NO:119 and a polypeptide of amino acid sequence SEQ ID NO:120.

In some embodiments of the methods described herein, the LAIR-1-binding agent comprises a heavy chain of amino acid sequence SEQ ID NO:134. In some embodiments of the methods described herein, the LAIR-1-binding agent comprises a light chain of amino acid sequence SEQ ID NO:136. In some embodiments of the methods described herein, the LAIR-1-binding agent comprises a heavy chain of amino acid sequence SEQ ID NO:134 and a light chain of amino acid sequence SEQ ID NO:136.

In some embodiments of the methods described herein, the LAIR-1-binding agent is an anti-LAIR-1 antibody that comprises a heavy chain of amino acid sequence SEQ ID NO:134. In some embodiments of the methods described herein, the LAIR-1-binding agent is an anti-LAIR-1 antibody that comprises a light chain of amino acid sequence SEQ ID NO:136. In some embodiments of the methods described herein, the LAIR-1-binding agent is an anti-LAIR-1 antibody that comprises a heavy chain of amino acid sequence SEQ ID NO:134 and a light chain of amino acid sequence SEQ ID NO:136.

In some embodiments of the methods described herein, the LAIR-1-binding agent is antibody 47H1. In some embodiments of the methods described herein, the LAIR-1-binding agent is a humanized version of antibody 47H1 (e.g., Hz47H1.v4). In some embodiments of the methods described herein, the LAIR-1-binding agent is a variant of antibody 47H1 or a variant of humanized 47H1. In some embodiments of the methods described herein, the LAIR-1-binding agent is antibody Hz47H1.v4.

In some embodiments of the methods described herein, the LAIR-1-binding agent comprises a heavy chain variable region CDR1, CDR2, and CDR3 and a light chain variable region CDR1, CDR2, and CDR3 of antibody 47A1.

In some embodiments of the methods described herein, the LAIR-1-binding agent comprises: (a) a heavy chain variable region comprising a heavy chain variable region CDR1 comprising the amino acid sequence GFTFNTYAIH (SEQ ID NO:9), a heavy chain variable region CDR2 comprising the amino acid sequence RIRSKSTNYATYY-ADSVKD (SEQ ID NO:10), and a heavy chain variable region CDR3 comprising the amino acid sequence ENWYYYALDY (SEQ ID NO:11), and (b) a light chain variable region comprising a light chain variable region CDR1 comprising the amino acid sequence RASGNIH-NYLT (SEQ ID NO:12), a light chain variable region CDR2 comprising the amino acid sequence NAKTLED (SEQ ID NO:13), and a light chain variable region CDR3 comprising the amino acid sequence QHFWSTPFT (SEQ ID NO:14).

In some embodiments of the methods described herein, the LAIR-1-binding agent comprises a heavy chain variable region of amino acid sequence SEQ ID NO:115 and a light chain variable region of amino acid sequence SEQ ID NO:116. In some embodiments of the methods described herein, the LAIR-1-binding agent comprises a polypeptide of amino acid sequence SEQ ID NO:115. In some embodiments of the methods described herein, the LAIR-1-binding agent comprises a polypeptide of amino acid sequence SEQ ID NO:116. In some embodiments of the methods described herein, the LAIR-1-binding agent comprises a polypeptide of amino acid sequence SEQ ID NO:115 and a polypeptide of amino acid sequence SEQ ID NO:116.

In some embodiments of the methods described herein, the LAIR-1-binding agent is antibody 47A1. In some embodiments of the methods described herein, the LAIR-1-binding agent is a humanized version of antibody 47A1. In some embodiments of the methods described herein, the LAIR-1-binding agent is a variant of antibody 47A1 or a variant of humanized 47A1.

In some embodiments of the methods described herein, the LAIR-1-binding agent comprises a heavy chain variable region CDR1, CDR2, and CDR3 and a light chain variable region CDR1, CDR2, and CDR3 of antibody 57D12.

In some embodiments of the methods described herein, the LAIR-1-binding agent comprises: (a) a heavy chain variable region comprising a heavy chain variable region CDR1 comprising the amino acid sequence GYSFTSFGIS (SEQ ID NO:46), a heavy chain variable region CDR2 comprising the amino acid sequence EIYPRSDNT-FYNEKFKG (SEQ ID NO:47), and a heavy chain variable region CDR3 comprising the amino acid sequence HFGSSSFDY (SEQ ID NO:48), and (b) a light chain variable region comprising a light chain variable region CDR1 comprising the amino acid sequence SASSSVSSIYFH (SEQ ID NO:49), a light chain variable region CDR2 comprising the amino acid sequence RASN-LAS (SEQ ID NO:50), and a light chain variable region CDR3 comprising the amino acid sequence QQWSGYPLT (SEQ ID NO:51).

In some embodiments of the methods described herein, the LAIR-1-binding agent comprises a heavy chain variable region of amino acid sequence SEQ ID NO:121 and a light chain variable region of amino acid sequence SEQ ID NO:122. In some embodiments of the methods described herein, the LAIR-1-binding agent comprises a polypeptide of amino acid sequence SEQ ID NO:121. In some embodiments of the methods described herein, the LAIR-1-binding agent comprises a polypeptide of amino acid sequence SEQ ID NO:122. In some embodiments of the methods described herein, the LAIR-1-binding agent comprises a polypeptide of amino acid sequence SEQ ID NO:121 and a polypeptide of amino acid sequence SEQ ID NO:122.

In some embodiments of the methods described herein, the LAIR-1-binding agent is antibody 57D12. In some embodiments of the methods described herein, the LAIR-1-binding agent is a humanized version of antibody 57D12. In some embodiments of the methods described herein, the LAIR-1-binding agent is a variant of antibody 57D12 or variant of humanized antibody 57D12.

In some embodiments of the methods described herein, the LAIR-1-binding agent comprises a heavy chain variable region CDR1, CDR2, and CDR3 and a light chain variable region CDR1, CDR2, and CDR3 of antibody 61H4.

In some embodiments of the methods described herein, the LAIR-1-binding agent comprises: (a) a heavy chain variable region comprising a heavy chain variable region CDR1 comprising the amino acid sequence GYTFTDYYYMN (SEQ ID NO:62), a heavy chain variable region CDR2 comprising the amino acid sequence YIYPNNGATSYNQKFKG (SEQ ID NO:63), and a heavy chain variable region CDR3 comprising the amino acid sequence DGYSSNYYTMDY (SEQ ID NO:64), and (b) a light chain variable region comprising a light chain variable region CDR1 comprising the amino acid sequence QASQGTSINLN (SEQ ID NO:65), a light chain variable region CDR2 comprising the amino acid sequence GASN-LED (SEQ ID NO:66), and a light chain variable region CDR3 comprising the amino acid sequence LQHTYLPYT (SEQ ID NO:67).

In some embodiments of the methods described herein, the LAIR-1-binding agent comprises a heavy chain variable region of amino acid sequence SEQ ID NO:123 and a light chain variable region of amino acid sequence SEQ ID NO:124. In some embodiments of the methods described herein, the LAIR-1-binding agent comprises a polypeptide of amino acid sequence SEQ ID NO:123. In some embodiments of the methods described herein, the LAIR-1-binding agent comprises a polypeptide of amino acid sequence SEQ ID NO:124. In some embodiments of the methods described herein, the LAIR-1-binding agent comprises a polypeptide of amino acid sequence SEQ ID NO:123 and a polypeptide of amino acid sequence SEQ ID NO:124.

In some embodiments of the methods described herein, the LAIR-1-binding agent is antibody 61H4. In some embodiments of the methods described herein, the LAIR-1-binding agent is a humanized version of antibody 61H4. In some embodiments of the methods described herein, the LAIR-1-binding agent is a variant of antibody 61H4 or a variant of humanized antibody 61H4.

In some embodiments of the methods described herein, the LAIR-1-binding agent comprises a heavy chain variable region CDR1, CDR2, and CDR3 and a light chain variable region CDR1, CDR2, and CDR3 of antibody 62G10 or a humanized version of antibody 62G10, (e.g., Hz62G10.v1).

In some embodiments of the methods described herein, the LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNFATYY-ADSVKD (SEQ ID NO:78), and a heavy chain variable region CDR3 comprising the amino acid sequence GPYFDY (SEQ ID NO:79), and (b) a light chain variable region comprising a light chain variable region CDR1 comprising the amino acid sequence LASQTIGTWLA (SEQ ID NO:80), a light chain variable region CDR2 comprising the amino acid sequence AATSLAD (SEQ ID NO:29), and a light chain variable region CDR3 comprising the amino acid sequence QQLYSTPYT (SEQ ID NO:81).

In some embodiments of the methods described herein, the LAIR-1-binding agent comprises a heavy chain variable region of amino acid sequence SEQ ID NO:125 and a light chain variable region of amino acid sequence SEQ ID NO:126. In some embodiments of the methods described herein, the LAIR-1-binding agent comprises a polypeptide of amino acid sequence SEQ ID NO:125. In some embodiments of the methods described herein, the LAIR-1-binding agent comprises a polypeptide of amino acid sequence SEQ ID NO:126. In some embodiments of the methods described herein, the LAIR-1-binding agent comprises a polypeptide of amino acid sequence SEQ ID NO:125 and a polypeptide of amino acid sequence SEQ ID NO:126.

In some embodiments of the methods described herein, the LAIR-1-binding agent comprises a heavy chain variable region of amino acid sequence SEQ ID NO:127 and a light chain variable region of amino acid sequence SEQ ID NO:128. In some embodiments of the methods described herein, the LAIR-1-binding agent comprises a polypeptide of amino acid sequence SEQ ID NO:127. In some embodiments of the methods described herein, the LAIR-1-binding agent comprises a polypeptide of amino acid sequence SEQ ID NO:128. In some embodiments of the methods described herein, the LAIR-1-binding agent comprises a polypeptide of amino acid sequence SEQ ID NO:127 and a polypeptide of amino acid sequence SEQ ID NO:128.

In some embodiments of the methods described herein, the LAIR-1-binding agent is antibody 62G10. In some embodiments of the methods described herein, the LAIR-1-binding agent is a humanized version of antibody 62G10 (e.g., Hz62G10). In some embodiments of the methods described herein, the LAIR-1-binding agent is a variant of antibody 62G10 or a variant of humanized antibody 62G10. In some embodiments of the methods described herein, the LAIR-1-binding agent is antibody Hz62G10.v1.

In some embodiments of the methods described herein, the LAIR-1-binding agent comprises a heavy chain variable region CDR1, CDR2, and CDR3 and a light chain variable region CDR1, CDR2, and CDR3 of antibody 108D10.

In some embodiments of the methods described herein, the LAIR-1-binding agent comprises: (a) a heavy chain variable region comprising a heavy chain variable region CDR1 comprising the amino acid sequence GFTFNINAMN (SEQ ID NO:25), a heavy chain variable region CDR2 comprising the amino acid sequence RIRTKNNNYATYY-ADSVKD (SEQ ID NO:88), and a heavy chain variable region CDR3 comprising the amino acid sequence DRYG-GAMAY (SEQ ID NO:89), and (b) a light chain variable region comprising a light chain variable region CDR1 comprising the amino acid sequence KASEDIYNRLA (SEQ ID NO:90), a light chain variable region CDR2 comprising the amino acid sequence SATSLET (SEQ ID NO:91), and a light chain variable region CDR3 comprising the amino acid sequence QQYWTIPYT (SEQ ID NO:92).

In some embodiments of the methods described herein, the LAIR-1-binding agent comprises a heavy chain variable region of amino acid sequence SEQ ID NO:129 and a light chain variable region of amino acid sequence SEQ ID NO:130. In some embodiments of the methods described herein, the LAIR-1-binding agent comprises a polypeptide of amino acid sequence SEQ ID NO:129. In some embodiments of the methods described herein, the anti-LAIR-1 antibody comprises a polypeptide of amino acid sequence SEQ ID NO:130. In some embodiments of the methods described herein, the LAIR-1-binding agent comprises a polypeptide of amino acid sequence SEQ ID NO:129 and a polypeptide of amino acid sequence SEQ ID NO:130.

In some embodiments of the methods described herein, the LAIR-1-binding agent is antibody 108D10. In some embodiments of the methods described herein, the LAIR-1-binding agent is a humanized version of antibody 108D10. In some embodiments of the methods described herein, the LAIR-1-binding agent is a variant of antibody 108D10 or a variant of humanized antibody 108D10.

In some embodiments of the methods described herein, the subject is human.

In some embodiments of the methods described herein, the LAIR-1-binding agent comprises a heavy chain variable region CDR1, CDR2, and CDR3 and a light chain variable region CDR1, CDR2, and CDR3 of antibody 43H2.

In some embodiments of the methods described herein, the LAIR-1-binding agent comprises: (a) a heavy chain variable region comprising a heavy chain variable region CDR1 comprising the amino acid sequence GFTFSNYGIH (SEQ ID NO:99), a heavy chain variable region CDR2 comprising the amino acid sequence SISPSGRSTY-FRDSVKG (SEQ ID NO:100), and a heavy chain variable region CDR3 comprising the amino acid sequence GINYSSFDY (SEQ ID NO:101), and (b) a light chain variable region comprising a light chain variable region CDR1 comprising the amino acid sequence KASQNVGSHVD (SEQ ID NO:102), a light chain variable region CDR2 comprising the amino acid sequence TASN-RYT (SEQ ID NO:103), and a light chain variable region CDR3 comprising the amino acid sequence MQSNSYPPT (SEQ ID NO:104).

In some embodiments of the methods described herein, the LAIR-1-binding agent comprises a heavy chain variable region of amino acid sequence SEQ ID NO:131 and a light chain variable region of amino acid sequence SEQ ID NO:132. In some embodiments of the methods described herein, the LAIR-1-binding agent comprises a polypeptide of amino acid sequence SEQ ID NO:131. In some embodiments of the methods described herein, the LAIR-1-binding agent comprises a polypeptide of amino acid sequence SEQ ID NO:132. In some embodiments of the methods described herein, the LAIR-1-binding agent comprises a polypeptide of amino acid sequence SEQ ID NO:131 and a polypeptide of amino acid sequence SEQ ID NO:132.

In some embodiments of the methods described herein, the LAIR-1-binding agent is antibody 43H2. In some embodiments of the methods described herein, the LAIR-1-binding agent is a humanized version of antibody 43H2. In some embodiments of the methods described herein, the LAIR-1-binding agent is a variant of antibody 43H2 or a variant of humanized antibody 43H2.

For the treatment of a disease, the appropriate dosage of a LAIR-1-binding agent of the present disclosure depends on the disorder or disease to be treated, the severity and course of the disorder or disease, the responsiveness of the disorder or disease, whether the agent is administered for therapeutic or preventative purposes, previous therapy, the patient's clinical history, and so on. A LAIR-1-binding agent can be administered one time or over a series of treatments lasting from several days to several months, or until a cure is effected or a diminution of the disease state is achieved.

In some embodiments, dosage of a LAIR-1-binding agent is from 0.01 µg/kg to 100 mg/kg of body weight, from 0.1 µg/kg to 100 mg/kg of body weight, from 1 µg/kg to 100 mg/kg of body weight, from 1 mg/kg to 100 mg/kg of body weight, 1 mg/kg to 80 mg/kg of body weight, from 1 mg/kg to 50 mg/kg of body weight, from 1 mg/kg to 25 mg/kg of body weight, from 1 mg/kg to 15 mg/kg of body weight, from 10 mg/kg to 100 mg/kg of body weight, from 10 mg/kg to 75 mg/kg of body weight, or from 10 mg/kg to 50 mg/kg of body weight. In some embodiments, dosage of a LAIR-1-binding agent is from about 0.1 mg to about 20 mg/kg of body weight. In some embodiments, dosage of a LAIR-1-binding agent is about 0.5 mg/kg of body weight. In some embodiments, dosage of a LAIR-1-binding agent is about 1 mg/kg of body weight. In some embodiments, dosage of a LAIR-1-binding agent is about 1.5 mg/kg of body weight. In some embodiments, dosage of a LAIR-1-binding agent is about 2 mg/kg of body weight. In some embodiments, dosage of a LAIR-1-binding agent is about 2.5 mg/kg of body weight. In some embodiments, dosage of a LAIR-1-binding agent is about 5 mg/kg of body weight. In some embodiments, dosage of a LAIR-1-binding agent is about 7.5 mg/kg of body weight. In some embodiments, dosage of a LAIR-1-binding agent is about 10 mg/kg of body weight. In some embodiments, dosage of a LAIR-1-binding agent is about 12.5 mg/kg of body weight. In some embodiments, dosage of a LAIR-1-binding agent is about 15 mg/kg of body weight.

In some embodiments, a LAIR-1-binding agent is dosed once or more daily, weekly, monthly, or yearly. In some embodiments, a LAIR-1-binding agent is dosed once every week, once every two weeks, once every three weeks, or once every four weeks. In some embodiments, a LAIR-1-binding agent is dosed once a week. In some embodiments, a LAIR-1-binding agent is dosed once every two weeks. In some embodiments, a LAIR-1-binding agent is dosed once every three weeks. In some embodiments, a LAIR-1-binding agent is dosed once every four weeks.

In some embodiments of the methods described herein, a method comprises administering a LAIR-1-binding agent described herein in combination with at least one additional therapeutic agent or therapeutic therapy. Treatment with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to an agent will develop.

In some embodiments of the methods described, the combination of a LAIR-1-binding agent described herein and at least one additional therapeutic agent results in additive or synergistic results. In some embodiments, the combination therapy results in an increase in the therapeutic index of the LAIR-1-binding agent. In some embodiments, the combination therapy results in an increase in the therapeutic index of the additional therapeutic agent(s). In some embodiments, the combination therapy results in a decrease in the toxicity and/or side effects of the LAIR-1-binding agent. In some embodiments, the combination therapy results in a decrease in the toxicity and/or side effects of the additional therapeutic agent(s). In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, a combination treatment comprises one additional therapeutic agent. In some embodiments of the methods described herein, a combination treatment comprises two or more additional therapeutic agents.

Useful classes of therapeutic agents include, but are not limited to, anti-tubulin agents, auristatins, DNA minor groove binders, DNA replication inhibitors, alkylating agents (e.g., platinum complexes such as cisplatin, mono (platinum), bis(platinum) and tri-nuclear platinum complexes and carboplatin), anthracyclines, antibiotics, anti-folates, anti-metabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In some embodiments, the second therapeutic agent is an alkylating agent, an antimetabolite, an antimitotic, a topoisomerase inhibitor, or an angiogenesis inhibitor.

Therapeutic agents that may be administered in combination with the LAIR-1-binding agents described herein include chemotherapeutic agents. Thus, in some embodiments, the method or treatment involves the administration of a LAIR-1-binding agent of the present disclosure in combination with a chemotherapeutic agent or in combination with a cocktail of chemotherapeutic agents.

Chemotherapeutic agents useful in the present disclosure include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; piranibicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT 11; topoisomerase inhibitor RFS 2000; difluoromethylomithine (DMFO); retinoic acid; esperamicins; capecitabine (XELODA); and pharmaceutically acceptable salts, acids or derivatives of any of the above.

Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above.

In some embodiments of the methods described herein, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In some embodiments, the additional therapeutic agent is gemcitabine.

In some embodiments of the methods described herein, the chemotherapeutic agent is an antimitotic agent, including, but not limited to, agents that bind tubulin. In some embodiments, the agent is a taxane. In some embodiments, the agent is paclitaxel or docetaxel, or a pharmaceutically acceptable salt, acid, or derivative of paclitaxel or docetaxel. In some embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In some embodiments, the additional therapeutic agent is paclitaxel. In some embodiments, the additional therapeutic agent is nab-paclitaxel.

In some embodiments of the methods described herein, an additional therapeutic agent comprises an agent such as a small molecule. For example, treatment can involve the combined administration of a LAIR-1-binding agent of the present disclosure with a small molecule that acts as an inhibitor against tumor-associated antigens including, but not limited to, EGFR, HER2 (ErbB2), and/or VEGF. In some embodiments, a LAIR-1-binding agent of the present disclosure is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In some embodiments of the methods described herein, an additional therapeutic agent comprises a biological molecule, such as an antibody. For example, treatment can involve the combined administration of a LAIR-1-binding agent of the present disclosure with antibodies against tumor-associated antigens including, but not limited to, antibodies that bind EGFR, HER2/ErbB2, and/or VEGF.

In some embodiments, the additional therapeutic agent is an antibody that is an angiogenesis inhibitor (e.g., an anti-VEGF or VEGF receptor antibody). In some embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

In some embodiments of the methods described herein, the additional therapeutic agent is an antibody that modulates the immune response. In some embodiments, the additional therapeutic agent is an anti-PD-1 antibody, an anti-PD-L1 antibody, an anti-PD-L2 antibody, an anti-CTLA-4 antibody, or an anti-TIGIT antibody.

Furthermore, treatment with a LAIR-1-binding agent described herein can include combination treatment with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician. In some embodiments, the additional therapeutic agent is an immunotherapeutic agent.

In some embodiments of the methods described herein, a LAIR-1-binding agent is combined with a growth factor selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-a, TGF-β, TNF-a, VEGF, PlGF, IL-1, IL-2, IL-3, IL-4, IL-5, IL-6, IL-7, IL-12, IL-15, and IL-18.

In some embodiments of the methods described herein, the additional therapeutic agent is an immunotherapeutic agent. In some embodiments, the immunotherapeutic agent is selected from the group consisting of granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), B7-1 (CD80), B7-2 (CD86), 4-1BB ligand, anti-CD3 antibody, anti-CTLA-4 antibody, anti-TIGIT antibody, anti-PD-1 antibody, anti-PD-L1 antibody, anti-LAG-3 antibody, and anti-TIM-3 antibody.

In some embodiments of the methods described herein, an immunotherapeutic agent is selected from the group consisting of: a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, and an immunostimulatory oligonucleotide.

In some embodiments of the methods described herein, an immunotherapeutic agent is selected from the group consisting of: a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, and/or an IDO1 antagonist.

In some embodiments of the methods described herein, the PD-1 antagonist is an antibody that specifically binds PD-1. In some embodiments, the antibody that binds PD-1 is pembrolizumab (KEYTRUDA, MK-3475), pidilizumab (CT-011), nivolumab (OPDIVO, BMS-936558, MDX-1106), MEDI0680 (AMP-514), REGN2810, BGB-A317, PDR-001, or STI-A1110. In some embodiments, the antibody that binds PD-1 is described in PCT Publication WO 2014/179664, for example, an antibody identified as APE2058, APE1922, APE1923, APE1924, APE 1950, or APE1963, or an antibody containing the CDR regions of any of these antibodies. In other embodiments, the PD-1 antagonist is a fusion protein that includes PD-L2, for example, AMP-224. In other embodiments, the PD-1 antagonist is a peptide inhibitor, for example, AU P-12.

In some embodiments, the PD-L1 antagonist is an antibody that specifically binds PD-L1. In some embodiments, the antibody that binds PD-L1 is atezolizumab (TECENTRIQ, RG7446, MPDL3280A), MEDI4736, BMS-936559 (MDX-1105), avelumab (BAVENCIO, MSB0010718C), durvalumab (IMFINZI), KD033, the antibody portion of KD033, or STI-A1014. In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies.

In some embodiments, the CTLA-4 antagonist is an antibody that specifically binds CTLA-4. In some embodiments, the antibody that binds CTLA-4 is ipilimumab (YERVOY) or tremelimumab (CP-675,206). In some embodiments, the CTLA-4 antagonist a CTLA-4 fusion protein, for example, KAHR-102.

In some embodiments, the LAG3 antagonist is an antibody that specifically binds LAG3. In some embodiments, the antibody that binds LAG3 is IMP701, IMP731, BMS-986016, LAG525, and GSK2831781. In some embodiments, the LAG3 antagonist includes a soluble LAG3 receptor, for example, IMP321.

In some embodiments, the KIR antagonist is an antibody that specifically binds KIR. In some embodiments, the antibody that binds KIR is lirilumab.

In some embodiments, an immunotherapeutic agent is selected from the group consisting of: a CD28 agonist, a 4-1BB agonist, an OX40 agonist, a CD27 agonist, a CD80 agonist, a CD86 agonist, a CD40 agonist, and a GITR agonist.

In some embodiments, the OX40 agonist includes OX40 ligand, or an OX40-binding portion thereof. For example, the OX40 agonist may be MEDI6383. In some embodiments, the OX40 agonist is an antibody that specifically binds OX40. In some embodiments, the antibody that binds OX40 is MEDI6469, MEDI0562, or MOXR0916 (RG7888). In some embodiments, the OX40 agonist is a vector (e.g., an expression vector or virus, such as an adenovirus) capable of expressing OX40 ligand. In some embodiments the OX40-expressing vector is tasadenoturev (DNX-2401).

In some embodiments, the 4-1BB (CD137) agonist is a binding molecule, such as an anticalin. In some embodiments, the anticalin is PRS-343. In some embodiments, the 4-1BB agonist is an antibody that specifically binds 4-1BB. In some embodiments, antibody that binds 4-1BB is PF-2566 (PF-05082566) or urelumab (BMS-663513).

In some embodiments, the CD27 agonist is an antibody that specifically binds CD27. In some embodiments, the antibody that binds CD27 is varlilumab (CDX-1127).

In some embodiments, the GITR agonist comprises a GITR ligand or a GITR-binding portion thereof. In some embodiments, the GITR agonist is an antibody that specifically binds GITR. In some embodiments, the antibody that binds GITR is TRX518, MK-4166, or INBRX-110.

In some embodiments, immunotherapeutic agents include, but are not limited to, cytokines such as chemokines, interferons, interleukins, lymphokines, and members of the tumor necrosis factor (TNF) family. In some embodiments, immunotherapeutic agents include immunostimulatory oligonucleotides, such as CpG dinucleotides.

In some embodiments, an immunotherapeutic agent includes, but is not limited to, anti-PD-1 antibodies, anti-PD-L1 antibodies, anti-PD-L2 antibodies, anti-CTLA-4 antibodies, anti-CD28 antibodies, anti-CD80 antibodies, anti-CD86 antibodies, anti-4-1BB antibodies, anti-OX40 antibodies, anti-KIR antibodies, anti-Tim-3 antibodies, anti-LAG3 antibodies, anti-CD27 antibodies, anti-CD40 antibodies, anti-GITR antibodies, anti-TIGIT antibodies, anti-CD20 antibodies, anti-CD96 antibodies, or anti-IDO1 antibodies.

It will be appreciated that the combination of a LAIR-1-binding agent described herein and at least one additional therapeutic agent may be administered in any order or concurrently. In some embodiments, a LAIR-1-binding agent is administered to subjects that have previously undergone treatment with a therapeutic agent. In some embodiments, a LAIR-1-binding agent and a second therapeutic agent are administered substantially simultaneously or concurrently. For example, a subject may be given a LAIR-1-binding agent while undergoing a course of treatment with a second therapeutic agent (e.g., a chemotherapeutic agent). In some embodiments, a LAIR-1-binding agent is administered within 1 year of the treatment with a second therapeutic agent. In some embodiments, a LAIR-1-binding agent is administered within 10, 8, 6, 4, or 2 months of any treatment with a second therapeutic agent. In some embodiments, a LAIR-1-binding agent is administered within 4, 3, 2, or 1 weeks of any treatment with a second therapeutic agent. In some embodiments, a LAIR-1-binding agent is administered within 5, 4, 3, 2, or 1 days of any treatment with a second therapeutic agent. It will further be appreciated that the two (or more) agents or treatments can be administered to the subject within a matter of hours or minutes (i.e., substantially simultaneously).

In some embodiments, treatment with a LAIR-1-binding agent can occur prior to, concurrently with, or subsequent to administration of the additional therapeutic agents. In some embodiments, combined administration includes co-administration, either in a single pharmaceutical formulation or using separate formulations, or consecutive administration in either order but generally within a time period such that all active agents can exert their biological activities. In some embodiments, preparation of agents and/or dosing schedules for additional therapeutic agents are according to manufacturers' instructions or as determined empirically by the skilled practitioner.

The present disclosure provides compositions comprising a LAIR-1-binding agent described herein. In some embodiments, a composition comprises an antibody selected from the group consisting of 47A1, 47H1, Hz47H1.v4, 57D11, 61H4, 62G10, Hz62G10.v1, 108D10, and 43H2. In some embodiments, a composition comprises antibody Hz47H1.v4. In some embodiments, a composition comprises antibody Hz62G10.v1.

The present disclosure provides pharmaceutical compositions comprising a LAIR-1-binding agent described herein and a pharmaceutically acceptable vehicle. In some embodiments, a pharmaceutical composition comprises an antibody selected from the group consisting of 47A1, 47H1, Hz47H1.v4, 57D11, 61H4, 62G10, Hz62G10.v1, 108D10, and 43H2 and a pharmaceutically acceptable vehicle. In some embodiments, a pharmaceutical composition comprises antibody Hz47H1.v4 and a pharmaceutically acceptable vehicle. In some embodiments, a pharmaceutical composition comprises antibody Hz62G10.v1 and a pharmaceutically acceptable vehicle.

Formulations are prepared for storage and use by combining a purified antibody or agent of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides; proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol. (*Remington: The Science and Practice of Pharmacy* 22$^{nd}$ *Edition.* 2012, Pharmaceutical Press, London.). In some embodiments, the formulation is in the form of an aqueous solution. In some embodiments, the formulation is stored in a lyophilized or in an alternative dried form.

The binding agents of the present disclosure can be formulated in any suitable form for delivery to a target cell/tissue. In some embodiments, a LAIR-1-binding agent can be formulated as a liposome, microparticle, microcapsule, albumin microsphere, microemulsion, nanoparticle, nanocapsule, or macroemulsion.

In some embodiments, a LAIR-1-binding agent is formulated with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE).

In some embodiments, a LAIR-1-binding agent is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

EXAMPLES

Example 1

Generation of Anti-LAIR-1 Antibodies

Anti-LAIR-1 antibodies were generated using the extracellular domain of human LAIR-1 as the immunogen. Recombinant constructs comprising the extracellular region of human LAIR-1 (aa 22-165 of SEQ ID NO:1) and cyno LAIR-1 (aa 22-165 of SEQ ID NO:5) were generated and expressed in mammalian cells. Mice were immunized with the LAIR-1-ECD proteins and were boosted several times to induce high titers. Blood was drawn from the immunized mice and antibody titers were determined by ELISA and FACS. Single cell suspensions of lymphocytes were obtained from the spleens and lymph nodes of immunized mice that had been determined to have suitably high antibody titers. Lymphocytes were fused with murine myeloma cells by standard methods (e.g., electrofusion). Cells were dispersed into 96-well plates in HAT-containing selection media.

ELISA and FACS assays were used to screen antibodies against human LAIR-1, cyno LAIR-1 and human LAIR-2.

Antibodies that bound to human LAIR-1 and cyno LAIR-1, but not to human LAIR-2 were selected.

Example 2

Binding Characteristics of Anti-Human LAIR-1 Antibodies

The binding affinities of purified anti-LAIR-1 antibodies to human LAIR-1 and cyno LAIR-1 were measured using a Biacore system (GE Healthcare LifeSciences). Briefly, anti-Fc antibody (Sigma-Aldrich) was immobilized on all four flow cells of a CM5 chip using amine coupling reagents (GE Healthcare LifeSciences). Antibodies were captured on flow cells 2, 3, and 4 using flow cell 1 as a reference. Concentrations ranging from 3.3-10 nM of human or cyno LAIR-1-ECD were injected at a flow rate of 530 µL/min at 25° C. Kinetic data were collected over time and fit using the simultaneous global fit equation to yield affinity constants ($K_D$ values) for each antibody.

Binding data is shown in Table 11.

TABLE 11

| | Human LAIR-1 | | |
| --- | --- | --- | --- |
| Antibody | $k_{on}$ $M^{-1}s^{-1}$ | $k_{off}$ $s^{-1}$ | $K_D$ M |
| 47A1 | $5.9 \times 10^5$ | $5.5 \times 10^{-4}$ | $9.2 \times 10^{-10}$ |
| 47H1 | $1.2 \times 10^6$ | $1.0 \times 10^{-4}$ | $8.7 \times 10^{-11}$ |
| 57D12 | $1.7 \times 10^5$ | $4.5 \times 10^{-5}$ | $2.7 \times 10^{-10}$ |
| 61H4 | $1.1 \times 10^5$ | $4.9 \times 10^{-5}$ | $4.6 \times 10^{-10}$ |
| 62G10 | $5.5 \times 10^5$ | $1.8 \times 10^{-4}$ | $3.2 \times 10^{-10}$ |
| 108D10 | $1.1 \times 10^6$ | $4.3 \times 10^{-4}$ | $4.0 \times 10^{-10}$ |

| | Cyno LAIR-1 | | |
| --- | --- | --- | --- |
| Antibody | $k_{on}$ $M^{-1}s^{-1}$ | $k_{off}$ $s^{-1}$ | $K_D$ M |
| 47A1 | $3.2 \times 10^5$ | $5.7 \times 10^{-3}$ | $1.8 \times 10^{-8}$ |
| 47H1 | $1.8 \times 10^5$ | $4.4 \times 10^{-4}$ | $2.5 \times 10^{-9}$ |
| 57D12 | $1.1 \times 10^5$ | $7.8 \times 10^{-4}$ | $7.3 \times 10^{-9}$ |
| 61H4 | $8.0 \times 10^4$ | $7.7 \times 10^{-4}$ | $9.6 \times 10^{-9}$ |
| 62G10 | $2.0 \times 10^5$ | $1.0 \times 10^{-3}$ | $5.1 \times 10^{-9}$ |
| 108D10 | $1.9 \times 10^5$ | $3.9 \times 10^{-3}$ | $2.1 \times 10^{-8}$ |

Example 3

Sequence Analyses of Anti-LAIR-1 Antibodies

Representative anti-LAIR-1 antibodies 47A1, 47H1, 57D12, 61H4, 62G10, and 108D10 were sequenced and the heavy chain variable region and light chain variable region amino acid sequences are disclosed herein and summarized in Table 12.

TABLE 12

| Antibody | Heavy Chain Variable Region | Light Chain Variable Region |
| --- | --- | --- |
| 47A1 | SEQ ID NO: 115 | SEQ ID NO: 116 |
| 47H1 | SEQ ID NO: 117 | SEQ ID NO: 118 |
| 57D12 | SEQ ID NO: 121 | SEQ ID NO: 122 |
| 61H4 | SEQ ID NO: 123 | SEQ ID NO: 124 |
| 62G10 | SEQ ID NO: 125 | SEQ ID NO: 126 |
| 108D10 | SEQ ID NO: 129 | SEQ ID NO: 130 |

The heavy chain and light chain variable region CDRs for the individual antibodies are disclosed in Tables 1-6 and as SEQ ID NOs:9-98.

Example 4

Generation of Humanized Antibodies

Two of the anti-LAIR-1 antibodies, 47H1 and 62G10, were humanized by methods known to those skilled in the art. These humanized antibodies are referred to herein as Hz47H1 and Hz62G10, respectively. Antibody 47H1 was found to have a potential deamidation site in the CDR2 of the heavy chain variable region, RIRTKNNNYATFY-ADSVKD (SEQ ID NO:26). In addition, antibody 47H1 was found to have a potential isomerization site in the CDR2 of the light chain variable region, AATSLAD (SEQ ID NO:29). During the humanization process, the heavy chain variable region CDR2 was reengineered to remove the deamidation site resulting in a heavy chain variable region CDR2 comprising RIRTKNYNYATFYADSVKD (SEQ ID NO:41). The light chain variable region CDR2 was also reengineered to remove the isomerization site resulting in a light chain variable region CDR2 comprising AATSLAE (SEQ ID NO:42). The Hz47H1 variant that comprises both of these modifications is referred to as Hz47H1.v4. The heavy chain variable sequence of Hz47H1.v4 comprises the amino acid sequence SEQ ID NO:119 and the light chain variable sequence of Hz47H1.v4 comprises the amino acid sequence SEQ ID NO:120; CDRs are disclosed in Table 2B.

The heavy chain sequence of antibody Hz47H1.v4 comprises four mutations in the constant region as compared to a wild-type IgG1 constant region. The heavy chain sequence of antibody Hz47H1.v4 is set forth as SEQ ID NO:133 and SEQ ID NO:134 (with and without signal sequence, respectively) and the light chain sequence of antibody Hz47H1.v4 is set forth as SEQ ID NO:135 and SEQ ID NO:136 (with and without signal sequence, respectively).

The heavy chain sequence of antibody Hz62G10.v1 comprises four mutations in the constant region as compared to a wild-type IgG1 constant region. The heavy chain sequence of antibody Hz62G10.v1 is set forth as SEQ ID NO:137 and SEQ ID NO:138 (with and without signal sequence, respectively) and the light chain sequence of antibody Hz62G10.v1 is set forth as SEQ ID NO:139 and SEQ ID NO:140 (with and without signal sequence, respectively).

The binding affinities of the humanized antibodies to human LAIR-1 were measured using a Biacore system as described herein. The binding affinities of antibodies Hz47H1.v4 and Hz62G10 are shown in Table 13 as compared with the parental antibodies.

TABLE 13

| | Human LAIR-1 | | |
| --- | --- | --- | --- |
| Antibody | $k_{on}$ $M^{-1}s^{-1}$ | $k_{off}$ $s^{-1}$ | $K_D$ M |
| ch47H1 | $1.5 \times 10^6$ | $5.1 \times 10^{-4}$ | $3.4 \times 10^{-10}$ |
| Hz47H1.v4 | $2.3 \times 10^6$ | $6.0 \times 10^{-4}$ | $2.6 \times 10^{-10}$ |
| ch62G10 | $7.7 \times 10^5$ | $6.9 \times 10^{-4}$ | $9.0 \times 10^{-10}$ |
| Hz62G10.v1 | $7.0 \times 10^5$ | $7.9 \times 10^{-4}$ | $1.1 \times 10^{-9}$ |

| | Cyno LAIR-1 | | |
| --- | --- | --- | --- |
| Antibody | $k_{on}$ $M^{-1}s^{-1}$ | $k_{off}$ $s^{-1}$ | $K_D$ M |
| ch47H1 | $2.2 \times 10^5$ | $1.0 \times 10^{-3}$ | $4.6 \times 10^{-9}$ |
| Hz47H1.v4 | $3.9 \times 10^5$ | $1.6 \times 10^{-3}$ | $4.3 \times 10^{-9}$ |
| ch62G10 | $2.8 \times 10^5$ | $4.3 \times 10^{-3}$ | $1.6 \times 10^{-8}$ |
| Hz62G10.v1 | $3.9 \times 10^5$ | $1.6 \times 10^{-3}$ | $4.3 \times 10^{-8}$ |

These results demonstrate that the humanization process for exemplary anti-LAIR-1 antibodies did not have a significant effect on the antibodies' binding capabilities to human or cynomolgus monkey LAIR-1.

Example 5

Characterization of LAIR-1 Ligands

Several potential novel binding partners of LAIR-1 have been identified. To characterize these proteins and assess whether they were functional ligands of LAIR-1, a reporter cell system was utilized. In this chimeric receptor system, potential ligands are coated onto plates and incubated with "reporter cells" expressing (i) a stable reporter system and (ii) a cell surface receptor of interest. The extracellular domain of the receptor of interest is fused with the transmembrane/intracellular domain of the human CD3ζ chain. When the chimeric receptor is activated by binding to a ligand, CD3ζ becomes phosphorylated and activates a NFAT-responsive promoter that drives GFP expression (see, e.g., Arase, et. al., 2002, *Science*, 296:1323-1326). For these experiments a human LAIR-1-CD3ζ-NFAT-GFP cell line and a cyno LAIR-1-CD3ζ-NFAT-GFP cell line were generated.

96-well Maxisorp (Nunc) plates were incubated overnight with the following proteins in PBS: 1 μg/mL human collagen type 1 (Millipore Sigma), 1 μg/mL human collagen type 4 (Millipore Sigma), 2 μg/mL recombinant human MARCO-his protein (R&D Systems or in house), 1 μg/mL recombinant human COLEC12 (R&D Systems), 2 μg/mL recombinant mannose-binding lectin (MBL) (R&D Systems), 2 μg/mL recombinant surfactant protein D (SP-D) (R&D Systems), or 3 μg/mL complement component C1 complex (C1; Complement Technologies). Plates were washed with PBS before adding $4 \times 10^5$ reporter cells in 80 μL RPMI 1640 (Corning) containing 10% heat-inactivated FBS (ThermoFisher Scientific), followed by overnight incubation at 37° C. GFP expression was measured by flow cytometry on LSRFortessa™ (BD Biosciences) and analyzed by FlowJo software. Negative and positive GFP signals were set based on the ability of a non-specific antibody or an anti-LAIR-1 antibody (clone DX26 or an in-house antibody) to activate reporter cells, respectively.

As shown in FIG. 1, GFP expression was induced when human LAIR-1 reporter cells were incubated with collagens 1 and 4, MBL, SP-D and C1 complex, all of which have been previously reported to bind LAIR-1. Additionally, GFP expression was strongly induced by MARCO and COLEC12. GFP expression was induced in cyno LAIR-1 reporter cells by collagens 1 and 4 as expected. Additionally, GFP expression was strongly induced with MARCO and COLEC12 to a lesser extent.

These data show that MARCO and COLEC12, which have been identified as novel binding partners of human LAIR-1, are biologically functional ligands for LAIR-1.

Example 6

Binding of LAIR-1-Fc and LAIR-2-Fc to Cell-Expressed Ligands

To investigate the binding interactions between LAIR-1 and cell-expressed MARCO, constructs were generated comprising LAIR-1 extracellular domain (aa 22-165 of SEQ ID NO:1) or LAIR-2 soluble protein (aa 22-152 of SEQ ID NO:225) fused to a Fc region (LAIR-1-Fc and LAIR-2-Fc, respectively). The LAIR-1-Fc and LAIR-2-Fc proteins were used to evaluate binding to cells expressing (i) MARCO or (ii) transmembrane domain-containing collagen 17A1 (COL17A1; used as positive control). Stable cell lines were generated by lentiviral transduction of constructs containing the full coding sequences of COL17A1 or MARCO into LCL 721.221 cells (ATCC). Cells were incubated with LAIR-1-Fc or LAIR2-Fc proteins at 10 μg/mL for 50 minutes on ice and washed. Binding was detected with a PE-labeled anti-Fc secondary antibody. Binding was measured by flow cytometry using a LSRFortessa™ instrument (BD Biosciences) and analyzed by FlowJo software.

Figure 2:
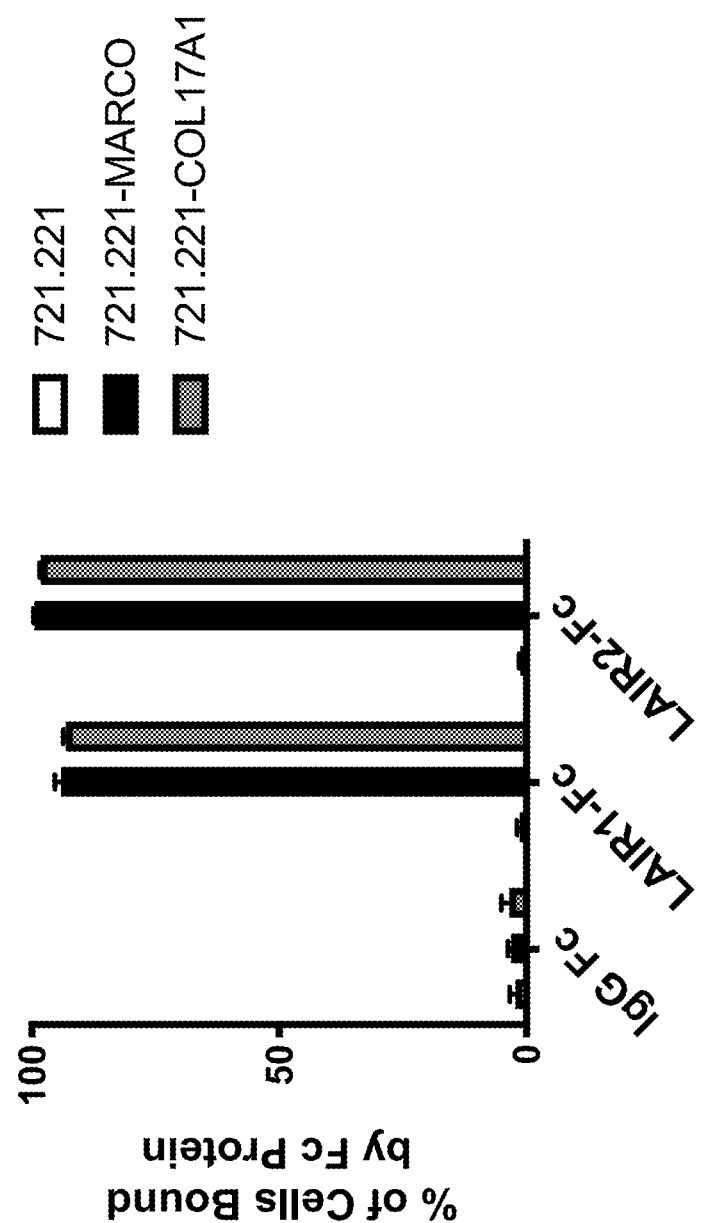
FIG. 2. Binding of LAIR-1-Fc and LAIR-2-Fc to cell-expressed ligands. Parental 721.221 cells (white bar) or 721.221 cells expressing MARCO (black bar) or COL17A1 (gray bar) were mixed with human LAIR-1-Fc and LAIR-2-Fc proteins at 10 μg/mL, then binding was detected with a PE-labeled anti-Fc secondary antibody. Binding of LAIR-1-Fc and LAIR-2-Fc proteins to cells was measured by flow cytometry and analyzed using FlowJo software.

As shown in FIG. 2, LAIR-1-Fc and LAIR2-Fc bound strongly to 721.221 cells expressing MARCO and COL17A1, but not the parental non-transduced 721.221 cell line.

These results demonstrate that LAIR-1 binds to MARCO when it is expressed on the surface of cells.

Example 7

Binding of Anti-LAIR-1 Antibodies to Cells Expressing LAIR-1

The binding of exemplary anti-LAIR-1 antibody ch47H1 and the humanized version Hz47H1.v4 to LAIR-1-expressing cells was evaluated by flow cytometry analysis. Human LAIR-1-CD3ζ-NFAT-GFP or cyno LAIR-1-CD3ζ-NFAT-GFP reporter cells (described herein) were used. Cells were washed in staining buffer (PBS/1% BSA/0.1% sodium azide) prior to incubation with antibody ch47H1, Hz47H1.v4, or control anti-KLH antibody at room temperature over a dose-response range. Cells were washed and stained with PE-anti-human Fc secondary antibody (Jackson ImmunoResearch) for 30 minutes at 4° C. Cells were washed in staining buffer and analyzed by flow cytometry on an Intellicyt instrument (Sartorius).

Figure 3:
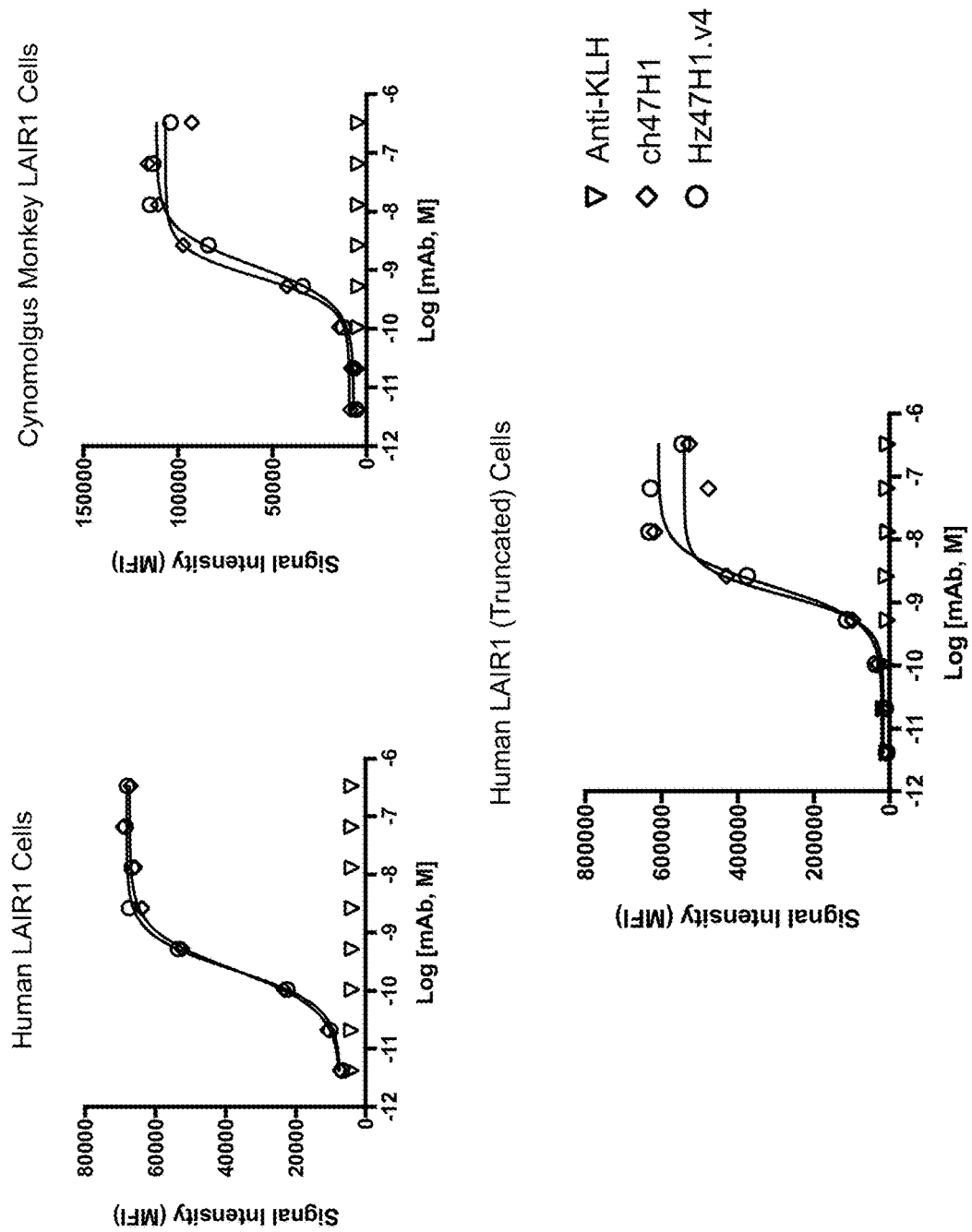
FIG. 3. Binding of anti-LAIR-1 antibodies to cells expressing LAIR-1. Human LAIR1-CD3ζ-NFAT-GFP reporter cells, cyno LAIR-1-CD3ζ-NFAT-GFP reporter cells, or human LAIR-1b-CD3ζ-NFAT-GFP reporter cells were incubated with a concentration range of anti-LAIR-1 antibodies ch47H1, Hz47H1.v4, or control anti-KLH antibody. GFP expression was measured by flow cytometry and analyzed using FlowJo software.

As shown in FIG. 3, an increase in fluorescence intensity was observed at increasing concentrations of antibody ch47H1 and antibody Hz47H1.v4 on cells expressing human LAIR-1 and cells expressing cyno LAIR-1. In comparison, an isotype control antibody demonstrated no additional signal intensity at increasing concentrations of antibody.

An alternative isoform of human LAIR-1 (LAIR-1b) has been described that lacks a 17 amino acid region in the extracellular domain between the Ig-like domain and the transmembrane domain (missing aa 122-138 of SEQ ID NO:1). To test binding to this unique isoform, a LAIR-1b construct containing the truncated sequence was generated and transfected into 293T cells using standard methods. These cells were stained in a similar method as described above.

An increase in fluorescence intensity was observed at increasing concentrations of antibody ch47H1 and antibody Hz47H1.v4 on cells expressing the alternative isoform of LAIR-1 (LAIR-1b), in a similar pattern as full length LAIR-1 (FIG. 3). The isotype control antibody demonstrated no detectable binding. Binding of the antibodies to cells expressing human LAIR-1 and cells expressing cyno LAIR-1 was comparable.

These results demonstrate that the exemplary anti-LAIR-1 antibodies recognize multiple isoforms of human LAIR-1 on intact cells and that there is comparable binding to both human and cyno LAIR-1, showing that monkeys will be a suitable model for future studies.

Example 8

Binding of Anti-LAIR-1 Antibodies to Primary Human Immune Cells

The binding of exemplary anti-LAIR-1 antibody 47H1 to human peripheral blood mononuclear cells (PBMCs) immune cells subsets was evaluated by flow cytometry analysis. Briefly, human PBMCs (from 9 donors) were prepared from Leukopaks (AllCells) using a Ficoll® Paque Plus (GE Healthcare) gradient method. Cells were cryopreserved in CryoStor® media (StemCell/Sigma) and maintained in liquid nitrogen. Antibody ch47H1 and a control anti-KLH antibody were labeled with Alexa Fluor 488 antibody labeling kit (Invitrogen). Cells were thawed in warm media (RPMI, 10% FBS, L-glutamine, pen/strep), washed, and resuspended in PBS. PBMCs were stained with Live/Dead Blue Fixable Dye (MermoFisher Scientific), washed in media with Fc Block™ (BD Biosciences), and stained with a cocktail of labeled antibodies to differentiate between different immune cell types. $1 \times 10^6$ cells/well were stained with fluorescently-labeled ch47H1 antibody (or control antibody) and incubated on ice for at least 20 minutes. The cells were washed and immediately analyzed by flow cytometry on a LSRFortessa™ Analyzer (BD Biosciences) and using FlowJo software. Live cells were gated before analysis. The percentage of live cells bound by the antibodies in each subset (% LAIR-1+) and the geometric mean fluorescence intensity (gMFI) for each positive subset (gated on LAIR-1+ cells) were calculated for each donor and an average was calculated.

Figure 4:
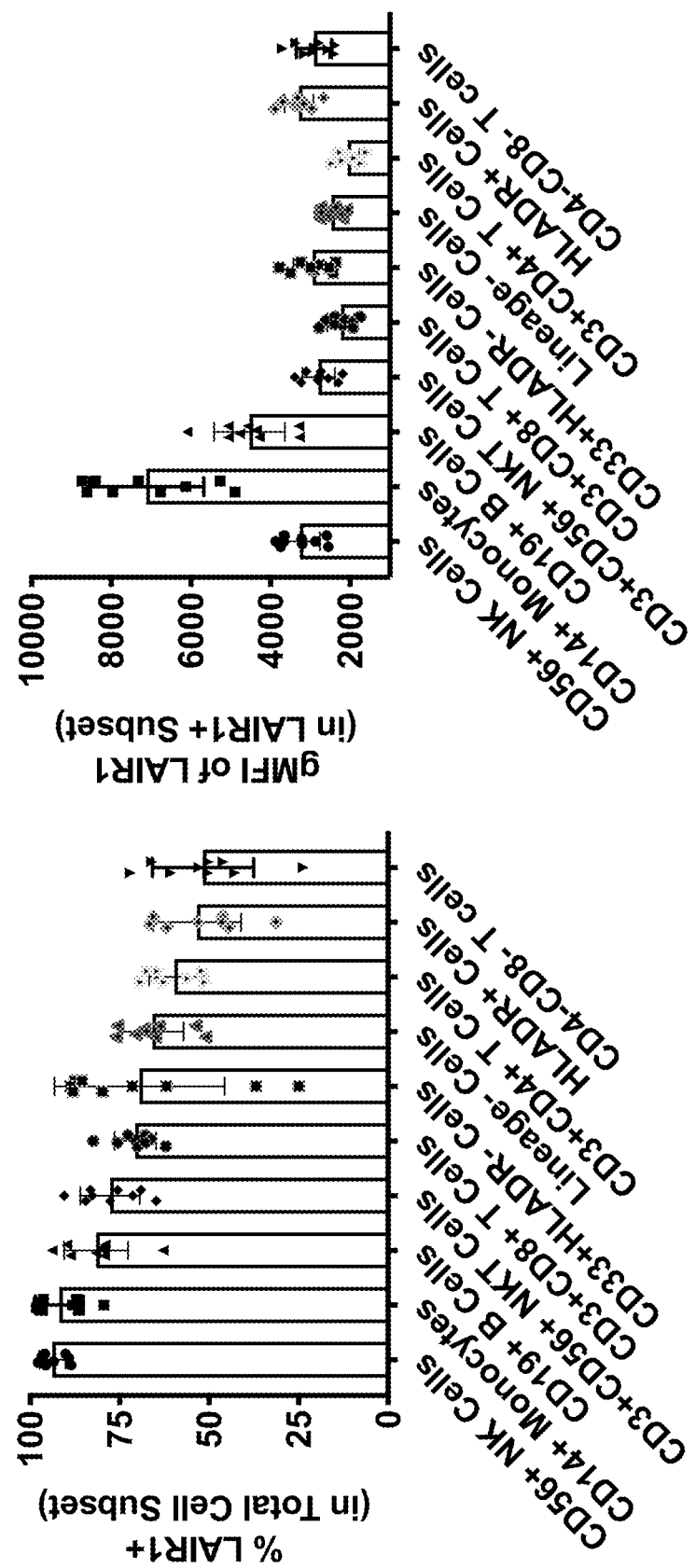
FIG. 4. Binding of anti-LAIR-1 antibody to primary human immune cells. PBMCs were stained with a cocktail of labeled antibodies to differentiate between different immune cell types. Labeled cells with incubated with anti-LAIR-1 antibody ch47H1. Percentage of LAIR-1-positive cells was measured by flow cytometry and analyzed using FlowJo software.

As shown in FIG. 4, antibody ch47H1 bound to a full spectrum of immune cells encompassing both lymphoid and myeloid lineage cells. The subset with the highest relative expression was determined to be CD14+ monocytes.

Example 9

Inhibition of the Interaction Between LAIR-1 and LAIR-1 Ligands by Anti-LAIR-1 Antibodies To investigate whether binding of anti-LAIR-1 antibodies blocked the interaction between LAIR-1 and collagen, ELISA blocking assays were performed. In brief, 96-well Maxisorp (Nunc) plates were coated with 5 µg/mL human collagen type 1 (Millipore Sigma) overnight at 4° C. in 50 µL PBS. Plates were washed with PBS and blocked for 1 hour at room temperature in blocking buffer (1% BSA in PBS). Anti-LAIR-1 antibodies ch47H1, Hz47H1.v4, ch57D12, ch62G10, Hz62G10.v1, and an anti-KLH control antibody were added to plates for 15 min. 1 µg/mL biotinylated human LAIR-1-Fc and cyno LAIR-1-Fc were added to plates and incubated for 60 minutes at room temperature. Plates were washed and incubated with HRP-conjugated streptavidin (Biorad) for 60 minutes at room temperature. Plates were washed and a detectable signal was developed with TMB chromogen solution (Life Technologies) for 5 minutes. Signal intensity was measured at 650 nM on a Spectramax plate reader (Molecular Devices).

Figure 5:
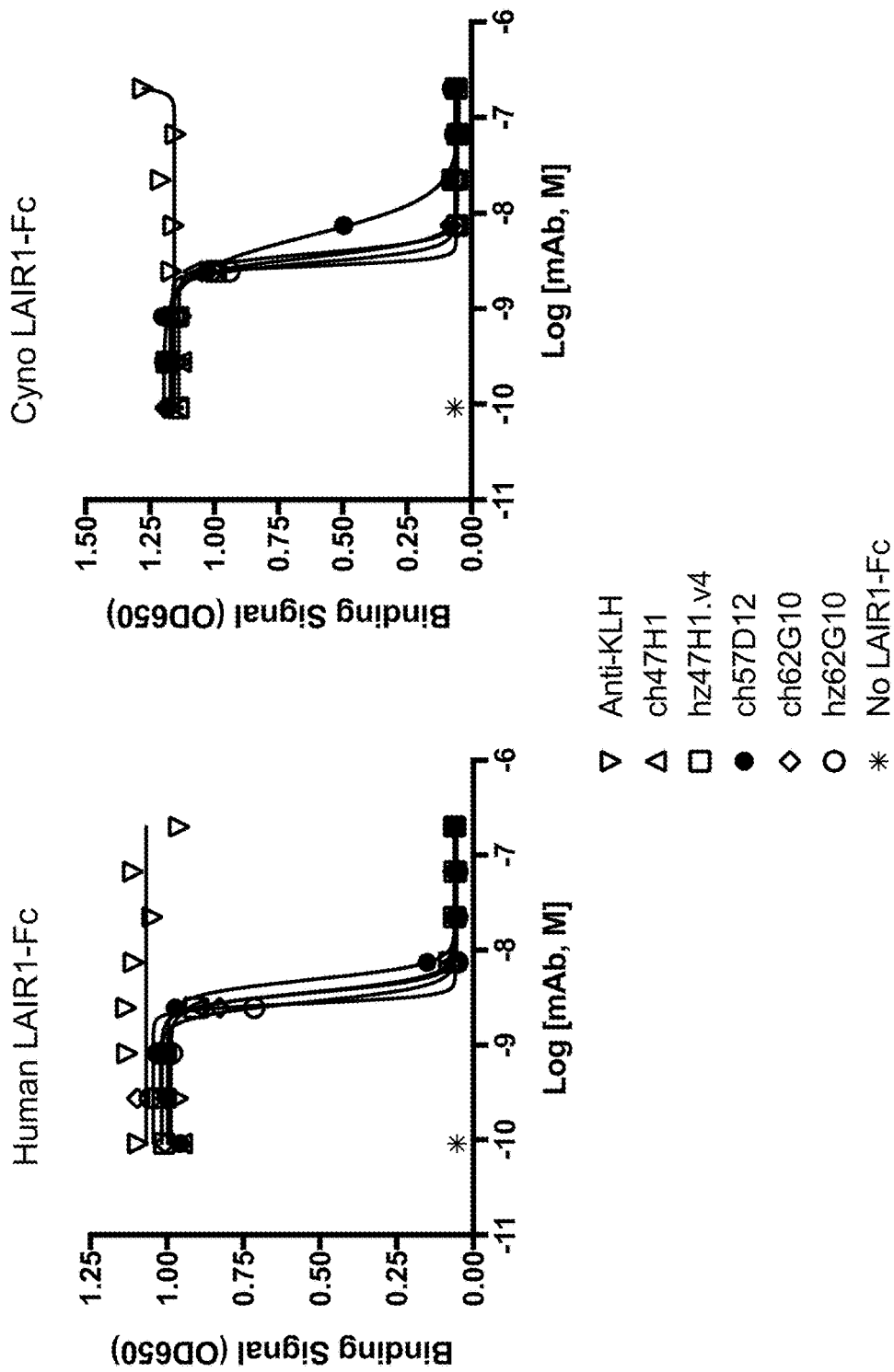
FIG. 5. Inhibition of the interaction between LAIR-1 and LAIR-1 ligands by anti-LAIR-1 antibodies. 96-well Maxisorp plates were coated with 5 μg/mL human collagen type 1. A concentration range of anti-LAIR-1 antibodies and anti-KLH control antibody was added to the plates: ch47H1, Hz47H1.v4, ch57D12, ch62G10, Hz62G10.v1, anti-KLH antibody. 1 μg/mL biotinylated human LAIR-1-Fc protein or cyno LAIR-1-Fc protein was added to plates. Plates were incubated with HRP-conjugated streptavidin. Signal was developed with TMB Chromogen Solution and binding signal was measured at 650 nM on a Spectramax plate reader.

As shown in FIG. 5, anti-LAIR-1 antibodies ch47H1, Hz47H1.v4, ch57D12, ch62G10, and Hz62G10 all blocked the binding of human LAIR-1-Fc and cyno LAIR-1-Fc proteins to collagen in a dose-dependent manner.

These results demonstrate that the exemplary anti-LAIR-1 antibodies described herein strongly inhibit LAIR-1 binding to collagen. Human LAIR-1 binding to collagen and cyno LAIR-1 binding to collagen were inhibited/blocked to similar levels, indicating that monkeys will be a suitable model for future studies.

The ability of anti-LAIR-1 antibodies to inhibit the functional interaction between LAIR-1 and collagen, as well as the interaction between LAIR-1 and MARCO, were evaluated using a reporter cell assay as described herein. 96-well Maxisorp (Nunc) plates were coated with 1 µg/mL of human collagen type 1 (Millipore Sigma), 1 µg/mL human collagen type 4 (Millipore Sigma), or 2 µg/mL recombinant human MARCO-his protein (R&D Systems) overnight at 4° C. in 50 µL PBS. Plates were washed twice before adding antibodies ch47A1, ch47H1, ch57D12, ch61H4, ch62G10, and ch108D10. Subsequently, $4 \times 10^5$ LAIR-1-CD3ζ-NFAT-GFP cells in 80 µL RPMI 1640 media containing 10% heat-inactivated FBS were added to the wells, followed by overnight incubation at 37° C. GFP expression was measured by flow cytometry using a LSRFortessa™ instrument (BD Biosciences) and analyzed by FlowJo software. Negative and positive GFP signals were gated using the activity measurements from non-specific immunoglobulin protein (negative control) and a reference anti-LAIR-1 antibody (positive control) to activate the reporter cells.

Figure 6:
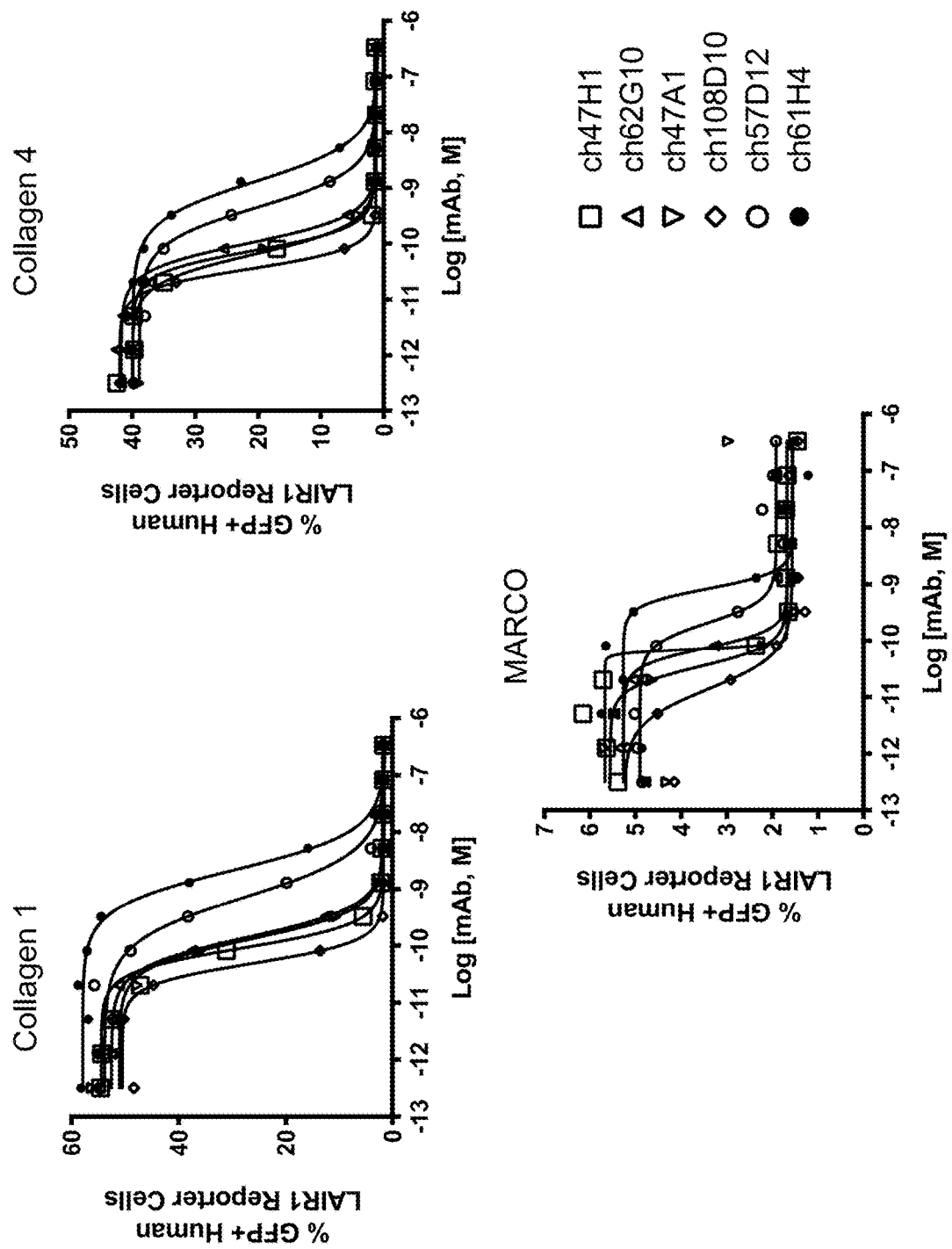
FIG. 6. Inhibition of the interaction between LAIR-1 and LAIR-1 ligands by anti-LAIR-1 antibodies. 96-well Maxisorp plates were coated with 1 μg/mL human collagen type 1, 1 μg/mL human collagen type 4, or 2 μg/mL recombinant human MARCO-his protein. A concentration range of anti-LAIR-1 antibodies was added to the plates: ch47H1, ch62G10, ch47A1, ch108D10, ch57D12, and ch61H4. Human LAIR-1-CD3ζ-NFAT-GFP reporter cells were added to the plates. GFP expression was measured by flow cytometry and analyzed using FlowJo software.

As shown in FIG. 6, GFP expression (% GFP+ cells) was induced when reporter cells were incubated with collagen 1, collagen 4, and MARCO. The exemplary anti-LAIR-1 antibodies strongly inhibited the interaction between LAIR-1 and all three ligands in a dose-dependent manner as assessed by GFP expression.

Another study was performed to evaluate the ability of exemplary anti-LAIR-1 antibodies described herein to inhibit the functional interaction between LAIR-1 and all of the previously reported ligands of LAIR-1 including collagen 1, collagen 4, MBL, SP-D, and C1, as well as the newly identified ligands MARCO and COLEC12. 96-well Maxisorp (Nunc) plates were coated with 1 µg/mL of human collagen type 1 (Millipore Sigma), 1 µg/mL human collagen type 4 (Millipore Sigma), 2 µg/mL recombinant human MARCO-his protein (R&D Systems), 1 µg/mL recombinant human COLEC12 (R&D Systems), 2 µg/mL recombinant MBL (R&D Systems), 2 µg/mL recombinant SP-D (R&D Systems), or 3 µg/mL C1 complex (Complement Technologies) overnight at 4° C. in 50 µL PBS. Plates were washed twice before adding antibodies ch47A1, ch47H1, Hz47H1.v4, ch108D10, and an anti-KLH control antibody. Subsequently, $4 \times 10^5$ LAIR-1-CD3ζ-NFAT-GFP cells in 80 µL RPMI 1640 media containing 10% heat-inactivated FBS were added to the wells, followed by overnight incubation at 37° C. GFP expression was measured by flow cytometry on a Fortessa Analyzer (BD Biosciences) as described above.

Figure 7:
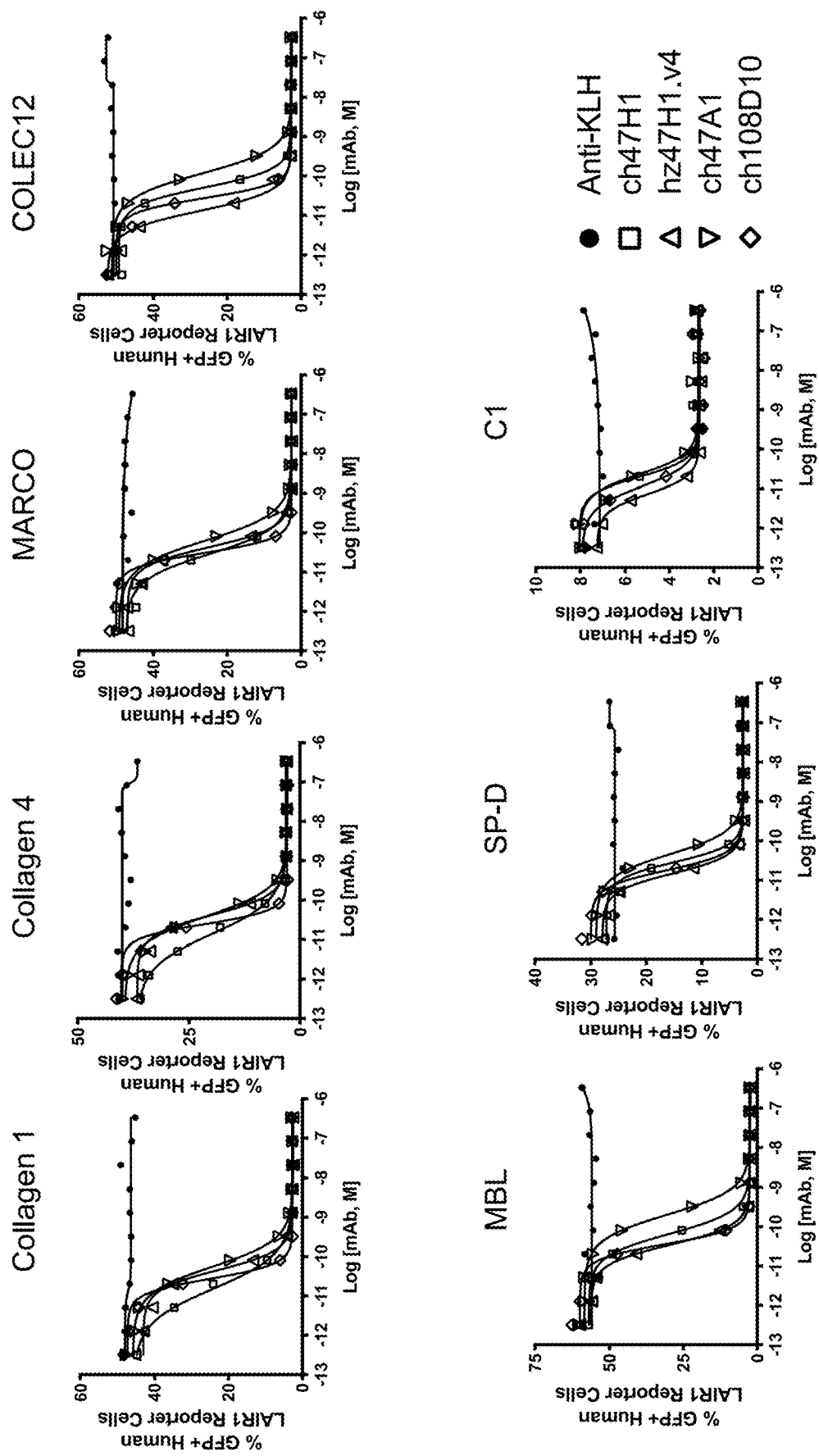
FIG. 7. Inhibition of the interaction between LAIR-1 and LAIR-1 ligands by anti-LAIR-1 antibodies. 96-well Maxisorp plates were coated with 1 μg/mL human collagen type 1, 1 μg/mL human collagen type 4, 2 μg/mL recombinant human MARCO-his protein, 1 μg/mL human COLEC12, 2 μg/mL MBL, 2 μg/mL SP-D, or 3 μg/mL C1 complex. A concentration range of anti-LAIR-1 antibodies was added to the plates: ch47H1, Hz47H1.v4, ch47A1, ch108D10, and anti-KLH antibody. Human LAIR1-CD3ζ-NFAT-GFP reporter cells were added to the plates. GFP expression was measured by flow cytometry and analyzed using FlowJo software.

As shown in FIG. 7, GFP expression was induced when reporter cells were incubated with all known ligands of LAIR-1 (collagen 1, collagen 4, MBL, SP-D and C1), as well as the newly identified ligands, MARCO and COLEC12. Anti-LAIR-1 antibodies strongly inhibited the interaction between LAIR-1 and all known ligands as well as MARCO and COLEC12 in a dose-dependent manner as assessed by GFP expression. Importantly, this study showed that the humanized antibody Hz47H1.v4 had a similar blocking effect as the parental antibody.

An additional study was performed to test the ability of anti-LAIR-1 antibodies to inhibit the functional interaction between human LAIR-1 with purified collagens and MARCO and compare that to inhibition of cyno LAIR-1 with purified collagens and MARCO. The study was set up under the same conditions as those described herein using anti-LAIR-1 antibodies ch47H1, Hz47H1.v4, ch57D12, ch62G10 and Hz62G10.

Figure 8:
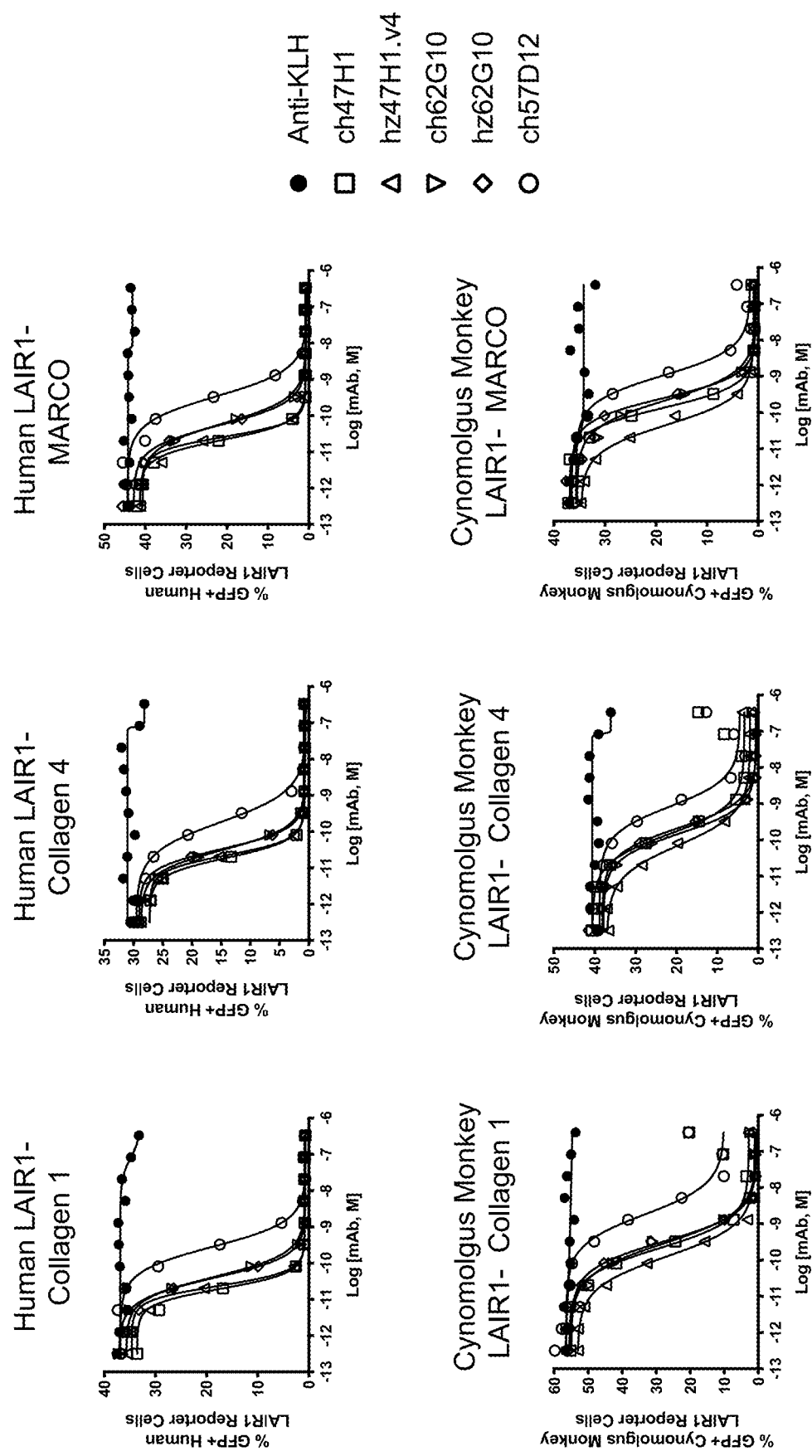
FIG. 8. Inhibition of the interaction between LAIR-1 and LAIR-1 ligands by anti-LAIR-1 antibodies. 96-well Maxisorp plates were coated with 1 μg/mL human collagen type 1, 1 μg/mL human collagen type 4, or 2 μg/mL recombinant human MARCO-his protein. A concentration range of anti-LAIR-1 antibodies was added to the plates: ch47H1, Hz47H1.v4, ch62G10, Hz62G10.v1, ch57D12, and anti-KLH antibody. Human LAIR1-CD3ζ-NFAT-GFP reporter cells or cyno LAIR1-CD3ζ-NFAT-GFP reporter cells were added to the plates. GFP expression was measured by flow cytometry and analyzed using FlowJo software.

As shown in FIG. 8, GFP expression was induced when human LAIR-1 CD3ζ-NFAT-GFP reporter cells or cyno LAIR-1 CD3ζ-NFAT-GFP reporter cells were incubated on purified collagen 1, collagen 4, or MARCO. Anti-LAIR-1 antibodies strongly inhibited the interaction between human LAIR-1 and cyno LAIR-1 and ligands collagen 1, collagen 4, and MARCO in a dose-dependent manner as assessed by GFP expression. The interactions between human LAIR-1 and ligands and cyno LAIR-1 and ligands were inhibited/blocked to a similar level.

In a real physiological setting, collagen often exists in a complex of extracellular matrix proteins. A study was performed to test the ability of anti-LAIR-1 antibodies to inhibit the functional interaction between LAIR-1 and ligand(s) naturally produced by cells. The bEnd.3 cell line (ATCC®) was originally generated from mouse cerebral cortex endothelial cells immortalized by transformation with polyomavirus middle T antigen. It has been shown that bEnd.3 cells express extracellular matrix proteins and cell surface adhesion molecules. A modified version of the previously described reporter cell assay was set up using these cells. $1\times10^5$ bEnd.3 cells were mixed with $4\times10^5$ human LAIR-1-CD3ζ-NFAT-GFP cells or cyno LAIR-1-CD3ζ-NFAT-GFP cells in a 96-well tissue culture-treated plate in RPMI 1640 media containing 10% heat-inactivated FBS. The reporter cells were labeled with CellTrace Violet (MermoFisher Scientific) to discriminate them from bEnd.3 cells. Antibodies ch47H1, Hz47H1.v4, ch62G10, or control anti-KLH antibody were added to the co-cultured cells and the plate was incubated overnight at 37° C. GFP expression was measured by flow cytometry on a Fortessa Analyzer (BD Bioscience).

Figure 9:
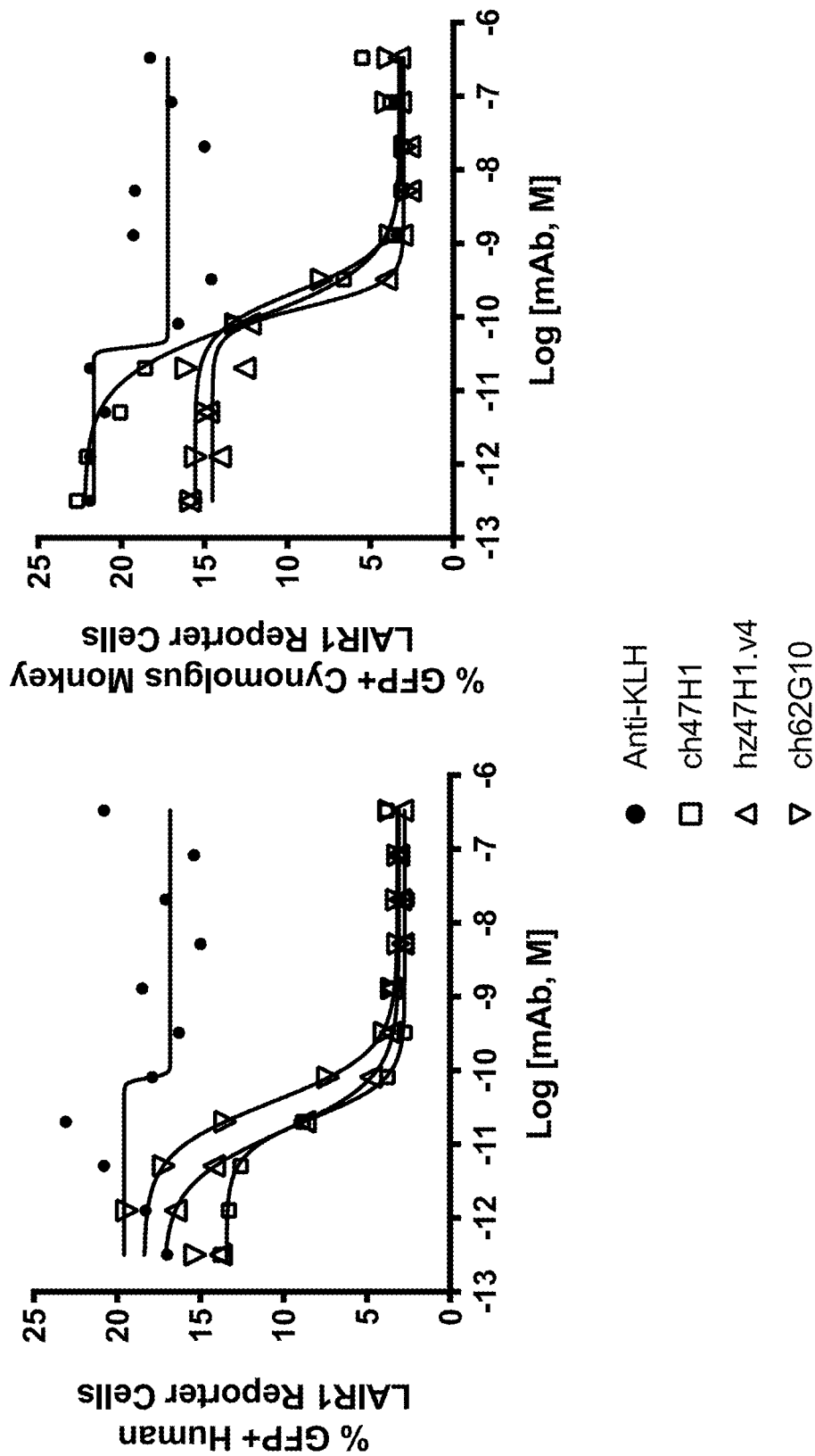
FIG. 9. Inhibition of the interaction between LAIR-1 and LAIR-1 ligands by anti-LAIR-1 antibodies. bEnd.3 cells were incubated with human LAIR1-CD3ζ-NFAT-GFP reporter cells or cyno LAIR1-CD3ζ-NFAT-GFP reporter cells. A concentration range of anti-LAIR-1 antibodies was added to the plates: ch47H1, Hz47H1.v4, ch62G10, and anti-KLH antibody. GFP expression was measured by flow cytometry and analyzed using FlowJo software.

As shown in FIG. 9, expression of GFP was induced by interaction of the bEnd.3 cells with the LAIR-1 reporter cells. This shows expression of a functional LAIR-1 ligand (s) by the bEnd.3 cells, likely, but not limited to, collagen, based on cell line gene expression data (CCLE from Harmonizome). Anti-LAIR-1 antibodies ch47H1, Hz47H1.v4, and ch62G10 inhibited and/or blocked the interaction of the bEnd.3 cells and LAIR-1 as evidenced by the reduced expression of GFP from the LAIR-1 expressing reporter cells. The inhibition was in a dose-dependent manner, with both human LAIR-1 and cyno LAIR-1 showing similar levels of inhibition. The inhibition of LAIR-1 and bEnd.3 ligand(s) interactions was similar with human LAIR-1 and cyno-LAIR-1.

Another study was performed to test the ability of anti-LAIR-1 antibodies to inhibit the functional interaction between LAIR-1 and a collagen matrix at a physiological density. Collagens often exist in a three-dimensional dense extracellular matrix. To duplicate this milieu, a highly concentrated and densely polymerized collagen matrix was generated and a modified version of the reporter cell assay was performed. In brief, a mixture of 4 mg/mL rat tail collagen (Corning) and 50 mM HEPES buffer diluted in RPMI 1640 containing 10% heat-inactivated FBS was prepared cold (on ice) and mixed gently to avoid bubbles. The collagen mixture was polymerized by adding 75 μL to the wells of a 96-well tissue culture-treated plate, then incubating the plate at 37° C. for 30 minutes. Next, $1\times10^5$ human LAIR-1-CD3ζ-NFAT-GFP or cyno LAIR-1-CD3ζ-NFAT-GFP reporter cells in RPMI 1640 containing 10% heat-inactivated FBS were added to the wells. Followed by the addition of anti-LAIR-1 antibodies ch47H1, Hz47H1.v4, ch57D12, ch62G10, Hz62G10.v1, and anti-KLH antibody. Cells and antibodies were incubated on the collagen matrix at 37° C. overnight and then gently removed from the plate by pipetting the liquid without disturbing the matrix. GFP expression was measured by flow cytometry on a Fortessa Analyzer (BD).

Figure 10:
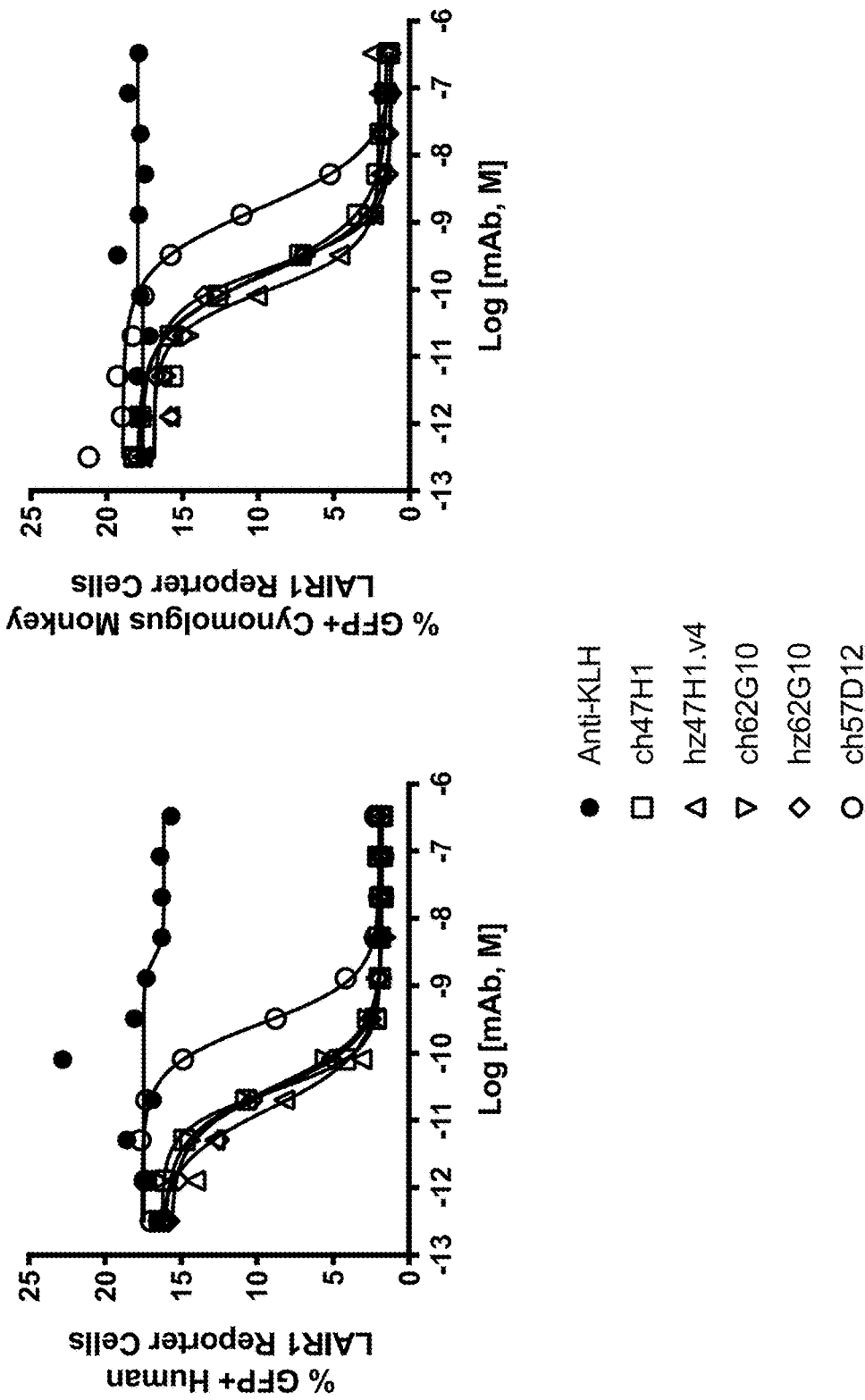
FIG. 10. Inhibition of the interaction between LAIR-1 and LAIR-1 ligands by anti-LAIR-1 antibodies. Plates were coated with high-density polymerized collagen. Human LAIR1-CD3ζ-NFAT-GFP reporter cells or cyno LAIR1-CD3ζ-NFAT-GFP reporter cells were added to the plates. A concentration range of anti-LAIR-1 antibodies was added to the plates: ch47H1, Hz47H1.v4, ch62G10, Hz62G10.v1, ch57D12, and anti-KLH antibody. GFP expression was measured by flow cytometry and analyzed using FlowJo software.

As shown in FIG. 10, the dense polymerized collagen matrix induced expression of GFP in LAIR-1 reporter cells, demonstrating the availability of a functional LAIR-1 ligand in the three-dimensional collagen matrix. Anti-LAIR-1 antibodies ch47H1, Hz47H1.v4, ch57D12, ch62G10, and Hz62G10.v1 inhibited and/or blocked the interaction of the LAIR-1 and the collagen matrix as evidenced by the reduced expression of GFP from the LAIR-1 expressing reporter cells. The inhibition was in a dose-dependent manner, with both human LAIR-1 and cyno LAIR-1 showing similar levels of inhibition.

Collectively, these results demonstrate that anti-LAIR-1 antibodies can block the functional interaction between LAIR-1 and LAIR-1 ligands in several relevant formats: purified proteins, cell-expressed proteins, and high concentration three-dimensional polymerized matrix. The degree of similarity between human and cyno LAIR-1 inhibition supports the utility of cynomolgus monkeys for future studies. Exemplary IC50s is shown in Table 14 for Hz47H1.v4 antibody, which blocks the functional interaction between LAIR-1 and LAIR-1 ligands.

TABLE 14

| $IC_{50}$ (M) | Hz47H1.v4 |
| --- | --- |
| Collagen 1 | $3.2 \times 10^{-11}$ |
| Collagen 4 | $3.2 \times 10^{-11}$ |
| Tumor Cell Collagens | $1.6 \times 10^{-11}$ |
| Polymerized Collagen Matrix | $3.0 \times 10^{-11}$ |
| MBL | $4.2 \times 10^{-11}$ |
| SPD | $2.0 \times 10^{-11}$ |
| C1 Complex | $1.5 \times 10^{-11}$ |
| MARCO | $3.2 \times 10^{-11}$ |
| COLEC12 | $1.2 \times 10^{-11}$ |

Example 10

Effect of Anti-LAIR-1 antibodies on MARCO- and collagen-dependent monocyte functions THP1 is a human monocytic cell line established from acute monocytic leukemia cells. These cells have been used extensively to study monocyte/macrophage functions, mechanisms, signaling pathways, and nutrient and drug transport (for review, see, Chanput et al., 2014, *Int. Immunopharmacol.*, 23:37-45). Activation of monocytes can be achieved by crosslinking of the Fc receptor (FcR) on the cell surface, which results in activation of NF-κB signaling, and ultimately inflammatory cytokine production. The effect of LAIR-1 interacting with collagen or MARCO was studied using THP1-Dual™ cells that contain a NF-κB-SEAP reporter (InvivoGen). The reporter is activated by interaction of the Fc region of an antibody and the FcR on the surface of THP-1 cells resulting in activation of the FcR signaling pathway and production of secreted embryonic alkaline phosphate (SEAP). In these studies, when LAIR-1 on the surface of THP-1 cells interacts with its ligand, i.e., collagen or MARCO, FcR signaling is suppressed and SEAP production is decreased. In addition, a LAIR-1 knock-out THP1 cell line (THP1-LAIR-1-KO) was generated for comparison to THP1 wild-type cells (THP1-WT).

To establish if MARCO could suppress FcR-based activation of THP1 cells, a study was set up using the reporter cells and MARCO. 96-well Maxisorp (Nunc) plates were coated with 5 μg/mL anti-KLH antibody, with or without 5 μg/mL human MARCO-his protein and incubated at 37° C. for 1.5 hrs at room temperature. Plates were washed in X-VIVO™ 15 media (Lonza) and $1\times10^5$ THP1-Dual™ NF-κB-SEAP reporter cells/well were added. Plates were incubated at 37° C. overnight. Reporter activity was measured by adding Quanti-Blue SEAP substrate (InvivoGen), incubating the plates at 37° C. for 2 hours, and reading the absorbance at 620 nm.

Figure 11:
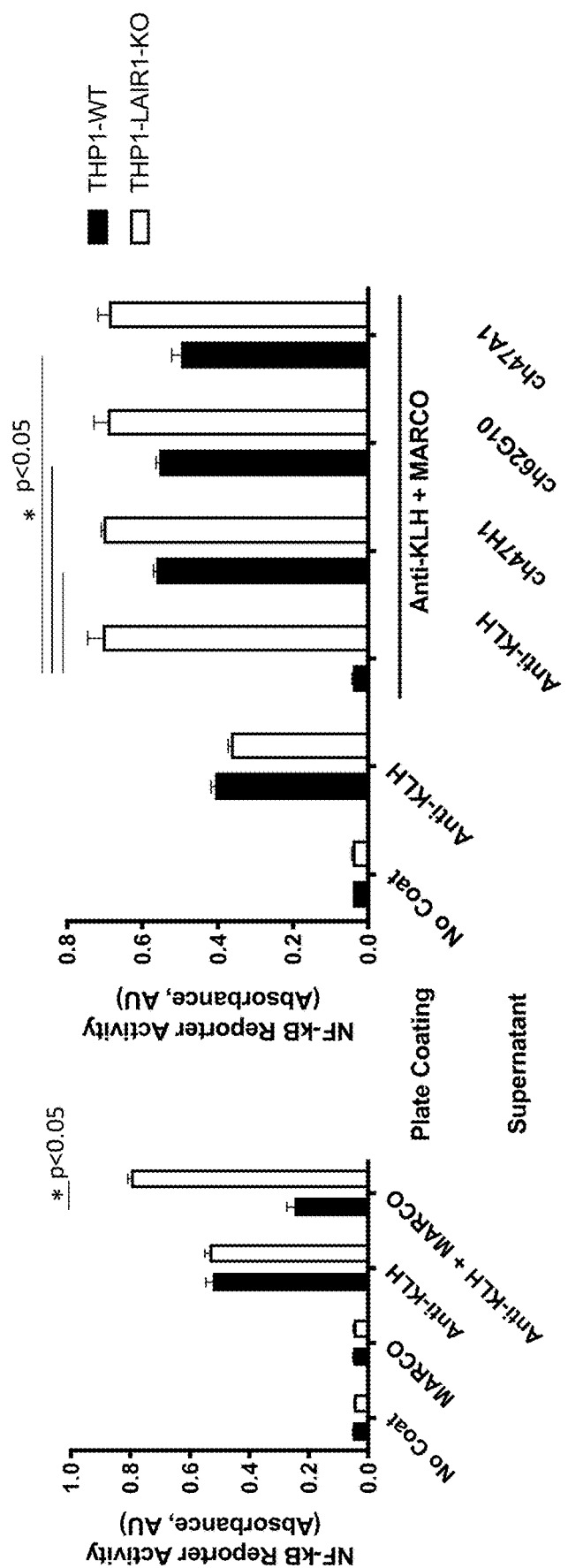
FIG. 11. Effect of anti-LAIR-1 antibodies monocyte function. 96-well Maxisorp plates were coated with 5 μg/mL anti-KLH antibody alone or a combination of anti-KLH antibody and 5 μg/mL human MARCO. THP1-Dual NF-κB-SEAP reporter cells or THP1-LAIR-1-KO-Dual NF-κB-SEAP reporter cells were added to the plates. In some samples, anti-LAIR-1 antibodies ch47H1, ch62G10 and ch47A1 (5 μg/mL) were added to the plates. Reporter cell activity was measured using Quanti-Blue SEAP substrate and reading the absorbance at 620 nm. *=p<0.05

As shown in FIG. 11, anti-KLH antibody activated reporter cell activity in both THP1-WT and THP-1-LAIR- 1-KO reporter cells. In contrast, MARCO by itself had no effect. When MARCO was co-coated with anti-KLH antibody, FcR activation was suppressed in THP1-WT cells, but not in THP1-LAIR-1-KO reporter cells.

These data demonstrate that MARCO can suppress FcR activation in monocytic cells and that the suppression was dependent on the presence of LAIR-1.

A follow-up study was performed to assess the ability of anti-LAIR-1 antibodies to restore FcR activity in MARCO-suppressed cells. As described above, 96-well Maxisorp (Nunc) plates were coated with 5 μg/mL anti-KLH antibody, with or without 5 μg/mL human MARCO-his protein and incubated at 37° C. for 1.5 hrs at room temperature. Plates were washed in X-VIVO™ 15 media (Lonza) and $1 \times 10^5$ THP1-Dual™ NF-κB-SEAP reporter cells per well were added. Anti-LAIR1 antibodies ch47A1, ch47H1, ch62G10, or a control antibody were added to the appropriate wells at 5 μg/mL. It should be noted that the anti-LAIR-1 antibodies ch47A1, ch47H1, and ch62G10 contain a mutation in the Fc region that renders them FcR binding-deficient. Plates were incubated at 37° C. overnight. Reporter activity was measured by adding Quanti-Blue™ SEAP substrate (InvivoGen), incubating the plates at 37° C. for 2 hours, and reading the absorbance at 620 nm.

The presence of anti-LAIR-1 antibodies was able to reverse the LAIR-1/MARCO-induced suppression THP1-WT cells. In the absence of LAIR-1 (THP1-LAIR1-KO cells) MARCO has no suppressive effect and thus the anti-LAIR-1 antibodies have no effect.

These data demonstrate the MARCO-mediated suppression of FcR activation by LAIR-1. Importantly, these results show that exemplary anti-LAIR-1 antibodies are capable of inhibiting and/or reversing the suppression.

Collagen was also tested for its ability to suppress FcR activation in a modified version of the same assay. 96-well Maxisorp (Nunc) plates were coated with 5 μg/mL anti-KLH antibody, with or without 1 μg/mL human collagen type 1 (Millipore Sigma). Plates were washed in X-VIVO™ 15 media (Lonza) and $1 \times 10^5$ THP1-Dual™ NF-κB-SEAP reporter cells per well were added. Anti-LAIR1 antibodies ch47H1, Hz47H1.v4, or a control antibody were added to the appropriate wells at 5 μg/mL. Plates were incubated at 37° C. overnight. Reporter activity was measured by adding Quanti-Blue™ SEAP substrate (InvivoGen), incubating the plates at 37° C. for 2 hours, and reading the absorbance at 620 nm.

Figure 12:
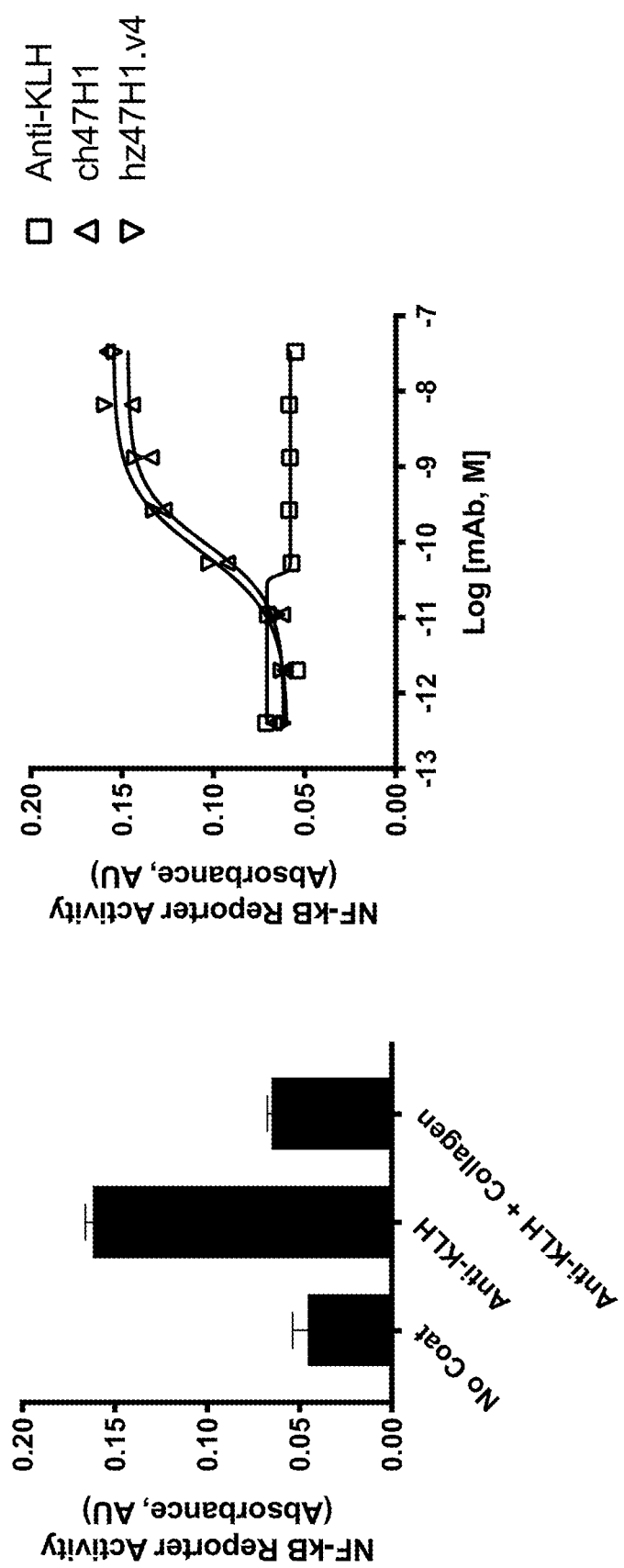
FIG. 12. Effect of anti-LAIR-1 antibodies monocyte function. 96-well Maxisorp plates were coated with 5 μg/mL anti-KLH antibody alone or a combination of anti-KLH antibody and 1 μg/mL collagen. THP1-Dual NF-κB-SEAP reporter cells were added to the plates. In some samples, a concentration range of anti-LAIR-1 antibodies ch47H1, Hz47H1.v4, or anti-KLH control antibody was added to the plates. Reporter cell activity was measured using Quanti-Blue SEAP substrate and reading the absorbance at 620 nm.

As shown in FIG. 12, an anti-KLH antibody induced Fc activation in THP1 cells as demonstrated by reporter activity and a suppressive effect was observed when collagen and anti-KLH were both present. The presence of anti-LAIR-1 antibodies was able to reverse the collagen-induced suppression in THP1 cells in a dose-dependent manner.

Collectively, these data demonstrate that MARCO and collagen can suppress FcR activation in a monocytic cell line in a LAIR-1-dependent manner. Importantly, these results show that exemplary anti-LAIR-1 antibodies are capable of inhibiting and/or reversing the suppression.

Example 11

Effect of Anti-LAIR-1 Antibodies on Dendritic Cell FcR Activation

Having established that LAIR-1 could suppress FcR activation in a monocytic THP1 cell line through interaction with MARCO or collagen, similar studies were undertaken with primary human dendritic cells. Human monocytes from PBMCs were purified using a human pan monocyte isolation kit (Miltenyi). Monocyte-derived dendritic cells (DCs) were generated by culturing the monocytes in X-VIVO™ 15 media (Lonza) containing 50 ng/mL recombinant human GM-CSF (Peprotech) and 50 ng/mL recombinant human IL-4 (Peprotech) for 5-7 days. 96-well MaxiSorp (Nunc) plates coated with 5 μg/mL anti-KLH antibody in the presence or absence of 5 μg/mL human collagen type 1 (Millipore Sigma) in 40 μL PBS/well for 1 hour at room temperature followed by a wash step. $1 \times 10^5$ DCs were added to the plates with anti-LAIR-1 antibodies ch47H1 and Hz47H1.v4 or a control antibody, and incubated overnight at 37° C. Supernatants were collected the next day and TNF-α production was measured using Luminex (ProcartaPlex system, ThermoFisher Scientific).

Figure 13:
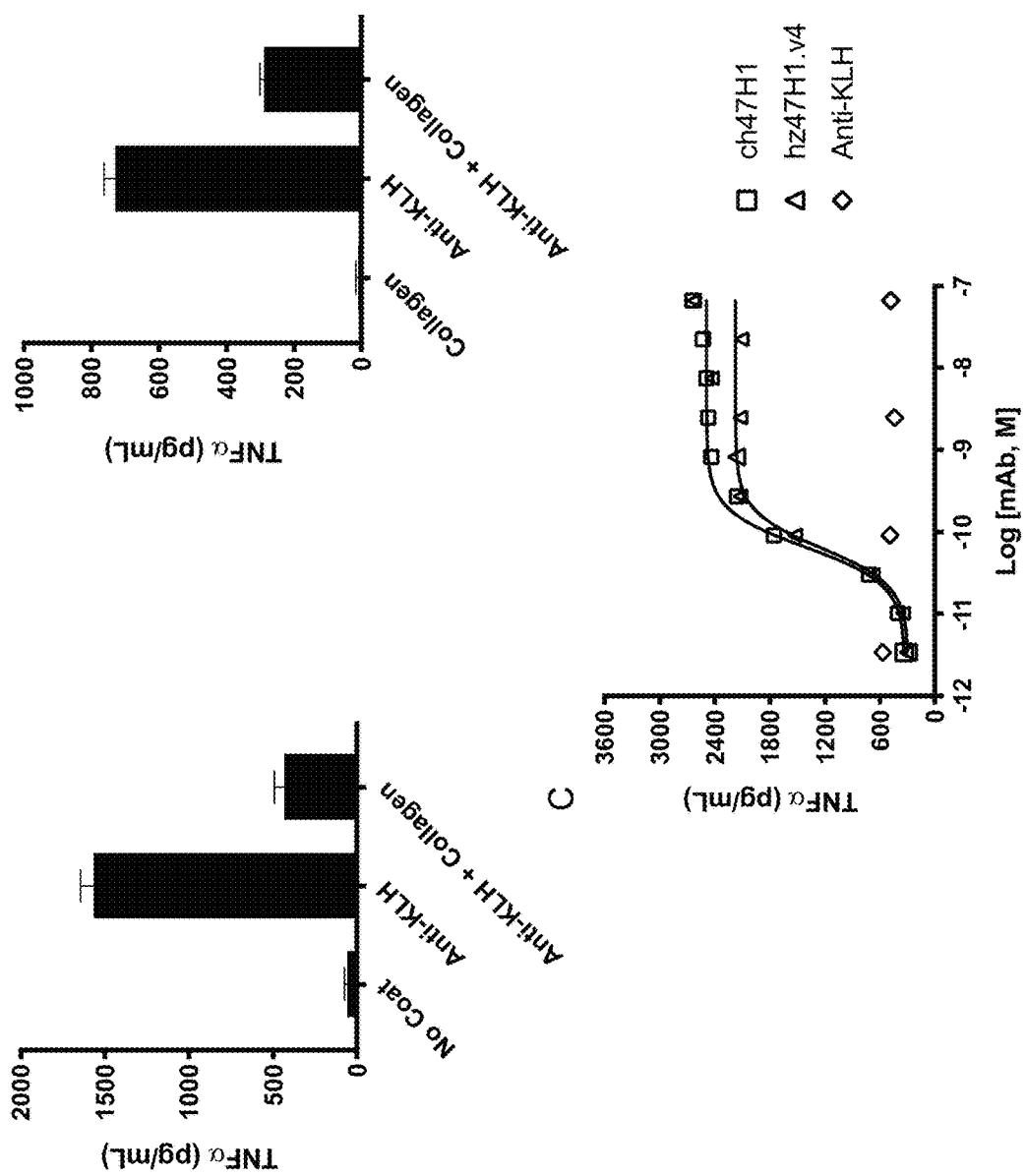
FIG. 13. Effect of anti-LAIR-1 antibodies on dendritic cell FcR activation. 96-well Maxisorp plates were coated with 5 μg/mL anti-KLH antibody in the presence or absence of 5 μg/mL human collagen type 1. Monocyte-derived dendritic cells were added the plates. In some samples, a concentration range of anti-LAIR-1 antibodies ch47H, Hz47H1.v4, or anti-KLH control antibody was added to the plates. Supernatants were collected and TNF-α production was measured using Luminex.

As shown in FIG. 13, anti-KLH antibody induced TNF-α secretion in monocyte-derived DCs. In contrast, when collagen was present, there was a reduction in TNF-α secretion. Collagen alone had no effect on TNF-α secretion, but collagen was able to suppress TNF-α secretion induced by anti-KLH antibody. Importantly, in the presence of exemplary anti-LAIR-1 antibodies ch47H1 and Hz47H1.v4, the suppression of TNF-α secretion was reversed in a dose-dependent manner; whereas a control antibody had no effect.

These data support the hypothesis that LAIR-1 and collagen interactions suppress FcR-mediated activation of primary human DCs, and that anti-LAIR-1 antibodies could restore activation in these cells.

Example 12

Effect of Anti-LAIR-1 Antibodies on Collagen-Polarized Primary Human Myeloid Cells In theory, collagen-polarized primary human myeloid cell activity would be expected to be suppressed due to the interaction of LAIR-1 and collagen. To evaluate the role of LAIR-1 in collagen-polarized myeloid cells, assays were performed in the absence or presence of anti-LAIR-1 antibodies and the amount of inflammatory cytokines produced by the primary human myeloid cells was determined as a marker of activation. Human monocytes from PBMCs were purified using a human pan monocyte isolation kit (Miltenyi). For generation of dendritic cells, purified monocytes were cultured in X-VIVO™ 15 media (Lonza) containing recombinant human 50 ng/mL of recombinant human GM-CSF and 50 ng/mL of recombinant human IL-4 (Peprotech). For generation of macrophage cells, purified monocytes were cultured in X-VIVO™ 15 media (Lonza) containing 50 ng/mL of recombinant human MCSF. Cells were cultured for 5-7 days. 96-well tissue culture-treated plates (Corning) were coated with 5 μg/mL human collagen type 1 (Millipore Sigma) in PBS overnight at 4° C. Plates were washed with PBS prior to addition of cells. $5 \times 10^4$ dendritic cells or macrophages were added to the plates in the presence of anti-LAIR-1 antibody ch47H1 or an anti-KLH control antibody (10 μg/mL). After 2-3 days incubation, cell supernatants were collected and cytokine/chemokine analysis was performed using Luminex (ProcartaPlex system; ThermoFisher Scientific).

Figure 14:
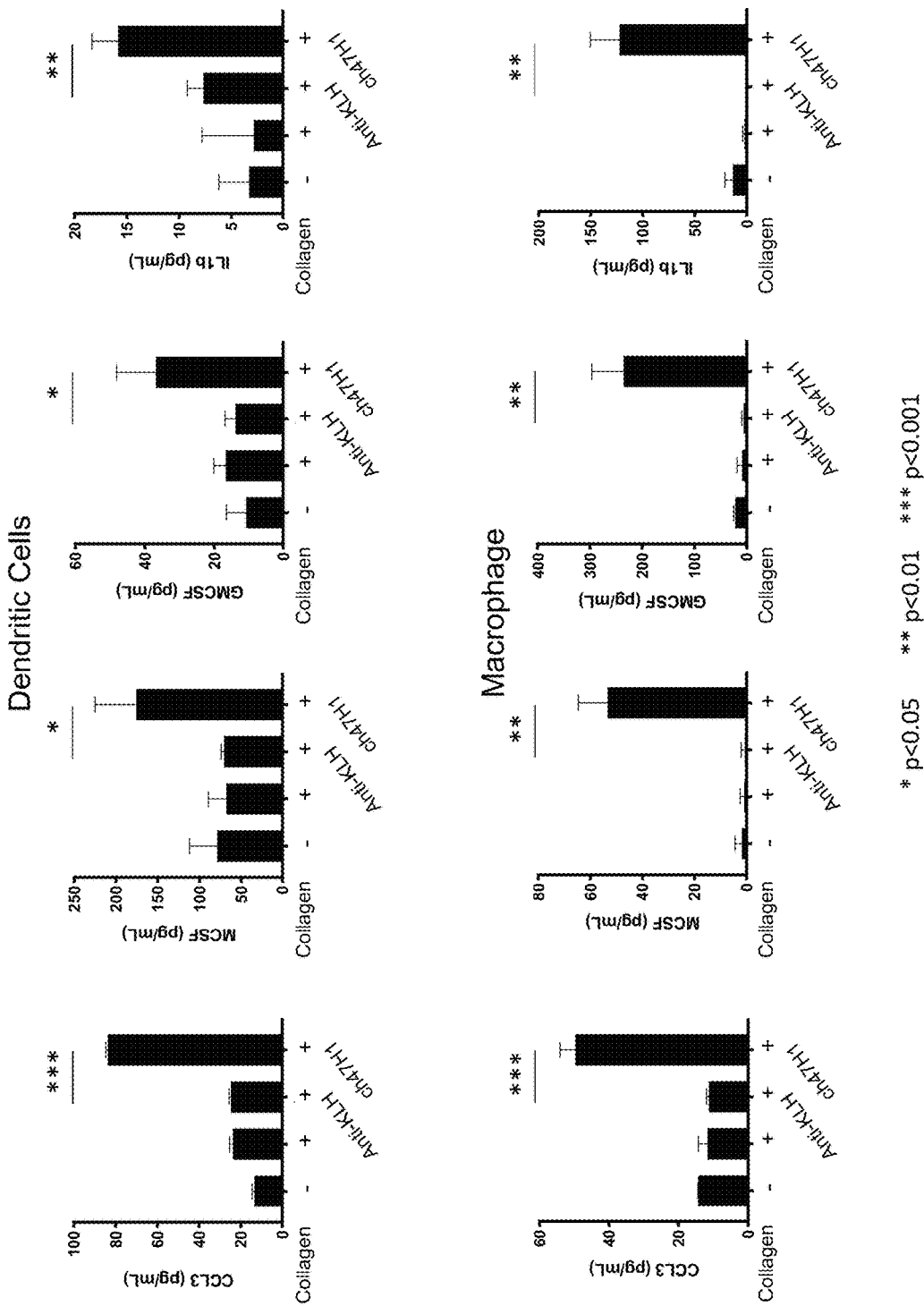
FIG. 14. Effect of anti-LAIR-1 antibodies on primary human myeloid cells activation. 96-well Maxisorp plates were coated with 5 μg/mL human collagen type 1. Monocyte-derived dendritic cells or macrophages were added the plates. Anti-LAIR-1 antibody ch47H1 or anti-KLH control antibody (10 μg/mL) was added to the plates. Supernatants were collected and cytokine/chemokine production was measured using Luminex. *=p<0.05=p<0.01*=p<0.001

As shown in FIG. 14, dendritic cells demonstrated no changes to CCL3/MIP1α, M-CSF (macrophage colony-stimulating factor), GM-CSF (granulocyte-macrophage colony-stimulating factor), or IL-IP secretion when incubated in the presence of collagen. In the presence of anti-LAIR-1 antibody ch47H1, there was a significant increase in the production of these representative cytokines/chemokines. Similar results were observed in macrophages.

In a follow-up experiment, dendritic cells were generated as described above. 96-well tissue culture-treated plates (Corning) were coated with human collagen type 1 (Millipore Sigma), fibronectin (Millipore Sigma), Laminin (Millipore Sigma) at 5 μg/mL each in PBS overnight at 4° C. $5 \times 10^4$ dendritic cells were added to the plates in the presence of anti-LAIR-1 antibody ch47A1, ch47H1, ch62G10, ch108D10, or an anti-KLH control antibody (10 μg/mL). After 2-3 days incubation, cell supernatants were collected and cytokine/chemokine analysis was performed using Luminex (ProcartaPlex system; ThermoFisher Scientific). A similar experiment was set up with anti-LAIR-1 antibody Hz47H1.v4.

Figure 15:
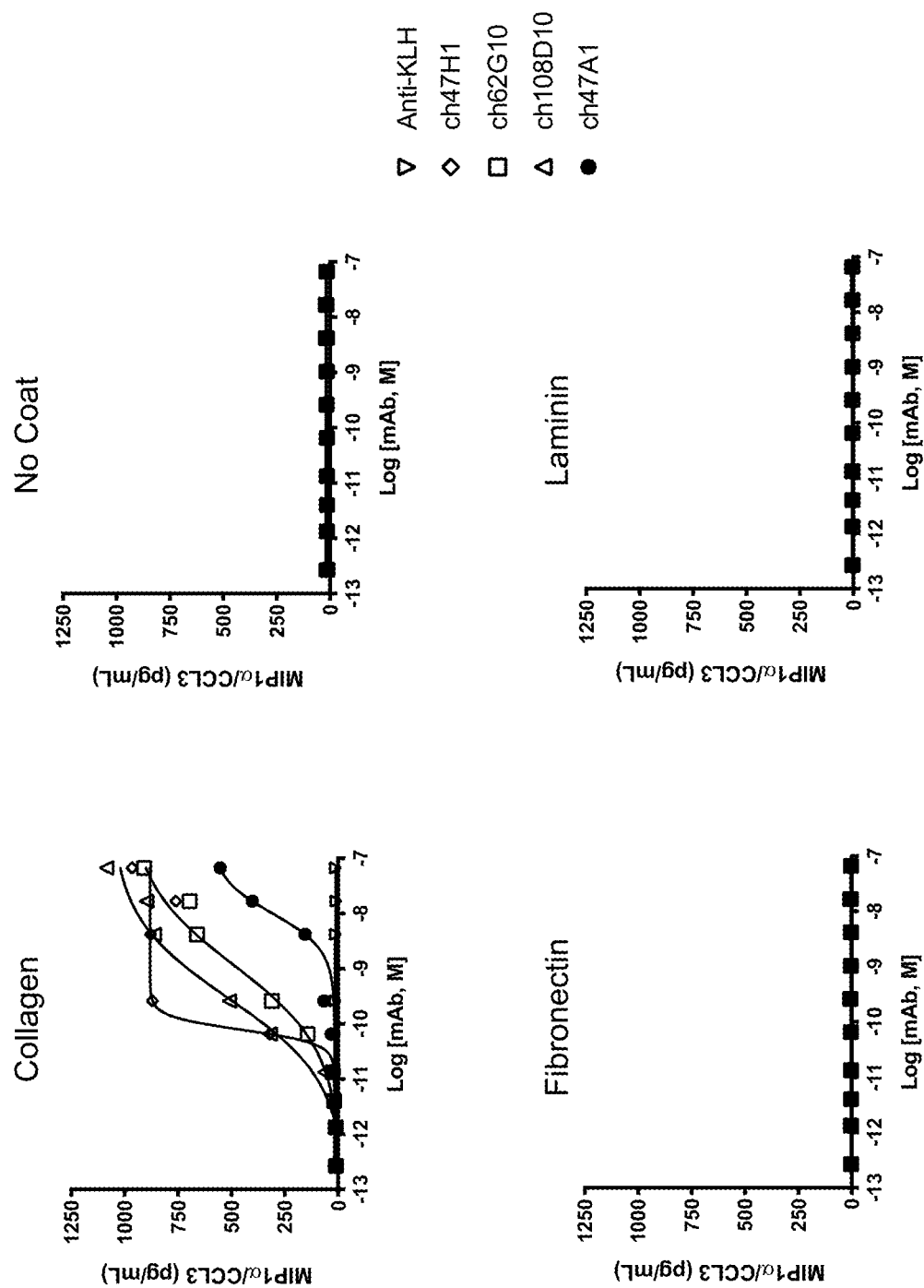
FIG. 15. Effect of anti-LAIR-1 antibodies on dendritic cells. 96-well Maxisorp plates were coated with 5 μg/mL human collagen type 1, 5 μg/mL fibronectin, or 5 μg/mL laminin. Monocyte-derived dendritic cells were added the plates. A concentration range of anti-LAIR-1 antibodies ch47H1, ch62G10, ch108D10, ch47A1, or anti-KLH antibody was added to the plates. Supernatants were collected and MIPα/CCL3 production was measured using Luminex.
Figure 16:
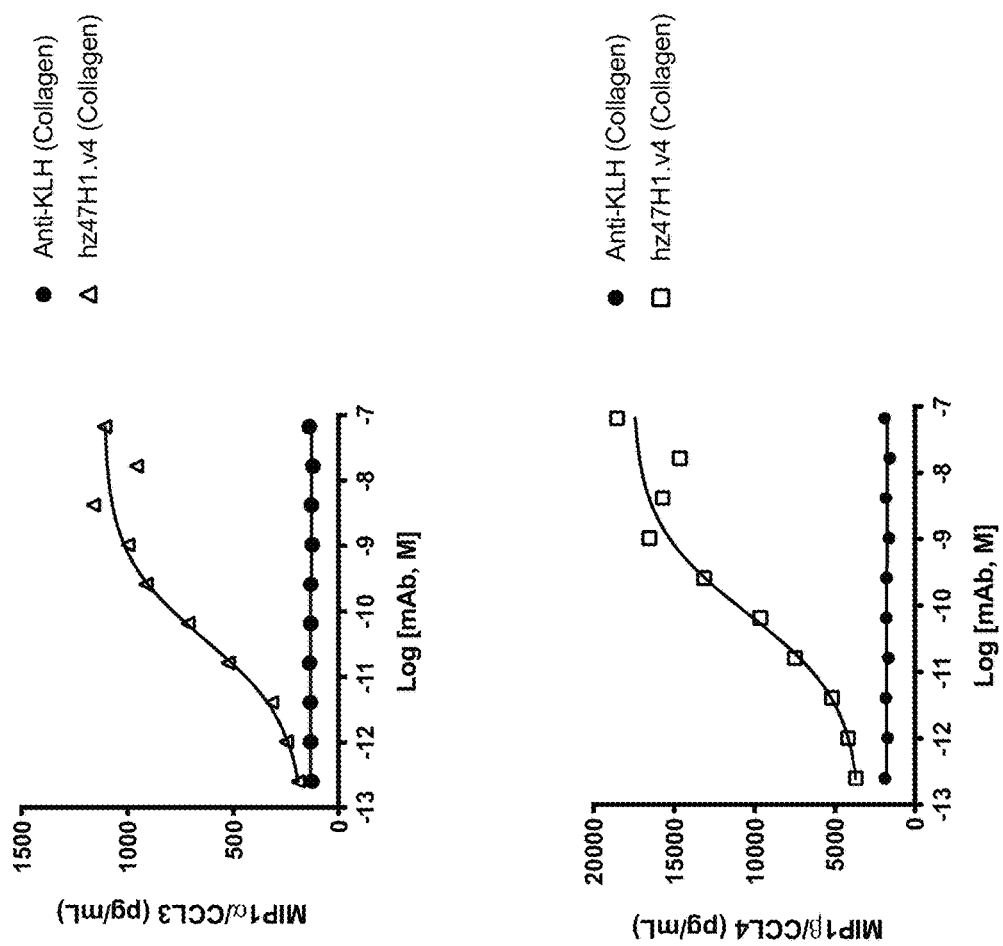
FIG. 16. Effect of anti-LAIR-1 antibodies on dendritic cells. 96-well Maxisorp plates were coated with 5 μg/mL human collagen type 1. Monocyte-derived dendritic cells were added the plates. A concentration range of anti-LAIR-1 antibody hz47H1.v4 or anti-KLH antibody was added to the plates. Supernatants were collected and levels of secreted MIPα/CCL3 and MIPs/CCL4 were measured using Luminex.

As shown in FIG. 15, anti-LAIR-1 antibodies ch47A1, ch47H1, ch62G10, and ch108D10 induced the secretion of CCL3/MIP1a by dendritic cells in a dose-dependent manner in the presence of collagen. There was no detectable production of CCL3/MIP1a in the presence of fibronectin or laminin or in the absence of a matrix protein. As shown in FIG. 16, the humanized Hz47H1.v4 antibody produced the very similar results as the chimeric antibody ch47H1. Hz47H1.v4 antibody induced secretion of CCL3/MIP1a and CCL4/MIP1β by dendritic cells in a dose-dependent manner in the presence of collagen.

Collectively these data show that collagen-polarized myeloid cells can be activated by exemplary anti-LAIR-1 antibodies and these activated cells produce inflammatory cytokines/chemokines.

Example 13

Effect of Anti-LAIR-1 Antibodies on Allogenic Mixed Lymphocyte Reactions

The mixed lymphocyte reaction (MLR) is a classic immunological assay used to investigate interactions between MHC-mismatched immune cells. The contribution of the LAIR-1 pathway in the context of a mixture of MHC-mismatched immune cells was investigated by performing MLR assays.

Monocyte-derived dendritic cells were generated as described herein. Allogeneic MHC-mismatched human T-cells were purified from PBMCs using a human pan T isolation kit (Miltenyi). Donor cells were pre-screened for MLR compatibility/incompatibility and collagen-responsiveness. 96-well plates were coated with 5 μg/mL human collagen type 1 (Millipore Sigma) in PBS overnight at 4° C. The plates were washed and $2.5 \times 10^4$ dendritic cells and $1 \times 10^5$ T-cells were added to each well. In some wells anti-LAIR-1 antibodies ch47A1, ch47H1, ch62G10, or an anti-KLH control antibody were added. The plates were incubated for 3-4 days at 37° C. To measure proliferation, fresh media containing tritiated thymidine ($^3$H-thymidine; Perkin-Elmer) was added at a concentration of 1 μCi/mL. After an additional overnight incubation, cells were harvested onto filters using a Harvester96™ (Tomtec) and $^3$H-thymidine incorporation was counted on a MicroBeta$^2$ microplate reader (PerkinElmer). A follow-up experiment was set up under similar conditions but in the presence of anti-LAIR-1 antibodies ch47H1 and humanized Hz47H1.v4.

Figure 17:
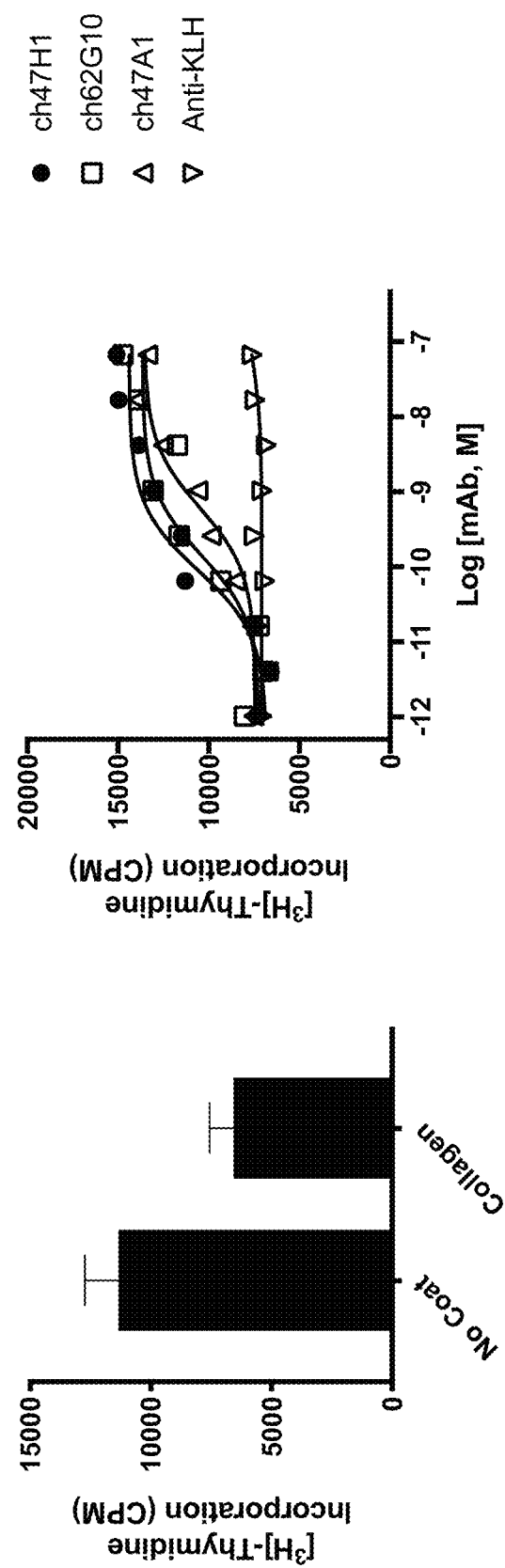
FIG. 17. Effect of anti-LAIR-1 antibodies on a MLR assay. 96-well plates were coated with 5 μg/mL human collagen type 1. Dendritic cells and allogeneic T-cells were added to the plates. In some samples, a concentration range of anti-LAIR-1 antibodies ch47H1, ch62G10, ch47A1, or anti-KLH control antibody was added to the plates. After 3-4 days, fresh media containing tritiated thymidine was added at a concentration of 1 μCi/mL. After an overnight incubation, cells were harvested onto filters and $3^H$-thymidine incorporation was counted on a MicroBeta2 microplate reader.
Figure 18:
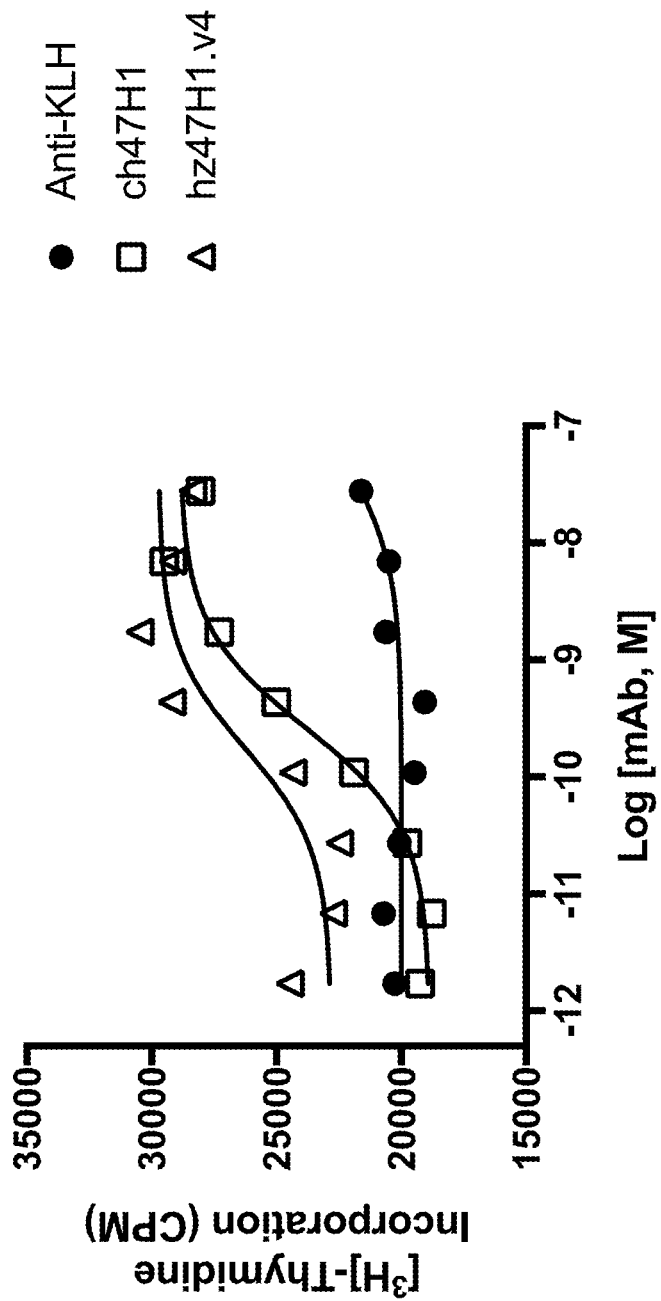
FIG. 18. Effect of anti-LAIR-1 antibodies on a MLR assay. 96-well plates were coated with 5 μg/mL human collagen type 1. Dendritic cells and allogeneic T-cells were added to the plates. A concentration range of anti-LAIR-1 antibodies ch47H1, Hz47H1.v4, or anti-KLH control antibody was added to the plates. After 3-4 days, fresh media containing tritiated thymidine at a concentration of 1 μCi/mL was added. After an overnight incubation, cells were harvested onto filters and $3^H$-thymidine incorporation was counted on a MicroBeta2 microplate reader.

As shown in FIG. 17, allogenic dendritic cell/T-cell pairs elicited a strong proliferative response. The proliferative response was weaker in the presence of collagen than in its absence (approximately 50% less proliferation). The presence of anti-LAIR1 antibodies increased proliferation in a dose-dependent manner. As shown in FIG. 18, anti-LAIR-1 antibodies ch47H1 and Hz47H1.v4 produced similar results in the MLR assays.

Figure 24:
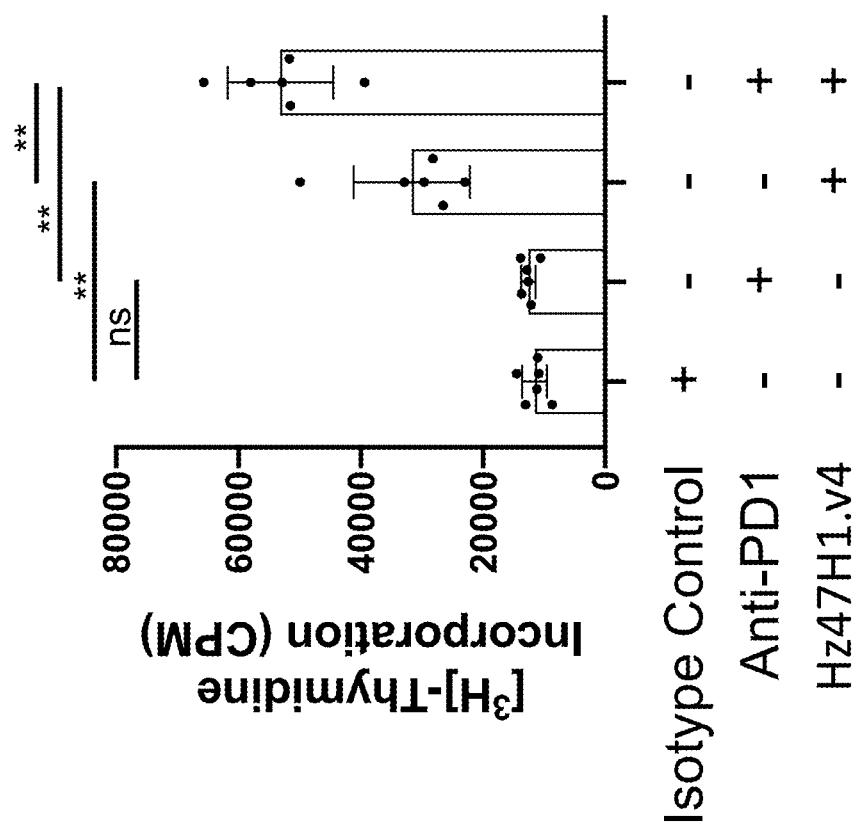
FIG. 24. Synergistic effect of an anti-LAIR-1 antibody and anti-PD1 antibody on proliferation of T cells in a MLR assay. 96-well plates were coated with human collagen type 1. Dendritic cells and allogeneic T-cells were added to the plates. Hz47H1.v4, pembrolizumab, Hz47H1.v4 in combination with pembrolizumab, or anti-KLH control antibody was added to the plates. T cell proliferation was measured by $3^H$-thymidine incorporation.

The MLR assay described herein was further developed to evaluate the potential synergistic effects of combining LAIR1 blockade with PD-1 blockade on DC-T cell MLRs in the presence of collagen. In this set of experiments, the MLRs were incubated in the presence of single dose of (1) an isotype control antibody, (2) Hz47H1.v4, (3) the anti-PD-1 antibody pembrolizumab, or (4) Hz47H1.v4 in combination with anti-PD-1 antibody (pembrolizumab). All antibodies were added at 5 μg/mL each. As shown in FIG. 24, anti-PD1 antibody had no effect, Hz47H1.v4 alone enhanced T cell proliferation. The combination of both treatments further increased proliferation above Hz47H1.v4 alone. These data demonstrate that the combination of Hz47H1.v4 and anti-PD1 antibody work synergistically to promote T cell proliferation in a DC-T cell MLR assay in the presence of collagen.

These results show that the interaction of LAIR-1 and collagen can suppress the activation of immune cells as demonstrated in an in vitro MLR assay and that exemplary anti-LAIR-1 antibodies can inhibit this suppression. These observations support the idea that anti-LAIR-1 antibodies can enhance immune responses in a microenvironment where there is a suppression from LAIR-1-ligand interactions. These data also show the ability of anti-LAIR-1 antibody to promote synergistic effects with an immune-checkpoint inhibitor to enhance immune responses in a microenvironment where there is a suppression from LAIR-1-ligand interactions.

Example 14

Effect of Anti-LAIR-1 Antibodies on T-Cell Activation

To investigate the role of LAIR1 on T-cell activation in the presence of collagen, the effects of anti-LAIR1 antibody (e.g., ch47H1 and Hz47H1.v4) was evaluated in an anti-CD3 antibody-induced T-cell activation assay. 96-well Maxisorp (Nunc) plates were coated with 10 μg/mL collagen from calf skin (Sigma) in water and incubated overnight at 4° C. Human T-cells were prepared from PBMCs using a human pan T-cell isolation kit (Miltenyi). Plates were washed, anti-CD3 antibody clone OKT3 (Biolegend) was coated on the plates in PBS over a range of concentrations, and incubated for 3 hours at 37° C. Plates were washed and $1 \times 10^5$ T-cells were added to the plates in RPMI 1640 (Corning) containing 10% heat-inactivated FBS (MermoFisher Scientific) in the presence of an anti-LAIR1 antibody or an anti-KLH control antibody (5 μg/mL). The plates were incubated for 3 days at 37° C., cell supernatants were collected, and cytokine analysis was performed using Luminex (ProcartaPlex system; ThermoFisher Scientific) or cytokine assay kits (MesoScale Diagnostics). To measure proliferation, fresh media containing tritiated thymidine ($3^H$-thymidine; Perkin-Elmer) was added. After an overnight incubation, cells were harvested onto filters using a Harvester96™ (Tomtec), and $^3$H-thymidine incorporation was counted on a MicroBeta2 microplate reader (PerkinElmer).

Figure 19A:
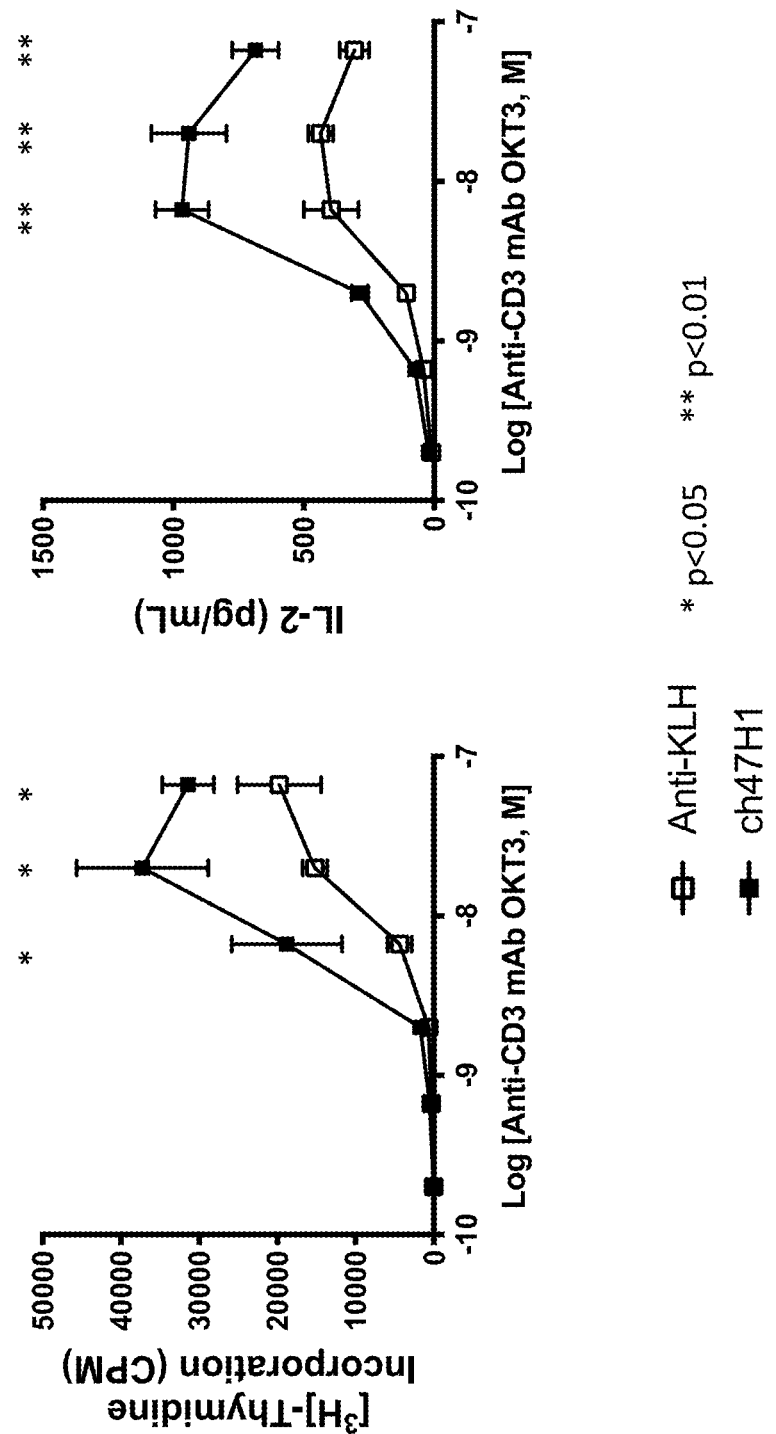
FIG. 19A-19B. Effect of anti-LAIR-1 antibodies on T-cell activation. 96-well plates were coated with 10 μg/mL collagen from calf skin. A concentration range of anti-CD3 antibody was subsequently added to the plates. T-cells with anti-LAIR-1 antibody ch47H1 or Hz47H1.v4 or anti-KLH control antibody were added to the plates. After 3-4 days, supernatants were collected for cytokine analysis. Fresh media containing tritiated thymidine at a concentration of 1 μCi/mL was added to the plates. After an overnight incubation, cells were harvested onto filters and $^3$H-thymidine incorporation was counted on a MicroBeta2 microplate reader.
Figure 19B:
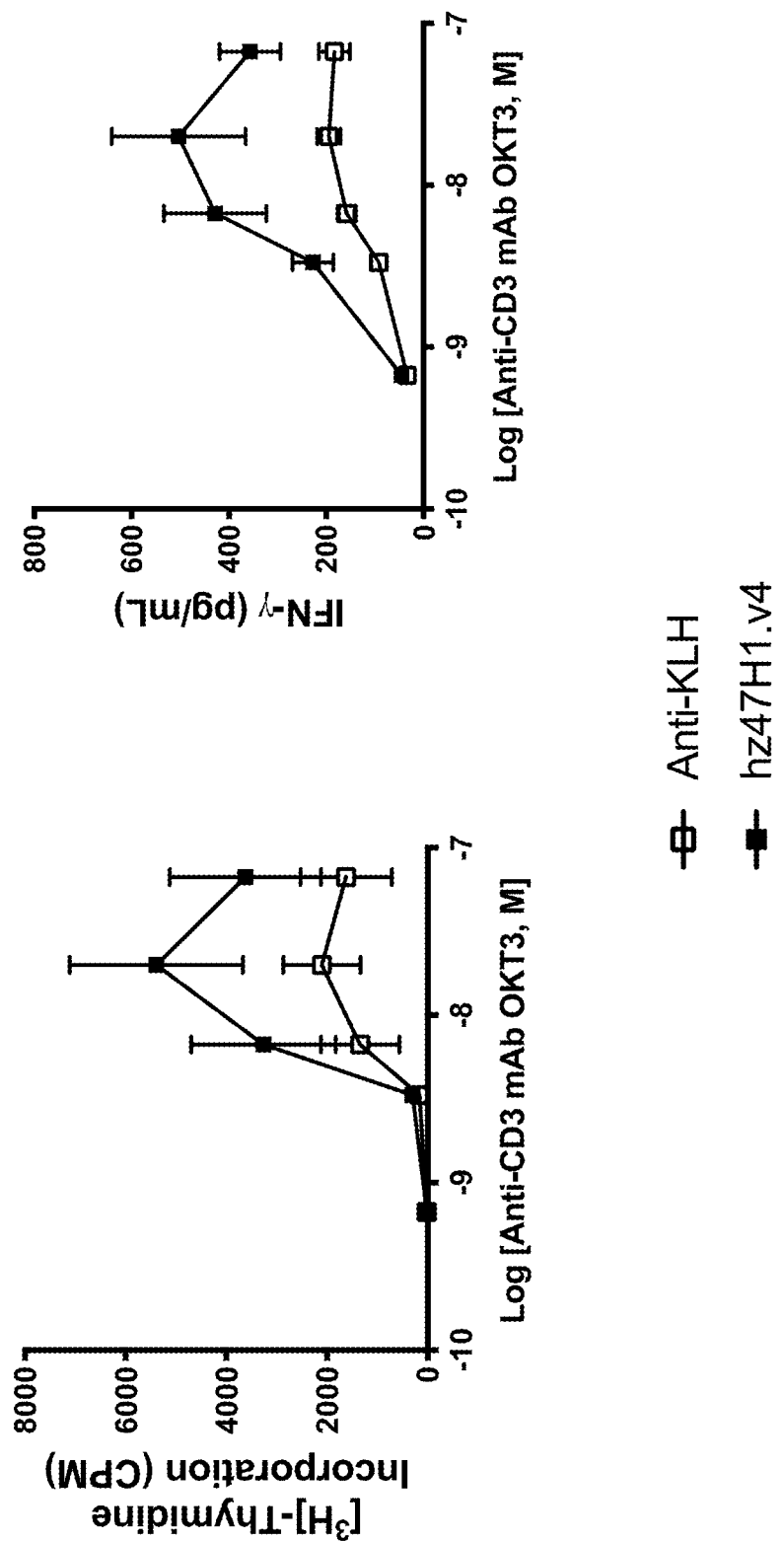

As shown in FIG. 19A, anti-CD3 antibody stimulated T-cell proliferation and IL-2 production. In the presence of anti-LAIR1 antibody ch47H1, proliferation and IL-2 production of T cells were increased relative to the control antibody across a range of anti-CD3 antibody stimulation. As shown in FIG. 19B, anti-CD3 antibody stimulated T-cell proliferation and interferon gamma (IFN-γ) production. In the presence of anti-LAIR1 antibody Hz47H1.v4, proliferation and IFN-γ production of T cells were increased relative to the control antibody across a range of anti-CD3 antibody stimulation.

These results show that the interaction of LAIR-1 and collagen can suppress the activation of T-cells in the presence of collagen and that exemplary anti-LAIR-1 antibodies described herein can inhibit this suppression. These observations support the idea that anti-LAIR-1 antibodies can enhance immune responses, including T cell proliferation and cytokine production, in a microenvironment where there is a suppression from LAIR-1-ligand interactions.

Example 15

Generation and Screening of Antibodies that Bind Mouse LAIR-1

The exemplary anti-LAIR-1 antibodies described herein bind human LAIR-1 and cyno LAIR-1, but do not bind mouse LAIR-1. Antibodies that specifically bind mouse LAIR-1 may be desired for studies in mouse models.

Anti-mouse LAIR-1 antibodies were generated using a fragment of mouse LAIR-1 as the immunogen. Recombinant constructs comprising a fragment of mouse LAIR-1 (aa 22-133 of SEQ ID NO:149) were generated and expressed in mammalian cells. Rats were immunized with the mouse LAIR-1 protein and were boosted several times to induce high titers. Blood was drawn from the immunized rats and antibody titers were determined. Single cell suspensions of lymphocytes were obtained from the spleens and lymph nodes of immunized rats that had been determined to have suitably high antibody titers. Lymphocytes were fused with murine myeloma cells by standard methods (e.g., electrofusion). Cells were dispersed into 96-well plates in HAT-containing selection media.

Anti-mouse LAIR-1 antibodies were screened for similar binding and functional characteristics as the exemplary anti-human LAIR-1 antibodies described herein. Similar characteristics are desirable for a surrogate antibody. A "surrogate antibody" is generally described as a functionally equivalent antibody to a therapeutic antibody candidate (e.g., anti-human LAIR-1 antibodies) while binding specifically to the target ortholog (e.g., mouse LAIR-1) expressed in the intended animal species.

ELISA and FACS assays were used to screen antibodies for binding to mouse LAIR-1. Exemplary antibody 43H2 was selected and the heavy chain and light chain variable regions were cloned into a mouse IgG2a backbone (ch43H2).

The binding affinity of purified ch43H2 to mouse LAIR-1 was measured using a Biacore system (GE Healthcare LifeSciences). Binding data is shown in Table 15.

TABLE 15

| | Mouse LAIR-1 | | |
|---|---|---|---|
| Antibody | $k_{on}$ $M^{-1}s^{-1}$ | $k_{off}$ $s^{-1}$ | $K_D$ M |
| ch43H2 | $5.3 \times 10^5$ | $5.7 \times 10^{-4}$ | $1.1 \times 10^{-9}$ |

Antibody 43H2 was sequenced and the heavy chain variable region and light chain variable region amino acid sequences are disclosed herein as SEQ ID NO:131 and SEQ ID NO:132, respectively. CDR sequences for antibody 43H2 are summarized in Table 7.

Example 16

Effect of Anti-Mouse LAIR-1 Antibodies on the Interaction Between Mouse LAIR-1 and LAIR-1 Ligands To examine whether the anti-mouse LAIR-1 antibody 43H2 could inhibitor block the binding of mouse LAIR-1 to collagen, ELISA assays were performed. Mouse collagen type 1 (BioRad) was coated onto a 384-well MaxiSorp (Nunc) plate at 2 µg/mL in PBS overnight at 4° C. The plate was washed with PBS/0.05% Tween® 20 and blocked with assay buffer (PBS/1% BSA) for 1 hour at room temperature. Antibody 43H2 was pre-incubated with 2 µg/mL mouse LAIR-1-hFc (Sino Biological) for 20 minutes at room temperature, added to the plate, and incubated for 1 hour at room temperature. The plate was washed and incubated with HRP-conjugated anti-human Fc secondary reagent (Jackson ImmunoResearch) for 1 hour at room temperature. The plate was washed and developed with TMB Chromogen solution (Life Technologies) for 5 min. The plate was read at 650 nm on a Spectramax plate reader (Molecular Devices).

To examine whether the anti-mouse LAIR-1 antibody 43H2 could inhibitor block the binding of mouse LAIR-1 to mouse MARCO expressed on cells, flow cytometry assays were performed. HEK-293T (ATCC) were transfected with 10 µg of plasmid DNA using standard methods. Cells were incubated for 2 days at 37° C. and then washed in staining buffer (PBS/1% BSA/0.1% sodium azide). Antibody 43H2 was pre-incubated with 2 µg/mL mouse LAIR-1-hFc (Sino Biological) for 20 minutes at room temperature. The antibody-protein mixture was then incubated with $1 \times 10^5$ cells/well for 1 hour at room temperature. Cells were washed with staining buffer and Alexa Fluor 647-conjugated anti-human Fc secondary reagent (Jackson ImmunoResearch) was added to cells for 30 min at 4° C. Cells were washed in staining buffer and signal was detected by flow cytometry on an Intellicyt instrument (Sartorius).

Figure 20:
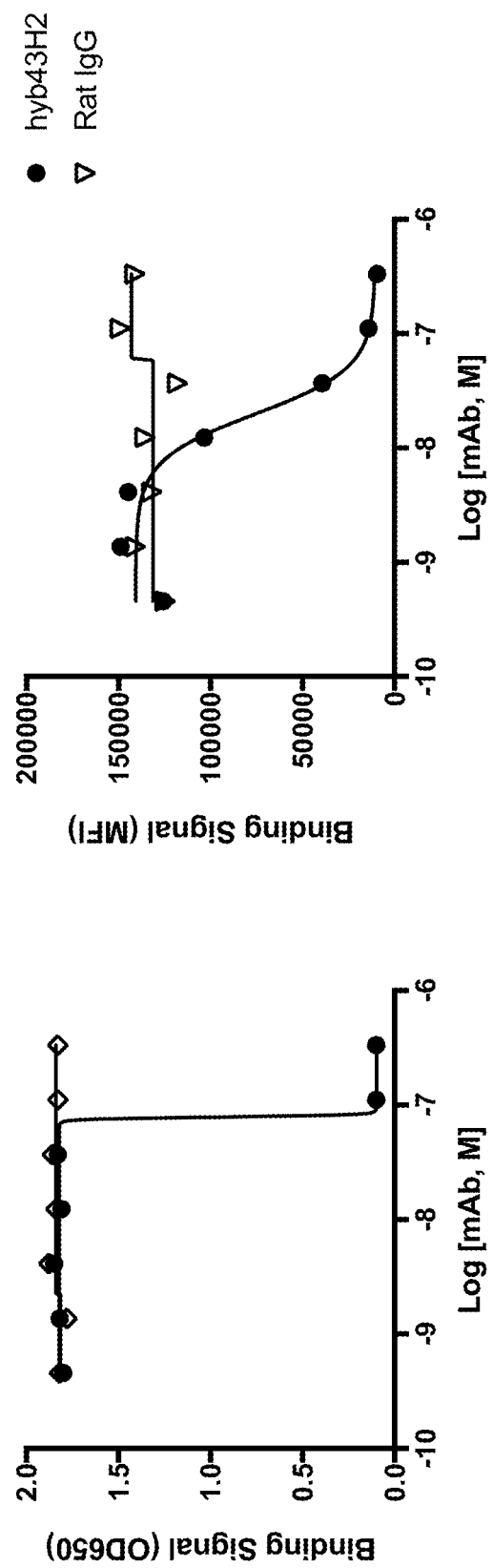
FIG. 20. Effect of anti-mouse LAIR-1 antibody on interaction between mouse LAIR-1 and LAIR-1 ligands. 384-well plates were coated with 2 μg/mL mouse collagen type 1. Antibody 43H2 or a control antibody were incubated with mouse LAIR-1-hFc protein and added to the plates. HRP-labeled anti-human Fc secondary antibody was added. TMB chromogen solution was added and the plates were read at 650 nm on a Spectramax plate reader.

As shown in FIG. 20, anti-mouse LAIR-1 antibody 43H2 inhibited the binding of mouse LAIR-1-Fc to collagen, whereas rat immunoglobulin (IgG) had no effect. Similarly, anti-mouse LAIR-1 antibody 43H2 inhibited the binding of mouse LAIR-1-Fc to MARCO expressed on cells in a dose-dependent manner. In contrast, rat IgG had no effect.

Example 17

Inhibition by Anti-Mouse LAIR-1 Antibody of the Interaction Between LAIR-1 and LAIR-1 Ligands To characterize the ability of 43H2 to inhibit the interaction between LAIR-1 and extracellular matrix proteins as well as MARCO, reporter cell assays were performed.

Mouse LAIR-1 reporter cells were generated in a manner similar to generation of the human and cyno LAIR-1 reporter cells described herein. However, the extracellular domain of mouse LAIR-1 was fused with the transmembrane/intracellular domain of PILRβ. When the chimeric receptor is activated by binding to ligand (e.g., collagen) DAP12 becomes phosphorylated and activates a NFAT-responsive promoter that drives GFP expression.

96-well Maxisorp (Nunc) plates were coated with 2 µg/mL of mouse collagen type 1 (YoProteins), 10 µg/mL of mouse collagen type 4 (Corning), or 2 µg/mL of recombinant human MARCO-his protein (in-house) overnight at 4° C. Plates were washed before adding a concentration range of anti-LAIR-1 antibody 43H2 or an anti-KLH control antibody. $4 \times 10^5$ mouse LAIR-1-PILRβ-GFP reporter cells in 80 µL RPMI 1640 containing 10% heat-inactivated FBS (Gibco) were added and plates were incubated overnight at 37° C. GFP expression was measured by flow cytometry on a LSRFortessa™ Instrument (BD Biosystems) and analyzed by FlowJo software. Negative and positive GFP signals were gated using the activity measurements from a non-specific immunoglobulin protein (negative control) and an anti-LAIR-1 antibody (positive control, ThermoFisher Scientific) on reporter cells.

Figure 21:
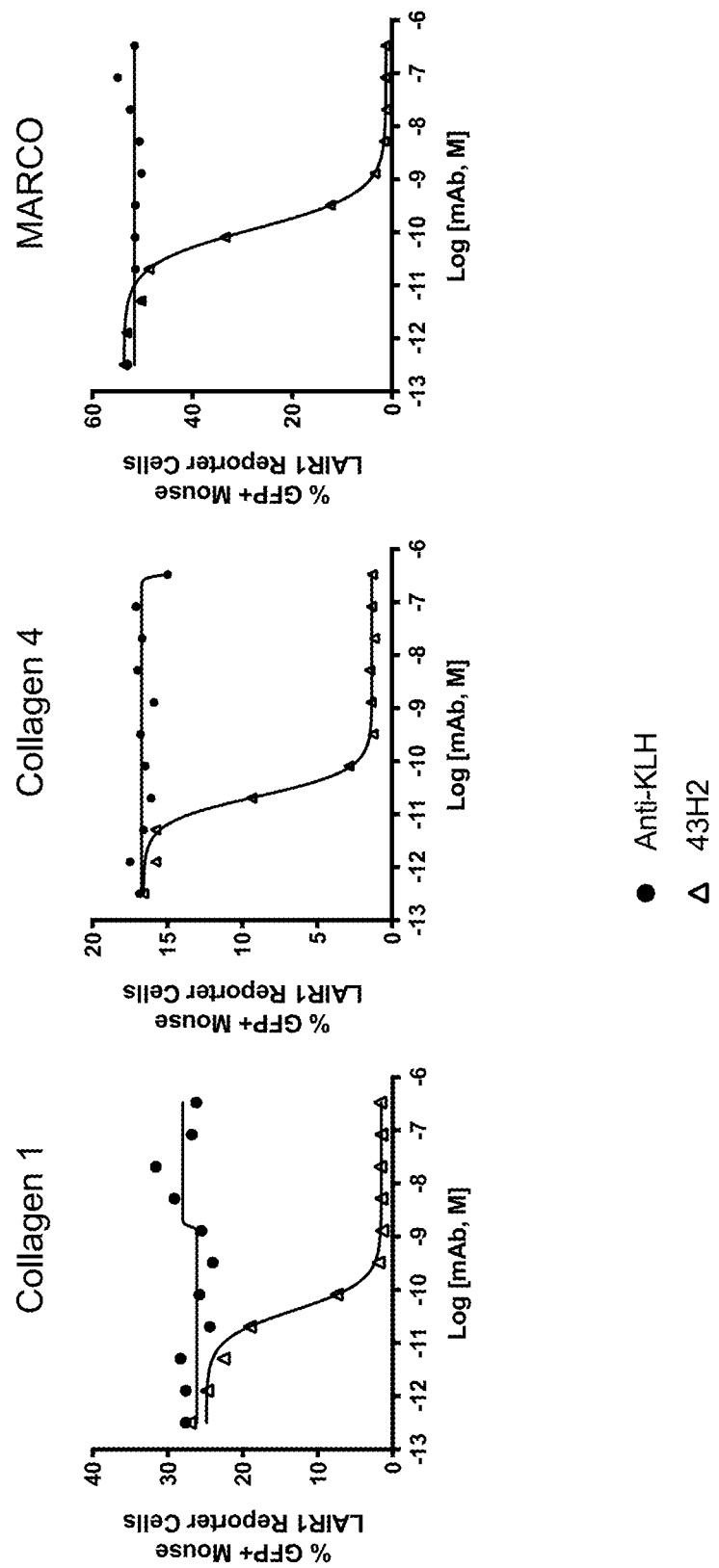
FIG. 21. Effect of anti-mouse LAIR-1 antibody on interaction between mouse LAIR-1 and LAIR-1 ligands. 96-well plates were coated with 2 μg/mL mouse collagen type 1, 10 μg/mL mouse collagen type 4, or 2 μg/mL human MARCO-his. Mouse-LAIR-1-PILRβ-GFP reporter cells were added to the plates with a concentration range of antibody 43H2 or a control antibody. GFP expression was measured by flow cytometry and analyzed using FlowJo software.

As shown in FIG. 21, GFP expression was induced when mouse LAIR-1 reporter cells were incubated with collagen 1, collagen 4, or MARCO. Anti-LAIR-1 antibody 43H2 inhibited GFP expression in a dose-dependent manner for all three proteins, while the control antibody had no effect.

Another study was performed to test the ability of anti-LAIR-1 43H2 antibody to inhibit the functional interaction between mouse LAIR-1 with proteins produced by bEnd.3 cells as described herein. A modified version of the reporter cell assay described above was performed. $1 \times 10^5$ bEnd.3 tumor cells (ATCC) were incubated with $4 \times 10^5$ mouse LAIR-1-PILRβ-GFP reporter cells and a concentration range of anti-LAIR-1 antibody 43H2 or an anti-KLH control antibody. The mouse LAIR-1-PILRβ-GFP reporter cells were labeled with CellTrace Violet (Thermo) to discriminate them from the bEnd.3 cells. Plates were incubated overnight at 37° C. GFP expression was measured by flow cytometry on a Fortessa Analyzer (BD). Negative and positive GFP signals were gated using the activity measurements from a non-specific immunoglobulin protein (negative control) and an anti-LAIR-1 antibody (positive control, ThermoFisher Scientific) on reporter cells.

Figure 22:
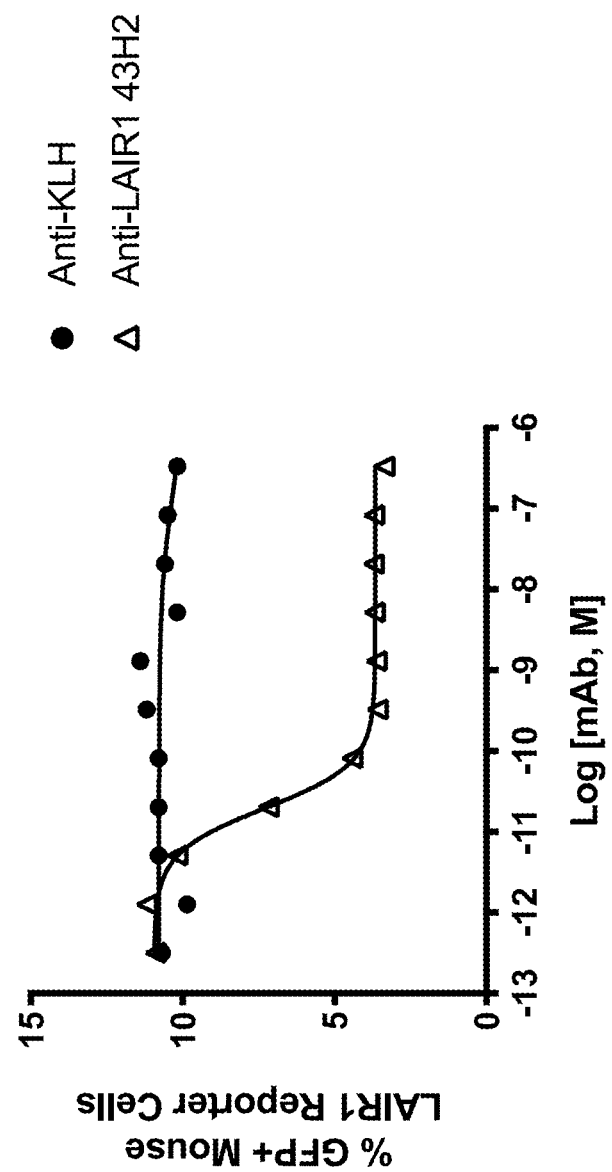
FIG. 22. Effect of anti-mouse LAIR-1 antibody on interaction between mouse LAIR-1 and LAIR-1 ligands. bEnd.3 cells were added to plates. Mouse-LAIR-1-PILRβ-GFP reporter cells were added to the plates with a concentration range of antibody 43H2 or a control antibody. GFP expression was measured by flow cytometry and analyzed using FlowJo software.

As shown in FIG. 22, bEnd.3 cells induced expression of GFP in mouse LAIR-1 reporter cells, demonstrating expression of at least one functional LAIR-1 ligand, likely a collagen(s). Anti-LAIR-1 antibody 43H2 inhibited the expression of GFP from the reporter cells in a dose-dependent manner.

Collectively, these results demonstrate that the anti-mouse LAIR-1 antibody 43H2 has similar characteristics as the exemplary anti-human LAIR-1 antibodies described herein. Importantly, antibody 43H2 appears to be a good surrogate antibody for future mouse studies.

Example 18

Generation and Screening of Anti-Human MARCO Antibodies

Anti-MARCO antibodies were generated using the extracellular domain of human MARCO as the immunogen (aa 79-520 of SEQ ID NO:154; R&D Systems). Mice were immunized with the MARCO-ECD-His protein and were boosted several times to induce high titers. Blood was drawn from the immunized mice and antibody titers were determined by ELISA and FACS. Single cell suspensions of lymphocytes were obtained from the spleens and lymph nodes of immunized mice that had been determined to have suitably high antibody titers. Lymphocytes were fused with murine myeloma cells by standard methods (e.g., electrofusion). Cells were dispersed into 96-well plates in HAT-containing selection media.

ELISA, FACS and IHC assays were used to screen antibodies for binding to human MARCO. Antibodies that bound to human MARCO but not to other SCARA (Scavenger Receptor class A) family proteins or collagens were selected for purification and further analysis.

Example 19

Characterization of Anti-Human MARCO Antibodies

Representative anti-MARCO antibodies 6D8, 10G4, and 15A3 were sequenced and the heavy chain variable region and light chain variable region amino acid sequences are disclosed herein and summarized in Table 16.

TABLE 16

| Antibody | Heavy Chain Variable Region | Light Chain Variable Region |
|---|---|---|
| 6D8 | SEQ ID NO: 160 | SEQ ID NO: 161 |
| 10G4 | SEQ ID NO: 162 | SEQ ID NO: 163 |
| 15A3 | SEQ ID NO: 164 | SEQ ID NO: 165 |

The heavy chain and light chain variable region CDRs for the individual antibodies are disclosed in Tables 8-10 and as SEQ ID NOs:178-224.

The binding of exemplary anti-MARCO antibodies 6D8, 10G4, and 15A3 to cells expressing MARCO was evaluated by flow cytometry. The cells included 721.221 cells stably expressing MARCO (721.221-MARCO described herein) and 293T cells were transiently transfected with MARCO or other scavenger receptor family member proteins (CD163L, MSR1, and SCARA5) using standard methods. 721.221 parental cells, 721.221-MARCO cells, 293T parental cells, 293T-CD163 cells, 293T-MSR1 cells, 293T-SCARA5 cells, and 293T-MARCO cells ($2 \times 10^5$ cells/well) were washed in PBS, labeled with Live/Dead Blue Fixable Dye (ThermoFisher Scientific), washed in staining buffer (PBS/2% FBS/0.1% sodium azide) with Fc Block™ (BD Biosciences), and incubated with 2.5 µg/mL of anti-MARCO antibodies 6D8, 10G4, or 15A3 for 30 minutes at room temperature. Binding was detected using an Alexa647-labeled anti-mouse IgG secondary antibody (Jackson ImmunoResearch). Cells were analyzed by flow cytometry on a LSRFortessa™ instrument (BD Biosciences) and using FlowJo software. Live cells were gated before analysis. The percentage of live cells bound by the antibodies in each subset (% mAb binding+) and the mean fluorescence intensity (MFI) were calculated. Non-specific background staining was determined with secondary antibody alone.

Figure 23:
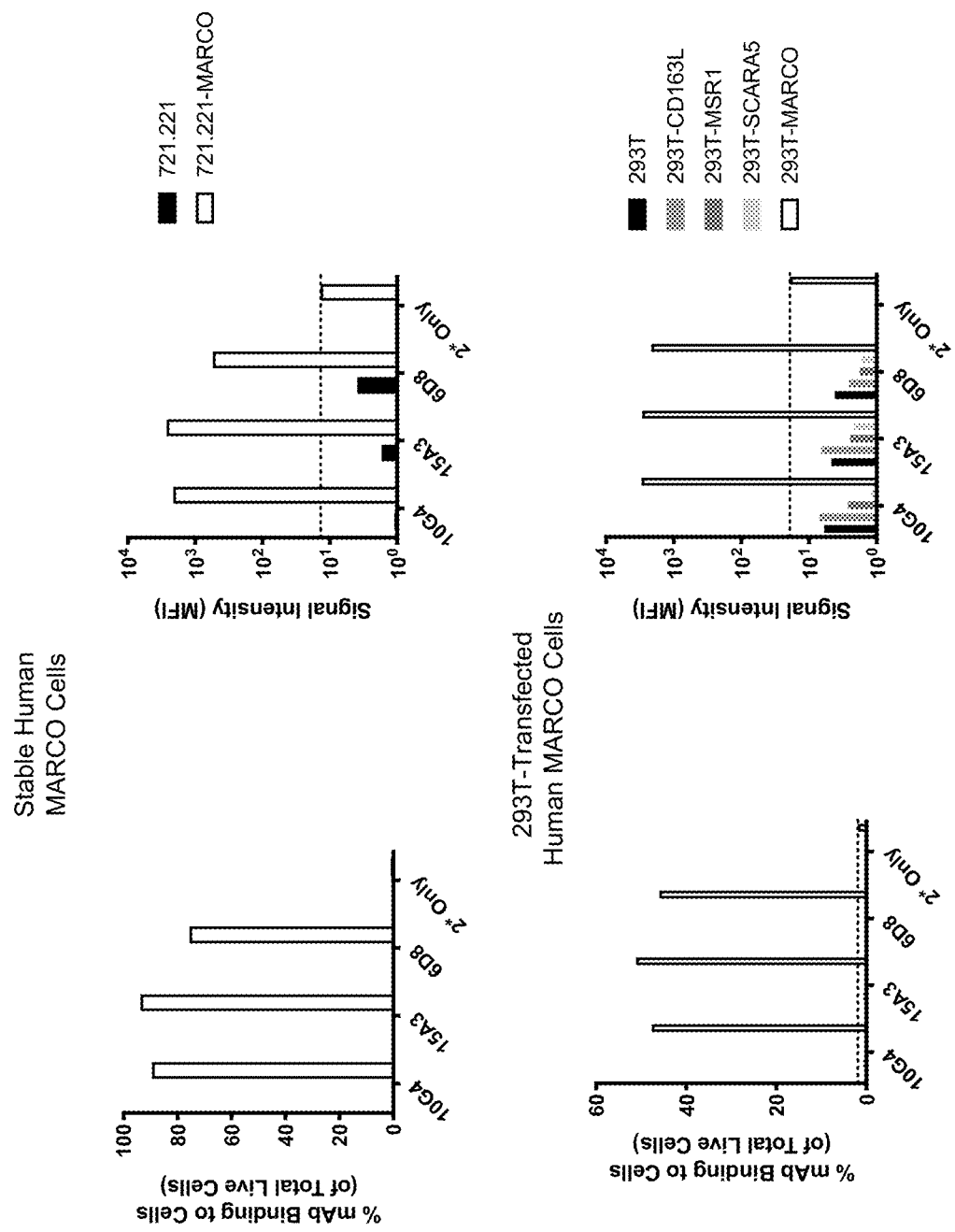
FIG. 23. Binding of anti-MARCO antibodies to MARCO-expressing cells. 721.221 cells were stably transfected with human MARCO. 293T cells were transiently transfected with CD163L, MSR1, or SCARA5. 721.221 parental cells, 721.221-MARCO cells, 293T parental cells, 293T-CD163L cells, 293T-MSR1 cells, and 293T-SCARA5 cells were added to plates. Anti-MARCO antibodies 6D8, 10G4, and 15A3 were added to the plates. An Alexa647-labeled anti-mouse IgG secondary antibody was added to the plates. Positive binding was measured by flow cytometry and analyzed using FlowJo software.

As shown in FIG. 23, anti-MARCO antibodies 6D8, 10G4 and 15A3 bound to 721.221-MARCO cells and 293T-MARCO cells. In contrast, the antibodies did not bind to 293T cells expressing CD163L, MSR1, or SCARA5 or to either of the parental cell lines. These data demonstrate the utility and specificity of these anti-MARCO antibodies for the purposes of flow cytometry.

Next, the binding of anti-MARCO antibodies 6D8, 10G4, and 15A3 to cells expressing MARCO was evaluated by immunohistochemistry (IHC). The cells included 721.221-MARCO, 721.221-COL17A1, parental 721.221, 293T-MARCO, 293T-SCARA5, 293T-COL13A1, and parental 293T.

For 293T transfected cells, cells were pelleted by centrifugation, the cell pellets were fixed overnight in 10% formalin at 4° C., encased in Histogel™ (Richard-Allan Scientific), processed in paraffin using a Leica tissue processor overnight, and embedded in stainless steel tissue molds using Leica HistoCore Arcadia. A biopsy punch was used to make cell pellet tissue microarrays, from which sections were cut and slides were prepared. Anti-MARCO antibodies 6D8, 10G4, and 15A3 were diluted 1:1 in antibody diluent (Biocare Medical) and IHC staining was performed using two-step mouse HRP-polymer detection. Samples were pre-treated with Diva Decloake and blocked with intelliPATH FLX™ peroxidase blocking solution and background Punisher (Biocare Medical). Antibodies 6D8, 10G4, and 15A3 were added and followed by intelliPATH™ mouse secondary reagent, HRP tertiary reagent, DAB chromogen, and hematoxylin counterstain (all from Biocare Medical). Tissues were washed and bluing reagent (Ventana) was added.

721.221 cells were assayed using the Leica BOND RX fully automated research stainer platform. Anti-MARCO antibodies 6D8, 10G4, and 15A3 were diluted 1:1 or prepared at 10 µg/mL in bond primary antibody diluent (Leica) and IHC staining was performed with a bond polymer refine detection kit (Leica). Samples were pre-treated with Diva Decloaker and blocked with intelliPATH FLX™ peroxidase blocking solution. Antibodies 6D8, 10G4, and 15A3 were added and followed by a rabbit anti-mouse IgG secondary reagent, an anti-rabbit Plot-HRP tertiary regent, DAB Refine chromogen and hematoxylin counterstain.

As summarized in Table 17, all three anti-MARCO antibodies specifically stained MARCO cells with no detectable signal in cells expressing other proteins, i.e., COL13A1, SCARA, or COL17A1. These data demonstrate the utility and specificity of these anti-MARCO antibody clones for the purposes of IHC.

TABLE 17

| Antibody | 293T - Transfected Cells | | | 721.221 Stable Cell Lines | | |
|---|---|---|---|---|---|---|
| | COL-13A1 | SCARA | MARCO | Parental | COL-17A1 | MARCO |
| 6D8 | − | − | +++ | − | − | +++ |
| 10G4 | − | − | +++ | − | − | +++ |
| 15A3 | − | − | +++ | − | − | +++ |

Although the foregoing present disclosure has been described in some detail by way of illustration and example for purposes of clarity of understanding, the descriptions and examples should not be construed as limiting the scope of the present disclosure. The embodiments of the present disclosure described herein are intended to be merely exemplary, and those skilled in the art will recognize numerous equivalents to the specific procedures described herein. All such equivalents are considered to be within the scope of the present disclosure and are covered by the embodiments.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are sequences disclosed in the application. CDR sequences are listed in Tables 1-10 as SEQ ID NOs: 9-114 and 178-224.

```
Human LAIR-1 amino acid sequence with predicted signal sequence underlined
                                                               (SEQ ID NO: 1)
MSPHPTALLGLVLCLAQTIHTQEEDLPRPSISAEPGTVIPLGSHVTFVCRGPVGVQTFRLE

RESRSTYNDTEDVSQASPSESEARFRIDSVSEGNAGPYRCIYYKPPKWSEQSDYLELLVK

ETSGGPDSPDTEPGSSAGPTQRPSDNSHNEHAPASQGLKAEHLYILIGVSVVFLFCLLLL

VLFCLHRQNQIKQGPPRSKDEEQKPQQRPDLAVDVLERTADKATVNGLPEKDRETDTS

ALAAGSSQEVTYAQLDHWALTQRTARAVSPQSTKPMAESITYAAVARH

Human LAIR-1 amino acid sequence without predicted signal sequence
                                                               (SEQ ID NO: 2)
QEEDLPRPSISAEPGTVIPLGSHVTFVCRGPVGVQTFRLERESRSTYNDTEDVSQASPSES

EARFRIDSVSEGNAGPYRCIYYKPPKWSEQSDYLELLVKETSGGPDSPDTEPGSSAGPTQ

RPSDNSHNEHAPASQGLKAEHLYILIGVSVVFLFCLLLLVLFCLHRQNQIKQGPPRSKDE

EQKPQQRPDLAVDVLERTADKATVNGLPEKDRETDTSALAAGSSQEVTYAQLDHWAL

TQRTARAVSPQSTKPMAESITYAAVARH

Human LAIR-1 extracellular domain (aa 22-165)
                                                               (SEQ ID NO: 3)
QEEDLPRPSISAEPGTVIPLGSHVTFVCRGPVGVQTFRLERESRSTYNDTEDVSQASPSES

EARFRIDSVSEGNAGPYRCIYYKPPKWSEQSDYLELLVKETSGGPDSPDTEPGSSAGPTQ

RPSDNSHNEHAPASQGLKAEHLY

Human LAIR-1 Ig-like C2-type domain amino acid sequence (aa 29-117)
                                                               (SEQ ID NO: 4)
PSISAEPGTVIPLGSHVTFVCRGPVGVQTFRLERESRSTYNDTEDVSQASPSESEARFRID

SVSEGNAGPYRCIYYKPPKWSEQSDYLE

Cyno LAIR-1 amino acid sequence with predicted signal sequence underlined
                                                               (SEQ ID NO: 5)
MSPHPTALLGLVLCLAQTIHAQEGPLPRPSISAEPGTVIPPGRPVTIVCRGPVGVDQFRLE

REDRSKFNDTKDVSQASPSESEARFRIDSVSEGNAGHYRCLYVKSTRWSEHSDYLDLV

VKETSGDTDSPVTEPDSSAGPTQRPSDNSHNEHAPASQGLSAEHLYILIGVSVVFLFCLL
```

```
-continued
LLVLFFLHRQNQMKQGPPRSKDEEQKLQQRPDLAVDVLERTADKATVNGLPEKDRET

DTSAPAAGSSQEVTYAQLDHWALTWRTAQAVSPQSTEPMAESSTYAAVARH
```

Cyno LAIR-1 amino acid sequence without predicted signal sequence
(SEQ ID NO: 6)
```
QEGPLPRPSISAEPGTVIPPGRPVTIVCRGPVGVDQFRLEREDRSKFNDTKDVSQASPSES

EARFRIDSVSEGNAGHYRCLYVKSTRWSEHSDYLDLVVKETSGDTDSPVTEPDSSAGPT

QRPSDNSHNEHAPASQGLSAEHLYILIGVSVVFLFCLLLLVLFFLHRQNQMKQGPPRSK

DEEQKLQQRPDLAVDVLERTADKATVNGLPEKDRETDTSAPAAGSSQEVTYAQLDHW

ALTWRTAQAVSPQSTEPMAESSTYAAVARH
```

Cyno LAIR-1 extracellular domain (aa 22-165)
(SEQ ID NO: 7)
```
QEGPLPRPSISAEPGTVIPPGRPVTIVCRGPVGVDQFRLEREDRSKFNDTKDVSQASPSES

EARFRIDSVSEGNAGHYRCLYVKSTRWSEHSDYLDLVVKETSGDTDSPVTEPDSSAGPT

QRPSDNSHNEHAPASQGLSAEH
```

Cyno LAIR-1 Ig-like C2-type domain amino acid sequence (aa 29-117)
(SEQ ID NO: 8)
```
EPGTVIPPGRPVTIVCRGPVGVDQFRLEREDRSKFNDTKDVSQASPSESEARFRIDSVSE

GNAGHYRCLYVKSTRWSEHSDYLDLVVK
```

47A1 Heavy chain variable region amino acid sequence
(SEQ ID NO: 115)
```
EVQLVESGGGLVQPKGSLKLSCAASGFTFNTYAIHWVRQAPGKGLEWVARIRSKSTNY

ATYYADSVKDRFTISRDDSQSMVFLQMNNLKTEDTAMYYCVRENWYYYALDYWGQ

GTSVTVSS
```

47A1 Light chain variable region amino acid sequence
(SEQ ID NO: 116)
```
DIQMTQSPASLSASVGETVTITCRASGNIHNYLTWYQQKQGKSPQVLVYNAKTLEDGV

PSRFSGSESGTQYSLKINSLQPEDFGSYYCQHFWSTPFTFGSGTKLEIK
```

47H1 Heavy chain variable region amino acid sequence
(SEQ ID NO: 117)
```
EVQLVETGGGLVQPKGSLKLSCAASGFTFNINAMNWVRQAPGKGLEWVARIRTKNNN

YATFYADSVKDRFTISRDDSQSMLYLQMNNLKTDDTAMYYCVRDRAGFFAYWGQGT

PVTVSA
```

47H1 Light chain variable region amino acid sequence
(SEQ ID NO: 118)
```
DIQMTQSPASQSASLGESVTITCLASQTIGTWLGWYRQKPGKSPQLLIYAATSLADGVP

SRFSGSGSGTKFSFKISSLQAEDFVIYYCQQLYSTPLTFGSGTKLEIK
```

Hz47H1.v4 Heavy chain variable region amino acid sequence
(SEQ ID NO: 119)
```
EVQLVESGGGLVQPGGSLRLSCAASGFTFNINAMNWVRQAPGKGLEWVARIRTKNYN

YATFYADSVKDRFTISRDDSKNSLYLQMNSLKTEDTAVYYCVRDRAGFFAYWGQGTT

VTVSS
```

Hz47H1.v4 Light chain variable region amino acid sequence
(SEQ ID NO: 120)
```
DIQMTQSPSSLSASVGDRVTITCLASQTIGTWLGWYQQKPGKAPKLLIYAATSLAEGVP

SRFSGSGSGTDFTLTISSLQPEDFATYYCQQLYSTPLTFGGGTKVEIK
```

57D12 Heavy chain variable region amino acid sequence
(SEQ ID NO: 121)
```
QVQLQQSGAELARPGASVNLSCRASGYSFTSFGISWVKQRTGQGLEWIGEIYPRSDNTF

YNEKFKGKATLTADKSSSTAYMELRSLTSEDSAVYFCARHFGSSSFDYWGQGTTLTVSS
```

57D12 Light chain variable region amino acid sequence
(SEQ ID NO: 122)
```
ENVLTQSPPIMAASLGQKVTMTCSASSSVSSIYFHWYQQKSGTSPKPLIHRASNLASGVP
```

```
ARFSGSGSGTSYSLTISSVEAEDDATYYCQQWSGYPLTFGGGTKLEIK

61H4 Heavy chain variable region amino acid sequence
                                                                    (SEQ ID NO: 123)
EVQLQQSGPEVLKPGASVKISCKASGYTFTDYYMNWVKQSHGKSLEWIGYIYPNNG

ATSYNQKFKGKATLTVDKSSSTAYMELRSLTSEDSAVYYCARDGYSSNYYTMDYWG

QGTSVTVSS

61H4 Light chain variable region amino acid sequence
                                                                    (SEQ ID NO: 124)
DVQMIQSPSSLSASLGDIVTMTCQASQGTSINLNWFQQKPGKAPKLLIYGASNLEDGVP

SRFSGSRYGTDFTLTISSLEDEDMATYFCLQHTYLPYTFGGGTKLEIK

62G10 Heavy chain variable region amino acid sequence
                                                                    (SEQ ID NO: 125)
EVQLVETGGGLVQPKGSLKLSCATSGFTFNINAMNWVRQAPGKGLEWVARIRTKNNN

FATYYADSVKDRFTISRDDSQSMLYLQMNNLKTEDTAMYYCVRGPYFDYWGQGTTLT

VSS

62G10 Light chain variable region amino acid sequence
                                                                    (SEQ ID NO: 126)
DIQMTQSPASQSASLGESVTITCLASQTIGTWLAWYQQKPGKSPQLLIYAATSLADGVP

SRFSGSGSGTKFSFKISNLQAEDFVTYYCQQLYSTPYTFGGGTKLEIK

Hz62G10.v1 Heavy chain variable region amino acid sequence
                                                                    (SEQ ID NO: 127)
EVQLVESGGGLVKPGGSLRLSCAASGFTFNINAMNWVRQAPGKGLEWVARIRTKNNN

FATYYADSVKDRFTISRDDSKNTLYLQMNSLKTEDTAVYYCVRGPYFDYWGQGTLVT

VSS

Hz62G10.v1 Light chain variable region amino acid sequence
                                                                    (SEQ ID NO: 128)
DIQMTQSPSSLSASVGDRVTITCLASQTIGTWLAWYQQKPGKAPKLLIYAATSLADGVP

SRFSGSGSGTDFTLTISSLQPEDFATYYCQQLYSTPYTFGGGTKVEIK

108D10 Heavy chain variable region amino acid sequence
                                                                    (SEQ ID NO: 129)
EVQLVETGGGLVQPKGSLKLSCAASGFTFNINAMNWVRQAPGKGLEWVARIRTKNNN

YATYYADSVKDRFTISRDDSESMLYLQMNNLKTEDTAMYYCVRDRYGGAMAYWGQ

GTSVTVSS

108D10 Light chain variable region amino acid sequence
                                                                    (SEQ ID NO: 130)
DIQMTQSSSSFSVSLGDRVTITCKASEDIYNRLAWYQQKPGNVPRLLISSATSLETGVPS

RFSGSGSGKDYTLSLTSLQSEDVATYYCQQYWTIPYTFGGGTKLEIK

43H2 Heavy chain variable region amino acid sequence
                                                                    (SEQ ID NO: 131)
EVQLVESGGGLVQPGRSLKVSCAASGFTFSNYGIHWIRQAPTKGLEWVASISPSGRTY

FRDSVKGRFTISRDNAKNTLYLQLDSLRSEDTATYYCATGINYSSFDYWGQGVMVTVSS

43H2 Light chain variable region amino acid sequence
                                                                    (SEQ ID NO: 132)
DIVMTQSPTSMSISVGDRVTMNCKASQNVGSHVDWYQQKTGQSPKLLISTASNRYTGV

PDRFTGSGSGTDFTFTINNMQTEDLAVYYCMQSNSYPPTFGGGTKLELK

Hz47H1.v4 Heavy chain amino acid sequence with signal sequence underlined
                                                                    (SEQ ID NO: 133)
MDMRVPAQLLGLLLLWLRGARCEVQLVESGGGLVQPGGSLRLSCAASGFTFNINAMN

WVRQAPGKGLEWVARIRTKNYNYATFYADSVKDRFTISRDDSKNSLYLQMNSLKTED

TAVYYCVRDRAGFFAYWGQGTTVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSN
```

-continued

TKVDKKVEPKSCDKTHTCPPCPAPELLGGPSVFLFPPKPKDTLMISRTPEVTCVVVDVS

HEDPEVKFNWYVDGVEVHNAKTKPREEQYGSTYRVVSVLTVLHQDWLNGKEYKCKV

SNKALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQKS

LSLSPGK

Hz47H1.v4 Heavy chain amino acid sequence without signal sequence
(SEQ ID NO: 134)

EVQLVESGGGLVQPGGSLRLSCAASGFTFNINAMNWVRQAPGKGLEWVARIRTKNYN

YATFYADSVKDRFTISRDDSKNSLYLQMNSLKTEDTAVYYCVRDRAGFFAYWGQGTT

VTVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVDGVEVHNAK

TKPREEQYGSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPPVLDSDGSFF

LYSKLTVDKSRWQQGNVFSCSVMHEALHNHYTQKSLSLSPGK

Hz47H1.v4 Light chain amino acid sequence with signal sequence underlined
(SEQ ID NO: 135)

<u>MDMRVPAQLLGLLLLWLRGARC</u>DIQMTQSPSSLSASVGDRVTITCLASQTIGTWLGWY

QQKPGKAPKLLIYAATSLAEGVPSRFSGSGSGTDFTLTISSLQPEDFATYYCQQLYSTPL

TFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

Hz47H1.v4 Light chain amino acid sequence without signal sequence
(SEQ ID NO: 136)

DIQMTQSPSSLSASVGDRVTITCLASQTIGTWLGWYQQKPGKAPKLLIYAATSLAEGVP

SRFSGSGSGTDFTLTISSLQPEDFATYYCQQLYSTPLTFGGGTKVEIKRTVAAPSVFIFPPS

DEQLKSGTASVVCLLNNFYPREAKVQWKVDNALQSGNSQESVTEQDSKDSTY SLSSTL

TLSKADYEKHKVYACEVTHQGLSSPVTKSFNRGEC

Hz62G10.v1 Heavy chain amino acid sequence with signal sequence underlined
(SEQ ID NO: 137)

<u>MDMRVPAQLLGLLLLWLRGARC</u>EVQLVESGGGLVKPGGSLRLSCAASGFTFNINAMN

WVRQAPGKGLEWVARIRTKNNNFATYYADSVKDRFTISRDDSKNTLYLQMNSLKTED

TAVYYCVRGPYFDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYICNVNHKPSNT

KVDKKVEPKSCDKTHTCPPCPAPELLGGPSVFLFPPKPKDTLMISRTPEVTCVVVDVSH

EDPEVKFNWYVDGVEVHNAKTKPREEQYGSTYRVVSVLTVLHQDWLNGKEYKCKVS

NKALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQKS

LSLSPGK

Hz62G10.v1 Heavy chain amino acid sequence without signal sequence
(SEQ ID NO: 138)

EVQLVESGGGLVKPGGSLRLSCAASGFTFNINAMNWVRQAPGKGLEWVARIRTKNNN

FATYYADSVKDRFTISRDDSKNTLYLQMNSLKTEDTAVYYCVRGPYFDYWGQGTLVT

VSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKP

REEQYGSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYS

KLTVDKSRWQQGNVFSCSVMHEALHNHYTQKSLSLSPGK

Hz62G10.v1 Light chain amino acid sequence with signal sequence underlined
(SEQ ID NO: 139)

<u>MDMRVPAQLLGLLLLWLRGARC</u>DIQMTQSPSSLSASVGDRVTITCLASQTIGTWLAWY

QQKPGKAPKLLIYAATSLADGVPSRFSGSGSGTDFTLTISSLQPEDFATYYCQQLYSTPY

TFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

Hz62G10.v1 Light chain amino acid sequence without signal sequence
(SEQ ID NO: 140)

DIQMTQSPSSLSASVGDRVTITCLASQTIGTWLAWYQQKPGKAPKLLIYAATSLADGVP

SRFSGSGSGTDFTLTISSLQPEDFATYYCQQLYSTPYTFGGGTKVEIKRTVAAPSVFIFPP

SDEQLKSGTASVVCLLNNFYPREAKVQWKVDNALQSGNSQESVTEQDSKDSTYSLSST

LTLSKADYEKHKVYACEVTHQGLSSPVTKSFNRGEC

Human IgG1 constant region-CH1, hinge, CH2, and CH3
(SEQ ID NO: 141)

ASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

Human IgG1 constant region E233A/L235A
(SEQ ID NO: 142)

ASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTCPPCPAPALA

GGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLYSKL

TVDKSRWQQGNVFSCSVMHEALHNHYTQKSLSLSPGK

Human IgG1 constant region L234A/L235A
(SEQ ID NO: 143)

ASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHT

CPPCPAPEAAGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYT

QKSLSLSPGK

Human IgG1 constant region L234A/L235A/P329G
(SEQ ID NO: 144)

ASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHT

CPPCPAPEAAGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALGA

PIEKTISKAKGQPREPQVYTLPPSREEMTKNQVSLTCLVKGFYPSDIAVEWESNG

-continued

QPENNYKTTPPVLDSDGSFFLYSKLTVDKSRWQQGNVFSCSVMHEALHNHYT

QKSLSLSPGK

Human IgG1 constant region N297G
(SEQ ID NO: 145)
ASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEVHNAKTKPREE

QYGSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

Human IgG1 constant region N297G/H310A
(SEQ ID NO: 146)
ASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEVHNAKTKPREE

QYGSTYRVVSVLTVLAQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGK

Human Kappa light chain constant region
(SEQ ID NO: 147)
RTVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC

Human Lambda light chain constant region
(SEQ ID NO: 148)
GQPKAAPSVTLFPPSSEELQANKATLVCLISDFYPGAVTVAWKADSSPVKAGVETTTPS

KQSNNKYAASSYLSLTPEQWKSHRSYSCQVTHEGSTVEKTVAPTECS

Mouse LAIR-1 amino acid sequence with predicted signal sequence underlined
(SEQ ID NO: 149)
MSLHPVILLVLVLCLGWKINTQEGSLPDITIFPNSSLMISQGTFVTVVCSYSDKHDLYNM

VRLEKDGSTFMEKSTEPYKTEDEFEIGPVNETITGHYSCIYSKGITWSERSKTLELKVIKE

NVIQTPAPGPTSDTSWLKTYSIYIFTVVSVIFLLCLSALLFCFLRHRQKKQGLPNNKRQQ

QRPEERLNLATNGLEMTPDIVADDRLPEDRWTETWTPVAGDLQEVTYIQLDHHSLTQR

AVGAVTSQSTDMAESSTYAAIIRH

Mouse LAIR-1 amino acid sequence without predicted signal sequence
(SEQ ID NO: 150)
QEGSLPDITIFPNSSLMISQGTFVTVVCSYSDKHDLYNMVRLEKDGSTFMEKSTEPYKTE

DEFEIGPVNETITGHYSCIYSKGITWSERSKTLELKVIKENVIQTPAPGPTSDTSWLKTYSI

YIFTVVSVIFLLCLSALLFCFLRHRQKKQGLPNNKRQQQRPEERLNLATNGLEMTPDIV

ADDRLPEDRWTETWTPVAGDLQEVTYIQLDHHSLTQRAVGAVTSQSTDMAESSTYAAIIRH

Mouse LAIR-1 extracellular domain (aa 22-144)
(SEQ ID NO: 151)
QEGSLPDITIFPNSSLMISQGTFVTVVCSYSDKHDLYNMVRLEKDGSTFMEKSTEPYKTE

DEFEIGPVNETITGHYSCIYSKGITWSERSKTLELKVIKENVIQTPAPGPTSDTSWLKTYSIY

Mouse LAIR-1 Ig-like C2-type domain amino acid sequence (aa 27-114)
(SEQ ID NO: 152)
PDITIFPNSSLMISQGTFVTVVCSYSDKHDLYNMVRLEKDGSTFMEKSTEPYKTEDEFEI

GPVNETITGHYSCIYSKGITWSERSKTL

Hexahistidine peptide tag
(SEQ ID NO: 153)
HHHHHH

-continued

Human MARCO (SEQ ID NO: 154)

MRNKKILKEDELLSETQQAAFHQIAMEPFEINVPKPKRRNGVNFSLAVVVIYLILLTAG
AGLLVVQVLNLQARLRVLEMYFLNDTLAAEDSPSFSLLQSAHPGEHLAQGASRLQVLQ
AQLTWVRVSHEHLLQRVDNFTQNPGMFRIKGEQGAPGLQGHKGAMGMPGAPGPPGPP
AEKGAKGAMGRDGATGPSGPQGPPGVKGEAGLQGPQGAPGKQGATGTPGPQGEKGS
KGDGGLIGPKGETGTKGEKGDLGLPGSKGDRGMKGDAGVMGPPGAQGSKGDFGRPG
PPGLAGFPGAKGDQGQPGLQGVPGPPGAVGHPGAKGEPGSAGSPGRAGLPGSPGSPGA
TGLKGSKGDTGLQGQQGRKGESGVPGPAGVKGEQGSPGLAGPKGAPGQAGQKGDQG
VKGSSGEQGVKGEKGERGENSVSVRIVGSSNRGRAEVYYSGTWGTICDDEWQNSDAI
VFCRMLGYSKGRALYKVGAGTGQIWLDNVQCRGTESTLWSCTKNSWGHHDCSHEED
AGVECSV

Human MARCO extracellular domain (aa 65-520) (SEQ ID NO: 155)

VQVLNLQARLRVLEMYFLNDTLAAEDSPSFSLLQSAHPGEHLAQGASRLQVLQAQLT
WVRVSHEHLLQRVDNFTQNPGMFRIKGEQGAPGLQGHKGAMGMPGAPGPPGPPAEK
GAKGAMGRDGATGPSGPQGPPGVKGEAGLQGPQGAPGKQGATGTPGPQGEKGSKGD
GGLIGPKGETGTKGEKGDLGLPGSKGDRGMKGDAGVMGPPGAQGSKGDFGRPGPPGL
AGFPGAKGDQGQPGLQGVPGPPGAVGHPGAKGEPGSAGSPGRAGLPGSPGSPGATGLK
GSKGDTGLQGQQGRKGESGVPGPAGVKGEQGSPGLAGPKGAPGQAGQKGDQGVKGS
SGEQGVKGEKGERGENSVSVRIVGSSNRGRAEVYYSGTWGTICDDEWQNSDAIVFCR
MLGYSKGRALYKVGAGTGQIWLDNVQCRGTESTLWSCTKNSWGHHDCSHEEDAGVE
CSV

Human MARCO collagen-like domain (aa 147-419) (SEQ ID NO: 156)

KGEQGAPGLQGHKGAMGMPGAPGPPGPPAEKGAKGAMGRDGATGPSGPQGPPGVKG
EAGLQGPQGAPGKQGATGTPGPQGEKGSKGDGGLIGPKGETGTKGEKGDLGLPGSKG
DRGMKGDAGVMGPPGAQGSKGDFGRPGPPGLAGFPGAKGDQGQPGLQGVPGPPGAV
GHPGAKGEPGSAGSPGRAGLPGSPGSPGATGLKGSKGDTGLQGQQGRKGESGVPGPA
GVKGEQGSPGLAGPKGAPGQAGQKGDQGVKGSSGEQGVKGEKGERGE

Human MARCO SRCR domain (aa 424-519) (SEQ ID NO: 157)

VRIVGSSNRGRAEVYYSGTWGTICDDEWQNSDAIVFCRMLGYSKGRALYKVGAGTGQ
IWLDNVQCRGTESTLWSCTKNSWGHHDCSHEEDAGVECS

Human IgG1 constant region L234F/L235E/P331G (SEQ ID NO: 158)

ASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPA
GIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHY
TQKSLSLSPGK

Human IgG1 constant region L234A/L235A/P331G (SEQ ID NO: 159)

ASTKGPSVFPLAPSSKSTSGGTAALGCLVKDYFPEPVTVSWNSGALTSGVHTFP

-continued

AVLQSSGLYSLSSVVTVPSSSLGTQTYICNVNHKPSNTKVDKKVEPKSCDKTHT

CPPCPAPEAAGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPA

GIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHY

TQKSLSLSPGK

6D8 Heavy chain variable region amino acid sequence
(SEQ ID NO: 160)
QVQLKESGPGLVAPSQSLSIACTVSGFSLTNYAISWVRQPPGKGLEWLGVIWTGGGTN

YNSTLKSRLSISKDNSKSQVFLKMNSLQTDDTARYNCARNSGDWYFDVWGPGTTVTV

SS

6D8 Light chain variable region amino acid sequence
(SEQ ID NO: 161)
DIVMSQSPSSLAVSVGEKVTMSCKSSQSLLYSSNQKNYLAWYQQKPGQSPHLLIYWAS

TRESGVPDRFIGSGSGTDFTLTISSVKAEDLAVYYCQQYYDYPPTFGSGTKLEIK

10G4 Heavy chain variable region amino acid sequence
(SEQ ID NO: 162)
QVQLKESGPGLVAPSQSLSITCTVSGFSLSSYPISWVRQPPGKGLEWLGIIWTGGGTNYN

SALKSRLSISKDNSKSQVFLKMNSLQTDDTARYYCASQNWDVNSALDYWGQGTSVTV

SS

10G4 Light chain variable region amino acid sequence
(SEQ ID NO: 163)
DIQMTQSPASLSVSVGETVTITCRASENIYSNLAWYQQKQGKSPQLLVYTATNLADGVP

SRFSGSGSGTQYSLRINRLQSEDFGNYYCQHFWNAPWTFGGGTKLEIK

15A3 Heavy chain variable region amino acid sequence
(SEQ ID NO: 164)
EIQLQQSGPELVKPGASVKVSCKASGYSFTDYNMYWVKQSHGKSLEWIGYIDPYNGGT

SYNQKFKGKATLTVDKSSSTAFMHLNSLTSEDSAVYYCARLSPYDYDRGDYVMDY

WGQGTSVTVSS

15A3 Light chain variable region amino acid sequence
(SEQ ID NO: 165)
DIVLTQSPASLAVSLGQRATISCRASKSVSTSGYTYMIHWYQQKPGQPPKLLIYLASNLE

SGVPARFSGSGSGTDFTLNIHPVEEEDAATYYCQHSRELPLTFGAGTKLELK

6D8 Heavy chain amino acid sequence with signal sequence underlined
(SEQ ID NO: 166)
MDMRVPAQLLGLLLLWLRGARCQVQLKESGPGLVAPSQSLSIACTVSGFSLTNYAISW

VRQPPGKGLEWLGVIWTGGGTNYNSTLKSRLSISKDNSKSQVFLKMNSLQTDDTARYN

CARNSGDWYFDVWGPGTTVTVSSAKTTAPSVYPLAPVCGDTTGSSVTLGCLVKGYFPE

PVTLTWNSGSLSSGVHTFPAVLQSDLYTLSSSVTVTSSTWPSQSITCNVAHPASSTKVDK

KIEPRGPTIKPCPPCKCPAPNAAGGPSVFIFPPKIKDVLMISLSPIVTCVVVDVSEDDPDV

QISWFVNNVEVHTAQTQTHREDYNSTLRVVSALPIQHQDWMSGKEFKCKVNNKDLGA

PIERTISKPKGSVRAPQVYVLPPPEEEMTKKQVTLTCMVTDFMPEDIYVEWTNNGKTEL

NYKNTEPVLDSDGSYFMYSKLRVEKKNWVERNSYSCSVVHEGLHNHHTTKSFSRTPGK

6D8 Heavy chain amino acid sequence without signal sequence
(SEQ ID NO: 167)
QVQLKESGPGLVAPSQSLSIACTVSGFSLTNYAISWVRQPPGKGLEWLGVIWTGGGTN

YNSTLKSRLSISKDNSKSQVFLKMNSLQTDDTARYNCARNSGDWYFDVWGPGTTVTV

SSAKTTAPSVYPLAPVCGDTTGSSVTLGCLVKGYFPEPVTLTWNSGSLSSGVHTFPAVL

QSDLYTLSSSVTVTSSTWPSQSITCNVAHPASSTKVDKKIEPRGPTIKPCPPCKCPAPNAA

```
GGPSVFIFPPKIKDVLMISLSPIVTCVVVDVSEDDPDVQISWFVNNVEVHTAQTQTHRED

YNSTLRVVSALPIQHQDWMSGKEFKCKVNNKDLGAPIERTISKPKGSVRAPQVYVLPPP

EEEMTKKQVTLTCMVTDFMPEDIYVEWTNNGKTELNYKNTEPVLDSDGSYFMYSKLR

VEKKNWVERNSYSCSVVHEGLHNHHTTKSFSRTPGK
```

6D8 Light chain amino acid sequence with signal sequence underlined
(SEQ ID NO: 168)
```
MDMRVPAQLLGLLLLWLRGARCDIVMSQSPSSLAVSVGEKVTMSCKSSQSLLYSSNQK

NYLAWYQQKPGQSPHLLIYWASTRESGVPDRFIGSGSGTDFTLTISSVKAEDLAVYYCQ

QYYDYPPTFGSGTKLEIKRADAAPTVSIFPPSSEQLTSGGASVVCFLNNFYPKDINVKWK

IDGSERQNGVLNSWTDQDSKDSTYSMSSTLTLTKDEYERHNSYTCEATHKTSTSPIVKS

FNRNEC
```

6D8 Light chain amino acid sequence without signal sequence
(SEQ ID NO: 169)
```
DIVMSQSPSSLAVSVGEKVTMSCKSSQSLLYSSNQKNYLAWYQQKPGQSPHLLIYWAS

TRESGVPDRFIGSGSGTDFTLTISSVKAEDLAVYYCQQYYDYPPTFGSGTKLEIKRADAA

PTVSIFPPSSEQLTSGGASVVCFLNNFYPKDINVKWKIDGSERQNGVLNSWTDQDSKDS

TYSMSSTLTLTKDEYERHNSYTCEATHKTSTSPIVKSFNRNEC
```

10G4 Heavy chain amino acid sequence with signal sequence underlined
(SEQ ID NO: 170)
```
MDMRVPAQLLGLLLLWLRGARCQVQLKESGPGLVAPSQSLSITCTVSGFSLSSYPISWV

RQPPGKGLEWLGIIWTGGGTNYNSALKSRLSISKDNSKSQVFLKMNSLQTDDTARYYC

ASQNWDVNSALDYWGQGTSVTVSSAKTTAPSVYPLAPVCGDTTGSSVTLGCLVKGYF

PEPVTLTWNSGSLSSGVHTFPAVLQSDLYTLSSSVTVTSSTWPSQSITCNVAHPASSTKV

DKKIEPRGPTIKPCPPCKCPAPNAAGGPSVFIFPPKIKDVLMISLSPIVTCVVVDVSEDDP

DVQISWFVNNVEVHTAQTQTHREDYNSTLRVVSALPIQHQDWMSGKEFKCKVNNKDL

GAPIERTISKPKGSVRAPQVYVLPPPEEEMTKKQVTLTCMVTDFMPEDIYVEWTNNGK

TELNYKNTEPVLDSDGSYFMYSKLRVEKKNWVERNSYSCSVVHEGLHNHHTTKSFSR

TPGK
```

10G4 Heavy chain amino acid sequence without signal sequence
(SEQ ID NO: 171)
```
QVQLKESGPGLVAPSQSLSITCTVSGFSLSSYPISWVRQPPGKGLEWLGIIWTGGGTNYN

SALKSRLSISKDNSKSQVFLKMNSLQTDDTARYYCASQNWDVNSALDYWGQGTSVTV

SSAKTTAPSVYPLAPVCGDTTGSSVTLGCLVKGYFPEPVTLTWNSGSLSSGVHTFPAVL

QSDLYTLSSSVTVTSSTWPSQSITCNVAHPASSTKVDKKIEPRGPTIKPCPPCKCPAPNAA

GGPSVFIFPPKIKDVLMISLSPIVTCVVVDVSEDDPDVQISWFVNNVEVHTAQTQTHRED

YNSTLRVVSALPIQHQDWMSGKEFKCKVNNKDLGAPIERTISKPKGSVRAPQVYVLPPP

EEEMTKKQVTLTCMVTDFMPEDIYVEWTNNGKTELNYKNTEPVLDSDGSYFMYSKLR

VEKKNWVERNSYSCSVVHEGLHNHEITTKSFSRTPGK
```

10G4 Light chain amino acid sequence with signal sequence underlined
(SEQ ID NO: 172)
```
MDMRVPAQLLGLLLLWLRGARCDIQMTQSPASLSVSVGETVTITCRASENIYSNLAWY

QQKQGKSPQLLVYTATNLADGVPSRFSGSGSGTQYSLRINRLQSEDFGNYYCQHFWNA

PWTFGGGTKLEIKRADAAPTVSIFPPSSEQLTSGGASVVCFLNNFYPKDINVKWKIDGSE

RQNGVLNSWTDQDSKDSTYSMSSTLTLTKDEYERHNSYTCEATHKTSTSPIVKSFNRNEC
```

10G4 Light chain amino acid sequence without signal sequence
(SEQ ID NO: 173)

-continued

DIQMTQSPASLSVSVGETVTITCRASENIYSNLAWYQQKQGKSPQLLVYTATNLADGVP

SRFSGSGSGTQYSLRINRLQSEDFGNYYCQHFWNAPWTFGGGTKLEIKRADAAPTVSIF

PPSSEQLTSGGASVVCFLNNFYPKDINVKWKIDGSERQNGVLNSWTDQDSKDSTYSMS

STLTLTKDEYERHNSYTCEATHKTSTSPIVKSFNRNEC

15A3 Heavy chain amino acid sequence with signal sequence underlined
(SEQ ID NO: 174)
<u>MDMRVPAQLLGLLLLWLRGARC</u>EIQLQQSGPELVKPGASVKVSCKASGYSFTDYNMY

WVKQSHGKSLEWIGYIDPYNGGTSYNQKFKGKATLTVDKSSSTAFMHLNSLTSEDSAV

YYCARLRSPYDYDRGDYVMDYWGQGTSVTVSSAKTTAPSVYPLAPVCGDTTGSSVTL

GCLVKGYFPEPVTLTWNSGSLSSGVHTFPAVLQSDLYTLSSSVTVTSSTWPSQSITCNVA

HPASSTKVDKKIEPRGPTIKPCPPCKCPAPNAAGGPSVFIFPPKIKDVLMISLSPIVTCVVV

DVSEDDPDVQISWFVNNVEVHTAQTQTHREDYNSTLRVVSALPIQHQDWMSGKEFKC

KVNNKDLGAPIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHEGLHNHH

TTKSFSRTPGK

15A3 Heavy chain amino acid sequence without signal sequence
(SEQ ID NO: 175)
EIQLQQSGPELVKPGASVKVSCKASGYSFTDYNMYWVKQSHGKSLEWIGYIDPYNGGT

SYNQKFKGKATLTVDKSSSTAFMHLNSLTSEDSAVYYCARLRSPYDYDRGDYVMDY

WGQGTSVTVSSAKTTAPSVYPLAPVCGDTTGSSVTLGCLVKGYFPEPVTLTWNSGSLSS

GVHTFPAVLQSDLYTLSSSVTVTSSTWPSQSITCNVAHPASSTKVDKKIEPRGPTIKPCPP

CKCPAPNAAGGPSVFIFPPKIKDVLMISLSPIVTCVVVDVSEDDPDVQISWFVNNVEVHT

AQTQTHREDYNSTLRVVSALPIQHQDWMSGKEFKCKVNNKDLGAPIERTISKPKGSVR

APQVYVLPPPEEEMTKKQVTLTCMVTDFMPEDIYVEWTNNGKTELNYKNTEPVLDSD

GSYFMYSKLRVEKKNWVERNSYSCSVVHEGLHNHHTTKSFSRTPGK

15A3 Light chain amino acid sequence with signal sequence underlined
(SEQ ID NO: 176)
<u>MDMRVPAQLLGLLLLWLRGARC</u>DIVLTQSPASLAVSLGQRATISCRASKSVSTSGYTY

MHWYQQKPGQPPKLLIYLASNLESGVPARFSGSGSGTDFTLNIHPVEEEDAATYYCQHS

RELPLTFGAGTKLELKRADAAPTVSIFPPSSEQLTSGGASVVCFLNNFYPKDINVKWKID

GSERQNGVLNSWTDQDSKDSTYSMSSTLTLTKDEYERHNSYTCEATHKTSTSPIVKSFN

RNEC

15A3 Light chain amino acid sequence without signal sequence
(SEQ ID NO: 177)
DIVLTQSPASLAVSLGQRATISCRASKSVSTSGYTYMHWYQQKPGQPPKLLIYLASNLE

SGVPARFSGSGSGTDFTLNIHPVEEEDAATYYCQHSRELPLTFGAGTKLELKRADAAPT

VSIFPPSSEQLTSGGASVVCFLNNFYPKDINVKWKIDGSERQNGVLNSWTDQDSKDSTY

SMSSTLTLTKDEYERHNSYTCEATHKTSTSPIVKSFNRNEC

Human LAIR-2 amino acid sequence with predicted signal sequence underlined
(SEQ ID NO: 225)
<u>MSPHLTALLGLVLCLAQTIHT</u>QEGALPRPSISAEPGTVISPGSHVTFMCRGPVGVQTFRL

EREDRAKYKDSYNVFRLGPSESEARFHIDSVSEGNAGLYRCLYYKPPGWSEHSDFLELL

VKESSGGPDSPDTEPGSSAGTVPGTEASGFDAP

Human LAIR-2 amino acid sequence without predicted signal sequence
(SEQ ID NO: 226)
QEGALPRPSISAEPGTVISPGSHVTFMCRGPVGVQTFRLEREDRAKYKDSYNVFRLGPSE

SEARFHIDSVSEGNAGLYRCLYYKPPGWSEHSDFLELLVKESSGGPDSPDTEPGSSAGT

-continued

VPGTEASGFDAP

Human LAIR-2 amino acid sequence Ig-like C2 type domain (aa 29-177)

(SEQ ID NO: 227)

PSISAEPGTVISPGSHVTFMCRGPVGVQTFRLEREDRAKYKDSYNVFRLGPSESEARFHI

DSVSEGNAGLYRCLYYKPPGWSEHSDFLE

The invention claimed is:

1. A binding agent that specifically binds the extracellular domain of human leukocyte-associated immunoglobulin-like receptor 1 (LAIR-1), wherein the binding agent comprises:
   (a) a heavy chain variable region (VH) comprising a VH-complementarity determining region (CDR) 1, a VH-CDR2, and a VH-CDR3 from the amino acid sequence of SEQ ID NO: 117; and a light chain variable region (VL) comprising a VL-CDR1, a VL-CDR2, and a VL-CDR3 from the amino acid sequence of SEQ ID NO: 118;
   (b) a VH comprising a VH-CDR1, a VH-CDR2, and a VH-CDR3 from the amino acid sequence of SEQ ID NO: 119; and a VL comprising a VL-CDR1, a VL-CDR2, and a VL-CDR3 from the amino acid sequence of SEQ ID NO: 120;
   (c) a VH comprising a VH-CDR1, a VH-CDR2, and a VH-CDR3 from the amino acid sequence of SEQ ID NO: 115; and a VL comprising a VL-CDR1, a VL-CDR2, and a VL-CDR3 from the amino acid sequence of SEQ ID NO: 116;
   (d) a VH comprising a VH-CDR1, a VH-CDR2, and a VH-CDR3 from the amino acid sequence of SEQ ID NO: 121; and a VL comprising a VL-CDR1, a VL-CDR2, and a VL-CDR3 from the amino acid sequence of SEQ ID NO: 122;
   (e) a VH comprising a VH-CDR1, a VH-CDR2, and a VH-CDR3 from the amino acid sequence of SEQ ID NO: 123; and a VL comprising a VL-CDR1, a VL-CDR2, and a VL-CDR3 from the amino acid sequence of SEQ ID NO: 124;
   (f) a VH comprising a VH-CDR1, a VH-CDR2, and a VH-CDR3 from the amino acid sequence of SEQ ID NO: 125; and a VL comprising a VL-CDR1, a VL-CDR2, and a VL-CDR3 from the amino acid sequence of SEQ ID NO: 126;
   (g) a VH comprising a VH-CDR1, a VH-CDR2, and a VH-CDR3 from the amino acid sequence of SEQ ID NO: 127; and a VL comprising a VL-CDR1, a VL-CDR2, and a VL-CDR3 from the amino acid sequence of SEQ ID NO: 128; or
   (h) a VH comprising a VH-CDR1, a VH-CDR2, and a VH-CDR3 from the amino acid sequence of SEQ ID NO: 129; and a VL comprising a VL-CDR1, a VL-CDR2, and a VL-CDR3 from the amino acid sequence of SEQ ID NO: 130.

2. The binding agent of claim 1, wherein:
   (a) (1) the VH comprises the VH-CDR1 comprising the amino acid sequence of SEQ ID NO:25, the VH-CDR2 comprising the amino acid sequence of SEQ ID NO:26, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:29, and the VL-CDR3 comprising the amino acid sequence of SEQ ID NO:30;
   (2) the VH comprises the VH-CDR1 comprising the amino acid sequence of SEQ ID NO:31, the VH-CDR2 comprising the amino acid sequence of SEQ ID NO:32, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:29, and the VL-CDR3 comprising the amino acid sequence of SEQ ID NO:30;
   (3) the VH comprises the VH-CDR1 comprising the amino acid sequence of SEQ ID NO:25, the VH-CDR2 comprising the amino acid sequence of SEQ ID NO:33, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:29, and the VL-CDR3 comprising the amino acid sequence of SEQ ID NO:30;
   (4) the VH comprises the VH-CDR1 comprising the amino acid sequence of SEQ ID NO:34, the VH-CDR2 comprising the amino acid sequence of SEQ ID NO:26, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:29, and the VL-CDR3 comprising the amino acid sequence of SEQ ID NO:30; or
   (5) the VH comprises the VH-CDR1 comprising the amino acid sequence of SEQ ID NO:35, the VH-CDR2 comprising the amino acid sequence of SEQ ID NO:36, and the VH-CDR3 comprising the amino acid sequence of SEQ ID NO:37; and the VL comprises the VL-CDR1 comprising the amino acid sequence of SEQ ID NO:38, the VL-CDR2 comprising the amino acid sequence of SEQ ID NO:39, and the VL-CDR3 comprising the amino acid sequence of SEQ ID NO:40;

(b) (1) the VH comprises the VH-CDR1 comprising the amino acid sequence of SEQ ID NO:25, the VH-CDR2 comprising the amino acid sequence of SEQ ID NO:41, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;

(2) the VH comprises the VH-CDR1 comprising the amino acid sequence of SEQ ID NO:31, the VH-CDR2 comprising the amino acid sequence of SEQ ID NO:43, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;

(3) the VH comprises the VH-CDR1 comprising the amino acid sequence of SEQ ID NO:25, the VH-CDR2 comprising the amino acid sequence of SEQ ID NO:44, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;

(4) the VH comprises the VH-CDR1 comprising the amino acid sequence of SEQ ID NO:34, the VH-CDR2 comprising the amino acid sequence of SEQ ID NO:41, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30; or (5) the VH comprises the VH-CDR1 comprising the amino acid sequence of SEQ ID NO:35, the VH-CDR2 comprising the amino acid sequence of SEQ ID NO:45, and the VH-CDR3 comprising the amino acid sequence of SEQ ID NO:37; and the VL comprises the VL-CDR1 comprising the amino acid sequence of SEQ ID NO:38, the VL-CDR2 comprising the amino acid sequence of SEQ ID NO:39, and the VL-CDR3 comprising the amino acid sequence of SEQ ID NO:40;

(c) (1) the VH comprises the VH-CDR1 comprising the amino acid sequence of SEQ ID NO:9, the VH-CDR2 comprising the amino acid sequence of SEQ ID NO:10, and the VH-CDR3 comprising the amino acid sequence of SEQ ID NO:11; and the VL comprises the VL-CDR1 comprising the amino acid sequence of SEQ ID NO:12, the VL-CDR2 comprising the amino acid sequence of SEQ ID NO:13, and the VL-CDR3 comprising the amino acid sequence of SEQ ID NO:14;

(2) the VH comprises the VH-CDR1 comprising the amino acid sequence of SEQ ID NO:15, the VH-CDR2 comprising the amino acid sequence of SEQ ID NO:16, and the VH-CDR3 comprising the amino acid sequence of SEQ ID NO:11; and the VL comprises the VL-CDR1 comprising the amino acid sequence of SEQ ID NO: 12, the VL-CDR2 comprising the amino acid sequence of SEQ ID NO:13, and the VL-CDR3 comprising the amino acid sequence of SEQ ID NO:14;

(3) the VH comprises the VH-CDR1 comprising the amino acid sequence of SEQ ID NO:9, the VH-CDR2 comprising the amino acid sequence of SEQ ID NO:17, and the VH-CDR3 comprising the amino acid sequence of SEQ ID NO:11; and the VL comprises the VL-CDR1 comprising the amino acid sequence of SEQ ID NO: 12, the VL-CDR2 comprising the amino acid sequence of SEQ ID NO: 13, and the VL-CDR3 comprising the amino acid sequence of SEQ ID NO:14;

(4) the VH comprises the VH-CDR1 comprising the amino acid sequence of SEQ ID NO:18, the VH-CDR2 comprising the amino acid sequence of SEQ ID NO:10, and the VH-CDR3 comprising the amino acid sequence of SEQ ID NO:11; and the VL comprises the VL-CDR1 comprising the amino acid sequence of SEQ ID NO:12, the VL-CDR2 comprising the amino acid sequence of SEQ ID NO: 13, and the VL-CDR3 comprising the amino acid sequence of SEQ ID NO: 14; or (5) the VH comprises the VH-CDR1 comprising the amino acid sequence of SEQ ID NO: 19, the VH-CDR2 comprising the amino acid sequence of SEQ ID NO:20, and the VH-CDR3 comprising the amino acid sequence of SEQ ID NO:21; and the VL comprises the VL-CDR1 comprising the amino acid sequence of SEQ ID NO:22, the VL-CDR2 comprising the amino acid sequence of SEQ ID NO:23, and the VL-CDR3 comprising the amino acid sequence of SEQ ID NO:24;

(d) (1) the VH comprises the VH-CDR1 comprising the amino acid sequence of SEQ ID NO:46, the VH-CDR2 comprising the amino acid sequence of SEQ ID NO:47, and the VH-CDR3 comprising the amino acid sequence of SEQ ID NO:48; and the VL comprises the VL-CDR1 comprising the amino acid sequence of SEQ ID NO:49, the VL-CDR2 comprising the amino acid sequence of SEQ ID NO:50, and the VL-CDR3 comprising the amino acid sequence of SEQ ID NO:51;

(2) the VH comprises the VH-CDR1 comprising the amino acid sequence of SEQ ID NO:52, the VH-CDR2 comprising the amino acid sequence of SEQ ID NO:53, and the VH-CDR3 comprising the amino acid sequence of SEQ ID NO:48; and the VL comprises the VL-CDR1 comprising the amino acid sequence of SEQ ID NO:49, the VL-CDR2 comprising the amino acid sequence of SEQ ID NO:50, and the VL-CDR3 comprising the amino acid sequence of SEQ ID NO:51;

(3) the VH comprises the VH-CDR1 comprising the amino acid sequence of SEQ ID NO:46, the VH-CDR2 comprising the amino acid sequence of SEQ ID NO:54, and the VH-CDR3 comprising the amino acid sequence of SEQ ID NO:48; and the VL comprises the VL-CDR1 comprising the amino acid sequence of SEQ ID NO:49, the VL-CDR2 comprising the amino acid sequence of SEQ ID NO:50, and the VL-CDR3 comprising the amino acid sequence of SEQ ID NO:51;

(4) the VH comprises the VH-CDR1 comprising the amino acid sequence of SEQ ID NO:55, the VH-CDR2 comprising the amino acid sequence of SEQ ID NO:47, and the VH-CDR3 comprising the amino acid sequence of SEQ ID NO:48; and the VL comprises the VL-CDR1 comprising the amino acid sequence of SEQ ID NO:49, the VL-CDR2 comprising the amino acid sequence of SEQ ID NO:50, and the VL-CDR3 comprising the amino acid sequence of SEQ ID NO:51; or (5) the VH comprises the VH-CDR1 comprising the amino acid sequence of SEQ ID NO:56, the VH-CDR2 comprising the amino acid sequence of SEQ ID NO:57, and the VH-CDR3 comprising the amino acid sequence of SEQ ID NO:58; and the VL comprises the VL-CDR1 comprising the amino acid sequence of SEQ ID NO:59, the VL-CDR2 comprising the amino acid sequence of SEQ ID NO:60, and the VL-CDR3 comprising the amino acid sequence of SEQ ID NO:61;

(e) (1) the VH comprises the VH-CDR1 comprising the amino acid sequence of SEQ ID NO:62, the VH-CDR2 comprising the amino acid sequence of SEQ ID NO:63, and the VH-CDR3 comprising the amino acid sequence of SEQ ID NO:64; and the VL comprises the VL-CDR1 comprising the amino acid sequence of SEQ ID NO:65, the VL-CDR2 comprising the amino acid sequence of SEQ ID NO:66, and the VL-CDR3 comprising the amino acid sequence of SEQ ID NO:67;

(2) the VH comprises the VH-CDR1 comprising the amino acid sequence of SEQ ID NO:68, the VH-CDR2 comprising the amino acid sequence of SEQ ID NO:69, and the VH-CDR3 comprising the amino acid sequence of SEQ ID NO:64; and the VL comprises the VL-CDR1 comprising the amino acid sequence of SEQ ID NO:65, the VL-CDR2 comprising the amino acid sequence of SEQ ID NO:66, and the VL-CDR3 comprising the amino acid sequence of SEQ ID NO:67;

(3) the VH comprises the VH-CDR1 comprising the amino acid sequence of SEQ ID NO:62, the VH-CDR2 comprising the amino acid sequence of SEQ ID NO:70, and the VH-CDR3 comprising the amino acid sequence of SEQ ID NO:64; and the VL comprises the VL-CDR1 comprising the amino acid sequence of SEQ ID NO:65, the VL-CDR2 comprising the amino acid sequence of SEQ ID NO:66, and the VL-CDR3 comprising the amino acid sequence of SEQ ID NO:67;

(4) the VH comprises the VH-CDR1 comprising the amino acid sequence of SEQ ID NO:71, the VH-CDR2 comprising the amino acid sequence of SEQ ID NO:63, and the VH-CDR3 comprising the amino acid sequence of SEQ ID NO:64; and the VL comprises the VL-CDR1 comprising the amino acid sequence of SEQ ID NO:65, the VL-CDR2 comprising the amino acid sequence of SEQ ID NO:66, and the VL-CDR3 comprising the amino acid sequence of SEQ ID NO:67; or (5) the VH comprises the VH-CDR1 comprising the amino acid sequence of SEQ ID NO:72, the VH-CDR2 comprising the amino acid sequence of SEQ ID NO:73, and the VH-CDR3 comprising the amino acid sequence of SEQ ID NO:74; and the VL comprises the VL-CDR1 comprising the amino acid sequence of SEQ ID NO:75, the VL-CDR2 comprising the amino acid sequence of SEQ ID NO:76, and the VL-CDR3 comprising the amino acid sequence of SEQ ID NO:77;

(f) (1) the VH comprises the VH-CDR1 comprising the amino acid sequence of SEQ ID NO:25 the VH-CDR2 comprising the amino acid sequence of SEQ ID NO:78, and the VH-CDR3 comprising the amino acid sequence of SEQ ID NO:79; and the VL comprises the VL-CDR1 comprising the amino acid sequence of SEQ ID NO:80, the VL-CDR2 comprising the amino acid sequence of SEQ ID NO:29, and the VL-CDR3 comprising the amino acid sequence of SEQ ID NO:81;

(2) the VH comprises the VH-CDR1 comprising the amino acid sequence of SEQ ID NO:31, the VH-CDR2 comprising the amino acid sequence of SEQ ID NO:82, and the VH-CDR3 comprising the amino acid sequence of SEQ ID NO:79; and the VL comprises the VL-CDR1 comprising the amino acid sequence of SEQ ID NO:80, the VL-CDR2 comprising the amino acid sequence of SEQ ID NO:29, and the VL-CDR3 comprising the amino acid sequence of SEQ ID NO:81;

(3) the VH comprises the VH-CDR1 comprising the amino acid sequence of SEQ ID NO:25, the VH-CDR2 comprising the amino acid sequence of SEQ ID NO:83, and the VH-CDR3 comprising the amino acid sequence of SEQ ID NO:79; and the VL comprises the VL-CDR1 comprising the amino acid sequence of SEQ ID NO:80, the VL-CDR2 comprising the amino acid sequence of SEQ ID NO:29, and the VL-CDR3 comprising the amino acid sequence of SEQ ID NO:81;

(4) the VH comprises the VH-CDR1 comprising the amino acid sequence of SEQ ID NO:34, the VH-CDR2 comprising the amino acid sequence of SEQ ID NO:78, and the VH-CDR3 comprising the amino acid sequence of SEQ ID NO:79; and the VL comprises the VL-CDR1 comprising the amino acid sequence of SEQ ID NO:80, the VL-CDR2 comprising the amino acid sequence of SEQ ID NO:29, and the VL-CDR3 comprising the amino acid sequence of SEQ ID NO:81; or (5) the VH comprises the VH-CDR1 comprising the amino acid sequence of SEQ ID NO:35, the VH-CDR2 comprising the amino acid sequence of SEQ ID NO:84, and the VH-CDR3 comprising the amino acid sequence of SEQ ID NO:85; and the VL comprises the VL-CDR1 comprising the amino acid sequence of SEQ ID NO:86, the VL-CDR2 comprising the amino acid sequence of SEQ ID NO:39, and the VL-CDR3 comprising the amino acid sequence of SEQ ID NO:87; or (g) (1) the VH comprises the VH-CDR1 comprising the amino acid sequence of SEQ ID NO:25 the VH-CDR2 comprising the amino acid sequence of SEQ ID NO:88, and the VH-CDR3 comprising the amino acid sequence of SEQ ID NO:89; and the VL comprises the VL-CDR1 comprising the amino acid sequence of SEQ ID NO:90, the VL-CDR2 comprising the amino acid sequence of SEQ ID NO:91, and the VL-CDR3 comprising the amino acid sequence of SEQ ID NO:92;

(2) the VH comprises the VH-CDR1 comprising the amino acid sequence of SEQ ID NO:31, the VH-CDR2 comprising the amino acid sequence of SEQ ID NO:32, and the VH-CDR3 comprising the amino acid sequence of SEQ ID NO:89; and the VL comprises the VL-CDR1 comprising the amino acid sequence of SEQ ID NO:90, the VL-CDR2 comprising the amino acid sequence of SEQ ID NO:91, and the VL-CDR3 comprising the amino acid sequence of SEQ ID NO:92;

(3) the VH comprises the VH-CDR1 comprising the amino acid sequence of SEQ ID NO:25, the VH-CDR2 comprising the amino acid sequence of SEQ ID NO:93, and the VH-CDR3 comprising the amino acid sequence of SEQ ID NO:89; and the VL comprises the VL-CDR1 comprising the amino acid sequence of SEQ ID NO:90, the VL-CDR2 comprising the amino acid sequence of SEQ ID NO:91, and the VL-CDR3 comprising the amino acid sequence of SEQ ID NO:92;

(4) the VH comprises the VH-CDR1 comprising the amino acid sequence of SEQ ID NO:34, the VH-CDR2 comprising the amino acid sequence of SEQ ID NO:88, and the VH-CDR3 comprising the amino acid sequence of SEQ ID NO:89; and the VL comprises the VL-CDR1 comprising the amino acid sequence of SEQ ID NO:90, the VL-CDR2 comprising the amino acid sequence of SEQ ID NO:91, and the VL-CDR3 comprising the amino acid sequence of SEQ ID NO:92; or (5) the VH comprises the VH-CDR1 comprising the amino acid sequence of SEQ ID NO:35, the VH-CDR2 comprising the amino acid sequence of SEQ ID NO:94, and the VH-CDR3 comprising the amino acid sequence of SEQ ID NO:95; and the VL comprises the VL-CDR1 comprising the amino acid sequence of SEQ ID NO:96, the VL-CDR2 comprising the amino acid sequence of SEQ ID NO:97, and the VL-CDR3 comprising the amino acid sequence of SEQ ID NO:98.

3. The binding agent of claim 1, wherein:
(1) the VH comprises the amino acid sequence of SEQ ID NO: 117 and/or the VL comprises the amino acid sequence of SEQ ID NO: 118;
(2) the VH comprises the amino acid sequence of SEQ ID NO: 119 and/or the VL comprises the amino acid sequence of SEQ ID NO: 120;
(3) the VH comprises the amino acid sequence of SEQ ID NO: 115 and/or the VL comprises the amino acid sequence of SEQ ID NO: 116;
(4) the VH comprises the amino acid sequence of SEQ ID NO: 121 and/or the VL comprises the amino acid sequence of SEQ ID NO: 122;
(5) the VH comprises the amino acid sequence of SEQ ID NO: 123 and/or the VL comprises the amino acid sequence of SEQ ID NO: 124;
(6) the VH comprises the amino acid sequence of SEQ ID NO: 125 and/or the VL comprises the amino acid sequence of SEQ ID NO: 126;
(7) the VH comprises the amino acid sequence of SEQ ID NO: 127 and/or the VL comprises the amino acid sequence of SEQ ID NO: 128; or
(8) the VH comprises the amino acid sequence of SEQ ID NO: 129 and/or the VL comprises the amino acid sequence of SEQ ID NO: 130.

4. The binding agent of claim 1, which is
(1) a whole antibody;
(2) an antibody fragment comprising at least one antigen-binding site;
(3) a chimeric antibody;
(4) a humanized antibody;
(5) a bispecific or multispecific antibody; or
(6) attached to a half-life extending moiety.

5. The binding agent of claim 1, comprising:
(a) a heavy chain comprising the amino acid sequence of SEQ ID NO: 134 and/or a light chain comprising the amino acid sequence of SEQ ID NO:136; or
(b) a heavy chain comprising the amino acid sequence of SEQ ID NO:138 and/or a light chain comprising the amino acid sequence of SEQ ID NO:140.

6. The binding agent of claim 1, which has at least one of the following properties:
(i) binding human LAIR-1;
(ii) binding cyno LAIR-1;
(iii) not binding mouse LAIR-1;
(iv) not binding human LAIR-2;
(v) being a LAIR-1 antagonist;
(vi) inhibiting LAIR-1 activity;
(vii) inhibiting LAIR-1 signaling in cells that express LAIR-1;
(viii) inhibiting binding of LAIR-1 to collagen;
(ix) inhibiting binding of LAIR-1 to macrophage receptor with collagenous structure (MARCO);
(x) inhibiting binding of LAIR-1 to collectin 12 (COLEC12);
(xi) inhibiting LAIR-1-induced suppression of myeloid cells;
(xii) inhibiting LAIR-1-induced suppression of myeloid cell activity;
(xiii) restoring FcR activation in myeloid cells;
(xiv) restoring cytokine and/or chemokine production in myeloid cells;
(XV) inhibiting LAIR-1-induced suppression of NK cells;
(xvi) inhibiting LAIR-1-induced suppression of NK activity;
(xvii) inhibiting LAIR-1-induced suppression of T-cell activity;
(xviii) inhibiting MDSC activity; and
(xix) inhibiting binding of LAIR-1 to one or more LAIR ligands, wherein the one or more LAIR ligands are selected from the group consisting of collagen, MARCO, COLEC12, mannose-binding lectin (MBL), surfactant protein D (SPD), and C1 complex.

7. A pharmaceutical composition that comprises the binding agent of claim 1 and a pharmaceutically acceptable carrier.

8. An isolated polynucleotide or polynucleotides encoding the binding agent of claim 1.

9. A vector or vectors comprising the polynucleotide or polynucleotides of claim 8.

10. An isolated cell comprising the polynucleotide or polynucleotides of claim 8.

11. An isolated cell comprising the vector or vectors of claim 9.

12. A method of making a binding agent that specifically binds to human LAIR-1, the method comprising:
(a) culturing the cell of claim 10 under conditions that result in the expression of the binding agent, and
(b) isolating the binding agent.

13. A method of making a binding agent that specifically binds to human LAIR-1, the method comprising:
(a) culturing the cell of claim 11 under conditions that result in the expression of the binding agent, and
(b) isolating the binding agent.

14. A method of disrupting, inhibiting, or blocking in a mixture of cells at least one of the following:
(a) the binding of LAIR-1 to collagen;
(b) the binding of LAIR-1 to MARCO;
(c) the binding of LAIR-1 to COLEC12; and
(d) collagen-induced LAIR-1 activity;
wherein the method comprises contacting the cell mixture with the binding agent of claim 1.

15. A method of disrupting, inhibiting, or blocking at least one of the following:

(a) LAIR-1-induced suppression of a myeloid cell or myeloid cell activity;
(b) LAIR-1-induced suppression of a natural killer cell or natural killer cell activity;
(c) LAIR-1-induced suppression of a T-cell or T-cell activity;
(d) the activity of a myeloid-derived suppressor cell (MDSC); and
(e) the activity of a regulatory T-cell (Treg);
wherein the method comprises contacting the myeloid cell, the natural killer cell, the T cell, the MDSC, or the Treg respectively with the binding agent of claim 1.

16. A method of disrupting, inhibiting, or blocking in a subject at least one of the following:
(a) the binding of LAIR-1 to collagen;
(b) the binding of LAIR-1 to MARCO;
(c) the binding of LAIR-1 to COLEC12;
(d) collagen-induced LAIR-1 activity;
(e) LAIR-1-induced suppression of a myeloid cell or myeloid cell activity;
(f) LAIR-1-induced suppression of a natural killer cell or natural killer cell activity;
(g) LAIR-1-induced suppression of a T-cell or T-cell activity;
(h) the activity of a MDSC; and
(i) the activity of a Treg;
wherein the method comprises administering to the subject the pharmaceutical composition of claim 7.

17. A method of:
(a) inhibiting tumor growth in a subject,
(b) increasing or enhancing an immune response to a tumor or tumor cells in a subject,
(c) activating or enhancing a persistent or long-term immune response to a tumor or tumor cells in a subject,
(d) inhibiting tumor relapse or tumor regrowth in a subject,
(e) inducing a persistent or long-term immunity that inhibits tumor relapse or tumor regrowth in a subject,
(f) activating myeloid cells in the tumor microenvironment in a subject with a tumor,
(g) activating T-cells in the tumor microenvironment in a subject with a tumor, wherein the method comprises administering to the subject a therapeutically effective amount of the pharmaceutical composition of claim 7, further comprising administering to the subject an anti-PD-1 antagonistic antibody.

18. The method of claim 17, wherein the tumor is pancreatic cancer, breast cancer, mesothelioma, gastric cancer, non-small cell lung cancer (NSCLC), cervical cancer, endocervical cancer, biliary duct cancer, squamous cell carcinoma of the head and neck (SCCHN), bladder urothelial cancer, colorectal cancer (CRC), esophageal cancer, ovarian cancer, renal cell carcinoma (RCC), prostate cancer, or melanoma.

19. The method of claim 17, wherein the anti-PD-1 antagonistic antibody is pembrolizumab.

20. A binding agent that specifically binds the extracellular domain of human LAIR-1, wherein the binding agent comprises a VH comprising a VH-CDR1, a VH-CDR2, and a VH-CDR3 from the amino acid sequence of SEQ ID NO:119; and a VL comprising a VL-CDR1, a VL-CDR2, and a VL-CDR3 from the amino acid sequence of SEQ ID NO: 120.

21. The binding agent of claim 20, wherein:
(1) the VH comprises the VH-CDR1 comprising the amino acid sequence of SEQ ID NO: 25, the VH-CDR2 comprising the amino acid sequence of SEQ ID NO:41, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;
(2) the VH comprises the VH-CDR1 comprising the amino acid sequence of SEQ ID NO: 31, the VH-CDR2 comprising the amino acid sequence of SEQ ID NO:43, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;
(3) the VH comprises the VH-CDR1 comprising the amino acid sequence of SEQ ID NO: 25, the VH-CDR2 comprising the amino acid sequence of SEQ ID NO:44, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;
(4) the VH comprises the VH-CDR1 comprising the amino acid sequence of SEQ ID NO: 34, the VH-CDR2 comprising the amino acid sequence of SEQ ID NO:41, and the VH-CDR3 comprising the amino acid sequence of SEQ ID NO:27; and the VL comprises the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30; or
(5) the VH comprises the VH-CDR1 comprising the amino acid sequence of SEQ ID NO: 35, the VH-CDR2 comprising the amino acid sequence of SEQ ID NO:45, and the VH-CDR3 comprising the amino acid sequence of SEQ ID NO:37; and the VL comprises the VL-CDR1 comprising the amino acid sequence of SEQ ID NO:38, the VL-CDR2 comprising the amino acid sequence of SEQ ID NO:39, and the VL-CDR3 comprising the amino acid sequence of SEQ ID NO:40.

22. The binding agent of claim 20, wherein the VH comprises the amino acid sequence of SEQ ID NO: 119, and the VL comprises the amino acid sequence of SEQ ID NO:120.

23. The binding agent of claim 20, comprising a heavy chain comprising the amino acid sequence of SEQ ID NO: 134, and a light chain comprising the amino acid sequence of SEQ ID NO: 136.

24. A pharmaceutical composition that comprises the binding agent of claim 20 and a pharmaceutically acceptable carrier.

25. A method of:
(a) inhibiting tumor growth in a subject,
(b) increasing or enhancing an immune response to a tumor or tumor cells in a subject,
(c) activating or enhancing a persistent or long-term immune response to a tumor or tumor cells in a subject,
(d) inhibiting tumor relapse or tumor regrowth in a subject,
(e) inducing a persistent or long-term immunity that inhibits tumor relapse or tumor regrowth in a subject,
(f) activating myeloid cells in the tumor microenvironment in a subject with a tumor, or
(g) activating T-cells in the tumor microenvironment in a subject with a tumor, wherein the method comprises administering to the subject a therapeutically effective amount of the pharmaceutical composition of claim 24, further comprising administering to the subject an anti-PD-1 antagonistic antibody.

26. The method of claim 25, wherein the tumor is pancreatic cancer, breast cancer, mesothelioma, gastric cancer, non-small cell lung cancer (NSCLC), cervical cancer, endocervical cancer, biliary duct cancer, squamous cell carcinoma of the head and neck (SCCHN), bladder urothelial cancer, colorectal cancer (CRC), esophageal cancer, ovarian cancer, renal cell carcinoma (RCC), prostate cancer, or melanoma.

27. The method of claim 25, wherein the anti-PD-1 antagonistic antibody is pembrolizumab.

28. An isolated cell comprising a polynucleotide or polynucleotides encoding the binding agent of claim 20.

29. A method for treating cancer in a subject comprising administering to the subject a therapeutically effective amount of the pharmaceutical composition of claim 24, further comprising administering to the subject an anti-PD-1 antagonistic antibody.

30. The method of claim 29, wherein the anti-PD-1 antagonistic antibody is pembrolizumab.

31. The method of claim 29, wherein the cancer is pancreatic cancer, breast cancer, mesothelioma, gastric cancer, non-small cell lung cancer (NSCLC), cervical cancer, endocervical cancer, biliary duct cancer, squamous cell carcinoma of the head and neck (SCCHN), bladder urothelial cancer, colorectal cancer (CRC), esophageal cancer, ovarian cancer, renal cell carcinoma (RCC), prostate cancer, or melanoma.

32. The method of claim 29, wherein the binding agent comprises:
  (1) the VH comprising the VH-CDR1 comprising the amino acid sequence of SEQ ID NO: 25, the VH-CDR2 comprising the amino acid sequence of SEQ ID NO:41, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;
  (2) the VH comprising the VH-CDR1 comprising the amino acid sequence of SEQ ID NO: 31, the VH-CDR2 comprising the amino acid sequence of SEQ ID NO:43, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;
  (3) the VH comprising the VH-CDR1 comprising the amino acid sequence of SEQ ID NO: 25, the VH-CDR2 comprising the amino acid sequence of SEQ ID NO:44, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;
  (4) the VH comprising the VH-CDR1 comprising the amino acid sequence of SEQ ID NO: 34, the VH-CDR2 comprising the amino acid sequence of SEQ ID NO:41, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30; or
  (5) the VH comprising the VH-CDR1 comprising the amino acid sequence of SEQ ID NO: 35, the VH-CDR2 comprising the amino acid sequence of SEQ ID NO:45, and the VH-CDR3 comprising the amino acid sequence of SEQ ID NO:37; and the VL comprising the VL-CDR1 comprising the amino acid sequence of SEQ ID NO:38, the VL-CDR2 comprising the amino acid sequence of SEQ ID NO:39, and the VL-CDR3 comprising the amino acid sequence of SEQ ID NO:40.

33. The method of claim 29, wherein the binding agent comprises the VH comprising the amino acid sequence of SEQ ID NO:119, and the VL comprising the amino acid sequence of SEQ ID NO:120.

34. The method of claim 29, wherein the binding agent comprises a heavy chain comprising the amino acid sequence of SEQ ID NO:134, and a light chain comprising the amino acid sequence of SEQ ID NO: 136.

35. A method for treating cancer in a subject, comprising administering to the subject a therapeutically effective amount of the pharmaceutical composition of claim 7, further comprising administering to the subject an anti-PD-1 antagonistic antibody.

36. The method of claim 35, wherein the anti-PD-1 antagonistic antibody is pembrolizumab.

37. The method of claim 35, wherein the cancer is pancreatic cancer, breast cancer, mesothelioma, gastric cancer, non-small cell lung cancer (NSCLC), cervical cancer, endocervical cancer, biliary duct cancer, squamous cell carcinoma of the head and neck (SCCHN), bladder urothelial cancer, colorectal cancer (CRC), esophageal cancer, ovarian cancer, renal cell carcinoma (RCC), prostate cancer, or melanoma.

38. The method of claim 35, wherein the binding agent comprises:
  (a) (1) the VH comprising the VH-CDR1 comprising the amino acid sequence of SEQ ID NO: 25, the VH-CDR2 comprising the amino acid sequence of SEQ ID NO:26, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:29, and the VL-CDR3 comprising the amino acid sequence of SEQ ID NO:30;
  (2) the VH comprising the VH-CDR1 comprising the amino acid sequence of SEQ ID NO: 31, the VH-CDR2 comprising the amino acid sequence of SEQ ID NO:32, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:29, and the VL-CDR3 comprising the amino acid sequence of SEQ ID NO:30;
  (3) the VH comprising the VH-CDR1 comprising the amino acid sequence of SEQ ID NO: 25, the VH-CDR2 comprising the amino acid sequence of SEQ ID NO:33, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:29, and the VL-CDR3 comprising the amino acid sequence of SEQ ID NO:30;
  (4) the VH comprising the VH-CDR1 comprising the amino acid sequence of SEQ ID NO: 34, the VH- CDR2 comprising the amino acid sequence of SEQ ID NO:26, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:29, and the VL-CDR3 comprising the amino acid sequence of SEQ ID NO:30; or (5) the VH comprising the VH-CDR1 comprising the amino acid sequence of SEQ ID NO: 35, the VH-CDR2 comprising the amino acid sequence of SEQ ID NO:36, and the VH-CDR3 comprising the amino acid sequence of SEQ ID NO:37; and the VL comprising the VL-CDR1 comprising the amino acid sequence of SEQ ID NO:38, the VL-CDR2 comprising the amino acid sequence of SEQ ID NO:39, and the VL-CDR3 comprising the amino acid sequence of SEQ ID NO:40;

(b) (1) the VH comprising the VH-CDR1 comprising the amino acid sequence of SEQ ID NO: 25, the VH-CDR2 comprising the amino acid sequence of SEQ ID NO:41, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;

(2) the VH comprising the VH-CDR1 comprising the amino acid sequence of SEQ ID NO: 31, the VH-CDR2 comprising the amino acid sequence of SEQ ID NO:43, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;

(3) the VH comprising the VH-CDR1 comprising the amino acid sequence of SEQ ID NO: 25, the VH-CDR2 comprising the amino acid sequence of SEQ ID NO:44, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30;

(4) the VH comprising the VH-CDR1 comprising the amino acid sequence of SEQ ID NO: 34, the VH-CDR2 comprising the amino acid sequence of SEQ ID NO:41, and the VH-CDR3 comprising the amino acid sequence of SEQ ID NO:27; and the VL comprising the VL-CDR1 comprising the amino acid sequence of SEQ ID NO:28, the VL-CDR2 comprising the amino acid sequence of SEQ ID NO:42, and the VL-CDR3 comprising the amino acid sequence of SEQ ID NO:30; or (5) the VH comprising the VH-CDR1 comprising the amino acid sequence of SEQ ID NO: 35, the VH-CDR2 comprising the amino acid sequence of SEQ ID NO:45, and the VH-CDR3 comprising the amino acid sequence of SEQ ID NO:37; and the VL comprising the VL-CDR1 comprising the amino acid sequence of SEQ ID NO:38, the VL-CDR2 comprising the amino acid sequence of SEQ ID NO:39, and the VL-CDR3 comprising the amino acid sequence of SEQ ID NO:40;

(c) (1) the VH comprising the VH-CDR1 comprising the amino acid sequence of SEQ ID NO: 9, the VH-CDR2 comprising the amino acid sequence of SEQ ID NO: 10, and the VH-CDR3 comprising the amino acid sequence of SEQ ID NO:11; and the VL comprising the VL-CDR1 comprising the amino acid sequence of SEQ ID NO: 12, the VL-CDR2 comprising the amino acid sequence of SEQ ID NO:13, and the VL-CDR3 comprising the amino acid sequence of SEQ ID NO:14;

(2) the VH comprising the VH-CDR1 comprising the amino acid sequence of SEQ ID NO: 15, the VH-CDR2 comprising the amino acid sequence of SEQ ID NO: 16, and the VH-CDR3 comprising the amino acid sequence of SEQ ID NO:11; and the VL comprising the VL-CDR1 comprising the amino acid sequence of SEQ ID NO: 12, the VL-CDR2 comprising the amino acid sequence of SEQ ID NO:13, and the VL-CDR3 comprising the amino acid sequence of SEQ ID NO:14;

(3) the VH comprising the VH-CDR1 comprising the amino acid sequence of SEQ ID NO: 9, the VH-CDR2 comprising the amino acid sequence of SEQ ID NO:17, and the VH-CDR3 comprising the amino acid sequence of SEQ ID NO:11; and the VL comprising the VL-CDR1 comprising the amino acid sequence of SEQ ID NO:12, the VL-CDR2 comprising the amino acid sequence of SEQ ID NO:13, and the VL-CDR3 comprising the amino acid sequence of SEQ ID NO:14;

(4) the VH comprising the VH-CDR1 comprising the amino acid sequence of SEQ ID NO: 18, the VH-CDR2 comprising the amino acid sequence of SEQ ID NO: 10, and the VH-CDR3 comprising the amino acid sequence of SEQ ID NO:11; and the VL comprising the VL-CDR1 comprising the amino acid sequence of SEQ ID NO: 12, the VL-CDR2 comprising the amino acid sequence of SEQ ID NO:13, and the VL-CDR3 comprising the amino acid sequence of SEQ ID NO:14; or (5) the VH comprising the VH-CDR1 comprising the amino acid sequence of SEQ ID NO: 19, the VH-CDR2 comprising the amino acid sequence of SEQ ID NO:20, and the VH-CDR3 comprising the amino acid sequence of SEQ ID NO:21; and the VL comprising the VL-CDR1 comprising the amino acid sequence of SEQ ID NO:22, the VL-CDR2 comprising the amino acid sequence of SEQ ID NO:23, and the VL-CDR3 comprising the amino acid sequence of SEQ ID NO:24;

(d) (1) the VH comprising the VH-CDR1 comprising the amino acid sequence of SEQ ID NO: 46, the VH-CDR2 comprising the amino acid sequence of SEQ ID NO:47, and the VH-CDR3 comprising the amino acid sequence of SEQ ID NO:48; and the VL comprising the VL-CDR1 comprising the amino acid sequence of SEQ ID NO:49, the VL-CDR2 comprising the amino acid sequence of SEQ ID NO:50, and the VL-CDR3 comprising the amino acid sequence of SEQ ID NO:51;

(2) the VH comprising the VH-CDR1 comprising the amino acid sequence of SEQ ID NO: 52, the VH-CDR2 comprising the amino acid sequence of SEQ ID NO:53, and the VH-CDR3 comprising the amino acid sequence of SEQ ID NO:48; and the VL comprising the VL-CDR1 comprising the amino acid sequence of SEQ ID NO:49, the VL-CDR2 comprising the amino acid sequence of SEQ ID NO:50, and the VL-CDR3 comprising the amino acid sequence of SEQ ID NO:51;
(3) the VH comprising the VH-CDR1 comprising the amino acid sequence of SEQ ID NO: 46, the VH-CDR2 comprising the amino acid sequence of SEQ ID NO:54, and the VH-CDR3 comprising the amino acid sequence of SEQ ID NO:48; and the VL comprising the VL-CDR1 comprising the amino acid sequence of SEQ ID NO:49, the VL-CDR2 comprising the amino acid sequence of SEQ ID NO:50, and the VL-CDR3 comprising the amino acid sequence of SEQ ID NO:51;
(4) the VH comprising the VH-CDR1 comprising the amino acid sequence of SEQ ID NO: 55, the VH-CDR2 comprising the amino acid sequence of SEQ ID NO:47, and the VH-CDR3 comprising the amino acid sequence of SEQ ID NO:48; and the VL comprising the VL-CDR1 comprising the amino acid sequence of SEQ ID NO:49, the VL-CDR2 comprising the amino acid sequence of SEQ ID NO:50, and the VL-CDR3 comprising the amino acid sequence of SEQ ID NO:51; or
(5) the VH comprising the VH-CDR1 comprising the amino acid sequence of SEQ ID NO: 56, the VH-CDR2 comprising the amino acid sequence of SEQ ID NO:57, and the VH-CDR3 comprising the amino acid sequence of SEQ ID NO:58; and the VL comprising the VL-CDR1 comprising the amino acid sequence of SEQ ID NO:59, the VL-CDR2 comprising the amino acid sequence of SEQ ID NO:60, and the VL-CDR3 comprising the amino acid sequence of SEQ ID NO:61;
(e) (1) the VH comprising the VH-CDR1 comprising the amino acid sequence of SEQ ID NO: 62, the VH-CDR2 comprising the amino acid sequence of SEQ ID NO:63, and the VH-CDR3 comprising the amino acid sequence of SEQ ID NO:64; and the VL comprising the VL-CDR1 comprising the amino acid sequence of SEQ ID NO:65, the VL-CDR2 comprising the amino acid sequence of SEQ ID NO:66, and the VL-CDR3 comprising the amino acid sequence of SEQ ID NO:67;
(2) the VH comprising the VH-CDR1 comprising the amino acid sequence of SEQ ID NO: 68, the VH-CDR2 comprising the amino acid sequence of SEQ ID NO:69, and the VH-CDR3 comprising the amino acid sequence of SEQ ID NO:64; and the VL comprising the VL-CDR1 comprising the amino acid sequence of SEQ ID NO:65, the VL-CDR2 comprising the amino acid sequence of SEQ ID NO:66, and the VL-CDR3 comprising the amino acid sequence of SEQ ID NO:67;
(3) the VH comprising the VH-CDR1 comprising the amino acid sequence of SEQ ID NO: 62, the VH-CDR2 comprising the amino acid sequence of SEQ ID NO:70, and the VH-CDR3 comprising the amino acid sequence of SEQ ID NO:64; and the VL comprising the VL-CDR1 comprising the amino acid sequence of SEQ ID NO:65, the VL-CDR2 comprising the amino acid sequence of SEQ ID NO:66, and the VL-CDR3 comprising the amino acid sequence of SEQ ID NO:67;
(4) the VH comprising the VH-CDR1 comprising the amino acid sequence of SEQ ID NO: 71, the VH-CDR2 comprising the amino acid sequence of SEQ ID NO:63, and the VH-CDR3 comprising the amino acid sequence of SEQ ID NO:64; and the VL comprising the VL-CDR1 comprising the amino acid sequence of SEQ ID NO:65, the VL-CDR2 comprising the amino acid sequence of SEQ ID NO:66, and the VL-CDR3 comprising the amino acid sequence of SEQ ID NO:67; or
(5) the VH comprising the VH-CDR1 comprising the amino acid sequence of SEQ ID NO: 72, the VH-CDR2 comprising the amino acid sequence of SEQ ID NO: 73, and the VH-CDR3 comprising the amino acid sequence of SEQ ID NO:74; and the VL comprising the VL-CDR1 comprising the amino acid sequence of SEQ ID NO:75, the VL-CDR2 comprising the amino acid sequence of SEQ ID NO:76, and the VL-CDR3 comprising the amino acid sequence of SEQ ID NO:77;
(f) (1) the VH comprising the VH-CDR1 comprising the amino acid sequence of SEQ ID NO: 25, the VH-CDR2 comprising the amino acid sequence of SEQ ID NO:78, and the VH-CDR3 comprising the amino acid sequence of SEQ ID NO:79; and the VL comprising the VL-CDR1 comprising the amino acid sequence of SEQ ID NO:80, the VL-CDR2 comprising the amino acid sequence of SEQ ID NO:29, and the VL-CDR3 comprising the amino acid sequence of SEQ ID NO:81;
(2) the VH comprising the VH-CDR1 comprising the amino acid sequence of SEQ ID NO: 31, the VH-CDR2 comprising the amino acid sequence of SEQ ID NO:82, and the VH-CDR3 comprising the amino acid sequence of SEQ ID NO:79; and the VL comprising the VL-CDR1 comprising the amino acid sequence of SEQ ID NO:80, the VL-CDR2 comprising the amino acid sequence of SEQ ID NO:29, and the VL-CDR3 comprising the amino acid sequence of SEQ ID NO:81;
(3) the VH comprising the VH-CDR1 comprising the amino acid sequence of SEQ ID NO: 25, the VH-CDR2 comprising the amino acid sequence of SEQ ID NO:83, and the VH-CDR3 comprising the amino acid sequence of SEQ ID NO:79; and the VL comprising the VL-CDR1 comprising the amino acid sequence of SEQ ID NO:80, the VL-CDR2 comprising the amino acid sequence of SEQ ID NO:29, and the VL-CDR3 comprising the amino acid sequence of SEQ ID NO:81;
(4) the VH comprising the VH-CDR1 comprising the amino acid sequence of SEQ ID NO: 34, the VH-CDR2 comprising the amino acid sequence of SEQ ID NO:78, and the VH-CDR3 comprising the amino acid sequence of SEQ ID NO:79; and the VL comprising the VL-CDR1 comprising the amino acid sequence of SEQ ID NO:80, the VL-CDR2 comprising the amino acid sequence of SEQ ID NO:29, and the VL-CDR3 comprising the amino acid sequence of SEQ ID NO:81; or
(5) the VH comprising the VH-CDR1 comprising the amino acid sequence of SEQ ID NO: 35, the VH-CDR2 comprising the amino acid sequence of SEQ ID NO:84, and the VH-CDR3 comprising the amino acid sequence of SEQ ID NO:85; and the VL comprising the VL-CDR1 comprising the amino acid sequence of SEQ ID NO:86, the VL-CDR2 comprising the amino acid sequence of SEQ ID NO:39, and the VL-CDR3 comprising the amino acid sequence of SEQ ID NO:87; or
(g) (1) the VH comprising the VH-CDR1 comprising the amino acid sequence of SEQ ID NO: 25 the VH-CDR2 comprising the amino acid sequence of SEQ ID NO:88, and the VH-CDR3 comprising the amino acid sequence of SEQ ID NO:89; and the VL comprising the VL-CDR1 comprising the amino acid sequence of SEQ ID NO:90, the VL-CDR2 comprising the amino acid sequence of SEQ ID NO:91, and the VL-CDR3 comprising the amino acid sequence of SEQ ID NO:92;

(2) the VH comprising the VH-CDR1 comprising the amino acid sequence of SEQ ID NO: 31, the VH-CDR2 comprising the amino acid sequence of SEQ ID NO:32, and the VH-CDR3 comprising the amino acid sequence of SEQ ID NO:89; and the VL comprising the VL-CDR1 comprising the amino acid sequence of SEQ ID NO:90, the VL-CDR2 comprising the amino acid sequence of SEQ ID NO:91, and the VL-CDR3 comprising the amino acid sequence of SEQ ID NO:92;

(3) the VH comprising the VH-CDR1 comprising the amino acid sequence of SEQ ID NO: 25, the VH-CDR2 comprising the amino acid sequence of SEQ ID NO:93, and the VH-CDR3 comprising the amino acid sequence of SEQ ID NO:89; and the VL comprising the VL-CDR1 comprising the amino acid sequence of SEQ ID NO:90, the VL-CDR2 comprising the amino acid sequence of SEQ ID NO:91, and the VL-CDR3 comprising the amino acid sequence of SEQ ID NO:92;

(4) the VH comprising the VH-CDR1 comprising the amino acid sequence of SEQ ID NO: 34, the VH-CDR2 comprising the amino acid sequence of SEQ ID NO:88, and the VH-CDR3 comprising the amino acid sequence of SEQ ID NO:89; and the VL comprising the VL-CDR1 comprising the amino acid sequence of SEQ ID NO:90, the VL-CDR2 comprising the amino acid sequence of SEQ ID NO:91, and the VL-CDR3 comprising the amino acid sequence of SEQ ID NO:92; or (5) the VH comprising the VH-CDR1 comprising the amino acid sequence of SEQ ID NO: 35, the VH-CDR2 comprising the amino acid sequence of SEQ ID NO:94, and the VH-CDR3 comprising the amino acid sequence of SEQ ID NO:95; and the VL comprising the VL-CDR1 comprising the amino acid sequence of SEQ ID NO:96, the VL-CDR2 comprising the amino acid sequence of SEQ ID NO:97, and the VL-CDR3 comprising the amino acid sequence of SEQ ID NO:98.

39. The method of claim 35, wherein the binding agent comprises:
(1) the VH comprising the amino acid sequence of SEQ ID NO: 117 and/or the VL comprising the amino acid sequence of SEQ ID NO: 118;
(2) the VH comprising the amino acid sequence of SEQ ID NO: 119 and/or the VL comprising the amino acid sequence of SEQ ID NO: 120;
(3) the VH comprising the amino acid sequence of SEQ ID NO: 115 and/or the VL comprising the amino acid sequence of SEQ ID NO: 116;
(4) the VH comprising the amino acid sequence of SEQ ID NO: 121 and/or the VL comprising the amino acid sequence of SEQ ID NO: 122;
(5) the VH comprising the amino acid sequence of SEQ ID NO: 123 and/or the VL comprising the amino acid sequence of SEQ ID NO: 124;
(6) the VH comprising the amino acid sequence of SEQ ID NO: 125 and/or the VL comprising the amino acid sequence of SEQ ID NO: 126;
(7) the VH comprising the amino acid sequence of SEQ ID NO: 127 and/or the VL comprising the amino acid sequence of SEQ ID NO: 128; or
(8) the VH comprising the amino acid sequence of SEQ ID NO: 129 and/or the VL comprising the amino acid sequence of SEQ ID NO: 130.

40. The method of claim 35, wherein the binding agent comprises:
(a) a heavy chain comprising the amino acid sequence of SEQ ID NO: 134 and/or a light chain comprising the amino acid sequence of SEQ ID NO:136; or
(b) a heavy chain comprising the amino acid sequence of SEQ ID NO:138 and/or a light chain comprising the amino acid sequence of SEQ ID NO:140.

41. A vector or vectors comprising a polynucleotide or polynucleotides encoding the binding agent of claim 20.

* * * * *

UNITED STATES PATENT AND TRADEMARK OFFICE
CERTIFICATE OF CORRECTION

| | | |
|---|---|---|
| PATENT NO. | : 12,240,899 B2 | |
| APPLICATION NO. | : 17/353295 | |
| DATED | : March 4, 2025 | |
| INVENTOR(S) | : Crawley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 135 days.

Signed and Sealed this
Sixth Day of January, 2026

John A. Squires
*Director of the United States Patent and Trademark Office*

SEQUENCE LISTING

<160> NUMBER OF SEQ ID NOS: 227

<210> SEQ ID NO 1
<211> LENGTH: 287
<212> TYPE: PRT
<213> ORGANISM: Homo sapiens

<400> SEQUENCE: 1

```
Met Ser Pro His Pro Thr Ala Leu Leu Gly Leu Val Leu Cys Leu Ala
1               5                   10                  15

Gln Thr Ile His Thr Gln Glu Glu Asp Leu Pro Arg Pro Ser Ile Ser
            20                  25                  30

Ala Glu Pro Gly Thr Val Ile Pro Leu Gly Ser His Val Thr Phe Val
        35                  40                  45

Cys Arg Gly Pro Val Gly Val Gln Thr Phe Arg Leu Glu Arg Glu Ser
    50                  55                  60

Arg Ser Thr Tyr Asn Asp Thr Glu Asp Val Ser Gln Ala Ser Pro Ser
65                  70                  75                  80

Glu Ser Glu Ala Arg Phe Arg Ile Asp Ser Val Ser Glu Gly Asn Ala
                85                  90                  95

Gly Pro Tyr Arg Cys Ile Tyr Tyr Lys Pro Pro Lys Trp Ser Glu Gln
            100                 105                 110

Ser Asp Tyr Leu Glu Leu Leu Val Lys Glu Thr Ser Gly Gly Pro Asp
            115                 120                 125

Ser Pro Asp Thr Glu Pro Gly Ser Ser Ala Gly Pro Thr Gln Arg Pro
        130                 135                 140

Ser Asp Asn Ser His Asn Glu His Ala Pro Ala Ser Gln Gly Leu Lys
145                 150                 155                 160

Ala Glu His Leu Tyr Ile Leu Ile Gly Val Ser Val Val Phe Leu Phe
                165                 170                 175

Cys Leu Leu Leu Leu Val Leu Phe Cys Leu His Arg Gln Asn Gln Ile
            180                 185                 190

Lys Gln Gly Pro Pro Arg Ser Lys Asp Glu Glu Gln Lys Pro Gln Gln
        195                 200                 205

Arg Pro Asp Leu Ala Val Asp Val Leu Glu Arg Thr Ala Asp Lys Ala
    210                 215                 220

Thr Val Asn Gly Leu Pro Glu Lys Asp Arg Glu Thr Asp Thr Ser Ala
225                 230                 235                 240

Leu Ala Ala Gly Ser Ser Gln Glu Val Thr Tyr Ala Gln Leu Asp His
                245                 250                 255

Trp Ala Leu Thr Gln Arg Thr Ala Arg Ala Val Ser Pro Gln Ser Thr
            260                 265                 270

Lys Pro Met Ala Glu Ser Ile Thr Tyr Ala Ala Val Ala Arg His
        275                 280                 285
```

<210> SEQ ID NO 2
<211> LENGTH: 266

```
<212> TYPE: PRT
<213> ORGANISM: Homo sapiens

<400> SEQUENCE: 2

Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
            20                  25                  30

Gly Val Gln Thr Phe Arg Leu Glu Arg Glu Ser Arg Ser Thr Tyr Asn
        35                  40                  45

Asp Thr Glu Asp Val Ser Gln Ala Ser Pro Ser Glu Ser Glu Ala Arg
    50                  55                  60

Phe Arg Ile Asp Ser Val Ser Glu Gly Asn Ala Gly Pro Tyr Arg Cys
65                  70                  75                  80

Ile Tyr Tyr Lys Pro Pro Lys Trp Ser Glu Gln Ser Asp Tyr Leu Glu
                85                  90                  95

Leu Leu Val Lys Glu Thr Ser Gly Gly Pro Asp Ser Pro Asp Thr Glu
            100                 105                 110

Pro Gly Ser Ser Ala Gly Pro Thr Gln Arg Pro Ser Asp Asn Ser His
        115                 120                 125

Asn Glu His Ala Pro Ala Ser Gln Gly Leu Lys Ala Glu His Leu Tyr
    130                 135                 140

Ile Leu Ile Gly Val Ser Val Val Phe Leu Phe Cys Leu Leu Leu Leu
145                 150                 155                 160

Val Leu Phe Cys Leu His Arg Gln Asn Gln Ile Lys Gln Gly Pro Pro
                165                 170                 175

Arg Ser Lys Asp Glu Glu Gln Lys Pro Gln Gln Arg Pro Asp Leu Ala
            180                 185                 190

Val Asp Val Leu Glu Arg Thr Ala Asp Lys Ala Thr Val Asn Gly Leu
        195                 200                 205

Pro Glu Lys Asp Arg Glu Thr Asp Thr Ser Ala Leu Ala Ala Gly Ser
    210                 215                 220

Ser Gln Glu Val Thr Tyr Ala Gln Leu Asp His Trp Ala Leu Thr Gln
225                 230                 235                 240

Arg Thr Ala Arg Ala Val Ser Pro Gln Ser Thr Lys Pro Met Ala Glu
                245                 250                 255

Ser Ile Thr Tyr Ala Ala Val Ala Arg His
            260                 265

<210> SEQ ID NO 3
<211> LENGTH: 144
<212> TYPE: PRT
<213> ORGANISM: Homo sapiens

<400> SEQUENCE: 3

Gln Glu Glu Asp Leu Pro Arg Pro Ser Ile Ser Ala Glu Pro Gly Thr
1               5                   10                  15

Val Ile Pro Leu Gly Ser His Val Thr Phe Val Cys Arg Gly Pro Val
            20                  25                  30

Gly Val Gln Thr Phe Arg Leu Glu Arg Glu Ser Arg Ser Thr Tyr Asn
        35                  40                  45

Asp Thr Glu Asp Val Ser Gln Ala Ser Pro Ser Glu Ser Glu Ala Arg
    50                  55                  60

Phe Arg Ile Asp Ser Val Ser Glu Gly Asn Ala Gly Pro Tyr Arg Cys
65                  70                  75                  80
```

Ile Tyr Tyr Lys Pro Pro Lys Trp Ser Glu Gln Ser Asp Tyr Leu Glu
                85                  90                  95

Leu Leu Val Lys Glu Thr Ser Gly Gly Pro Asp Ser Pro Asp Thr Glu
            100                 105                 110

Pro Gly Ser Ser Ala Gly Pro Thr Gln Arg Pro Ser Asp Asn Ser His
            115                 120                 125

Asn Glu His Ala Pro Ala Ser Gln Gly Leu Lys Ala Glu His Leu Tyr
            130                 135                 140

<210> SEQ ID NO 4
<211> LENGTH: 89
<212> TYPE: PRT
<213> ORGANISM: Homo sapiens

<400> SEQUENCE: 4

Pro Ser Ile Ser Ala Glu Pro Gly Thr Val Ile Pro Leu Gly Ser His
1               5                   10                  15

Val Thr Phe Val Cys Arg Gly Pro Val Gly Val Gln Thr Phe Arg Leu
            20                  25                  30

Glu Arg Glu Ser Arg Ser Thr Tyr Asn Asp Thr Glu Asp Val Ser Gln
        35                  40                  45

Ala Ser Pro Ser Glu Ser Glu Ala Arg Phe Arg Ile Asp Ser Val Ser
    50                  55                  60

Glu Gly Asn Ala Gly Pro Tyr Arg Cys Ile Tyr Tyr Lys Pro Pro Lys
65                  70                  75                  80

Trp Ser Glu Gln Ser Asp Tyr Leu Glu
                85

<210> SEQ ID NO 5
<211> LENGTH: 287
<212> TYPE: PRT
<213> ORGANISM: Macaca fascicularis

<400> SEQUENCE: 5

Met Ser Pro His Pro Thr Ala Leu Leu Gly Leu Val Leu Cys Leu Ala
1               5                   10                  15

Gln Thr Ile His Ala Gln Glu Gly Pro Leu Pro Arg Pro Ser Ile Ser
            20                  25                  30

Ala Glu Pro Gly Thr Val Ile Pro Pro Gly Arg Pro Val Thr Ile Val
            35                  40                  45

Cys Arg Gly Pro Val Gly Val Asp Gln Phe Arg Leu Glu Arg Glu Asp
        50                  55                  60

Arg Ser Lys Phe Asn Asp Thr Lys Asp Val Ser Gln Ala Ser Pro Ser
65                  70                  75                  80

Glu Ser Glu Ala Arg Phe Arg Ile Asp Ser Val Ser Glu Gly Asn Ala
                85                  90                  95

Gly His Tyr Arg Cys Leu Tyr Val Lys Ser Thr Arg Trp Ser Glu His
            100                 105                 110

Ser Asp Tyr Leu Asp Leu Val Val Lys Glu Thr Ser Gly Asp Thr Asp
            115                 120                 125

Ser Pro Val Thr Glu Pro Asp Ser Ser Ala Gly Pro Thr Gln Arg Pro
            130                 135                 140

Ser Asp Asn Ser His Asn Glu His Ala Pro Ala Ser Gln Gly Leu Ser
145                 150                 155                 160

Ala Glu His Leu Tyr Ile Leu Ile Gly Val Ser Val Val Phe Leu Phe
                165                 170                 175

```
Cys Leu Leu Leu Leu Val Leu Phe Phe Leu His Arg Gln Asn Gln Met
            180                 185                 190

Lys Gln Gly Pro Pro Arg Ser Lys Asp Glu Gln Lys Leu Gln Gln
        195                 200                 205

Arg Pro Asp Leu Ala Val Asp Val Leu Glu Arg Thr Ala Asp Lys Ala
        210                 215                 220

Thr Val Asn Gly Leu Pro Glu Lys Asp Arg Glu Thr Asp Thr Ser Ala
225                 230                 235                 240

Pro Ala Ala Gly Ser Ser Gln Glu Val Thr Tyr Ala Gln Leu Asp His
                245                 250                 255

Trp Ala Leu Thr Trp Arg Thr Ala Gln Ala Val Ser Pro Gln Ser Thr
            260                 265                 270

Glu Pro Met Ala Glu Ser Ser Thr Tyr Ala Ala Val Ala Arg His
        275                 280                 285

<210> SEQ ID NO 6
<211> LENGTH: 266
<212> TYPE: PRT
<213> ORGANISM: Macaca fascicularis

<400> SEQUENCE: 6

Gln Glu Gly Pro Leu Pro Arg Pro Ser Ile Ser Ala Glu Pro Gly Thr
1               5                   10                  15

Val Ile Pro Pro Gly Arg Pro Val Thr Ile Val Cys Arg Gly Pro Val
            20                  25                  30

Gly Val Asp Gln Phe Arg Leu Glu Arg Glu Asp Arg Ser Lys Phe Asn
        35                  40                  45

Asp Thr Lys Asp Val Ser Gln Ala Ser Pro Ser Glu Ser Glu Ala Arg
    50                  55                  60

Phe Arg Ile Asp Ser Val Ser Glu Gly Asn Ala Gly His Tyr Arg Cys
65                  70                  75                  80

Leu Tyr Val Lys Ser Thr Arg Trp Ser Glu His Ser Asp Tyr Leu Asp
                85                  90                  95

Leu Val Val Lys Glu Thr Ser Gly Asp Thr Asp Ser Pro Val Thr Glu
            100                 105                 110

Pro Asp Ser Ser Ala Gly Pro Thr Gln Arg Pro Ser Asp Asn Ser His
        115                 120                 125

Asn Glu His Ala Pro Ala Ser Gln Gly Leu Ser Ala Glu His Leu Tyr
    130                 135                 140

Ile Leu Ile Gly Val Ser Val Val Phe Leu Phe Cys Leu Leu Leu Leu
145                 150                 155                 160

Val Leu Phe Phe Leu His Arg Gln Asn Gln Met Lys Gln Gly Pro Pro
                165                 170                 175

Arg Ser Lys Asp Glu Glu Gln Lys Leu Gln Gln Arg Pro Asp Leu Ala
            180                 185                 190

Val Asp Val Leu Glu Arg Thr Ala Asp Lys Ala Thr Val Asn Gly Leu
        195                 200                 205

Pro Glu Lys Asp Arg Glu Thr Asp Thr Ser Ala Pro Ala Ala Gly Ser
    210                 215                 220

Ser Gln Glu Val Thr Tyr Ala Gln Leu Asp His Trp Ala Leu Thr Trp
225                 230                 235                 240

Arg Thr Ala Gln Ala Val Ser Pro Gln Ser Thr Glu Pro Met Ala Glu
                245                 250                 255

Ser Ser Thr Tyr Ala Ala Val Ala Arg His
            260                 265
```

<210> SEQ ID NO 7
<211> LENGTH: 142
<212> TYPE: PRT
<213> ORGANISM: Macaca fascicularis

<400> SEQUENCE: 7

```
Gln Glu Gly Pro Leu Pro Arg Pro Ser Ile Ser Ala Glu Pro Gly Thr
1               5                   10                  15

Val Ile Pro Pro Gly Arg Pro Val Thr Ile Val Cys Arg Gly Pro Val
            20                  25                  30

Gly Val Asp Gln Phe Arg Leu Glu Arg Glu Asp Arg Ser Lys Phe Asn
        35                  40                  45

Asp Thr Lys Asp Val Ser Gln Ala Ser Pro Ser Glu Ser Glu Ala Arg
    50                  55                  60

Phe Arg Ile Asp Ser Val Ser Glu Gly Asn Ala Gly His Tyr Arg Cys
65                  70                  75                  80

Leu Tyr Val Lys Ser Thr Arg Trp Ser Glu His Ser Asp Tyr Leu Asp
                85                  90                  95

Leu Val Val Lys Glu Thr Ser Gly Asp Thr Asp Ser Pro Val Thr Glu
            100                 105                 110

Pro Asp Ser Ser Ala Gly Pro Thr Gln Arg Pro Ser Asp Asn Ser His
        115                 120                 125

Asn Glu His Ala Pro Ala Ser Gln Gly Leu Ser Ala Glu His
    130                 135                 140
```

<210> SEQ ID NO 8
<211> LENGTH: 88
<212> TYPE: PRT
<213> ORGANISM: Macaca fascicularis

<400> SEQUENCE: 8

```
Glu Pro Gly Thr Val Ile Pro Pro Gly Arg Pro Val Thr Ile Val Cys
1               5                   10                  15

Arg Gly Pro Val Gly Val Asp Gln Phe Arg Leu Glu Arg Glu Asp Arg
            20                  25                  30

Ser Lys Phe Asn Asp Thr Lys Asp Val Ser Gln Ala Ser Pro Ser Glu
        35                  40                  45

Ser Glu Ala Arg Phe Arg Ile Asp Ser Val Ser Glu Gly Asn Ala Gly
    50                  55                  60

His Tyr Arg Cys Leu Tyr Val Lys Ser Thr Arg Trp Ser Glu His Ser
65                  70                  75                  80

Asp Tyr Leu Asp Leu Val Val Lys
                85
```

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Gly Phe Thr Phe Asn Thr Tyr Ala Ile His
1               5                   10
```

<210> SEQ ID NO 10
<211> LENGTH: 19

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ile Arg Ser Lys Ser Thr Asn Tyr Ala Thr Tyr Tyr Ala Asp Ser
1               5                   10                  15

Val Lys Asp

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Asn Trp Tyr Tyr Tyr Ala Leu Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Gly Asn Ile His Asn Tyr Leu Thr
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Ala Lys Thr Leu Glu Asp
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln His Phe Trp Ser Thr Pro Phe Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Gly Phe Thr Phe Asn Thr Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Lys Ser Thr Asn Tyr Ala
1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ile Arg Ser Lys Ser Thr Asn Tyr Ala Thr Tyr
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Tyr Ala Ile His
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Thr Tyr Ala Ile His
1               5

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Val Ala Arg Ile Arg Ser Lys Ser Thr Asn Tyr Ala Thr Tyr
1               5                   10                  15

<210> SEQ ID NO 21
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 21

Val Arg Glu Asn Trp Tyr Tyr Tyr Ala Leu Asp
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

His Asn Tyr Leu Thr Trp Tyr
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Leu Val Tyr Asn Ala Lys Thr Leu Glu
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln His Phe Trp Ser Thr Pro Phe
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Phe Thr Phe Asn Ile Asn Ala Met Asn
1               5                   10

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ile Arg Thr Lys Asn Asn Asn Tyr Ala Thr Phe Tyr Ala Asp Ser
1               5                   10                  15
```

Val Lys Asp

```
<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Arg Ala Gly Phe Phe Ala Tyr
1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Ala Ser Gln Thr Ile Gly Thr Trp Leu Gly
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Thr Ser Leu Ala Asp
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Leu Tyr Ser Thr Pro Leu Thr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Thr Phe Asn Ile Asn
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 32

Arg Thr Lys Asn Asn Asn Tyr Ala
1               5

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ile Arg Thr Lys Asn Asn Asn Tyr Ala Thr Phe
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Asn Ala Met Asn
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asn Ile Asn Ala Met Asn
1               5

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Val Ala Arg Ile Arg Thr Lys Asn Asn Asn Tyr Ala Thr Phe
1               5                   10                  15

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Arg Asp Arg Ala Gly Phe Phe Ala
1               5

<210> SEQ ID NO 38
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Thr Trp Leu Gly Trp Tyr
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Leu Ile Tyr Ala Ala Thr Ser Leu Ala
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Leu Tyr Ser Thr Pro Leu
1               5

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ile Arg Thr Lys Asn Tyr Asn Tyr Ala Thr Phe Tyr Ala Asp Ser
1               5                   10                  15

Val Lys Asp

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Ala Thr Ser Leu Ala Glu
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 43

Arg Thr Lys Asn Tyr Asn Tyr Ala
1               5

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ile Arg Thr Lys Asn Tyr Asn Tyr Ala Thr Phe
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Val Ala Arg Ile Arg Thr Lys Asn Tyr Asn Tyr Ala Thr Phe
1               5                   10                  15

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Ser Phe Thr Ser Phe Gly Ile Ser
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Ile Tyr Pro Arg Ser Asp Asn Thr Phe Tyr Asn Glu Lys Phe Lys
1               5                   10                  15

Gly

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Phe Gly Ser Ser Ser Phe Asp Tyr
1               5

<210> SEQ ID NO 49
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Ala Ser Ser Ser Val Ser Ser Ile Tyr Phe His
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ala Ser Asn Leu Ala Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Trp Ser Gly Tyr Pro Leu Thr
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Tyr Ser Phe Thr Ser Phe
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Tyr Pro Arg Ser Asp Asn
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

```
Glu Ile Tyr Pro Arg Ser Asp Asn Thr Phe
1               5                   10

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Phe Gly Ile Ser
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Ser Phe Gly Ile Ser
1               5

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Trp Ile Gly Glu Ile Tyr Pro Arg Ser Asp Asn Thr Phe
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Arg His Phe Gly Ser Ser Ser Phe Asp
1               5                   10

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Ser Ile Tyr Phe His Trp Tyr
1               5

<210> SEQ ID NO 60
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 60

Pro Leu Ile His Arg Ala Ser Asn Leu Ala
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Gln Trp Ser Gly Tyr Pro Leu
1               5

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Tyr Thr Phe Thr Asp Tyr Tyr Tyr Met Asn
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Ile Tyr Pro Asn Asn Gly Ala Thr Ser Tyr Asn Gln Lys Phe Lys
1               5                   10                  15

Gly

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Gly Tyr Ser Ser Asn Tyr Tyr Thr Met Asp Tyr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ala Ser Gln Gly Thr Ser Ile Asn Leu Asn
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ala Ser Asn Leu Glu Asp
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Gln His Thr Tyr Leu Pro Tyr Thr
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Tyr Thr Phe Thr Asp Tyr Tyr
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Pro Asn Asn Gly Ala
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Ile Tyr Pro Asn Asn Gly Ala Thr Ser
1               5                   10

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 71

Asp Tyr Tyr Tyr Met Asn
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Asp Tyr Tyr Tyr Met Asn
1               5

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Trp Ile Gly Tyr Ile Tyr Pro Asn Asn Gly Ala Thr Ser
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Arg Asp Gly Tyr Ser Ser Asn Tyr Tyr Thr Met Asp
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Ile Asn Leu Asn Trp Phe
1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Leu Ile Tyr Gly Ala Ser Asn Leu Glu
1               5                   10

<210> SEQ ID NO 77
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Gln His Thr Tyr Leu Pro Tyr
1               5

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ile Arg Thr Lys Asn Asn Asn Phe Ala Thr Tyr Tyr Ala Asp Ser
1               5                   10                  15

Val Lys Asp

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Pro Tyr Phe Asp Tyr
1               5

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Ala Ser Gln Thr Ile Gly Thr Trp Leu Ala
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Gln Leu Tyr Ser Thr Pro Tyr Thr
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82
```

```
Arg Thr Lys Asn Asn Asn Phe Ala
1               5

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ile Arg Thr Lys Asn Asn Asn Phe Ala Thr Tyr
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Val Ala Arg Ile Arg Thr Lys Asn Asn Asn Phe Ala Thr Tyr
1               5                   10                  15

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Arg Gly Pro Tyr Phe Asp
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Thr Trp Leu Ala Trp Tyr
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Gln Leu Tyr Ser Thr Pro Tyr
1               5

<210> SEQ ID NO 88
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 88

Arg Ile Arg Thr Lys Asn Asn Asn Tyr Ala Thr Tyr Tyr Ala Asp Ser
1               5                   10                  15

Val Lys Asp

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Arg Tyr Gly Gly Ala Met Ala Tyr
1               5

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Ala Ser Glu Asp Ile Tyr Asn Arg Leu Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Ala Thr Ser Leu Glu Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln Tyr Trp Thr Ile Pro Tyr Thr
1               5

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ile Arg Thr Lys Asn Asn Asn Tyr Ala Thr Tyr
```

```
<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Val Ala Arg Ile Arg Thr Lys Asn Asn Asn Tyr Ala Thr Tyr
1               5                   10                  15

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Arg Asp Arg Tyr Gly Gly Ala Met Ala
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Asn Arg Leu Ala Trp Tyr
1               5

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Leu Ile Ser Ser Ala Thr Ser Leu Glu
1               5                   10

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gln Tyr Trp Thr Ile Pro Tyr
1               5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
          peptide

<400> SEQUENCE: 99

Gly Phe Thr Phe Ser Asn Tyr Gly Ile His
1               5                   10

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ile Ser Pro Ser Gly Arg Ser Thr Tyr Phe Arg Asp Ser Val Lys
1               5                   10                  15

Gly

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ile Asn Tyr Ser Ser Phe Asp Tyr
1               5

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Ala Ser Gln Asn Val Gly Ser His Val Asp
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Ala Ser Asn Arg Tyr Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Met Gln Ser Asn Ser Tyr Pro Pro Thr
1               5
```

```
<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Phe Thr Phe Ser Asn Tyr
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Pro Ser Gly Arg Ser
1               5

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Ile Ser Pro Ser Gly Arg Ser Thr Tyr
1               5                   10

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asn Tyr Gly Ile His
1               5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Asn Tyr Gly Ile His
1               5

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 110

Trp Val Ala Ser Ile Ser Pro Ser Gly Arg Ser Thr Tyr
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Thr Gly Ile Asn Tyr Ser Ser Phe Asp
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Ser His Val Asp Trp Tyr
1               5

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Leu Leu Ile Ser Thr Ala Ser Asn Arg Tyr
1               5                   10

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Met Gln Ser Asn Ser Tyr Pro Pro
1               5

<210> SEQ ID NO 115
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Ile His Trp Val Arg Gln Ala Pro Gly Lys Gly Leu Glu Trp Val
```

```
                35                  40                  45
Ala Arg Ile Arg Ser Lys Ser Thr Asn Tyr Ala Thr Tyr Tyr Ala Asp
 50                  55                  60

Ser Val Lys Asp Arg Phe Thr Ile Ser Arg Asp Asp Ser Gln Ser Met
 65                  70                  75                  80

Val Phe Leu Gln Met Asn Asn Leu Lys Thr Glu Asp Thr Ala Met Tyr
                 85                  90                  95

Tyr Cys Val Arg Glu Asn Trp Tyr Tyr Tyr Ala Leu Asp Tyr Trp Gly
            100                 105                 110

Gln Gly Thr Ser Val Thr Val Ser Ser
            115                 120
```

<210> SEQ ID NO 116
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Asp Ile Gln Met Thr Gln Ser Pro Ala Ser Leu Ser Ala Ser Val Gly
 1               5                  10                  15

Glu Thr Val Thr Ile Thr Cys Arg Ala Ser Gly Asn Ile His Asn Tyr
                 20                  25                  30

Leu Thr Trp Tyr Gln Gln Lys Gln Gly Lys Ser Pro Gln Val Leu Val
             35                  40                  45

Tyr Asn Ala Lys Thr Leu Glu Asp Gly Val Pro Ser Arg Phe Ser Gly
 50                  55                  60

Ser Glu Ser Gly Thr Gln Tyr Ser Leu Lys Ile Asn Ser Leu Gln Pro
 65                  70                  75                  80

Glu Asp Phe Gly Ser Tyr Tyr Cys Gln His Phe Trp Ser Thr Pro Phe
                 85                  90                  95

Thr Phe Gly Ser Gly Thr Lys Leu Glu Ile Lys
            100                 105
```

<210> SEQ ID NO 117
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Glu Val Gln Leu Val Glu Thr Gly Gly Gly Leu Val Gln Pro Lys Gly
 1               5                  10                  15

Ser Leu Lys Leu Ser Cys Ala Ala Ser Gly Phe Thr Phe Asn Ile Asn
                 20                  25                  30

Ala Met Asn Trp Val Arg Gln Ala Pro Gly Lys Gly Leu Glu Trp Val
             35                  40                  45

Ala Arg Ile Arg Thr Lys Asn Asn Tyr Ala Thr Phe Tyr Ala Asp
 50                  55                  60

Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Asp Asp Thr Ala Met Tyr
                 85                  90                  95

Tyr Cys Val Arg Asp Arg Ala Gly Phe Phe Ala Tyr Trp Gly Gln Gly
```

Thr Pro Val Thr Val Ser Ala
            115

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Gly Trp Tyr Arg Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ile Tyr Tyr Cys Gln Gln Leu Tyr Ser Thr Pro Leu
                85                  90                  95

Thr Phe Gly Ser Gly Thr Lys Leu Glu Ile Lys
            100                 105

<210> SEQ ID NO 119
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Thr Lys Asn Tyr Asn Tyr Ala Thr Phe Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg Asp Arg Ala Gly Phe Phe Ala Tyr Trp Gly Gln Gly
            100                 105                 110

Thr Thr Val Thr Val Ser Ser
        115

<210> SEQ ID NO 120
<211> LENGTH: 107
<212> TYPE: PRT
<213> ORGANISM: Artificial Sequence
<220> FEATURE:
<223> OTHER INFORMATION: Description of Artificial Sequence: Synthetic

```
                polypeptide

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Gly Trp Tyr Gln Gln Lys Pro Gly Lys Ala Pro Lys Leu Leu Ile
        35                  40                  45

Tyr Ala Ala Thr Ser Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Leu
                85                  90                  95

Thr Phe Gly Gly Gly Thr Lys Val Glu Ile Lys
            100                 105

<210> SEQ ID NO 121
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Gln Gln Ser Gly Ala Glu Leu Ala Arg Pro Gly Ala
1               5                   10                  15

Ser Val Asn Leu Ser Cys Arg Ala Ser Gly Tyr Ser Phe Thr Ser Phe
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Asp Asn Thr Phe Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg His Phe Gly Ser Ser Phe Asp Tyr Trp Gly Gln Gly Thr
            100                 105                 110

Thr Leu Thr Val Ser Ser
        115

<210> SEQ ID NO 122
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Asn Val Leu Thr Gln Ser Pro Pro Ile Met Ala Ala Ser Leu Gly
1               5                   10                  15

Gln Lys Val Thr Met Thr Cys Ser Ala Ser Ser Ser Val Ser Ser Ile
            20                  25                  30

Tyr Phe His Trp Tyr Gln Gln Lys Ser Gly Thr Ser Pro Lys Pro Leu
        35                  40                  45
```

Ile His Arg Ala Ser Asn Leu Ala Ser Gly Val Pro Ala Arg Phe Ser
            50                  55                  60

Gly Ser Gly Ser Gly Thr Ser Tyr Ser Leu Thr Ile Ser Ser Val Glu
 65                  70                  75                  80

Ala Glu Asp Asp Ala Thr Tyr Tyr Cys Gln Gln Trp Ser Gly Tyr Pro
                85                  90                  95

Leu Thr Phe Gly Gly Gly Thr Lys Leu Glu Ile Lys
            100                 105

<210> SEQ ID NO 123
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Gln Gln Ser Gly Pro Glu Val Leu Lys Pro Gly Ala
 1               5                  10                  15

Ser Val Lys Ile Ser Cys Lys Ala Ser Gly Tyr Thr Phe Thr Asp Tyr
            20                  25                  30

Tyr Tyr Met Asn Trp Val Lys Gln Ser His Gly Lys Ser Leu Glu Trp
        35                  40                  45

Ile Gly Tyr Ile Tyr Pro Asn Asn Gly Ala Thr Ser Tyr Asn Gln Lys
    50                  55                  60

Phe Lys Gly Lys Ala Thr Leu Thr Val Asp Lys Ser Ser Ser Thr Ala
 65                  70                  75                  80

Tyr Met Glu Leu Arg Ser Leu Thr Ser Glu Asp Ser Ala Val Tyr Tyr
                85                  90                  95

Cys Ala Arg Asp Gly Tyr Ser Ser Asn Tyr Tyr Thr Met Asp Tyr Trp
            100                 105                 110

Gly Gln Gly Thr Ser Val Thr Val Ser Ser
        115                 120

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Val Gln Met Ile Gln Ser Pro Ser Ser Leu Ser Ala Ser Leu Gly
 1               5                  10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Gly Ala Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
 65                  70                  75                  80

Glu Asp Met Ala Thr Tyr Phe Cys Leu Gln His Thr Tyr Leu Pro Tyr
                85                  90                  95

Thr Phe Gly Gly Gly Thr Lys Leu Glu Ile Lys
            100                 105

<210> SEQ ID NO 125
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Thr Gly Gly Gly Leu Val Gln Pro Lys Gly
1               5                   10                  15

Ser Leu Lys Leu Ser Cys Ala Thr Ser Gly Phe Thr Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Thr Lys Asn Asn Asn Phe Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gly Pro Tyr Phe Asp Tyr Trp Gln Gly Thr Thr
            100                 105                 110

Leu Thr Val Ser Ser
        115

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Asn Leu Gln Ala
65                  70                  75                  80

Glu Asp Phe Val Thr Tyr Tyr Cys Gln Gln Leu Tyr Ser Thr Pro Tyr
                85                  90                  95

Thr Phe Gly Gly Gly Thr Lys Leu Glu Ile Lys
            100                 105

<210> SEQ ID NO 127
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Thr Lys Asn Asn Asn Phe Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Val Arg Gly Pro Tyr Phe Asp Tyr Trp Gly Gln Gly Thr Leu
        100                 105                 110

Val Thr Val Ser Ser
            115
```

<210> SEQ ID NO 128
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Tyr
            85                  90                  95

Thr Phe Gly Gly Gly Thr Lys Val Glu Ile Lys
            100                 105
```

<210> SEQ ID NO 129
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Thr Lys Asn Asn Asn Tyr Ala Thr Tyr Tyr Ala Asp
    50                  55                  60
```

-continued

Ser Val Lys Asp Arg Phe Thr Ile Ser Arg Asp Asp Ser Glu Ser Met
65                  70                  75                  80

Leu Tyr Leu Gln Met Asn Asn Leu Lys Thr Glu Asp Thr Ala Met Tyr
                85                  90                  95

Tyr Cys Val Arg Asp Arg Tyr Gly Gly Ala Met Ala Tyr Trp Gly Gln
            100                 105                 110

Gly Thr Ser Val Thr Val Ser Ser
            115                 120

<210> SEQ ID NO 130
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
                20                  25                  30

Leu Ala Trp Tyr Gln Gln Lys Pro Gly Asn Val Pro Arg Leu Leu Ile
            35                  40                  45

Ser Ser Ala Thr Ser Leu Glu Thr Gly Val Pro Ser Arg Phe Ser Gly
        50                  55                  60

Ser Gly Ser Gly Lys Asp Tyr Thr Leu Ser Leu Thr Ser Leu Gln Ser
65                  70                  75                  80

Glu Asp Val Ala Thr Tyr Tyr Cys Gln Gln Tyr Trp Thr Ile Pro Tyr
                85                  90                  95

Thr Phe Gly Gly Gly Thr Lys Leu Glu Ile Lys
            100                 105

<210> SEQ ID NO 131
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Val Glu Ser Gly Gly Leu Val Gln Pro Gly Arg
1               5                   10                  15

Ser Leu Lys Val Ser Cys Ala Ala Ser Gly Phe Thr Phe Ser Asn Tyr
                20                  25                  30

Gly Ile His Trp Ile Arg Gln Ala Pro Thr Lys Gly Leu Glu Trp Val
            35                  40                  45

Ala Ser Ile Ser Pro Ser Gly Arg Ser Thr Tyr Phe Arg Asp Ser Val
        50                  55                  60

Lys Gly Arg Phe Thr Ile Ser Arg Asp Asn Ala Lys Asn Thr Leu Tyr
65                  70                  75                  80

Leu Gln Leu Asp Ser Leu Arg Ser Glu Asp Thr Ala Thr Tyr Tyr Cys
                85                  90                  95

Ala Thr Gly Ile Asn Tyr Ser Ser Phe Asp Tyr Trp Gly Gln Gly Val
            100                 105                 110

Met Val Thr Val Ser Ser
            115

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Val Met Thr Gln Ser Pro Thr Ser Met Ser Ile Ser Val Gly
1               5                   10                  15

Asp Arg Val Thr Met Asn Cys Lys Ala Ser Gln Asn Val Gly Ser His
            20                  25                  30

Val Asp Trp Tyr Gln Gln Lys Thr Gly Gln Ser Pro Lys Leu Leu Ile
        35                  40                  45

Ser Thr Ala Ser Asn Arg Tyr Thr Gly Val Pro Asp Arg Phe Thr Gly
    50                  55                  60

Ser Gly Ser Gly Thr Asp Phe Thr Phe Thr Ile Asn Asn Met Gln Thr
65                  70                  75                  80

Glu Asp Leu Ala Val Tyr Tyr Cys Met Gln Ser Asn Ser Tyr Pro Pro
                85                  90                  95

Thr Phe Gly Gly Gly Thr Lys Leu Glu Leu Lys
            100                 105

<210> SEQ ID NO 133
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Asn Ile Asn Ala Met Asn Trp Val Arg Gln Ala Pro Gly
    50                  55                  60

Lys Gly Leu Glu Trp Val Ala Arg Ile Arg Thr Lys Asn Tyr Asn Tyr
65                  70                  75                  80

Ala Thr Phe Tyr Ala Asp Ser Val Lys Asp Arg Phe Thr Ile Ser Arg
                85                  90                  95

Asp Asp Ser Lys Asn Ser Leu Tyr Leu Gln Met Asn Ser Leu Lys Thr
            100                 105                 110

Glu Asp Thr Ala Val Tyr Tyr Cys Val Arg Asp Arg Ala Gly Phe Phe
        115                 120                 125

Ala Tyr Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

```
Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Gly Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 134
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Thr Lys Asn Tyr Asn Tyr Ala Thr Phe Tyr Ala Asp
    50                  55                  60

Ser Val Lys Asp Arg Phe Thr Ile Ser Arg Asp Asp Ser Lys Asn Ser
65                  70                  75                  80
```

```
Leu Tyr Leu Gln Met Asn Ser Leu Lys Thr Glu Asp Thr Ala Val Tyr
                85                  90                  95

Tyr Cys Val Arg Asp Arg Ala Gly Phe Phe Ala Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 135
<211> LENGTH: 236
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 135

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Leu Ala Ser
        35                  40                  45

Gln Thr Ile Gly Thr Trp Leu Gly Trp Tyr Gln Gln Lys Pro Gly Lys
50                  55                  60

Ala Pro Lys Leu Leu Ile Tyr Ala Ala Thr Ser Leu Ala Glu Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Leu Tyr Ser Thr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 136
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Gly Trp Tyr Gln Gln Lys Pro Gly Lys Ala Pro Lys Leu Leu Ile
        35                  40                  45

Tyr Ala Ala Thr Ser Leu Ala Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Tyr Ser Thr Pro Leu
                85                  90                  95

Thr Phe Gly Gly Gly Thr Lys Val Glu Ile Lys Arg Thr Val Ala Ala

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 137
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
                20                  25                  30

Leu Val Lys Pro Gly Gly Ser Leu Arg Leu Ser Cys Ala Ala Ser Gly
            35                  40                  45

Phe Thr Phe Asn Ile Asn Ala Met Asn Trp Val Arg Gln Ala Pro Gly
        50                  55                  60

Lys Gly Leu Glu Trp Val Ala Arg Ile Arg Thr Lys Asn Asn Asn Phe
65                  70                  75                  80

Ala Thr Tyr Tyr Ala Asp Ser Val Lys Asp Arg Phe Thr Ile Ser Arg
                85                  90                  95

Asp Asp Ser Lys Asn Thr Leu Tyr Leu Gln Met Asn Ser Leu Lys Thr
            100                 105                 110

Glu Asp Thr Ala Val Tyr Tyr Cys Val Arg Gly Pro Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240
```

```
Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
        260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Gly Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 138
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Thr Lys Asn Asn Asn Phe Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Val Arg Gly Pro Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125
```

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Gly Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 139
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Leu Ala Ser

-continued

```
                35                  40                  45
Gln Thr Ile Gly Thr Trp Leu Ala Trp Tyr Gln Gln Lys Pro Gly Lys
 50                  55                  60
Ala Pro Lys Leu Leu Ile Tyr Ala Ala Thr Ser Leu Ala Asp Gly Val
 65                  70                  75                  80
Pro Ser Arg Phe Ser Gly Ser Gly Ser Gly Thr Asp Phe Thr Leu Thr
                 85                  90                  95
Ile Ser Ser Leu Gln Pro Glu Asp Phe Ala Thr Tyr Tyr Cys Gln Gln
                100                 105                 110
Leu Tyr Ser Thr Pro Tyr Thr Phe Gly Gly Gly Thr Lys Val Glu Ile
                115                 120                 125
Lys Arg Thr Val Ala Ala Pro Ser Val Phe Ile Phe Pro Pro Ser Asp
130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
                180                 185                 190
Ser Thr Tyr Ser Leu Ser Ser Thr Leu Thr Leu Ser Lys Ala Asp Tyr
                195                 200                 205
Glu Lys His Lys Val Tyr Ala Cys Glu Val Thr His Gln Gly Leu Ser
210                 215                 220
Ser Pro Val Thr Lys Ser Phe Asn Arg Gly Glu Cys
225                 230                 235

<210> SEQ ID NO 140
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ile Gln Met Thr Gln Ser Pro Ser Ser Leu Ser Ala Ser Val Gly
 1                5                  10                  15
Asp Arg Val Thr Ile Thr Cys Leu Ala Ser Gln Thr Ile Gly Thr Trp
                 20                  25                  30
Leu Ala Trp Tyr Gln Gln Lys Pro Gly Lys Ala Pro Lys Leu Leu Ile
                 35                  40                  45
Tyr Ala Ala Thr Ser Leu Ala Asp Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Leu Tyr Ser Thr Pro Tyr
                 85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 141
<211> LENGTH: 330
<212> TYPE: PRT
<213> ORGANISM: Homo sapiens

<400> SEQUENCE: 141

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

-continued

```
Gln Lys Ser Leu Ser Leu Ser Pro Gly Lys
            325                 330

<210> SEQ ID NO 142
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Ala Leu Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

```
<210> SEQ ID NO 143
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 144
<211> LENGTH: 330
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 144

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 145
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 146
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gly Ser Thr Tyr Arg Val Val Ser Val Leu Thr Val Leu
            180                 185                 190

Ala Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 147
<211> LENGTH: 107
<212> TYPE: PRT
<213> ORGANISM: Homo sapiens

<400> SEQUENCE: 147

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu

-continued

```
                65                  70                  75                  80
Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105

<210> SEQ ID NO 148
<211> LENGTH: 106
<212> TYPE: PRT
<213> ORGANISM: Homo sapiens

<400> SEQUENCE: 148

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 149
<211> LENGTH: 263
<212> TYPE: PRT
<213> ORGANISM: Mus sp.

<400> SEQUENCE: 149

Met Ser Leu His Pro Val Ile Leu Leu Val Leu Val Leu Cys Leu Gly
1               5                   10                  15

Trp Lys Ile Asn Thr Gln Glu Gly Ser Leu Pro Asp Ile Thr Ile Phe
                20                  25                  30

Pro Asn Ser Ser Leu Met Ile Ser Gln Gly Thr Phe Val Thr Val Val
            35                  40                  45

Cys Ser Tyr Ser Asp Lys His Asp Leu Tyr Asn Met Val Arg Leu Glu
        50                  55                  60

Lys Asp Gly Ser Thr Phe Met Glu Lys Ser Thr Glu Pro Tyr Lys Thr
65                  70                  75                  80

Glu Asp Glu Phe Glu Ile Gly Pro Val Asn Glu Thr Ile Thr Gly His
                85                  90                  95

Tyr Ser Cys Ile Tyr Ser Lys Gly Ile Thr Trp Ser Glu Arg Ser Lys
                100                 105                 110

Thr Leu Glu Leu Lys Val Ile Lys Glu Asn Val Ile Gln Thr Pro Ala
            115                 120                 125

Pro Gly Pro Thr Ser Asp Thr Ser Trp Leu Lys Thr Tyr Ser Ile Tyr
        130                 135                 140

Ile Phe Thr Val Val Ser Val Ile Phe Leu Leu Cys Leu Ser Ala Leu
145                 150                 155                 160

Leu Phe Cys Phe Leu Arg His Arg Gln Lys Lys Gln Gly Leu Pro Asn
                165                 170                 175

Asn Lys Arg Gln Gln Gln Arg Pro Glu Glu Arg Leu Asn Leu Ala Thr
```

```
                180                 185                 190
Asn Gly Leu Glu Met Thr Pro Asp Ile Val Ala Asp Asp Arg Leu Pro
            195                 200                 205

Glu Asp Arg Trp Thr Glu Thr Trp Thr Pro Val Ala Gly Asp Leu Gln
210                 215                 220

Glu Val Thr Tyr Ile Gln Leu Asp His His Ser Leu Thr Gln Arg Ala
225                 230                 235                 240

Val Gly Ala Val Thr Ser Gln Ser Thr Asp Met Ala Glu Ser Ser Thr
            245                 250                 255

Tyr Ala Ala Ile Ile Arg His
            260

<210> SEQ ID NO 150
<211> LENGTH: 242
<212> TYPE: PRT
<213> ORGANISM: Mus sp.

<400> SEQUENCE: 150

Gln Glu Gly Ser Leu Pro Asp Ile Thr Ile Phe Pro Asn Ser Ser Leu
1               5                   10                  15

Met Ile Ser Gln Gly Thr Phe Val Thr Val Val Cys Ser Tyr Ser Asp
            20                  25                  30

Lys His Asp Leu Tyr Asn Met Val Arg Leu Glu Lys Asp Gly Ser Thr
        35                  40                  45

Phe Met Glu Lys Ser Thr Glu Pro Tyr Lys Thr Glu Asp Glu Phe Glu
    50                  55                  60

Ile Gly Pro Val Asn Glu Thr Ile Thr Gly His Tyr Ser Cys Ile Tyr
65                  70                  75                  80

Ser Lys Gly Ile Thr Trp Ser Glu Arg Ser Lys Thr Leu Glu Leu Lys
                85                  90                  95

Val Ile Lys Glu Asn Val Ile Gln Thr Pro Ala Pro Gly Pro Thr Ser
            100                 105                 110

Asp Thr Ser Trp Leu Lys Thr Tyr Ser Ile Tyr Ile Phe Thr Val Val
        115                 120                 125

Ser Val Ile Phe Leu Leu Cys Leu Ser Ala Leu Leu Phe Cys Phe Leu
130                 135                 140

Arg His Arg Gln Lys Lys Gln Gly Leu Pro Asn Asn Lys Arg Gln Gln
145                 150                 155                 160

Gln Arg Pro Glu Glu Arg Leu Asn Leu Ala Thr Asn Gly Leu Glu Met
                165                 170                 175

Thr Pro Asp Ile Val Ala Asp Asp Arg Leu Pro Glu Asp Arg Trp Thr
            180                 185                 190

Glu Thr Trp Thr Pro Val Ala Gly Asp Leu Gln Glu Val Thr Tyr Ile
        195                 200                 205

Gln Leu Asp His His Ser Leu Thr Gln Arg Ala Val Gly Ala Val Thr
    210                 215                 220

Ser Gln Ser Thr Asp Met Ala Glu Ser Ser Thr Tyr Ala Ala Ile Ile
225                 230                 235                 240

Arg His

<210> SEQ ID NO 151
<211> LENGTH: 123
<212> TYPE: PRT
<213> ORGANISM: Mus sp.

<400> SEQUENCE: 151
```

Gln Glu Gly Ser Leu Pro Asp Ile Thr Ile Phe Pro Asn Ser Ser Leu
1               5                   10                  15

Met Ile Ser Gln Gly Thr Phe Val Thr Val Cys Ser Tyr Ser Asp
            20                  25                  30

Lys His Asp Leu Tyr Asn Met Val Arg Leu Glu Lys Asp Gly Ser Thr
            35                  40                  45

Phe Met Glu Lys Ser Thr Glu Pro Tyr Lys Thr Glu Asp Glu Phe Glu
50                  55                  60

Ile Gly Pro Val Asn Glu Thr Ile Thr Gly His Tyr Ser Cys Ile Tyr
65                  70                  75                  80

Ser Lys Gly Ile Thr Trp Ser Glu Arg Ser Lys Thr Leu Glu Leu Lys
                85                  90                  95

Val Ile Lys Glu Asn Val Ile Gln Thr Pro Ala Pro Gly Pro Thr Ser
            100                 105                 110

Asp Thr Ser Trp Leu Lys Thr Tyr Ser Ile Tyr
            115                 120

<210> SEQ ID NO 152
<211> LENGTH: 88
<212> TYPE: PRT
<213> ORGANISM: Mus sp.

<400> SEQUENCE: 152

Pro Asp Ile Thr Ile Phe Pro Asn Ser Ser Leu Met Ile Ser Gln Gly
1               5                   10                  15

Thr Phe Val Thr Val Cys Ser Tyr Ser Asp Lys His Asp Leu Tyr
            20                  25                  30

Asn Met Val Arg Leu Glu Lys Asp Gly Ser Thr Phe Met Glu Lys Ser
            35                  40                  45

Thr Glu Pro Tyr Lys Thr Glu Asp Glu Phe Glu Ile Gly Pro Val Asn
        50                  55                  60

Glu Thr Ile Thr Gly His Tyr Ser Cys Ile Tyr Ser Lys Gly Ile Thr
65                  70                  75                  80

Trp Ser Glu Arg Ser Lys Thr Leu
                85

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 153

His His His His His His
1               5

<210> SEQ ID NO 154
<211> LENGTH: 520
<212> TYPE: PRT
<213> ORGANISM: Homo sapiens

<400> SEQUENCE: 154

Met Arg Asn Lys Lys Ile Leu Lys Glu Asp Glu Leu Leu Ser Glu Thr
1               5                   10                  15

Gln Gln Ala Ala Phe His Gln Ile Ala Met Glu Pro Phe Glu Ile Asn
            20                  25                  30

-continued

```
Val Pro Lys Pro Lys Arg Arg Asn Gly Val Asn Phe Ser Leu Ala Val
         35                  40                  45

Val Val Ile Tyr Leu Ile Leu Leu Thr Ala Gly Ala Gly Leu Leu Val
 50                  55                  60

Val Gln Val Leu Asn Leu Gln Ala Arg Leu Arg Val Leu Glu Met Tyr
65                   70                  75                  80

Phe Leu Asn Asp Thr Leu Ala Ala Glu Asp Ser Pro Ser Phe Ser Leu
                 85                  90                  95

Leu Gln Ser Ala His Pro Gly Glu His Leu Ala Gln Gly Ala Ser Arg
                100                 105                 110

Leu Gln Val Leu Gln Ala Gln Leu Thr Trp Val Arg Val Ser His Glu
                115                 120                 125

His Leu Leu Gln Arg Val Asp Asn Phe Thr Gln Asn Pro Gly Met Phe
130                 135                 140

Arg Ile Lys Gly Glu Gln Gly Ala Pro Gly Leu Gln Gly His Lys Gly
145                 150                 155                 160

Ala Met Gly Met Pro Gly Ala Pro Gly Pro Gly Pro Pro Ala Glu
                165                 170                 175

Lys Gly Ala Lys Gly Ala Met Gly Arg Asp Gly Ala Thr Gly Pro Ser
                180                 185                 190

Gly Pro Gln Gly Pro Pro Gly Val Lys Gly Glu Ala Gly Leu Gln Gly
                195                 200                 205

Pro Gln Gly Ala Pro Gly Lys Gln Gly Ala Thr Gly Thr Pro Gly Pro
210                 215                 220

Gln Gly Glu Lys Gly Ser Lys Gly Asp Gly Gly Leu Ile Gly Pro Lys
225                 230                 235                 240

Gly Glu Thr Gly Thr Lys Gly Glu Lys Gly Asp Leu Gly Leu Pro Gly
                245                 250                 255

Ser Lys Gly Asp Arg Gly Met Lys Gly Asp Ala Gly Val Met Gly Pro
                260                 265                 270

Pro Gly Ala Gln Gly Ser Lys Gly Asp Phe Gly Arg Pro Gly Pro Pro
                275                 280                 285

Gly Leu Ala Gly Phe Pro Gly Ala Lys Gly Asp Gln Gly Gln Pro Gly
                290                 295                 300

Leu Gln Gly Val Pro Gly Pro Pro Gly Ala Val Gly His Pro Gly Ala
305                 310                 315                 320

Lys Gly Glu Pro Gly Ser Ala Gly Ser Pro Gly Arg Ala Gly Leu Pro
                325                 330                 335

Gly Ser Pro Gly Ser Pro Gly Ala Thr Gly Leu Lys Gly Ser Lys Gly
                340                 345                 350

Asp Thr Gly Leu Gln Gly Gln Gly Arg Lys Gly Glu Ser Gly Val
                355                 360                 365

Pro Gly Pro Ala Gly Val Lys Gly Glu Gln Gly Ser Pro Gly Leu Ala
370                 375                 380

Gly Pro Lys Gly Ala Pro Gly Gln Ala Gly Lys Gly Asp Gln Gly
385                 390                 395                 400

Val Lys Gly Ser Ser Gly Glu Gln Gly Val Lys Gly Glu Lys Gly Glu
                405                 410                 415

Arg Gly Glu Asn Ser Val Ser Val Arg Ile Val Gly Ser Ser Asn Arg
                420                 425                 430

Gly Arg Ala Glu Val Tyr Tyr Ser Gly Thr Trp Gly Thr Ile Cys Asp
                435                 440                 445

Asp Glu Trp Gln Asn Ser Asp Ala Ile Val Phe Cys Arg Met Leu Gly
```

```
            450                 455                 460
Tyr Ser Lys Gly Arg Ala Leu Tyr Lys Val Gly Ala Gly Thr Gly Gln
465                 470                 475                 480

Ile Trp Leu Asp Asn Val Gln Cys Arg Gly Thr Glu Ser Thr Leu Trp
                485                 490                 495

Ser Cys Thr Lys Asn Ser Trp Gly His His Asp Cys Ser His Glu Glu
                500                 505                 510

Asp Ala Gly Val Glu Cys Ser Val
            515                 520

<210> SEQ ID NO 155
<211> LENGTH: 456
<212> TYPE: PRT
<213> ORGANISM: Homo sapiens

<400> SEQUENCE: 155

Val Gln Val Leu Asn Leu Gln Ala Arg Leu Arg Val Leu Glu Met Tyr
1               5                   10                  15

Phe Leu Asn Asp Thr Leu Ala Ala Glu Asp Ser Pro Ser Phe Ser Leu
                20                  25                  30

Leu Gln Ser Ala His Pro Gly Glu His Leu Ala Gln Gly Ala Ser Arg
            35                  40                  45

Leu Gln Val Leu Gln Ala Gln Leu Thr Trp Val Arg Val Ser His Glu
        50                  55                  60

His Leu Leu Gln Arg Val Asp Asn Phe Thr Gln Asn Pro Gly Met Phe
65                  70                  75                  80

Arg Ile Lys Gly Glu Gln Gly Ala Pro Gly Leu Gln Gly His Lys Gly
                85                  90                  95

Ala Met Gly Met Pro Gly Ala Pro Gly Pro Gly Pro Pro Ala Glu
                100                 105                 110

Lys Gly Ala Lys Gly Ala Met Gly Arg Asp Gly Ala Thr Gly Pro Ser
            115                 120                 125

Gly Pro Gln Gly Pro Pro Gly Val Lys Gly Glu Ala Gly Leu Gln Gly
        130                 135                 140

Pro Gln Gly Ala Pro Gly Lys Gln Gly Ala Thr Gly Thr Pro Gly Pro
145                 150                 155                 160

Gln Gly Glu Lys Gly Ser Lys Gly Asp Gly Gly Leu Ile Gly Pro Lys
                165                 170                 175

Gly Glu Thr Gly Thr Lys Gly Glu Lys Gly Asp Leu Gly Leu Pro Gly
                180                 185                 190

Ser Lys Gly Asp Arg Gly Met Lys Gly Asp Ala Gly Val Met Gly Pro
            195                 200                 205

Pro Gly Ala Gln Gly Ser Lys Gly Asp Phe Gly Arg Pro Gly Pro Pro
        210                 215                 220

Gly Leu Ala Gly Phe Pro Gly Ala Lys Gly Asp Gln Gly Gln Pro Gly
225                 230                 235                 240

Leu Gln Gly Val Pro Gly Pro Pro Gly Ala Val Gly His Pro Gly Ala
                245                 250                 255

Lys Gly Glu Pro Gly Ser Ala Gly Ser Pro Gly Arg Ala Gly Leu Pro
                260                 265                 270

Gly Ser Pro Gly Ser Pro Gly Ala Thr Gly Leu Lys Gly Ser Lys Gly
            275                 280                 285

Asp Thr Gly Leu Gln Gly Gln Gln Gly Arg Lys Gly Glu Ser Gly Val
        290                 295                 300
```

```
Pro Gly Pro Ala Gly Val Lys Gly Glu Gln Gly Ser Pro Gly Leu Ala
305                 310                 315                 320

Gly Pro Lys Gly Ala Pro Gly Gln Ala Gly Gln Lys Gly Asp Gln Gly
            325                 330                 335

Val Lys Gly Ser Ser Gly Glu Gln Gly Val Lys Gly Glu Lys Gly Glu
            340                 345                 350

Arg Gly Glu Asn Ser Val Ser Val Arg Ile Val Gly Ser Ser Asn Arg
            355                 360                 365

Gly Arg Ala Glu Val Tyr Tyr Ser Gly Thr Trp Gly Thr Ile Cys Asp
        370                 375                 380

Asp Glu Trp Gln Asn Ser Asp Ala Ile Val Phe Cys Arg Met Leu Gly
385                 390                 395                 400

Tyr Ser Lys Gly Arg Ala Leu Tyr Lys Val Gly Ala Gly Thr Gly Gln
            405                 410                 415

Ile Trp Leu Asp Asn Val Gln Cys Arg Gly Thr Glu Ser Thr Leu Trp
            420                 425                 430

Ser Cys Thr Lys Asn Ser Trp Gly His His Asp Cys Ser His Glu Glu
            435                 440                 445

Asp Ala Gly Val Glu Cys Ser Val
    450                 455

<210> SEQ ID NO 156
<211> LENGTH: 273
<212> TYPE: PRT
<213> ORGANISM: Homo sapiens

<400> SEQUENCE: 156

Lys Gly Glu Gln Gly Ala Pro Gly Leu Gln Gly His Lys Gly Ala Met
1               5                   10                  15

Gly Met Pro Gly Ala Pro Gly Pro Gly Pro Ala Glu Lys Gly
            20                  25                  30

Ala Lys Gly Ala Met Gly Arg Asp Gly Ala Thr Gly Pro Ser Gly Pro
            35                  40                  45

Gln Gly Pro Pro Gly Val Lys Gly Glu Ala Gly Leu Gln Gly Pro Gln
50                  55                  60

Gly Ala Pro Gly Lys Gln Gly Ala Thr Gly Thr Pro Gly Pro Gln Gly
65                  70                  75                  80

Glu Lys Gly Ser Lys Gly Asp Gly Gly Leu Ile Gly Pro Lys Gly Glu
            85                  90                  95

Thr Gly Thr Lys Gly Glu Lys Gly Asp Leu Gly Leu Pro Gly Ser Lys
            100                 105                 110

Gly Asp Arg Gly Met Lys Gly Asp Ala Gly Val Met Gly Pro Pro Gly
            115                 120                 125

Ala Gln Gly Ser Lys Gly Asp Phe Gly Arg Pro Gly Pro Pro Gly Leu
            130                 135                 140

Ala Gly Phe Pro Gly Ala Lys Gly Asp Gln Gly Gln Pro Gly Leu Gln
145                 150                 155                 160

Gly Val Pro Gly Pro Pro Gly Ala Val Gly His Pro Gly Ala Lys Gly
            165                 170                 175

Glu Pro Gly Ser Ala Gly Ser Pro Gly Arg Ala Gly Leu Pro Gly Ser
            180                 185                 190

Pro Gly Ser Pro Gly Ala Thr Gly Leu Lys Gly Ser Lys Gly Asp Thr
            195                 200                 205

Gly Leu Gln Gly Gln Gln Gly Arg Lys Gly Glu Ser Gly Val Pro Gly
        210                 215                 220
```

```
Pro Ala Gly Val Lys Gly Glu Gln Gly Ser Pro Gly Leu Ala Gly Pro
225                 230                 235                 240

Lys Gly Ala Pro Gly Gln Ala Gly Gln Lys Gly Asp Gln Gly Val Lys
            245                 250                 255

Gly Ser Ser Gly Glu Gln Gly Val Lys Gly Glu Lys Gly Glu Arg Gly
        260                 265                 270

Glu
```

<210> SEQ ID NO 157
<211> LENGTH: 96
<212> TYPE: PRT
<213> ORGANISM: Homo sapiens

<400> SEQUENCE: 157

```
Val Arg Ile Val Gly Ser Ser Asn Arg Gly Arg Ala Glu Val Tyr Tyr
1               5                   10                  15

Ser Gly Thr Trp Gly Thr Ile Cys Asp Asp Glu Trp Gln Asn Ser Asp
            20                  25                  30

Ala Ile Val Phe Cys Arg Met Leu Gly Tyr Ser Lys Gly Arg Ala Leu
        35                  40                  45

Tyr Lys Val Gly Ala Gly Thr Gly Gln Ile Trp Leu Asp Asn Val Gln
    50                  55                  60

Cys Arg Gly Thr Glu Ser Thr Leu Trp Ser Cys Thr Lys Asn Ser Trp
65                  70                  75                  80

Gly His His Asp Cys Ser His Glu Glu Asp Ala Gly Val Glu Cys Ser
                85                  90                  95
```

<210> SEQ ID NO 158
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
        195                 200                 205
Lys Ala Leu Pro Ala Gly Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 159
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Ala Ala Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Gly Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 160
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Lys Glu Ser Gly Pro Gly Leu Val Ala Pro Ser Gln
1               5                   10                  15

Ser Leu Ser Ile Ala Cys Thr Val Ser Gly Phe Ser Leu Thr Asn Tyr
            20                  25                  30

Ala Ile Ser Trp Val Arg Gln Pro Pro Gly Lys Gly Leu Glu Trp Leu
        35                  40                  45

Gly Val Ile Trp Thr Gly Gly Gly Thr Asn Tyr Asn Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Asn Cys Ala
                85                  90                  95

Arg Asn Ser Gly Asp Trp Tyr Phe Asp Val Trp Gly Pro Gly Thr Thr
            100                 105                 110

Val Thr Val Ser Ser
        115

<210> SEQ ID NO 161
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

```
Ser Asn Gln Lys Asn Tyr Leu Ala Trp Tyr Gln Gln Lys Pro Gly Gln
            35                  40                  45

Ser Pro His Leu Leu Ile Tyr Trp Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Asp Tyr Pro Pro Thr Phe Gly Ser Gly Thr Lys Leu Glu Ile
            100                 105                 110

Lys

<210> SEQ ID NO 162
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ser Ser Tyr
                20                  25                  30

Pro Ile Ser Trp Val Arg Gln Pro Pro Gly Lys Gly Leu Glu Trp Leu
            35                  40                  45

Gly Ile Ile Trp Thr Gly Gly Gly Thr Asn Tyr Asn Ser Ala Leu Lys
 50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Arg Tyr Tyr Cys Ala
                 85                  90                  95

Ser Gln Asn Trp Asp Val Asn Ser Ala Leu Asp Tyr Trp Gly Gln Gly
            100                 105                 110

Thr Ser Val Thr Val Ser Ser
        115

<210> SEQ ID NO 163
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
                20                  25                  30

Leu Ala Trp Tyr Gln Gln Lys Gln Gly Lys Ser Pro Gln Leu Leu Val
            35                  40                  45

Tyr Thr Ala Thr Asn Leu Ala Asp Gly Val Pro Ser Arg Phe Ser Gly
        50                  55                  60

Ser Gly Ser Gly Thr Gln Tyr Ser Leu Arg Ile Asn Arg Leu Gln Ser
 65                  70                  75                  80
```

Glu Asp Phe Gly Asn Tyr Tyr Cys Gln His Phe Trp Asn Ala Pro Trp
                85                  90                  95

Thr Phe Gly Gly Gly Thr Lys Leu Glu Ile Lys
            100                 105

<210> SEQ ID NO 164
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Gly Thr Ser Tyr Asn Gln Lys Phe
        50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Leu Arg Ser Pro Tyr Asp Tyr Asp Arg Gly Asp Tyr Val Met
                100                 105                 110

Asp Tyr Trp Gly Gln Gly Thr Ser Val Thr Val Ser Ser
            115                 120                 125

<210> SEQ ID NO 165
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Thr Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
                100                 105                 110

<210> SEQ ID NO 166
<211> LENGTH: 469
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 166

```
Met Asp Met Arg Val Pro Ala Gln Leu Leu Gly Leu Leu Leu Leu Trp
1               5                   10                  15

Leu Arg Gly Ala Arg Cys Gln Val Gln Leu Lys Glu Ser Gly Pro Gly
            20                  25                  30

Leu Val Ala Pro Ser Gln Ser Leu Ser Ile Ala Cys Thr Val Ser Gly
        35                  40                  45

Phe Ser Leu Thr Asn Tyr Ala Ile Ser Trp Val Arg Gln Pro Pro Gly
    50                  55                  60

Lys Gly Leu Glu Trp Leu Gly Val Ile Trp Thr Gly Gly Thr Asn
65                  70                  75                  80

Tyr Asn Ser Thr Leu Lys Ser Arg Leu Ser Ile Ser Lys Asp Asn Ser
                85                  90                  95

Lys Ser Gln Val Phe Leu Lys Met Asn Ser Leu Gln Thr Asp Asp Thr
            100                 105                 110

Ala Arg Tyr Asn Cys Ala Arg Asn Ser Gly Asp Trp Tyr Phe Asp Val
        115                 120                 125

Trp Gly Pro Gly Thr Thr Val Thr Val Ser Ser Ala Lys Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
    210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Ala
                245                 250                 255

Ala Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
    290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Gly Ala
            340                 345                 350

Pro Ile Glu Arg Thr Ile Ser Lys Pro Lys Gly Ser Val Arg Ala Pro
        355                 360                 365

Gln Val Tyr Val Leu Pro Pro Pro Glu Glu Glu Met Thr Lys Lys Gln
    370                 375                 380

Val Thr Leu Thr Cys Met Val Thr Asp Phe Met Pro Glu Asp Ile Tyr
385                 390                 395                 400
```

```
Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
    450                 455                 460

Arg Thr Pro Gly Lys
465

<210> SEQ ID NO 167
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Lys Glu Ser Gly Pro Gly Leu Val Ala Pro Ser Gln
1               5                   10                  15

Ser Leu Ser Ile Ala Cys Thr Val Ser Gly Phe Ser Leu Thr Asn Tyr
            20                  25                  30

Ala Ile Ser Trp Val Arg Gln Pro Pro Gly Lys Gly Leu Glu Trp Leu
        35                  40                  45

Gly Val Ile Trp Thr Gly Gly Thr Asn Tyr Asn Ser Thr Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Asn Cys Ala
                85                  90                  95

Arg Asn Ser Gly Asp Trp Tyr Phe Asp Val Trp Gly Pro Gly Thr Thr
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Ala Ala Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
```

|     |     |     |     |     | 275 |     |     |     |     | 280 |     |     |     |     | 285 |     |     |

Thr Gln Thr His Arg Glu Asp Tyr Asn Ser Thr Leu Arg Val Val Ser
        290                     295                 300

Ala Leu Pro Ile Gln His Gln Asp Trp Met Ser Gly Lys Glu Phe Lys
305                     310                 315                 320

Cys Lys Val Asn Asn Lys Asp Leu Gly Ala Pro Ile Glu Arg Thr Ile
                    325                 330                 335

Ser Lys Pro Lys Gly Ser Val Arg Ala Pro Gln Val Tyr Val Leu Pro
                340                 345                 350

Pro Pro Glu Glu Glu Met Thr Lys Lys Gln Val Thr Leu Thr Cys Met
                355                 360                 365

Val Thr Asp Phe Met Pro Glu Asp Ile Tyr Val Glu Trp Thr Asn Asn
        370                     375                 380

Gly Lys Thr Glu Leu Asn Tyr Lys Asn Thr Glu Pro Val Leu Asp Ser
385                     390                 395                 400

Asp Gly Ser Tyr Phe Met Tyr Ser Lys Leu Arg Val Glu Lys Lys Asn
                    405                 410                 415

Trp Val Glu Arg Asn Ser Tyr Ser Cys Ser Val Val His Glu Gly Leu
                420                 425                 430

His Asn His His Thr Thr Lys Ser Phe Ser Arg Thr Pro Gly Lys
                435                 440                 445

<210> SEQ ID NO 168
<211> LENGTH: 242
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 168

Met Asp Met Arg Val Pro Ala Gln Leu Leu Gly Leu Leu Leu Leu Trp
1               5                   10                  15

Leu Arg Gly Ala Arg Cys Asp Ile Val Met Ser Gln Ser Pro Ser Ser
                20                  25                  30

Leu Ala Val Ser Val Gly Glu Lys Val Thr Met Ser Cys Lys Ser Ser
                35                  40                  45

Gln Ser Leu Leu Tyr Ser Ser Asn Gln Lys Asn Tyr Leu Ala Trp Tyr
            50                  55                  60

Gln Gln Lys Pro Gly Gln Ser Pro His Leu Leu Ile Tyr Trp Ala Ser
65                  70                  75                  80

Thr Arg Glu Ser Gly Val Pro Asp Arg Phe Ile Gly Ser Gly Ser Gly
                85                  90                  95

Thr Asp Phe Thr Leu Thr Ile Ser Ser Val Lys Ala Glu Asp Leu Ala
            100                 105                 110

Val Tyr Tyr Cys Gln Gln Tyr Tyr Asp Tyr Pro Pro Thr Phe Gly Ser
        115                     120                 125

Gly Thr Lys Leu Glu Ile Lys Arg Ala Asp Ala Ala Pro Thr Val Ser
    130                     135                 140

Ile Phe Pro Pro Ser Ser Glu Gln Leu Thr Ser Gly Gly Ala Ser Val
145                     150                 155                 160

Val Cys Phe Leu Asn Asn Phe Tyr Pro Lys Asp Ile Asn Val Lys Trp
                    165                 170                 175

Lys Ile Asp Gly Ser Glu Arg Gln Asn Gly Val Leu Asn Ser Trp Thr
                180                 185                 190

Asp Gln Asp Ser Lys Asp Ser Thr Tyr Ser Met Ser Ser Thr Leu Thr
            195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 169
<211> LENGTH: 220
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 169

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Lys Pro Gly Gln
        35                  40                  45

Ser Pro His Leu Leu Ile Tyr Trp Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asp Tyr Pro Pro Thr Phe Gly Ser Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 170
<211> LENGTH: 471
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 170

Met Asp Met Arg Val Pro Ala Gln Leu Leu Gly Leu Leu Leu Leu Trp
1               5                   10                  15

Leu Arg Gly Ala Arg Cys Gln Val Gln Leu Lys Glu Ser Gly Pro Gly

```
            20                  25                  30
Leu Val Ala Pro Ser Gln Ser Leu Ser Ile Thr Cys Thr Val Ser Gly
        35                  40                  45
Phe Ser Leu Ser Ser Tyr Pro Ile Ser Trp Val Arg Gln Pro Pro Gly
        50                  55                  60
Lys Gly Leu Glu Trp Leu Gly Ile Ile Trp Thr Gly Gly Gly Thr Asn
65                  70                  75                  80
Tyr Asn Ser Ala Leu Lys Ser Arg Leu Ser Ile Ser Lys Asp Asn Ser
                85                  90                  95
Lys Ser Gln Val Phe Leu Lys Met Asn Ser Leu Gln Thr Asp Asp Thr
                100                 105                 110
Ala Arg Tyr Tyr Cys Ala Ser Gln Asn Trp Asp Val Asn Ser Ala Leu
            115                 120                 125
Asp Tyr Trp Gly Gln Gly Thr Ser Val Thr Val Ser Ser Ala Lys Thr
    130                 135                 140
Thr Ala Pro Ser Val Tyr Pro Leu Ala Pro Val Cys Gly Asp Thr Thr
145                 150                 155                 160
Gly Ser Ser Val Thr Leu Gly Cys Leu Val Lys Gly Tyr Phe Pro Glu
                165                 170                 175
Pro Val Thr Leu Thr Trp Asn Ser Gly Ser Leu Ser Ser Gly Val His
                180                 185                 190
Thr Phe Pro Ala Val Leu Gln Ser Asp Leu Tyr Thr Leu Ser Ser Ser
            195                 200                 205
Val Thr Val Thr Ser Ser Thr Trp Pro Ser Gln Ser Ile Thr Cys Asn
    210                 215                 220
Val Ala His Pro Ala Ser Ser Thr Lys Val Asp Lys Lys Ile Glu Pro
225                 230                 235                 240
Arg Gly Pro Thr Ile Lys Pro Cys Pro Pro Cys Lys Cys Pro Ala Pro
                245                 250                 255
Asn Ala Ala Gly Gly Pro Ser Val Phe Ile Phe Pro Pro Lys Ile Lys
                260                 265                 270
Asp Val Leu Met Ile Ser Leu Ser Pro Ile Val Thr Cys Val Val Val
            275                 280                 285
Asp Val Ser Glu Asp Asp Pro Asp Val Gln Ile Ser Trp Phe Val Asn
    290                 295                 300
Asn Val Glu Val His Thr Ala Gln Thr Gln Thr His Arg Glu Asp Tyr
305                 310                 315                 320
Asn Ser Thr Leu Arg Val Val Ser Ala Leu Pro Ile Gln His Gln Asp
                325                 330                 335
Trp Met Ser Gly Lys Glu Phe Lys Cys Lys Val Asn Asn Lys Asp Leu
                340                 345                 350
Gly Ala Pro Ile Glu Arg Thr Ile Ser Lys Pro Lys Gly Ser Val Arg
            355                 360                 365
Ala Pro Gln Val Tyr Val Leu Pro Pro Pro Glu Glu Glu Met Thr Lys
    370                 375                 380
Lys Gln Val Thr Leu Thr Cys Met Val Thr Asp Phe Met Pro Glu Asp
385                 390                 395                 400
Ile Tyr Val Glu Trp Thr Asn Asn Gly Lys Thr Glu Leu Asn Tyr Lys
                405                 410                 415
Asn Thr Glu Pro Val Leu Asp Ser Asp Gly Ser Tyr Phe Met Tyr Ser
                420                 425                 430
Lys Leu Arg Val Glu Lys Lys Asn Trp Val Glu Arg Asn Ser Tyr Ser
            435                 440                 445
```

```
Cys Ser Val Val His Glu Gly Leu His Asn His His Thr Thr Lys Ser
    450                 455                 460

Phe Ser Arg Thr Pro Gly Lys
465                 470

<210> SEQ ID NO 171
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Pro Ile Ser Trp Val Arg Gln Pro Pro Gly Lys Gly Leu Glu Trp Leu
        35                  40                  45

Gly Ile Ile Trp Thr Gly Gly Gly Thr Asn Tyr Asn Ser Ala Leu Lys
50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Ser Gln Asn Trp Asp Val Asn Ser Ala Leu Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
210                 215                 220

Pro Cys Pro Pro Cys Lys Cys Pro Ala Pro Asn Ala Ala Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Gly Ala Pro Ile Glu Arg
```

```
                        325                 330                 335
Thr Ile Ser Lys Pro Lys Gly Ser Val Arg Ala Pro Gln Val Tyr Val
                340                 345                 350
Leu Pro Pro Glu Glu Met Thr Lys Lys Gln Val Thr Leu Thr
            355                 360                 365
Cys Met Val Thr Asp Phe Met Pro Glu Asp Ile Tyr Val Glu Trp Thr
370                 375                 380
Asn Asn Gly Lys Thr Glu Leu Asn Tyr Lys Asn Thr Glu Pro Val Leu
385                 390                 395                 400
Asp Ser Asp Gly Ser Tyr Phe Met Tyr Ser Lys Leu Arg Val Glu Lys
                405                 410                 415
Lys Asn Trp Val Glu Arg Asn Ser Tyr Ser Cys Ser Val Val His Glu
                420                 425                 430
Gly Leu His Asn His His Thr Thr Lys Ser Phe Ser Arg Thr Pro Gly
                435                 440                 445
Lys

<210> SEQ ID NO 172
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Met Asp Met Arg Val Pro Ala Gln Leu Leu Gly Leu Leu Leu Leu Trp
1               5                   10                  15
Leu Arg Gly Ala Arg Cys Asp Ile Gln Met Thr Gln Ser Pro Ala Ser
                20                  25                  30
Leu Ser Val Ser Val Gly Glu Thr Val Thr Ile Thr Cys Arg Ala Ser
            35                  40                  45
Glu Asn Ile Tyr Ser Asn Leu Ala Trp Tyr Gln Gln Lys Gln Gly Lys
        50                  55                  60
Ser Pro Gln Leu Leu Val Tyr Thr Ala Thr Asn Leu Ala Asp Gly Val
65                  70                  75                  80
Pro Ser Arg Phe Ser Gly Ser Gly Ser Gly Thr Gln Tyr Ser Leu Arg
                85                  90                  95
Ile Asn Arg Leu Gln Ser Glu Asp Phe Gly Asn Tyr Tyr Cys Gln His
                100                 105                 110
Phe Trp Asn Ala Pro Trp Thr Phe Gly Gly Gly Thr Lys Leu Glu Ile
            115                 120                 125
Lys Arg Ala Asp Ala Ala Pro Thr Val Ser Ile Phe Pro Pro Ser Ser
130                 135                 140
Glu Gln Leu Thr Ser Gly Gly Ala Ser Val Val Cys Phe Leu Asn Asn
145                 150                 155                 160
Phe Tyr Pro Lys Asp Ile Asn Val Lys Trp Lys Ile Asp Gly Ser Glu
                165                 170                 175
Arg Gln Asn Gly Val Leu Asn Ser Trp Thr Asp Gln Asp Ser Lys Asp
                180                 185                 190
Ser Thr Tyr Ser Met Ser Ser Thr Leu Thr Leu Thr Lys Asp Glu Tyr
            195                 200                 205
Glu Arg His Asn Ser Tyr Thr Cys Glu Ala Thr His Lys Thr Ser Thr
        210                 215                 220
Ser Pro Ile Val Lys Ser Phe Asn Arg Asn Glu Cys
```

<210> SEQ ID NO 173
<211> LENGTH: 214
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 173

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Thr Ala Thr Asn Leu Ala Asp Gly Val Pro Ser Arg Phe Ser Gly
    50                  55                  60

Ser Gly Ser Gly Thr Gln Tyr Ser Leu Arg Ile Asn Arg Leu Gln Ser
65                  70                  75                  80

Glu Asp Phe Gly Asn Tyr Tyr Cys Gln His Phe Trp Asn Ala Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 174
<211> LENGTH: 477
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 174

Met Asp Met Arg Val Pro Ala Gln Leu Leu Gly Leu Leu Leu Leu Trp
1               5                   10                  15

Leu Arg Gly Ala Arg Cys Glu Ile Gln Leu Gln Gln Ser Gly Pro Glu
            20                  25                  30

Leu Val Lys Pro Gly Ala Ser Val Lys Val Ser Cys Lys Ala Ser Gly
        35                  40                  45

Tyr Ser Phe Thr Asp Tyr Asn Met Tyr Trp Val Lys Gln Ser His Gly
    50                  55                  60

Lys Ser Leu Glu Trp Ile Gly Tyr Ile Asp Pro Tyr Asn Gly Gly Thr

```
                65                  70                  75                  80
        Ser Tyr Asn Gln Lys Phe Lys Gly Lys Ala Thr Leu Thr Val Asp Lys
                        85                  90                  95

Ser Ser Ser Thr Ala Phe Met His Leu Asn Ser Leu Thr Ser Glu Asp
                        100                 105                 110

Ser Ala Val Tyr Tyr Cys Ala Arg Leu Arg Ser Pro Tyr Asp Tyr Asp
                        115                 120                 125

Arg Gly Asp Tyr Val Met Asp Tyr Trp Gly Gln Gly Thr Ser Val Thr
                130                 135                 140

Val Ser Ser Ala Lys Thr Thr Ala Pro Ser Val Tyr Pro Leu Ala Pro
        145                 150                 155                 160

Val Cys Gly Asp Thr Thr Gly Ser Ser Val Thr Leu Gly Cys Leu Val
                                165                 170                 175

Lys Gly Tyr Phe Pro Glu Pro Val Thr Leu Thr Trp Asn Ser Gly Ser
                        180                 185                 190

Leu Ser Ser Gly Val His Thr Phe Pro Ala Val Leu Gln Ser Asp Leu
                        195                 200                 205

Tyr Thr Leu Ser Ser Ser Val Thr Val Thr Ser Ser Thr Trp Pro Ser
                210                 215                 220

Gln Ser Ile Thr Cys Asn Val Ala His Pro Ala Ser Ser Thr Lys Val
        225                 230                 235                 240

Asp Lys Lys Ile Glu Pro Arg Gly Pro Thr Ile Lys Pro Cys Pro Pro
                        245                 250                 255

Cys Lys Cys Pro Ala Pro Asn Ala Ala Gly Pro Ser Val Phe Ile
                        260                 265                 270

Phe Pro Pro Lys Ile Lys Asp Val Leu Met Ile Ser Leu Ser Pro Ile
                        275                 280                 285

Val Thr Cys Val Val Val Asp Val Ser Glu Asp Pro Asp Val Gln
                290                 295                 300

Ile Ser Trp Phe Val Asn Asn Val Glu Val His Thr Ala Gln Thr Gln
        305                 310                 315                 320

Thr His Arg Glu Asp Tyr Asn Ser Thr Leu Arg Val Val Ser Ala Leu
                        325                 330                 335

Pro Ile Gln His Gln Asp Trp Met Ser Gly Lys Glu Phe Lys Cys Lys
                        340                 345                 350

Val Asn Asn Lys Asp Leu Gly Ala Pro Ile Glu Arg Thr Ile Ser Lys
                        355                 360                 365

Pro Lys Gly Ser Val Arg Ala Pro Gln Val Tyr Val Leu Pro Pro Pro
                370                 375                 380

Glu Glu Glu Met Thr Lys Lys Gln Val Thr Leu Thr Cys Met Val Thr
        385                 390                 395                 400

Asp Phe Met Pro Glu Asp Ile Tyr Val Glu Trp Thr Asn Asn Gly Lys
                        405                 410                 415

Thr Glu Leu Asn Tyr Lys Asn Thr Glu Pro Val Leu Asp Ser Asp Gly
                        420                 425                 430

Ser Tyr Phe Met Tyr Ser Lys Leu Arg Val Glu Lys Lys Asn Trp Val
                        435                 440                 445

Glu Arg Asn Ser Tyr Ser Cys Ser Val Val His Glu Gly Leu His Asn
                        450                 455                 460

His His Thr Thr Lys Ser Phe Ser Arg Thr Pro Gly Lys
        465                 470                 475

<210> SEQ ID NO 175
```

```
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175
```

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Leu Arg Ser Pro Tyr Asp Tyr Asp Arg Gly Asp Tyr Val Met
            100                 105                 110

Asp Tyr Trp Gly Gln Gly Thr Ser Val Thr Val Ser Ser Ala Lys Thr
        115                 120                 125

Thr Ala Pro Ser Val Tyr Pro Leu Ala Pro Val Cys Gly Asp Thr Thr
    130                 135                 140

Gly Ser Ser Val Thr Leu Gly Cys Leu Val Lys Gly Tyr Phe Pro Glu
145                 150                 155                 160

Pro Val Thr Leu Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Thr Ser Ser Thr Trp Pro Ser Gln Ser Ile Thr Cys Asn
        195                 200                 205

Val Ala His Pro Ala Ser Ser Thr Lys Val Asp Lys Lys Ile Glu Pro
    210                 215                 220

Arg Gly Pro Thr Ile Lys Pro Cys Pro Pro Cys Lys Cys Pro Ala Pro
225                 230                 235                 240

Asn Ala Ala Gly Gly Pro Ser Val Phe Ile Phe Pro Pro Lys Ile Lys
                245                 250                 255

Asp Val Leu Met Ile Ser Leu Ser Pro Ile Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Lys Asp Leu
                325                 330                 335

Gly Ala Pro Ile Glu Arg Thr Ile Ser Lys Pro Lys Gly Ser Val Arg
            340                 345                 350

Ala Pro Gln Val Tyr Val Leu Pro Pro Pro Glu Glu Glu Met Thr Lys
        355                 360                 365

Lys Gln Val Thr Leu Thr Cys Met Val Thr Asp Phe Met Pro Glu Asp

```
                370                 375                 380
Ile Tyr Val Glu Trp Thr Asn Asn Gly Lys Thr Glu Leu Asn Tyr Lys
385                 390                 395                 400

Asn Thr Glu Pro Val Leu Asp Ser Asp Gly Ser Tyr Phe Met Tyr Ser
                405                 410                 415

Lys Leu Arg Val Glu Lys Asn Trp Val Glu Arg Asn Ser Tyr Ser
                420                 425                 430

Cys Ser Val Val His Glu Gly Leu His Asn His His Thr Thr Lys Ser
                435                 440                 445

Phe Ser Arg Thr Pro Gly Lys
    450                 455

<210> SEQ ID NO 176
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Met Asp Met Arg Val Pro Ala Gln Leu Leu Gly Leu Leu Leu Leu Trp
1               5                   10                  15

Leu Arg Gly Ala Arg Cys Asp Ile Val Leu Thr Gln Ser Pro Ala Ser
                20                  25                  30

Leu Ala Val Ser Leu Gly Gln Arg Ala Thr Ile Ser Cys Arg Ala Ser
                35                  40                  45

Lys Ser Val Ser Thr Ser Gly Tyr Thr Tyr Met His Trp Tyr Gln Gln
50                  55                  60

Lys Pro Gly Gln Pro Pro Lys Leu Leu Ile Tyr Leu Ala Ser Asn Leu
65                  70                  75                  80

Glu Ser Gly Val Pro Ala Arg Phe Ser Gly Ser Gly Ser Gly Thr Asp
                85                  90                  95

Phe Thr Leu Asn Ile His Pro Val Glu Glu Asp Ala Ala Thr Tyr
                100                 105                 110

Tyr Cys Gln His Ser Arg Glu Leu Pro Leu Thr Phe Gly Ala Gly Thr
                115                 120                 125

Lys Leu Glu Leu Lys Arg Ala Asp Ala Ala Pro Thr Val Ser Ile Phe
130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
                180                 185                 190

Asp Ser Lys Asp Ser Thr Tyr Ser Met Ser Ser Thr Leu Thr Leu Thr
                195                 200                 205

Lys Asp Glu Tyr Glu Arg His Asn Ser Tyr Thr Cys Glu Ala Thr His
                210                 215                 220

Lys Thr Ser Thr Ser Pro Ile Val Lys Ser Phe Asn Arg Asn Glu Cys
225                 230                 235                 240

<210> SEQ ID NO 177
<211> LENGTH: 218
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 177

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Thr Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys Arg
                100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
        130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
                180                 185                 190

His Asn Ser Tyr Thr Cys Glu Ala Thr His Lys Thr Ser Thr Ser Pro
            195                 200                 205

Ile Val Lys Ser Phe Asn Arg Asn Glu Cys
        210                 215

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Phe Ser Leu Thr Asn Tyr Ala Ile Ser
1               5                   10

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Val Ile Trp Thr Gly Gly Gly Thr Asn Tyr Asn Ser Thr Leu Lys Ser
1               5                   10                  15

<210> SEQ ID NO 180
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 180

Asn Ser Gly Asp Trp Tyr Phe Asp Val
1               5

<210> SEQ ID NO 181
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Lys Ser Ser Gln Ser Leu Leu Tyr Ser Ser Asn Gln Lys Asn Tyr Leu
1               5                   10                  15

Ala

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Trp Ala Ser Thr Arg Glu Ser
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Gln Tyr Tyr Asp Tyr Pro Pro Thr
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Phe Ser Leu Thr Asn Tyr
1               5

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

```
Trp Thr Gly Gly Gly
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Val Ile Trp Thr Gly Gly Gly Thr Asn
1               5

<210> SEQ ID NO 187
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asn Tyr Ala Ile Ser
1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Thr Asn Tyr Ala Ile Ser
1               5

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Trp Leu Gly Val Ile Trp Thr Gly Gly Gly Thr Asn
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Arg Asn Ser Gly Asp Trp Tyr Phe Asp
1               5                   10

<210> SEQ ID NO 191
<211> LENGTH: 13
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 191

Leu Tyr Ser Ser Asn Gln Lys Asn Tyr Leu Ala Trp Tyr
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Leu Leu Ile Tyr Trp Ala Ser Thr Arg Glu
1               5                   10

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Gln Tyr Tyr Asp Tyr Pro Pro
1               5

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Phe Ser Leu Ser Ser Tyr Pro Ile Ser
1               5                   10

<210> SEQ ID NO 195
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ile Ile Trp Thr Gly Gly Gly Thr Asn Tyr Asn Ser Ala Leu Lys Ser
1               5                   10                  15

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Asn Trp Asp Val Asn Ser Ala Leu Asp Tyr
1               5                   10

```
<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Arg Ala Ser Glu Asn Ile Tyr Ser Asn Leu Ala
1               5                   10

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Thr Ala Thr Asn Leu Ala Asp
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln His Phe Trp Asn Ala Pro Trp Thr
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Phe Ser Leu Ser Ser Tyr
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ile Ile Trp Thr Gly Gly Gly Thr Asn
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202
```

Ser Tyr Pro Ile Ser
1               5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Ser Tyr Pro Ile Ser
1               5

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Trp Leu Gly Ile Ile Trp Thr Gly Gly Gly Thr Asn
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Ser Gln Asn Trp Asp Val Asn Ser Ala Leu Asp
1               5                   10

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Tyr Ser Asn Leu Ala Trp Tyr
1               5

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Leu Leu Val Tyr Thr Ala Thr Asn Leu Ala
1               5                   10

<210> SEQ ID NO 208
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 208

Gln His Phe Trp Asn Ala Pro Trp
1               5

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Tyr Ser Phe Thr Asp Tyr Asn Met Tyr
1               5                   10

<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Tyr Ile Asp Pro Tyr Asn Gly Gly Thr Ser Tyr Asn Gln Lys Phe Lys
1               5                   10                  15

Gly

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Leu Arg Ser Pro Tyr Asp Tyr Asp Arg Gly Asp Tyr Val Met Asp Tyr
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Arg Ala Ser Lys Ser Val Ser Thr Ser Gly Tyr Thr Tyr Met His
1               5                   10                  15

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Leu Ala Ser Asn Leu Glu Ser
```

```
1               5
```

```
<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln His Ser Arg Glu Leu Pro Leu Thr
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Tyr Ser Phe Thr Asp Tyr
1               5

<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Asp Pro Tyr Asn Gly Gly
1               5

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Tyr Ile Asp Pro Tyr Asn Gly Gly Thr Ser
1               5                   10

<210> SEQ ID NO 218
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Asp Tyr Asn Met Tyr
1               5

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 219

Thr Asp Tyr Asn Met Tyr
1               5

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Trp Ile Gly Tyr Ile Asp Pro Tyr Asn Gly Gly Thr Ser
1               5                   10

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ala Arg Leu Arg Ser Pro Tyr Asp Tyr Asp Arg Gly Asp Tyr Val Met
1               5                   10                  15

Asp

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Thr Ser Gly Tyr Thr Tyr Met His Trp Tyr
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Leu Leu Ile Tyr Leu Ala Ser Asn Leu Glu
1               5                   10

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gln His Ser Arg Glu Leu Pro Leu
1               5

<210> SEQ ID NO 225
<211> LENGTH: 152
<212> TYPE: PRT
<213> ORGANISM: Homo sapiens

<400> SEQUENCE: 225

Met Ser Pro His Leu Thr Ala Leu Leu Gly Leu Val Leu Cys Leu Ala
1               5                   10                  15

Gln Thr Ile His Thr Gln Glu Gly Ala Leu Pro Arg Pro Ser Ile Ser
            20                  25                  30

Ala Glu Pro Gly Thr Val Ile Ser Pro Gly Ser His Val Thr Phe Met
        35                  40                  45

Cys Arg Gly Pro Val Gly Val Gln Thr Phe Arg Leu Glu Arg Glu Asp
    50                  55                  60

Arg Ala Lys Tyr Lys Asp Ser Tyr Asn Val Phe Arg Leu Gly Pro Ser
65                  70                  75                  80

Glu Ser Glu Ala Arg Phe His Ile Asp Ser Val Ser Glu Gly Asn Ala
                85                  90                  95

Gly Leu Tyr Arg Cys Leu Tyr Tyr Lys Pro Pro Gly Trp Ser Glu His
            100                 105                 110

Ser Asp Phe Leu Glu Leu Leu Val Lys Glu Ser Ser Gly Gly Pro Asp
        115                 120                 125

Ser Pro Asp Thr Glu Pro Gly Ser Ser Ala Gly Thr Val Pro Gly Thr
    130                 135                 140

Glu Ala Ser Gly Phe Asp Ala Pro
145                 150

<210> SEQ ID NO 226
<211> LENGTH: 131
<212> TYPE: PRT
<213> ORGANISM: Homo sapiens

<400> SEQUENCE: 226

Gln Glu Gly Ala Leu Pro Arg Pro Ser Ile Ser Ala Glu Pro Gly Thr
1               5                   10                  15

Val Ile Ser Pro Gly Ser His Val Thr Phe Met Cys Arg Gly Pro Val
            20                  25                  30

Gly Val Gln Thr Phe Arg Leu Glu Arg Glu Asp Arg Ala Lys Tyr Lys
        35                  40                  45

Asp Ser Tyr Asn Val Phe Arg Leu Gly Pro Ser Glu Ser Glu Ala Arg
    50                  55                  60

Phe His Ile Asp Ser Val Ser Glu Gly Asn Ala Gly Leu Tyr Arg Cys
65                  70                  75                  80

Leu Tyr Tyr Lys Pro Pro Gly Trp Ser Glu His Ser Asp Phe Leu Glu
                85                  90                  95

Leu Leu Val Lys Glu Ser Ser Gly Gly Pro Asp Ser Pro Asp Thr Glu
            100                 105                 110

Pro Gly Ser Ser Ala Gly Thr Val Pro Gly Thr Glu Ala Ser Gly Phe
        115                 120                 125

Asp Ala Pro
    130

<210> SEQ ID NO 227
<211> LENGTH: 89
<212> TYPE: PRT
<213> ORGANISM: Homo sapiens

```
<400> SEQUENCE: 227

Pro Ser Ile Ser Ala Glu Pro Gly Thr Val Ile Ser Pro Gly Ser His
1               5                   10                  15

Val Thr Phe Met Cys Arg Gly Pro Val Gly Val Gln Thr Phe Arg Leu
                20                  25                  30

Glu Arg Glu Asp Arg Ala Lys Tyr Lys Asp Ser Tyr Asn Val Phe Arg
            35                  40                  45

Leu Gly Pro Ser Glu Ser Glu Ala Arg Phe His Ile Asp Ser Val Ser
    50                  55                  60

Glu Gly Asn Ala Gly Leu Tyr Arg Cys Leu Tyr Tyr Lys Pro Pro Gly
65                      70                  75                  80

Trp Ser Glu His Ser Asp Phe Leu Glu
                85
```